(12) United States Patent
Holmes et al.

(10) Patent No.: US 11,158,429 B2
(45) Date of Patent: Oct. 26, 2021

(54) INTEGRATED HEALTH DATA CAPTURE AND ANALYSIS SYSTEM

(71) Applicant: Labrador Diagnostics LLC, Wilmington, DE (US)

(72) Inventors: Elizabeth A. Holmes, Palo Alto, CA (US); Ian Gibbons; Daniel Young, Palo Alto, CA (US); Seth G. Michelson, San Jose, CA (US)

(73) Assignee: Labrador Diagnostics LLC, Wilmington, DE (US)

(*) Notice: Subject to any disclaimer, the term of this patent is extended or adjusted under 35 U.S.C. 154(b) by 0 days.

(21) Appl. No.: 15/952,957

(22) Filed: Apr. 13, 2018

(65) Prior Publication Data

US 2018/0308585 A1 Oct. 25, 2018

Related U.S. Application Data

(63) Continuation of application No. 15/246,401, filed on Aug. 24, 2016, which is a continuation of application (Continued)

(51) Int. Cl.
*G16H 50/50* (2018.01)
*G16H 50/70* (2018.01)
(Continued)

(52) U.S. Cl.
CPC .............. *G16H 50/50* (2018.01); *G06F 19/00* (2013.01); *G16H 50/20* (2018.01); *G16H 50/70* (2018.01); *G16H 50/80* (2018.01); *Y02A 90/10* (2018.01)

(58) Field of Classification Search
CPC ........ G16H 50/50; G16H 50/80; G16H 50/20; G16H 50/70; G06F 19/00; Y02A 90/22;
(Continued)

(56) References Cited

U.S. PATENT DOCUMENTS

| 4,003,379 A | 1/1977 | Ellinwood, Jr. |
| 4,146,029 A | 3/1979 | Ellinwood, Jr. |
| (Continued) | | |

FOREIGN PATENT DOCUMENTS

| CN | 1146017 A | 3/1997 |
| CN | 1173776 A | 2/1998 |
| (Continued) | | |

OTHER PUBLICATIONS

ABCNews, Ex-Theranos CEO Elizabeth Holmes says 'I don't know' 600+ times in never-before-broadcast deposition tapes, Retrieved from Internet: <http://sandhillsexpress.com/abc_business/extheranos-ceo-elizabeth-holmes-says-i-dont-know-600-times-in-neverbeforebroadcast-deposition-tapes-abcid36151095/> (Year: 2019).*

(Continued)

*Primary Examiner* — Juan C Ochoa
(74) *Attorney, Agent, or Firm* — Sterne, Kessler, Goldstein & Fox P.L.L.C.

(57) ABSTRACT

The present invention provides an integrated health care surveillance and monitoring system that provides real-time sampling, modeling, analysis, and recommended interventions. The system can be used to monitor infectious and chronic diseases. When faced with outbreak of an infectious disease agent, e.g., influenza virus, the system can identify active cases through pro-active sampling in high risk locations, such as schools or crowded commercial areas. The system can notify appropriate entities, e.g., local, regional and national governments, when an event is detected, thereby allowing for proactive management of a possible outbreak. The system also predicts the best response for deployment of scarce resources.

20 Claims, 37 Drawing Sheets

Related U.S. Application Data

No. 14/511,753, filed on Oct. 14, 2014, now Pat. No. 9,460,263, which is a continuation of application No. 12/906,975, filed on Oct. 18, 2010, now Pat. No. 8,862,448.

(60) Provisional application No. 61/253,015, filed on Oct. 19, 2009.

(51) Int. Cl.
  *G16H 50/80* (2018.01)
  *G16H 50/20* (2018.01)
  *G06F 19/00* (2018.01)

(58) Field of Classification Search
  CPC ........ Y02A 90/26; Y02A 90/24; Y02A 90/10; G06Q 50/22; G06Q 50/265; G16Z 99/00; A61B 5/00
  USPC .......................................... 703/6, 11; 702/19
  See application file for complete search history.

(56) References Cited

U.S. PATENT DOCUMENTS

| | | |
|---|---|---|
| 4,347,176 A | 8/1982 | Mehta |
| 4,731,726 A | 3/1988 | Allen |
| 4,793,825 A | 12/1988 | Benjamin et al. |
| 4,910,131 A | 3/1990 | Mellman et al. |
| 4,920,213 A | 4/1990 | Dale et al. |
| 4,946,795 A | 8/1990 | Gibbons et al. |
| 5,061,381 A | 10/1991 | Burd |
| 5,089,229 A | 2/1992 | Heidt et al. |
| 5,104,813 A | 4/1992 | Besemer et al. |
| 5,122,284 A | 6/1992 | Braynin et al. |
| 5,130,238 A | 7/1992 | Malek et al. |
| 5,162,237 A | 11/1992 | Messenger et al. |
| 5,173,193 A | 12/1992 | Schembri |
| 5,242,606 A | 9/1993 | Braynin et al. |
| 5,270,184 A | 12/1993 | Walker et al. |
| 5,273,905 A | 12/1993 | Muller et al. |
| 5,279,607 A | 1/1994 | Schentag et al. |
| 5,281,395 A | 1/1994 | Markart et al. |
| 5,380,487 A | 1/1995 | Thoperena et al. |
| 5,403,415 A | 4/1995 | Schembri |
| 5,443,790 A | 8/1995 | Coeurveille et al. |
| 5,455,166 A | 10/1995 | Walker |
| 5,472,603 A | 12/1995 | Schembri |
| 5,478,750 A | 12/1995 | Bernstein et al. |
| 5,527,670 A | 6/1996 | Stanley |
| 5,554,539 A | 9/1996 | Chadney et al. |
| 5,578,269 A | 11/1996 | Yaremko et al. |
| 5,590,052 A | 12/1996 | Kopf-Sill et al. |
| 5,591,643 A | 1/1997 | Schembri |
| 5,599,411 A | 2/1997 | Schembri |
| 5,624,850 A | 4/1997 | Kumar et al. |
| 5,648,211 A | 7/1997 | Fraiser et al. |
| 5,670,375 A | 9/1997 | Seaton et al. |
| 5,674,698 A | 10/1997 | Zarling et al. |
| 5,687,716 A | 11/1997 | Kaufmann et al. |
| 5,693,233 A | 12/1997 | Schembri |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,854,033 A | 12/1998 | Lizardi |
| 5,863,502 A | 1/1999 | Southgate et al. |
| 5,874,046 A | 2/1999 | Megerle |
| 5,874,214 A | 2/1999 | Nova et al. |
| 5,876,675 A | 3/1999 | Kennedy |
| 5,885,470 A | 3/1999 | Parce et al. |
| 5,891,734 A | 4/1999 | Gill et al. |
| 5,899,855 A | 5/1999 | Brown |
| 5,902,549 A | 5/1999 | Mimura et al. |
| 5,939,291 A | 8/1999 | Loewy et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,046,056 A | 4/2000 | Parce et al. |
| 6,074,616 A | 6/2000 | Buechler et al. |
| 6,108,635 A * | 8/2000 | Herren .................. G06Q 40/08 705/2 |
| 6,123,861 A | 9/2000 | Santini, Jr. et al. |
| 6,156,181 A | 12/2000 | Parce et al. |
| 6,168,948 B1 | 1/2001 | Anderson et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |
| 6,221,677 B1 | 4/2001 | Wu et al. |
| 6,235,531 B1 | 5/2001 | Kopf-Sill et al. |
| 6,245,057 B1 | 6/2001 | Sieben et al. |
| 6,267,858 B1 | 7/2001 | Parce et al. |
| 6,295,506 B1 | 9/2001 | Heinonen et al. |
| 6,299,839 B1 | 10/2001 | Karunaratne et al. |
| 6,312,929 B1 | 11/2001 | McMillan |
| 6,319,668 B1 | 11/2001 | Nova et al. |
| 6,340,588 B1 | 1/2002 | Nova et al. |
| 6,352,854 B1 | 3/2002 | Nova et al. |
| 6,361,958 B1 | 3/2002 | Shieh et al. |
| 6,368,275 B1 | 4/2002 | Sliwa et al. |
| 6,368,871 B1 | 4/2002 | Christel et al. |
| 6,369,893 B1 | 4/2002 | Christel et al. |
| 6,372,428 B1 | 4/2002 | Nova et al. |
| 6,375,469 B1 | 4/2002 | Brown |
| 6,396,416 B1 | 5/2002 | Kuusela et al. |
| 6,403,338 B1 | 6/2002 | Knapp et al. |
| 6,413,213 B1 | 7/2002 | Essenpreis et al. |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,471,916 B1 | 10/2002 | Noblett |
| 6,482,593 B2 | 11/2002 | Walt et al. |
| 6,484,104 B2 | 11/2002 | Abraham-Fuchs et al. |
| 6,491,666 B1 | 12/2002 | Santini et al. |
| 6,494,830 B1 | 12/2002 | Wessel |
| 6,503,231 B1 | 1/2003 | Prausnitz et al. |
| 6,527,762 B1 | 3/2003 | Santini, Jr. et al. |
| 6,542,717 B1 | 4/2003 | Zimmerman et al. |
| 6,544,732 B1 | 4/2003 | Chee et al. |
| 6,551,838 B2 | 4/2003 | Santini et al. |
| 6,565,815 B1 | 5/2003 | Chang et al. |
| 6,591,124 B2 | 7/2003 | Sherman et al. |
| 6,632,216 B2 | 10/2003 | Houzego et al. |
| 6,641,533 B2 | 11/2003 | Causey, III et al. |
| 6,649,358 B1 | 11/2003 | Parce et al. |
| 6,663,003 B2 | 12/2003 | Johnson et al. |
| 6,664,104 B2 | 12/2003 | Pourahmadi et al. |
| 6,699,188 B2 | 3/2004 | Wessel |
| 6,752,961 B2 | 6/2004 | Kopf-Sill et al. |
| 6,789,510 B1 | 9/2004 | Lee |
| 6,832,296 B2 | 12/2004 | Hooker |
| 6,849,237 B2 | 2/2005 | Housefield et al. |
| 6,878,540 B2 | 4/2005 | Pourahmadi et al. |
| 6,878,755 B2 | 4/2005 | Singh et al. |
| 6,881,541 B2 | 4/2005 | Petersen et al. |
| 6,887,202 B2 | 5/2005 | Currie et al. |
| 6,887,693 B2 | 5/2005 | McMillan et al. |
| 6,893,879 B2 | 5/2005 | Petersen et al. |
| 6,923,764 B2 | 8/2005 | Aceti et al. |
| 6,927,851 B2 | 8/2005 | Mccaffrey et al. |
| 6,929,636 B1 | 8/2005 | Von Alten |
| 6,940,598 B2 | 9/2005 | Christel et al. |
| 6,949,377 B2 | 9/2005 | Ho |
| 6,966,880 B2 | 11/2005 | Boecker et al. |
| 6,979,424 B2 | 12/2005 | Northrup et al. |
| 7,024,370 B2 | 4/2006 | Epler et al. |
| 7,039,453 B2 | 5/2006 | Mullick et al. |

(56) References Cited

U.S. PATENT DOCUMENTS

| | | | |
|---|---|---|---|
| 7,052,831 B2 | 5/2006 | Fletcher et al. |
| 7,105,183 B2 | 9/2006 | Mcgrath |
| 7,112,444 B2 | 9/2006 | Beebe et al. |
| 7,135,144 B2 | 11/2006 | Christel et al. |
| 7,177,767 B2 | 2/2007 | Ostoich et al. |
| 7,178,386 B1 | 2/2007 | Gamble et al. |
| 7,188,001 B2 | 3/2007 | Young et al. |
| 7,201,872 B2 | 4/2007 | Meron |
| 7,209,835 B1 | 4/2007 | Pearlman |
| 7,249,006 B2 | 7/2007 | Lombardo et al. |
| 7,255,833 B2 | 8/2007 | Chang et al. |
| 7,266,484 B2 | 9/2007 | Lombardo et al. |
| 7,289,944 B1 | 10/2007 | Genovese |
| 7,291,497 B2 | 11/2007 | Holmes et al. |
| 7,343,302 B2 | 3/2008 | Aratow et al. |
| 7,349,808 B1 | 3/2008 | Kreiswirth et al. |
| 7,399,276 B1 | 7/2008 | Brown et al. |
| 7,406,453 B2 | 7/2008 | Mundie et al. |
| 7,412,461 B2 | 8/2008 | Sholl et al. |
| 7,457,731 B2 | 11/2008 | Rao |
| 7,459,305 B2 | 12/2008 | Levy |
| 7,497,997 B2 | 3/2009 | Glezer et al. |
| 7,569,346 B2 | 8/2009 | Petersen et al. |
| 7,635,594 B2 | 12/2009 | Holmes et al. |
| 7,636,667 B2 | 12/2009 | Brown |
| 7,666,355 B2 | 2/2010 | Alavie et al. |
| 7,759,067 B2 | 7/2010 | Andersson et al. |
| 7,765,069 B2 | 7/2010 | Ostoich et al. |
| 7,771,658 B2 | 8/2010 | Larsen |
| 7,807,197 B2 | 10/2010 | Lee et al. |
| 7,887,750 B2 | 2/2011 | Blatt et al. |
| 7,888,125 B2 | 2/2011 | Gibbons et al. |
| 7,914,994 B2 | 3/2011 | Petersen et al. |
| 7,998,411 B2 | 8/2011 | Kopf-Sill et al. |
| 8,029,733 B2 | 10/2011 | Chang et al. |
| 8,055,329 B2 | 11/2011 | Kimchy et al. |
| 8,158,430 B1 | 4/2012 | Roy et al. |
| 8,247,176 B2 | 8/2012 | Petersen et al. |
| 8,283,155 B2 | 10/2012 | Holmes et al. |
| 8,346,482 B2 | 1/2013 | Fernandez |
| 8,389,297 B2 | 3/2013 | Pamula et al. |
| 8,394,608 B2 | 3/2013 | Ririe et al. |
| 8,538,778 B2 * | 9/2013 | Neville ............. G06F 19/3481 705/3 |
| 8,580,559 B2 | 11/2013 | Petersen et al. |
| 8,592,157 B2 | 11/2013 | Petersen et al. |
| 8,617,873 B2 | 12/2013 | Solomon |
| 8,862,448 B2 | 10/2014 | Holmes et al. |
| 9,156,032 B2 | 10/2015 | Petersen et al. |
| 9,789,481 B2 | 10/2017 | Petersen et al. |
| 10,533,994 B2 | 1/2020 | Holmes et al. |
| 2001/0012612 A1 | 8/2001 | Petersen et al. |
| 2001/0019831 A1 | 9/2001 | Phillips et al. |
| 2001/0045355 A1 | 11/2001 | Gephart et al. |
| 2001/0051340 A1 | 12/2001 | Singh et al. |
| 2001/0051766 A1 | 12/2001 | Gazdzinski |
| 2001/0053535 A1 | 12/2001 | Bashir et al. |
| 2002/0001854 A1 | 1/2002 | Lee |
| 2002/0019060 A1 | 2/2002 | Petersen et al. |
| 2002/0025576 A1 | 2/2002 | Northrup et al. |
| 2002/0034757 A1 | 3/2002 | Cubicciotti |
| 2002/0035459 A1 | 3/2002 | Grass et al. |
| 2002/0039783 A1 | 4/2002 | McMillan et al. |
| 2002/0042125 A1 | 4/2002 | Petersen et al. |
| 2002/0045246 A1 | 4/2002 | McMillan et al. |
| 2002/0055094 A1 | 5/2002 | Reece et al. |
| 2002/0055127 A1 | 5/2002 | Gindilis |
| 2002/0055167 A1 | 5/2002 | Pourahmadi et al. |
| 2002/0059030 A1 | 5/2002 | Otworth et al. |
| 2002/0072733 A1 | 6/2002 | Flaherty |
| 2002/0092770 A1 | 7/2002 | Hedberg et al. |
| 2002/0109844 A1 | 8/2002 | Christel et al. |
| 2002/0110496 A1 | 8/2002 | Samsoondar |
| 2002/0111741 A1 | 8/2002 | Abraham-Fuchs et al. |
| 2002/0114739 A1 | 8/2002 | Weigl et al. |
| 2002/0120183 A1 | 8/2002 | Abraham-Fuchs et al. |
| 2002/0120187 A1 | 8/2002 | Eiffert et al. |
| 2002/0132226 A1 | 9/2002 | Nair et al. |
| 2002/0143437 A1 | 10/2002 | Handique et al. |
| 2002/0148477 A1 | 10/2002 | Kwoen |
| 2002/0175079 A1 | 11/2002 | Christel et al. |
| 2002/0187074 A1 | 12/2002 | O'Connor et al. |
| 2003/0009088 A1 | 1/2003 | Korth et al. |
| 2003/0014362 A1 | 1/2003 | Yim |
| 2003/0032077 A1 | 2/2003 | Itoh et al. |
| 2003/0049833 A1 | 3/2003 | Chen et al. |
| 2003/0049849 A1 | 3/2003 | Mori et al. |
| 2003/0049865 A1 | 3/2003 | Santini et al. |
| 2003/0061687 A1 | 4/2003 | Hansen et al. |
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0112432 A1 | 6/2003 | Yguerabide et al. |
| 2003/0114735 A1 | 6/2003 | Silver et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0148530 A1 | 8/2003 | Lauks |
| 2003/0152492 A1 | 8/2003 | Chang et al. |
| 2003/0153900 A1 | 8/2003 | Aceti et al. |
| 2003/0167000 A1 | 9/2003 | Mullick et al. |
| 2003/0177038 A1 | 9/2003 | Rao |
| 2003/0185706 A1 | 10/2003 | Ribi |
| 2003/0191430 A1 | 10/2003 | D Andrea et al. |
| 2003/0207457 A1 | 11/2003 | Kopf-Sill et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0211618 A1 | 11/2003 | Patel |
| 2003/0212379 A1 | 11/2003 | Bylund et al. |
| 2003/0214057 A1 | 11/2003 | Huang |
| 2004/0005247 A1 | 1/2004 | Karp |
| 2004/0005582 A1 | 1/2004 | Shipwash |
| 2004/0008125 A1 | 1/2004 | Aratow et al. |
| 2004/0014202 A1 | 1/2004 | King et al. |
| 2004/0024612 A1 | 2/2004 | Gerntholtz |
| 2004/0030672 A1 | 2/2004 | Galvin |
| 2004/0033553 A1 | 2/2004 | Littarru et al. |
| 2004/0053290 A1 | 3/2004 | Terbrueggen et al. |
| 2004/0078145 A1 | 4/2004 | Ostoich et al. |
| 2004/0086872 A1 | 5/2004 | Childers et al. |
| 2004/0096959 A1 | 5/2004 | Stiene et al. |
| 2004/0109793 A1 | 6/2004 | Mcneely et al. |
| 2004/0121305 A1 | 6/2004 | Wiegand et al. |
| 2004/0122486 A1 | 6/2004 | Stahmann et al. |
| 2004/0122559 A1 | 6/2004 | Young et al. |
| 2004/0132220 A1 | 7/2004 | Fish |
| 2004/0166023 A1 | 8/2004 | Lappe et al. |
| 2004/0209374 A1 | 10/2004 | Kopf-Sill et al. |
| 2004/0213825 A1 | 10/2004 | Levy |
| 2004/0228766 A1 | 11/2004 | Witty et al. |
| 2004/0236604 A1 | 11/2004 | Mcnair |
| 2004/0260204 A1 | 12/2004 | Boecker et al. |
| 2005/0009101 A1 | 1/2005 | Blackburn |
| 2005/0009191 A1 | 1/2005 | Swenson et al. |
| 2005/0019836 A1 | 1/2005 | Vogel et al. |
| 2005/0024437 A1 | 2/2005 | Silverbrook |
| 2005/0033196 A1 | 2/2005 | Alroy |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1 | 5/2005 | Holmes |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | Mcdevitt et al. |
| 2005/0137481 A1 | 6/2005 | Sheard et al. |
| 2005/0147559 A1 | 7/2005 | Von Alten |
| 2005/0148091 A1 | 7/2005 | Kitaguchi et al. |
| 2005/0194316 A1 | 9/2005 | Pourahmadi et al. |
| 2005/0203353 A1 | 9/2005 | Ma et al. |
| 2005/0209565 A1 | 9/2005 | Yuzhakov et al. |

(56) References Cited

U.S. PATENT DOCUMENTS

| | | |
|---|---|---|
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2005/0283318 A1 | 12/2005 | Ostoich et al. |
| 2006/0019319 A1 | 1/2006 | Billadeau et al. |
| 2006/0029924 A1 | 2/2006 | Brewster et al. |
| 2006/0036619 A1 | 2/2006 | Fuerst et al. |
| 2006/0062852 A1 | 3/2006 | Holmes |
| 2006/0073605 A1 | 4/2006 | Horan et al. |
| 2006/0078998 A1 | 4/2006 | Puskas et al. |
| 2006/0106316 A1 | 5/2006 | Patti |
| 2006/0177873 A1 | 8/2006 | Dowd et al. |
| 2006/0182738 A1 | 8/2006 | Holmes |
| 2006/0206010 A1 | 9/2006 | Iida et al. |
| 2006/0211933 A1 | 9/2006 | Zimmermann et al. |
| 2006/0218010 A1 | 9/2006 | Michon et al. |
| 2006/0222567 A1 | 10/2006 | Kloepfer et al. |
| 2006/0257941 A1 | 11/2006 | Mcdevitt et al. |
| 2006/0264779 A1 | 11/2006 | Kemp et al. |
| 2006/0264780 A1 | 11/2006 | Holmes et al. |
| 2006/0264782 A1 | 11/2006 | Holmes et al. |
| 2006/0264783 A1 | 11/2006 | Holmes et al. |
| 2006/0271407 A1 | 11/2006 | Rosenfeld et al. |
| 2007/0009388 A1 | 1/2007 | Oda |
| 2007/0026426 A1 | 2/2007 | Fuernkranz et al. |
| 2007/0054270 A1 | 3/2007 | Inganas et al. |
| 2007/0059196 A1 | 3/2007 | Brister et al. |
| 2007/0166195 A1 | 7/2007 | Padmanabhan et al. |
| 2007/0179349 A1 | 8/2007 | Hoyme et al. |
| 2007/0222599 A1 | 9/2007 | Coveley et al. |
| 2007/0224084 A1 | 9/2007 | Holmes et al. |
| 2007/0255756 A1 | 11/2007 | Satomura et al. |
| 2007/0264629 A1 | 11/2007 | Holmes et al. |
| 2008/0009766 A1 | 1/2008 | Holmes et al. |
| 2008/0020379 A1 | 1/2008 | Agan et al. |
| 2008/0044893 A1 | 2/2008 | Pollack et al. |
| 2008/0057572 A1 | 3/2008 | Petersen et al. |
| 2008/0077474 A1 | 3/2008 | Dumas et al. |
| 2008/0091471 A1 | 4/2008 | Michon et al. |
| 2008/0113391 A1 | 5/2008 | Gibbons et al. |
| 2008/0176217 A1 | 7/2008 | Bogoch et al. |
| 2008/0215705 A1 | 9/2008 | Liu et al. |
| 2008/0254532 A1 | 10/2008 | Chang et al. |
| 2008/0270200 A1 | 10/2008 | Khan et al. |
| 2008/0279420 A1 | 11/2008 | Masticola et al. |
| 2008/0306770 A1 | 12/2008 | Sysko et al. |
| 2008/0312515 A1 | 12/2008 | Youn et al. |
| 2009/0055150 A1 | 2/2009 | Prior et al. |
| 2009/0076851 A1 | 3/2009 | Rao |
| 2009/0088336 A1* | 4/2009 | Burd .......... B01J 19/0046 506/9 |
| 2009/0104643 A1* | 4/2009 | Bartholomeusz .... G01N 21/07 435/29 |
| 2009/0203117 A1 | 8/2009 | Crees |
| 2009/0216747 A1 | 8/2009 | Li et al. |
| 2009/0216860 A1 | 8/2009 | Li et al. |
| 2009/0318775 A1* | 12/2009 | Michelson .......... G06Q 10/00 600/301 |
| 2010/0009394 A1 | 1/2010 | Guo |
| 2010/0068706 A1 | 3/2010 | Pourahmadi et al. |
| 2010/0074799 A1 | 3/2010 | Kemp et al. |
| 2010/0081144 A1 | 4/2010 | Holmes et al. |
| 2010/0138160 A1 | 6/2010 | Jacquez et al. |
| 2010/0192683 A1 | 8/2010 | Elkins |
| 2010/0248277 A1 | 9/2010 | Gibbons et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |
| 2011/0275079 A1* | 11/2011 | Palma .............. C12Q 1/6883 435/6.12 |
| 2012/0034598 A1 | 2/2012 | Holmes et al. |
| 2012/0142020 A1 | 6/2012 | Miller |
| 2012/0171758 A1 | 7/2012 | Petersen et al. |
| 2012/0252005 A1 | 10/2012 | Chiang et al. |
| 2012/0258472 A1 | 10/2012 | Roy et al. |
| 2012/0295269 A1 | 11/2012 | Pourahmadi et al. |
| 2013/0115685 A1 | 5/2013 | Holmes et al. |
| 2013/0220931 A1 | 8/2013 | Petersen et al. |
| 2013/0236907 A1 | 9/2013 | Petersen et al. |
| 2014/0141424 A1 | 5/2014 | Pourahmadi et al. |
| 2017/0053091 A1 | 2/2017 | Holmes |
| 2018/0111123 A1 | 4/2018 | Chatterjee et al. |

FOREIGN PATENT DOCUMENTS

| | | |
|---|---|---|
| CN | 1253625 A | 5/2000 |
| CN | 1262606 A | 8/2000 |
| CN | 1341244 A | 3/2002 |
| CN | 1415964 A | 5/2003 |
| CN | 1416528 A | 5/2003 |
| CN | 2559986 | 7/2003 |
| CN | 2559986 Y | 7/2003 |
| CN | 1499949 A | 5/2004 |
| CN | 1526074 A | 9/2004 |
| CN | 1173776 C | 11/2004 |
| CN | 1572320 A | 2/2005 |
| CN | 1192567 C | 3/2005 |
| CN | 1746675 A | 3/2006 |
| CN | 1748217 A | 3/2006 |
| CN | 1751309 A | 3/2006 |
| CN | 1806253 A | 7/2006 |
| EP | 0478319 A1 | 4/1992 |
| EP | 0541340 A2 | 5/1993 |
| EP | 0564254 A1 | 10/1993 |
| EP | 0571225 A2 | 11/1993 |
| EP | 0576602 A1 | 1/1994 |
| EP | 0631137 A2 | 12/1994 |
| EP | 0636685 A2 | 2/1995 |
| EP | 0637996 A1 | 2/1995 |
| EP | 0637998 A1 | 2/1995 |
| EP | 0639223 A1 | 2/1995 |
| EP | 0640826 A1 | 3/1995 |
| EP | 0640828 A1 | 3/1995 |
| EP | 0652600 A1 | 5/1995 |
| EP | 0684315 A1 | 11/1995 |
| EP | 0693560 A2 | 1/1996 |
| EP | 0723146 A1 | 7/1996 |
| EP | 0734017 A1 | 9/1996 |
| EP | 0844475 A2 | 5/1998 |
| EP | 0962773 A1 | 12/1999 |
| EP | 0971039 A2 | 1/2000 |
| EP | 1002229 A1 | 5/2000 |
| EP | 1086719 A1 | 3/2001 |
| EP | 1106244 A2 | 6/2001 |
| EP | 1174078 A2 | 1/2002 |
| EP | 1202057 A2 | 5/2002 |
| EP | 1203959 A1 | 5/2002 |
| EP | 1225442 A2 | 7/2002 |
| EP | 1346686 A2 | 9/2003 |
| EP | 1360931 A1 | 11/2003 |
| EP | 1415788 A1 | 5/2004 |
| EP | 1498067 A | 1/2005 |
| JP | S6247555 A | 3/1987 |
| JP | H0727700 A | 1/1995 |
| JP | H07103959 A | 4/1995 |
| JP | H07120393 A | 5/1995 |
| JP | H07151101 A | 6/1995 |
| JP | H07196314 A | 8/1995 |
| JP | H07304799 A | 11/1995 |
| JP | H08211071 A | 8/1996 |
| JP | H08334505 A | 12/1996 |
| JP | H0968533 A | 3/1997 |
| JP | H0980021 A | 3/1997 |
| JP | H09113511 A | 5/1997 |
| JP | H09192218 A | 7/1997 |
| JP | H09244055 A | 9/1997 |
| JP | H09253056 A | 9/1997 |
| JP | H09281078 A | 10/1997 |
| JP | H1072628 A | 3/1998 |
| JP | H10132712 A | 5/1998 |
| JP | H10239240 A | 9/1998 |
| JP | H10267888 A | 10/1998 |
| JP | H10305016 A | 11/1998 |

(56) References Cited

FOREIGN PATENT DOCUMENTS

| | | |
|---|---|---|
| JP | H1157560 A | 3/1999 |
| JP | H11352094 A | 12/1999 |
| JP | 2000314719 A | 11/2000 |
| JP | 2001065458 A | 3/2001 |
| JP | 2001157855 A | 6/2001 |
| JP | 2001165752 A | 6/2001 |
| JP | 2001319560 A | 11/2001 |
| JP | 2002010990 A | 1/2002 |
| JP | 2002031055 A | 1/2002 |
| JP | 2002041654 A | 2/2002 |
| JP | 2002044007 A | 2/2002 |
| JP | 2002511965 A | 4/2002 |
| JP | 2002161856 A | 6/2002 |
| JP | 2002263185 A | 9/2002 |
| JP | 2002266762 A | 9/2002 |
| JP | 2002279076 A | 9/2002 |
| JP | 2002282217 A | 10/2002 |
| JP | 2002538440 A | 11/2002 |
| JP | 2002371955 A | 12/2002 |
| JP | 2003057244 A | 2/2003 |
| JP | 2003504618 A | 2/2003 |
| JP | 2003166910 A | 6/2003 |
| JP | 2003167960 A | 6/2003 |
| JP | 2003207454 A | 7/2003 |
| JP | 2003222611 A | 8/2003 |
| JP | 2003315348 A | 11/2003 |
| JP | 2003322653 A | 11/2003 |
| JP | 2003329696 A | 11/2003 |
| JP | 2004028589 A | 1/2004 |
| JP | 2004101381 A | 4/2004 |
| JP | 2004527825 A | 9/2004 |
| JP | 2004317498 A | 11/2004 |
| JP | 2004333452 A | 11/2004 |
| JP | 2004358261 A | 12/2004 |
| JP | 2005010179 A | 1/2005 |
| JP | 2005015243 A | 1/2005 |
| JP | 2005030983 A | 2/2005 |
| JP | 2005056395 A | 3/2005 |
| JP | 2005104750 A | 4/2005 |
| JP | 2005130855 A | 5/2005 |
| JP | 2005140681 A | 6/2005 |
| JP | 2005291954 A | 10/2005 |
| JP | 2007187677 A | 7/2007 |
| WO | 9401165 A | 1/1994 |
| WO | 2000051066 A1 | 8/2000 |
| WO | WO 00/78454 A1 | 12/2000 |
| WO | WO 01/13127 A1 | 2/2001 |
| WO | 0135928 A | 5/2001 |
| WO | 0164344 A2 | 9/2001 |
| WO | 0219246 A | 3/2002 |
| WO | 02064038 A | 8/2002 |
| WO | WO 02/064038 A2 | 8/2002 |
| WO | WO 02/064826 A2 | 8/2002 |
| WO | 03043494 A | 5/2003 |
| WO | 03066128 A | 8/2003 |
| WO | 03083727 A | 10/2003 |
| WO | 03098399 A | 11/2003 |
| WO | 2004/098402 A1 | 11/2004 |
| WO | 2005024437 A1 | 3/2005 |
| WO | 2005025413 A2 | 3/2005 |
| WO | 2005031355 A | 4/2005 |
| WO | 2005065157 A2 | 7/2005 |
| WO | 2005065538 A2 | 7/2005 |
| WO | 2005076957 A | 8/2005 |
| WO | 2005079122 A | 8/2005 |
| WO | WO 2005074161 A1 | 8/2005 |
| WO | 2005121367 A | 12/2005 |
| WO | 2006045004 A | 4/2006 |
| WO | WO 2006/116455 A2 | 11/2006 |
| WO | 2007011412 A | 1/2007 |
| WO | WO 2007/092713 A2 | 8/2007 |
| WO | 2007106588 A | 9/2007 |
| WO | 2007120904 A | 10/2007 |
| WO | 2007139895 A | 12/2007 |
| WO | 2008013553 A | 1/2008 |
| WO | 2008105848 A | 9/2008 |
| WO | 2008119182 A | 10/2008 |
| WO | 2009029599 A | 3/2009 |
| WO | 2009053868 A2 | 4/2009 |

OTHER PUBLICATIONS

US Northern District Court Of CA, CR 18 002 58, Indictment, Retrieved from Internet: <https://www.justice.gov/file/1072521/download>, 15 pages (Year: 2019).*

SEC vs. Elizabeth Holmes and Theranos, Case 5:18-cv-01602 Document 1 Filed Mar. 14, 2018, Retrieved from Internet: <https://www.sec.gov/litigation/complaints/2018/comp-pr2018-41-theranos-holmes.pdf>, 24 pages (Year: 2018).* https://www.youtube.com/watch?v=PvznWSEKoEE, Published on Jan. 24, 2019, [online] screenshot, 1 page (Year: 2019).*

Paul Yager et al., Point-of-Care Diagnostics for Global Health, 2008, Annu. Rev. Biomed. Eng. 2008.10, pp. 107-144.*

Katherine A. Erickson and Peter Wilding, "Evaluation of a novel point-of-care system, the i-STAT portable clinical analyzer", 1993, Clinical Chemistry 39.2, pp. 283-287.*

Nichols et al., Evaluation of the enterprise point-of-care (EPOC) system for blood gas and electrolyte analysis, 2008, Point Care 7(1), pp. 7-11.*

Perumalla et al., Reversible parallel discrete-event execution of large-scale epidemic outbreak models, May 17, 2010, Proceedings of the IEEE Workshop on Principles of Advanced and Distributed Simulation, IEEE Computer Society, pp. 1-8.*

Bisset et al. "Modeling interaction between individuals, social networks and public policy to support public health epidemiology", 2009, Proceedings of the Winter Simulation Conference (WSC) IEEE, pp. 2020-2031.*

Barrett et al., "Estimating the impact of public and private strategies for controlling an epidemic: A multi-agent approach", 2009, Twenty-First IAAI Conference, pp. 34-39.*

Bisset et al., "EpiFast: a fast algorithm for large scale realistic epidemic simulations on distributed memory systems", 2009, Proceedings of the 23rd international conference on Supercomputing, ACM, pp. 430-439.*

"Products," Cepheid, Inc., Sunnyvale, California, United States, https://web.archive.org/web/20040407201033/http://cepheid.com:80/pages/products html, archived Apr. 7, 2004.

"Cepheid—Products," Cepheid, Inc., Sunnyvale, California, United States, https ://web.archive.org/web/2004/0614174818/https://www.cepheid.com:80/Sites/cepheid/content.cfm?id=158, archived Jun. 14, 2004.

Belgrader, P., et al., "A microfluidic cartridge to prepare spores for PCR analysis," Biosensors & Bioelectronics, vol. 14: 849-852 (2000).

Ulrich, M. P., et al., "Evaluation of the Cepheid GeneXpert® system for detecting Bacillu antracis," Journal of Applied Microbiology, vol. 100: 1011-1016 (2006).

McMillan, W. A., "Real-time point-of-care molecular detection of infectious disease agents," American Clinical Laboratory, vol. 21(1): 29-31 (2002).

Meehan, P. J., et al., "Responding to Detection of Aerosolized Bacillus anthracis by Autonomous Detection Systems in the Workplace," Morbidity and Mortality Weekly Report: Recommendations and Reports, vol. 53 (7): 1-12 (2004).

Petersen, K., et al., "IVD systems in bioterrorism response," IVDT: Beyond Clinical Diagnostics, vol. 8(4): 35-40 (2002).

"Cepheid Granted US Patent Covering Key Internal Control Method for Ensuring Accurate DNA Test Results," Cepheid Inc., Sunnyvale, California, United States, Nov. 27, 2001.

Piccolo® Operator's Manual, Abaxis, Inc., Union City, California, United States, Mar. 2001.

Von Schenck, H., et al., "Evaluation of "HemoCue," a New Device for Determining Hemoglobin," Clin. Chem., vol. 32(3): 526-529 (1986).

Neufeld, L., et al., "Hemoglobin measured by Hemocue and a reference method in venous and capillary blood: A validation study," Salud Publica de Mexico, vol. 44(3): 219-227 (2002).

(56) References Cited

OTHER PUBLICATIONS

HemoCue Hb 201+ Operating Manual, HomeCue AB, Angelholm Sweden, www.hemocue.com.
Inganäs, M., et al., "Integrated Microfluidic Compact Disc Device with Potential Use in Both Centralized and Point-of-Care Laboratory Settings," Clinical Chemistry, vol. 51(10): 1985-1987 (2005).
Cheng, S. B., et al., "Development of a Multichannel Microfluidic Analysis System Employing Affinity Capillary Electrophoresis for Immunoassay," *Anal. Chem.*, vol. 73(7): 1472-1479 (2001).
Clayton, J., "Go with the microflow," *Nature Methods*, vol. 2(8): 621-622 (2005).
Hong, J. W., et al., "A nanoliter-scale nucleic acid processor with parallel architecture," *Nature Biotechnology*, vol. 22(4): 435-439 (2004).
Sara Yemimah Del Valle, "Effects of behavioral changes and mixing patterns in mathematical models for smallpox epidemics", 2005, pp. 1-112.
S. Y. Del Valle et al., "Mixing Patterns Between Age Groups Using Social Networks", 2006, pp. 1-24.
W. John Edmunds et al., "The pre-vaccination epidemiology of measles, mumps and rubella in Europe: implications for modelling studies", 2000, Epidemiology & Infection 125.3, pp. 635-650.
UnifiedPatents blog post dated May 7, 2020, available at https://www.unifiedpatents.com/insights/2020/5/7/1/prior-art-theranos-covid.
UnifiedPatents PATROLL Winning Submission; (Holmes I), linked to UnifiedPatents blog post dated May 7, 2020.
UnifiedPatents PATROLL Winning Submission; (Holmes II), linked to UnifiedPatents blog post dated May 7, 2020.
APEX Standards Enterprise; Pseudo Claim Charting; U.S. Pat. No. 10,533,994 B2, linked to UnifiedPatents blog post dated May 7, 2020.
APEX Standards Enterprise; Pseudo Claim Charting; U.S. Pat. No. 8,283,155 B2, linked to UnifiedPatents blog post dated May 7, 2020.
Schuette et al., "Modeling the effects of varicella vaccination programs on the incidence of chickenpox and shingles", 1999, Bulletin of mathematical biology 61.6, pp. 1031-1064.
Office Action dated Jul. 27, 2011 for U.S. Appl. No. 11/554,509.
Office Action dated Jul. 28, 2009 for U.S. Appl. No. 11/202,206.
Office Action dated Jul. 29, 2011 for U.S. Appl. No. 12/986,954.
Office Action dated Aug. 24, 2010 for U.S. Appl. No. 11/388,415.
Office Action dated Aug. 27, 2010 for U.S. Appl. No. 11/388,823.
Office Action dated Aug. 29, 2008 for U.S. Appl. No. 11/388,823.
Office Action dated Aug. 31, 2011 for U.S. Appl. No. 12/221,816.
Office Action dated Sep. 1, 2005 for U.S. Appl. No. 10/937,872.
Office Action dated Sep. 11, 2008 for U.S. Appl. No. 11/389,409.
Office Action dated Sep. 22, 2011 for U.S. Appl. No. 12/576,197.
Office Action dated Sep. 30, 2016 for U.S. Appl. No. 13/647,325.
Office Action dated Sep. 4, 2013 for U.S. Appl. No. 11/388,823.
Office Action dated Sep. 5, 2008 for U.S. Appl. No. 11/388,723.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Pal, et al. An integrated microfluidic device for influenza and other genetic analyses. Lab Chip. Oct. 2005;5(10):1024-32. Epub Aug. 18, 2005.
Patolsky, et al. Electrical detection of single viruses. Proc Natl Acad Sci USA. Sep. 28, 2004;101(39):14017-22. Epub Sep. 13, 2004.
Pescovitz, D. Sniffing out airborne disease. Lab Note: Research from the College of Engineering, University of California, Berkeley, 2004. Available online at http://www.coe.berkeley.edu/labnotes/0904/pisano.html. Accessed Jan. 28, 2011.
Preininger, et al. Polymer-coated optical fibres for application in a direct evanescent wave immunoassay. Analytica Chimica Acta, 2000; 403; 67-76.
Price et al, "Improving Healthcare Accessibility Through Point-of-Care Technologies", Clinical Chemistry, 53:9, pp. 1665-1675, 2007.
Rai-Choudhury, ed., Handbook of Microlithography, Micromachining & Microfabrication. SPIE Optical Engineering Press. Bellingham, Wash. 1997. (Cover pages and table of contents only).
Ray, et al. Distinct hemagglutinin and neuraminidase epitopes involved in antigenic variation of recent human parainfluenza virus type 2 isolates. Virus Res. Jun. 1992;24(1):107-13.
Red Herring. Stopping bad reactions. Red Herring. Dec. 26, 2005.
Runyan, et al. Seminconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74 (5):1061-8.
Scheurle, et al. HER-2/neu expression in archival non-small cell lung carcinomas using FDA-approved hercep test. Anticancer Res. 2000; 20:2091-2096.
Sista et al, "Development of a Digital Microfluidic Platform for Point of Care Testing", Lab Chip, vol. 8, pp. 2091-2104, 2008.
Spira, et al. The identification of monoclonal class switch variants by sib selection and an ELISA assay. J Immunol Methods. 1984;74(2):307-15.
Steplewski, et al. Isolation and characterization of anti-monosialoganglioside monoclonal antibody 19-9 class-switch variants. Proc Nati Acad Sci U S A. 1985; 82(24):8653-7.
Stevens, et al. Glycan microarray analysis of the hemagglutinins from modern and pandemic influenza viruses reveals different receptor specificities. J Mol Biol. Feb. 3, 2006;355(5):1143-55.
Tedeschi, et al. Antibody immobilisation on fibre optic TIRF sensors. Biosens Bioelectron. 2003; 19(2):85-93.
Yan, el al. Multiplexed flow cytometric immunoassay for influenza virus detection and differentiation. Anal Chem. Dec. 1, 2005;77(23):7673-8.
Office Action dated Oct. 17, 2008 for U.S. Appl. No. 11/389,410.
Office Action dated Oct. 26, 2006 for U.S. Appl. No. 10/937,872.
Office Action dated Oct. 31, 2013 for U.S. Appl. No. 12/986,954.
Office Action dated Oct. 6, 2008 for U.S. Appl. No. 11/746,535.
Office Action dated Nov. 22, 2011 for U.S. Appl. No. 11/202,231.
Office Action dated Nov. 30, 2015 for U.S. Appl. No. 14/511,753.
Office Action dated Nov. 5, 2009 for U.S. Appl. No. 11/202,231.
Office Action dated Nov. 9, 2011 for U.S. Appl. No. 11/388,823.
Office Action dated Dec. 11, 2012 for U.S. Appl. No. 12/750,518.
Office Action dated Dec. 19, 2008 for U.S. Appl. No. 11/202,206.
Office Action dated Dec. 22, 2009 for U.S. Appl. No. 11/388,823.
Office Action dated Dec. 22, 2010 for U.S. Appl. No. 11/554,509.
Office Action dated Dec. 9, 2013 for U.S. Appl. No. 12/625,430.
Office Action dated Feb. 1, 2013 for U.S. Appl. No. 13/187,960.
Office Action dated Feb. 17, 2009 for U.S. Appl. No. 11/202,231.
Office Action dated Feb. 2, 2011 for U.S. Appl. No. 11/746,535.
Office Action dated Feb. 22, 2008 for U.S. Appl. No. 11/202,231.
Office Action dated Feb. 22, 2008 for U.S. Appl. No. 11/746,535.
Office Action dated Feb. 27, 2009 for U.S. Appl. No. 11/388,723.
Office Action dated Mar. 6, 2011 for U.S. Appl. No. 11/202,231.
Office Action dated Mar. 17, 2009 for U.S. Appl. No. 11/388,415.
Office Action dated Mar. 18, 2008 for U.S. Appl. No. 11/202,206.
Office Action dated Mar. 21, 2008 for U.S. Appl. No. 11/388,723.
Office Action dated Mar. 21, 2011 for U.S. Appl. No. 11/388,415.
Office Action dated Mar. 22, 2010 for U.S. Appl. No. 11/202,206.
Office Action dated Mar. 3, 2011 for U.S. Appl. No. 11/202,206.
Office Action dated Mar. 5, 2009 for U.S. Appl. No. 11/388,823.
Office Action dated Mar. 5, 2010 for U.S. Appl. No. 11/746,535.
Office Action dated Mar. 7, 2006 for U.S. Appl. No. 10/937,872.
Office Action dated Apr. 1, 2010 for U.S. Appl. No. 11/388,824.
Office Action dated Apr. 13, 2012 for U.S. Appl. No. 11/554,509.
Office Action dated Apr. 18, 2007 for U.S. Appl. No. 10/937,872.
Office Action dated Apr. 29, 2009 for U.S. Appl. No. 11/389,409.
Office Action dated Apr. 30, 2009 for U.S. Appl. No. 11/388,824.
Office Action dated Apr. 30, 2013 for U.S. Appl. No. 13/647,325.
Office Action dated Apr. 4, 2013 for U.S. Appl. No. 12/986,954.
Office Action dated Apr. 5, 2010 for U.S. Appl. No. 11/554,509.
Office Action dated Apr. 8, 2009 for U.S. Appl. No. 11/389,410.
Office Action dated May 22, 2009 for U.S. Appl. No. 11/746,535.

(56) References Cited

OTHER PUBLICATIONS

Office Action dated May 29, 2012 for U.S. Appl. No. 12/986,954.
Office Action dated Jun. 1, 2007 for U.S. Appl. No. 11/389,409.
Office Action dated Jun. 1, 2012 for U.S. Appl. No. 11/388,823.
Office Action dated Jun. 11, 2012 for U.S. Appl. No. 11/388,415.
Office Action dated Jun. 19, 2015 for U.S. Appl. No. 13/647,325.
Office Action dated Jun. 21, 2007 for U.S. Appl. No. 11/202,231.
Office Action dated Jun. 24, 2013 for U.S. Appl. No. 13/436,568.
Office Action dated Jun. 5, 2013 for U.S. Appl. No. 12/750,518.
Office Action dated Jun. 9, 2010 for U.S. Appl. No. 11/746,535.
Office Action dated Jul. 18, 2012 for U.S. Appl. No. 12/576,197.
Office Action dated Jul. 25, 2008 for U.S. Appl. No. 11/389,409.
Akhgar et al, Leveraging StoLPaN Host Environment for Portable Diagnostic Health-Care Platform, IKE, 2008.
Barrett et al. EpiSimdemics: An Efficient Algorithm for Simulating the Spread of Infectious Disease Over Large Realistic Social Networks, SC2008, Nov. 2008.
Bawendi, et al. The quantum-mechanics of larger semiconductor clusters. Annu. Rev. Phys. Chem. 1990; 41:477-496.
BD Biosciences, Directigen FluA&B Assay Manual. Oct. 11, 2016, pp. 1-11.
Beier, et al. Versatile derivatisation of solid support media for covalent bonding on DNA-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifuntional crosslinkers for immobilization of antibodies on silica surfaces. Anal Biochem. 1989; 178(2):408-13.
Bosma et al, "Designing Smart Health Care Technology into the Home of the Future", Sandia National Laboratories, Mar. 25, 1999.
Broadcaster Moira Gunn with Elizabeth Holmes, recorded Mar. 5, 2005 on Biotech Nation.
Bruchez, et al. Semiconductor nanocrystals as fluorescent biological labels. Science. 1998; 281(5385):2013-6.
Celebre, et al. A comparative sudy of efficiencies of fibre optic and prism TIRF sensors. Meas. Sci. Technol. 1992; 3:1166-1173.
Chan. Quantum dot bioconjugates for ultrasensitive nonisotopic detection. Science. 1998;281(5385):2016-8.
Chang, et al. Micromachining & Microfabrication. SPIE Optical Engineering Press. Bellingham, Wash. 1997. (Cover pages and table of contents only).
Charles, et al. Synthesis of a flurescent analog of polychlorinated biphenyls for use in a continuous flow immunosensor assay. Bioconjug Chem. 1995; 6(6):691-4.
Duffy, et al. Rapid Prototyping of Microfluidic Systems in Poly(dimethylsiloxane). Analytical Chemistry. 1998; 70 (23);4974-4084.
European search report and search opinion dated Feb. 7, 2012 for EP Application No. 11180769.9.
European search report and search opinion dated Mar. 6, 2012 for EP Application No. 10179887.4.
European search report and search opinion dated May 29, 2012 for EP Application No. 11180769.9.
European search report dated Jun. 2, 2009 for Application No. 07762092.
Gavin, et al. Review of Rapid Diagnostic Tests for Influenza. Clinical and Applied Immunology Reviews. 2004; 4(3):151-172.
Geddes, et al. The impedance of stainless-steel electrodes. Med Biol Eng. Sep. 1971;9(5):511-21.

Gonzalez et al. SINCO: Intelligent System in Disease Prevention and Control. An Architectual Approach, ISBMDA 2004, LNCS 3337, pp. 129-140.
Gutierrez. Agent-Based Simulation of Disease Spread Aboard Ship, Thesis, Naval Postgraduate School, Mar. 2005.
Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
Hirsh, et al. The electrical conductivity of blood. I: Relationship to erythrocyte concentration. Blood. Nov. 1950;5(11):1017-35.
International search report and written opinion dated Feb. 23, 2011 for PCT/US10/53088.
International search report and written opinion dated Sep. 16, 2008 for PCT/US2007/009878.
International search report dated Jan. 22, 2008 for PCT/US06/42563.
International search report dated Dec. 8, 2008 for PCT/US06/11090.
International search report dated Jul. 4, 2005 for PCT/US04/029462.
International search report dated Aug. 11, 2008 for PCT/US07/68665.
International search report dated Sep. 9, 2008 for PCT/US07/23904.
Jaeger. Introduction to Microelectronic fabrication. Addison-Wesley Publishing Co. Reading Mass. 1988. (Cover pages and table of Contents only).
Jenvald et al. Simulation as Decision Support in Pandemic Influenza Preparedness and Response, Proceedings ISCRAM, 2007.
Kessler, et al. Use of the DNA flow-thru chip, a three-dimensional biochip, for typing and subtyping of influenza viruses. J Clin Microbiol. May 2004;42(5):2173-85.
Khan, et al. Detection of influenza virus neuraminidase-specific antibodies by an enzyme-linked immunosorbent assay. J Clin Microbiol. Jul. 1982;16(1): 115-22.
Kilbourne, et al. Independent and disparate evolution in nature of influenza A virus hemagglutinin and neuraminidase glycoproteins. Proc Natl Acad Sci U S A. Jan. 1990;87(2):786-90.
Lee, et al. Microfluidic enzyme-linked immunosorbent assay technology. Adv Clin Chem. 2006;42:255-95.
Liu, et al. Validation of a fully integrated microfluidic array device for influenza A subtype identification and sequencing. Anal Chem. Jun. 15, 2006;78(12):4184-93.
Lupiani, et al. Improved diagnostic tests for Avian influenza surveillance, 2005. Proceedings of the Institute of Food Technologies' First Annual Forod protection and Defense Research Conference.
Mohapatra, et al. Blood resistivity and its implications for the calculation of cardic output by the thoracic electrical impedance technique. Intensive Care Med. Aug. 1977;3(2):63-7.
Mukerjee, et al. Microneedle array for transdermal biological fluid extraction and in situ analysis. Sensors and Actuators A. 2004; 114:267-275.
Notice of Allowance dated Jun. 17, 2016 for U.S. Appl. No. 14/511,753.
Notice of allowance dated Feb. 28, 2014 for U.S. Appl. No. 12/906,975.
Office Action dated Jan. 12, 2016 for U.S. Appl. No. 13/647,325.
Office Action dated Jan. 13, 2015 for U.S. Appl. No. 13/647,325.
Office Action dated Jan. 16, 2014 for U.S. Appl. No. 13/647,325.
Office Action dated Jan. 5, 2010 for U.S. Appl. No. 11/388,415.
Office Action dated Jan. 8, 2013 for U.S. Appl. No. 11/388,415.

* cited by examiner

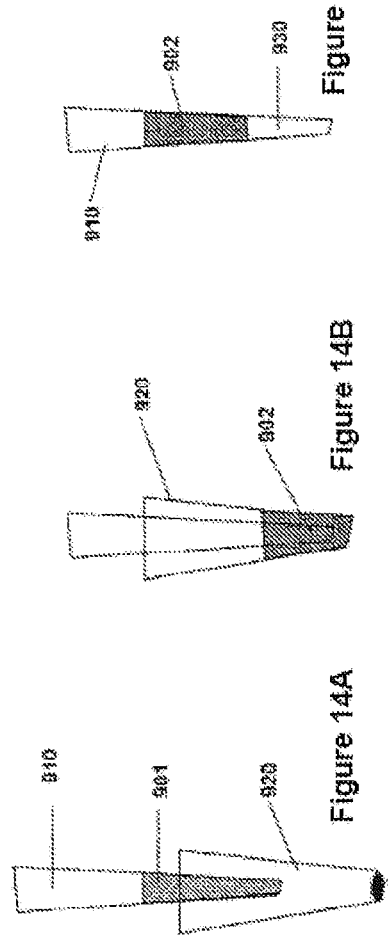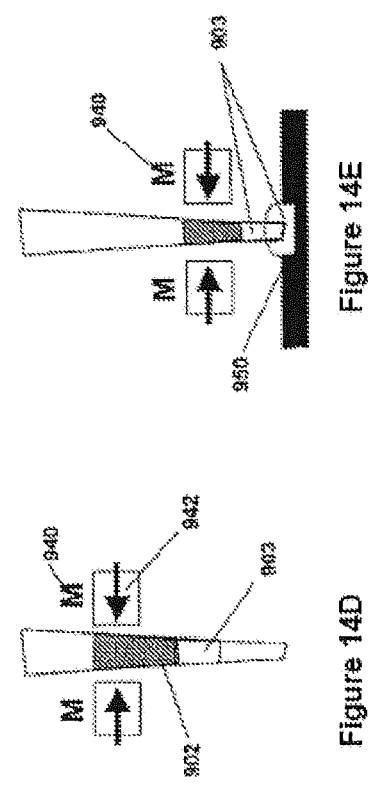
FIGURES 14A-E

INTEGRATED HEALTH DATA CAPTURE AND ANALYSIS SYSTEM

CROSS-REFERENCE TO RELATED APPLICATIONS AND INCORPORATION BY REFERENCE

This application is a continuation of U.S. application Ser. No. 15/246,401, filed Aug. 24, 2016, which is a continuation of U.S. application Ser. No. 14/511,753, filed Oct. 10, 2014, now U.S. Pat. No. 9,460,263, issued Oct. 4, 2016, which is a continuation of Ser. No. 12/906,975, filed Oct. 18, 2010, now U.S. Pat. No. 8,862,448, issued Oct. 14, 2014, which claims the benefit of U.S. Provisional Application No. 61/253,015, filed Oct. 19, 2009, which are incorporated by reference herein in their entirety.

FIELD OF THE INVENTION

The present disclosure is generally in the field of electronic medical assistance and field testing.

BACKGROUND OF THE INVENTION

An epidemic of infectious diseases capable of spreading across a large region, e.g., a continent or the entire world, can be hugely costly to societies. Such incidences include pandemics of influenza, smallpox, tuberculosis, human immune deficiency virus (HIV), and Severe Acute Respiratory Syndrome (SARS). The World Bank estimated in 2008 that a flu pandemic could cost $3 trillion and result in a nearly 5% drop in world gross domestic product (GDP). The World Bank further estimated that more than 70 million people could die worldwide in a severe pandemic. Others have estimated that a flu pandemic could cause an economic recession in the United States, costing the country at least $500 billion to $675 billion in the near term. In 2003, SARS disrupted travel, trade and the workplace in the Asia Pacific region and cost the region about $40 billion. The SARS pandemic lasted for six months, killing at least 1000 of the 8,000 people it infected in 25 countries. The city of Toronto, Calif. was closed to air traffic for several weeks and suffered significant financial loss.

In 2009, the spring flu season cost billions of dollars even though it only lasted only a few weeks. The 2009-2010 winter flu season is anticipated to start by late August and could run through April 2010. Even if working vaccines are available, their supplies are expected to be limited and cannot be expected to stop the flu for several months. Economic losses can be minimized if the flu can be contained through proactive screening that allows for effective anti-viral administration and narrowly targeted quarantines.

Economic loss due to "avoidance behaviors" is even greater than the cost of treating flu victims. The cost includes reducing air travel, avoiding travel to infected destinations and reducing consumption of services, such as mass transit, dining out, shopping, etc. According to the World Bank, if a flu epidemic approached the 2.5% mortality rates similar to 1918-19 flu, avoidance behaviors would cost a region five times more than losses from mortality or work absenteeism.

SUMMARY OF THE INVENTION

There is a pressing need for an infrastructure to mitigate the spread of infectious diseases such as influenza when it occurs. The present invention meets this need through an integrated system that provides real-time sampling, modeling, analysis, and/or recommended interventions. The system can identify active cases in an outbreak through proactive sampling in high risk locations, such as schools or crowded commercial areas, and can allow for sampling and quarantine of surrounding cases to help eradicate the outbreak. The system can also suggest an appropriate response for deployment of scarce resources and predict the impact of such mitigation both in terms of reduction of mortality and morbidity and economic impact. Furthermore, the systems of the present invention can help the government provide accurate, more reliable, and timely information that may reduce unnecessary avoidance behavior and save billions of dollars.

In one aspect, the present invention provides a system for modeling a progression of a disease within a population, comprising: a static database component comprising static data related to the disease and/or the population; a dynamic database component comprising dynamic data about the population and individual subjects; and a computer modeling component that is configured to model the data in the static database component and the dynamic database component, thereby modeling the disease within the population. The disease can be an infectious disease or a chronic disease.

In some embodiments, the infectious disease agent or an analyte thereof comprises an adenovirus, *Bordella pertussis, Chlamydia pneumoiea, Chlamydia trachomatis*, Cholera Toxin, Cholera Toxin β, *Campylobacter jejuni*, Cytomegalovirus, Diptheria Toxin, Epstein-Barr NA, Epstein-Barr EA, Epstein-Barr VCA, *Helicobacter Pylori*, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3 KD, Hepatitis E virus (HEV) orf2 6 KD, Hepatitis E virus (HEV) orf3 3KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, *Leishmania donovani*, Lyme disease, Mumps, *M. pneumoniae, M. tuberculosis*, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15 kd, *T. pallidum* p47, *T. cruzi, Toxoplasma*, or *Varicella Zoster*.

In other embodiments, the disease is an infectious disease comprising a microrganism, a microbe, a virus, a bacterium, an archaeum, a protozoan, a protist, a fungus or a microscopic plant. The virus can comprise influenza or HIV. The bacterium can comprise *Mycobacterium tuberculosis*. The protozoan can comprise malaria.

In still other embodiments, the disease is a chronic disease or condition comprising diabetes, prediabetes, insulin resistance, metabolic disorder, obesity, or cardiovascular disease.

The static database component of the invention can include information about the individuals in the population. The information about the individuals in the population can include one or more of age, race, sex, location, genetic factors, single nucleotide polymorphisms (SNPs), family history, disease history or therapeutic history.

The static database component can also comprise information about the disease. The information about the disease can include one or more of virulence, contagiousness, mode of transmission, treatment availability, vaccine availability, death rate, recovery time, cost of treatment, infectivity, rate of spread, rate of mutation, and past outbreak.

In some embodiments, the data in the dynamic database component is updated in real-time. In some embodiments, the data in the dynamic database component comprises an indication of the disease state of the individuals in the population. The indication of the disease state of an individual can be determined by measuring a biomarker, a physiological parameter, or a combination thereof.

When the disease monitored by the invention is influenza, the biomarker/s can include hemagglutinin and/or neuraminidase. The hemagglutinin can be selected from the group consisting of H, H2, H3, H4, H5, H6, H7, H8, H9, H10, H11, H12, H13, H14, H15, and H16, and the neuraminidase can be selected from the group consisting of N1, N2, N3, N4, and N5. In some embodiments, the hemagglutinin comprises H1 and the neuraminidase comprises N1. In some embodiments, the hemagglutinin comprises H5 and the neuraminidase comprises N1.

The biomarker measured by the invention can be a host antibody. For example, the biomarker can be an IgM antibody, an IgG antibody or an IgA antibody against a disease marker.

In some embodiments, the biomarker comprises a marker of inflammation. Such marker of inflammation can be a cytokine or C-reactive protein. The marker of inflammation can also be IL-1β, IL-6, IL-8, IL-10, or TNFα.

In some embodiments, the biomarker is measured in a sample of bodily fluid from the individual. Exemplary bodily fluids include without limitation blood, plasma, serum, sputum, urine, feces, semen, mucous, lymph, saliva, or nasal lavage.

In some embodiments, the physiological parameter measured by the invention comprises one or more of body weight, temperature, heart rate, blood pressure, mobility, hydration, ECG, or alcohol use.

The biomarker or physiological parameter can be determined using a point-of-care device. The point of care devices can be deployed according to instructions determined by the computer modeling component. The point of care device can perform without limitation one or more of cartridge assays, real time PCR, rapid antigen tests, viral culture, and immunoassays. The point of care device can measure more than one biomarker with more than 30% better accuracy and/or precision than standard methods. In some embodiments, the system comprises a plurality of point of care devices. The point of care devices can be positioned at one or more of a school, a workplace, a shopping center, a community center, a religious institution, a hospital, a health clinic, a mobile unit, or a home.

The point of care device can comprise a portable instrument. For example, the point of care device can include a portable cartridge. In some embodiments, the cartridge is configured to accept reagents for measuring the biomarkers. The biomarkers can be measured according to a protocol communicated from the computer modeling component. In some embodiments, the cartridge is configured to measure a set of biomarkers from a plurality of bodily fluid samples.

The point of care device of the invention can include a graphical user interface configured for data entry.

In some embodiments, the point of care device is configured to communicate the biomarker or physiological parameter measurements to the computer modeling component. The communication can include wireless communication, wired communication, or a combination thereof. Wireless communication comprises without limitation WiFi, Bluetooth, Zigbee, cellular, satellite, and/or WWAN. The communication can also be performed over a secure internet communication. In some embodiments, the point of care device is configured to perform two way communications with the computer modeling component.

In some embodiments of the system of the invention, the modeling results are updated in real time when updated dynamic data becomes available, e.g., after the computer modeling component receives updated information from a point of care device.

The computer modeling component can be configured to present the modeling results to one or more of healthcare professionals, government agencies and individual human subjects. The computer modeling component can also be configured to predict one or more courses of action based on the modeling results. The one or more courses of action are ranked according to a ranking parameter, including without limitation ranking by financial considerations, number of affected individuals, quality-adjusted life year (QALY), and/or quality-adjusted life year (QALY) per economic cost unit.

The one or more courses of action comprise a strategy to control the spread of the disease. The strategy to control the spread of the disease can include one or more of household quarantine, individual quarantine, geographic quarantine, social distancing, hospitalization, school closure, work place closure, travel restrictions, public transit closure, therapeutic treatment or intervention, prophylactic treatment or intervention, vaccination, provision of protective clothing, provision of masks, and additional point-of-care testing. The strategy to control the spread of the disease can further include one or more of counseling at risk or affected individuals for behavior modification, repeated biomarker and/or physiological measurements, and reward for the individual. Still further, the strategy to control the spread of the disease can include one or more of patient triage recommendations, resource management, efficacy index for each strategy, costs of each strategy, return on investment for each strategy. The strategy to control the spread of the disease can be one or more of targeted prophylaxis, blanket prophylaxis, targeted antibiotic prophylaxis, blanket antibiotic prophylaxis, targeted anti-viral prophylaxis, blanket anti-viral prophylaxis, targeted vaccination, and blanket vaccination. The targeted prophylaxis or vaccination can be targeting the prophylaxis or vaccination to children between 1-4 yrs of age, children between 5-14 yrs of age, pregnant women, young adults between 15-30 yrs of age, first-line medical response workers, individuals identified to at high risk of mortality, or geriatric individuals.

In some embodiments of the invention, the computer modeling component is configured to estimate a surveillance strategy based on the modeling results. The surveillance strategy can include determining the disease status of an individual or group of individuals using a point of care device. The surveillance strategy can be updated when a diseased individual is detected. In some embodiments, the updated strategy comprises one or more of testing a household comprising the diseased individual, testing a school comprising the diseased individual, and testing a work place comprising the diseased individual. The updated strategy can further be one or more of quarantine, prophylaxis or hospitalization.

In some embodiments, the computer modeling component comprises a graphical interface for displaying modeling results to a user.

The computer modeling component can include a plurality of nonlinear ordinary differential equations, and/or a plurality of parameters. In some embodiments, the computer modeling component comprises a learning machine that updates the plurality of parameters when the static data and/or dynamic data are updated.

The model of the data can be configured to include a plurality of states. In some embodiments, the plurality of states comprises one or more of: susceptible individuals, early exposed individuals, late exposed individuals, early infected individuals, late infected individuals, recovered individuals, individuals who died due to the infection and/or associated complications, asymptomatic individuals, individuals given therapeutic treatment, individuals given therapeutic treatment and quarantined, individuals treated prophylactically, vaccinated individuals, individuals protected due to vaccination, early infected individuals who are hospitalized, late infected individuals who are hospitalized, susceptible individuals who are home quarantined, early exposed individuals who are home quarantined, late exposed individuals who are home quarantined, early infected individuals who are home quarantined, late infected individuals who are home quarantined, asymptomatic individuals who are home quarantined, susceptible individuals quarantined in the whole neighborhood, early exposed individuals quarantined in the whole neighborhood, late exposed individuals quarantined in the whole neighborhood, early infected individuals quarantined in the whole neighborhood, late infected individuals quarantined in the whole neighborhood, asymptomatic individuals quarantined in the whole neighborhood, amount of therapeutic drug doses available, amount of antivirals and/or antibiotics available to the target population, home quarantined individuals that are vaccinated, home quarantined individuals that are protected due to vaccination, home quarantined individuals that recovered, susceptible individuals earmarked by mitigation policies for action, early exposed individuals earmarked by mitigation policies for action, late exposed individuals earmarked by mitigation policies for action, asymptomatic individuals earmarked by mitigation policies for action, early infected individuals earmarked by mitigation policies for action, late infected individuals earmarked by mitigation policies for action, prophylactic-treated individuals earmarked by mitigation policies for action, vaccinated individuals earmarked by mitigation policies for action, protected individuals earmarked by mitigation policies for action, recovered individuals earmarked by mitigation policies for action, susceptible individuals earmarked for therapeutic treatment, early exposed individuals earmarked for therapeutic treatment, late exposed individuals earmarked for therapeutic treatment, asymptomatic individuals earmarked for therapeutic treatment, early infected individuals earmarked for therapeutic treatment, late infected individuals earmarked for therapeutic treatment, susceptible individuals earmarked for surveillance, early exposed individuals earmarked for surveillance, late exposed individuals earmarked for surveillance, asymptomatic individuals earmarked for surveillance, early infected individuals earmarked for surveillance, late infected individuals earmarked for surveillance, prophylactic individuals earmarked for surveillance, vaccinated individuals earmarked for surveillance, protected individuals earmarked for surveillance, susceptible individuals in whole neighborhood quarantine earmarked by mitigation policies for action, early exposed individuals in whole neighborhood quarantine earmarked by mitigation policies for action, late exposed individuals in whole neighborhood quarantine earmarked by mitigation policies for action, asymptomatic individuals in whole neighborhood quarantine earmarked by mitigation policies for action, early infected individuals in whole neighborhood quarantine earmarked by mitigation policies for action, late infected individuals in whole neighborhood quarantine earmarked by mitigation policies for action, prophylactic-treated individuals in whole neighborhood quarantine individuals earmarked by mitigation policies for action, cumulative number of therapeutic doses administered, cumulative number of antivirals and/or antibiotics administered, cumulative number of home quarantined asymptomatic individuals, cumulative number of home quarantined symptomatic individuals, cumulative number of total infected individuals, cumulative number of infected individuals who are not quarantined, cumulative number of infected individuals with some action taken, cumulative number of hospitalized individuals, and cumulative number of deaths.

In another aspect, the present invention provides a system for controlling spread of influenza within a population, comprising: a static database component comprising static data related to the influenza and/or the population; a dynamic database component comprising dynamic data about the population; and a computer modeling component that is configured to model the data in the static database component and the dynamic database component, thereby modeling the incidence of the influenza within the population.

In still another aspect, the present invention provides a system for controlling spread of human immunodeficiency virus (HIV) within a population, comprising: a static database component comprising static data related to the HIV and/or the population; a dynamic database component comprising dynamic data about the population; a computer modeling component that is configured to model the data in the static database component and the dynamic database component, thereby modeling the incidence of the HIV within the population.

In yet another aspect, the present invention provides a system for controlling spread of hepatitis within a population, comprising: a static database component comprising static data related to the hepatitis and/or the population; a dynamic database component comprising dynamic data about the population; and a computer modeling component that is configured to model the data in the static database component and the dynamic database component, thereby modeling the incidence of the hepatitis within the population.

In an aspect, the present invention provides a system for controlling spread of diabetes within a population, comprising: a static database component comprising static data related to the diabetes and/or the population; a dynamic database component comprising dynamic data about the population; and a computer modeling component that is configured to model the data in the static database component and the dynamic database component, thereby modeling the incidence of the diabetes within the population.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS/FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 4A:
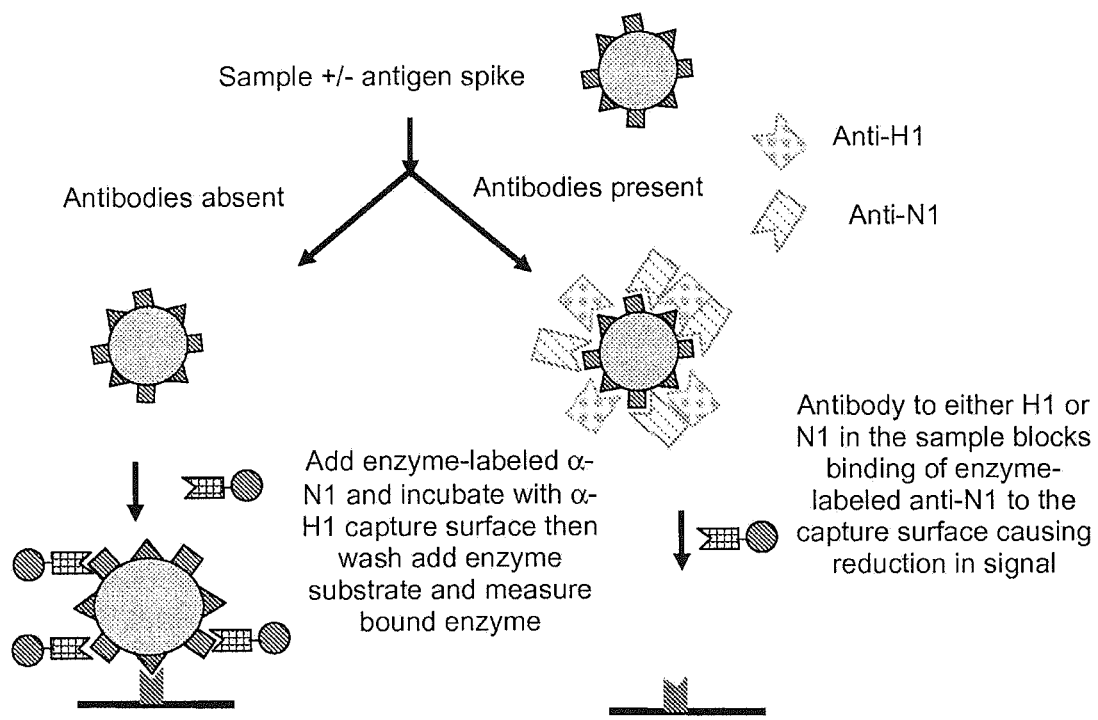
Figure 4B:
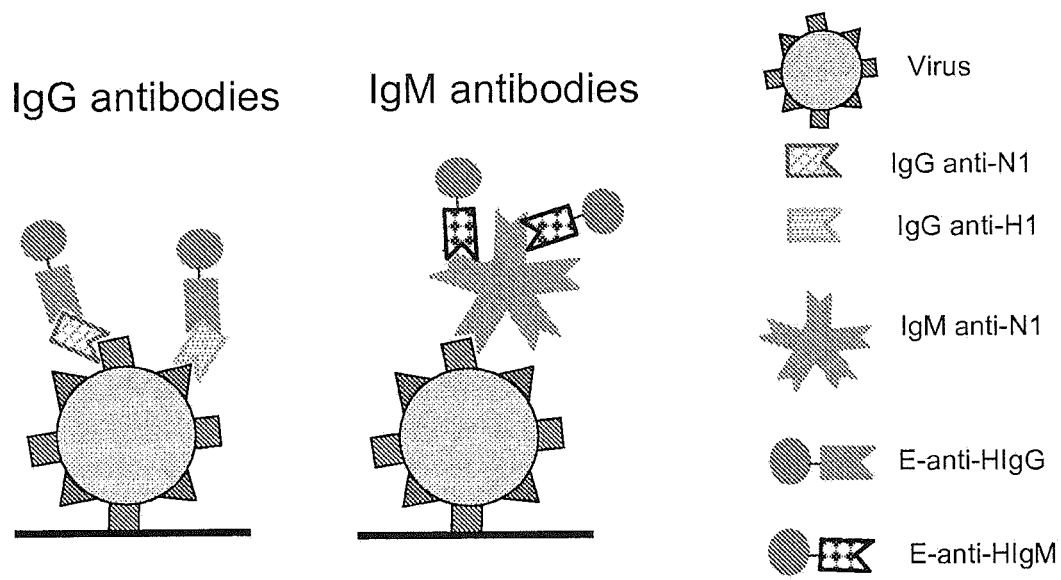

FIG. 4A illustrates an assay for host anti-virus antibodies. The figure illustrates a spike recovery assay for host anti-H1N1 antibodies. Shown is a version using α-H1/α-N1 configuration. FIG. 4B illustrates direct assays for α-H1N1 antibodies illustrating sandwich complexes.

Figure 5:
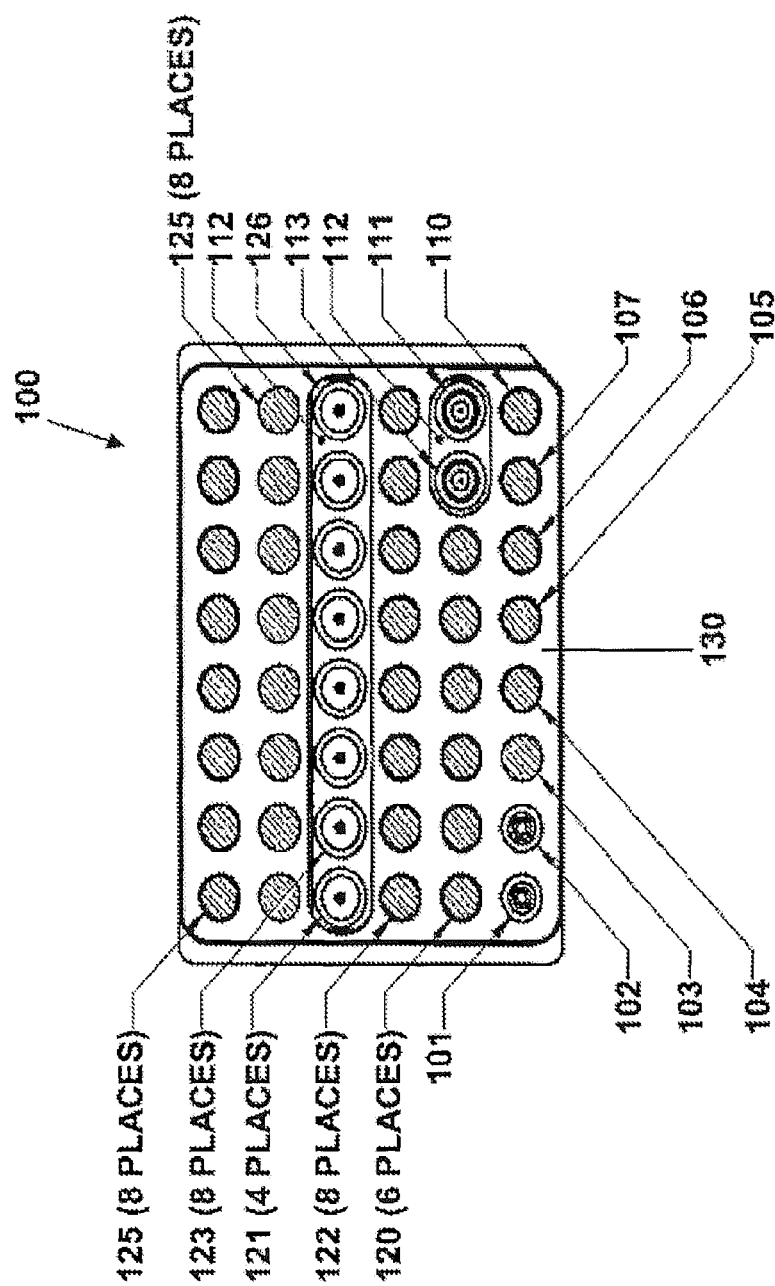

FIG. 5 illustrates an exemplary device that can be used in the present invention. The exemplary devices comprise assay units, reagents unit, and other modular components.

Figure 6:
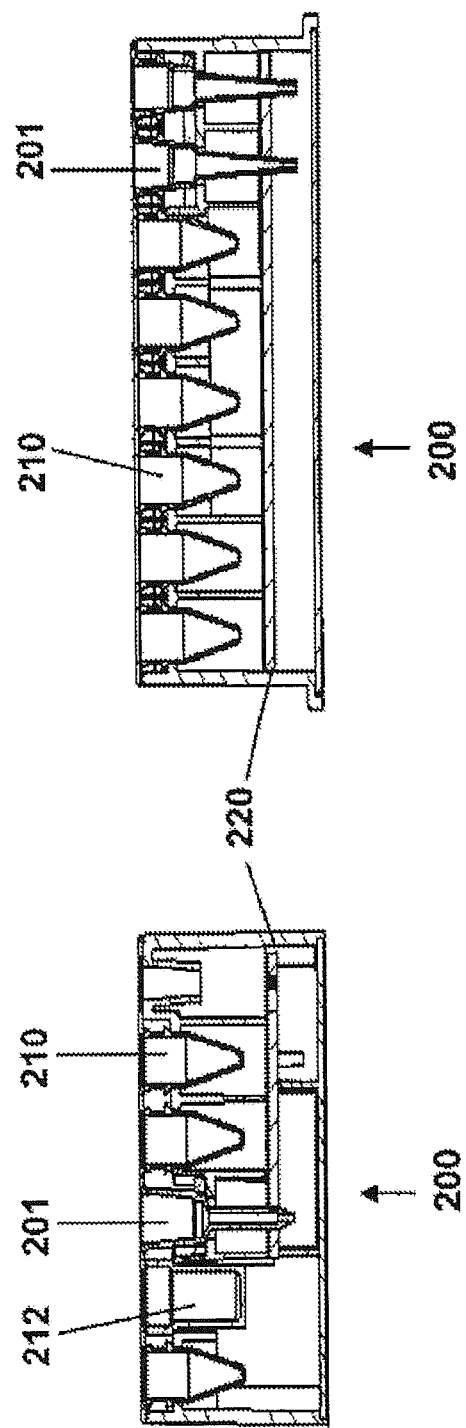

FIG. 6 illustrates two side-cut away views of the exemplary device that can be used in the present invention. The exemplary device comprises cavities in the housing of the device shaped to accommodate an assay unit, a reagent unit, and a sample tip.

Figure 7A:
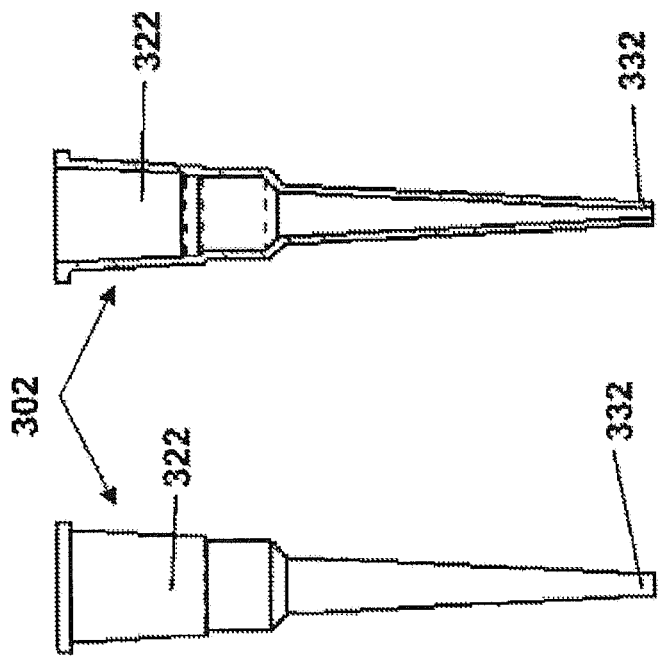
Figure 7B:
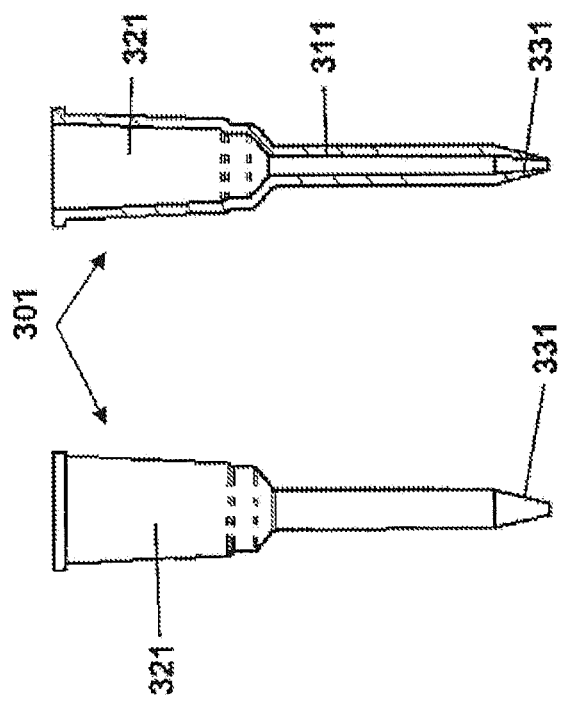

FIG. 7A demonstrates an exemplary assay unit that comprises a small tip or tubular formation. FIG. 7B demonstrates an example of a sample tip as described herein.

Figure 8A:
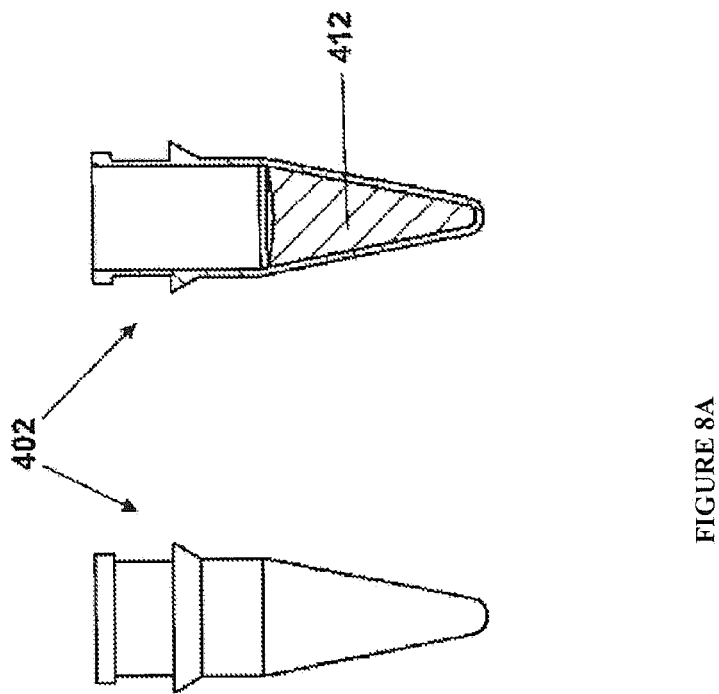
Figure 8B:
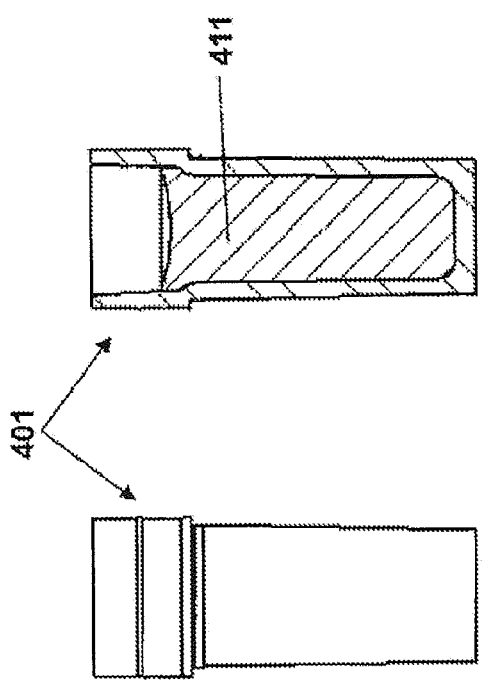

FIGS. 8A and 8B illustrate two examples of a reagent unit comprising a cup.

Figure 9:
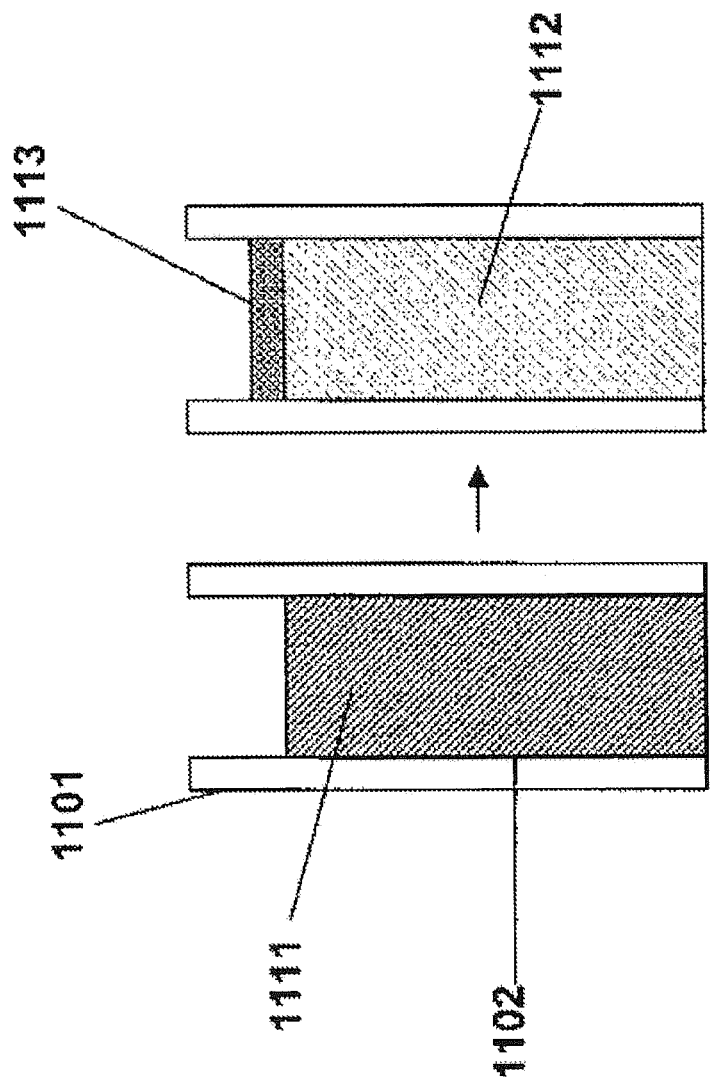

FIG. 9 illustrates a thin film, for example, contamination, within the tip when a liquid is expelled and another liquid aspirated.

Figure 10:
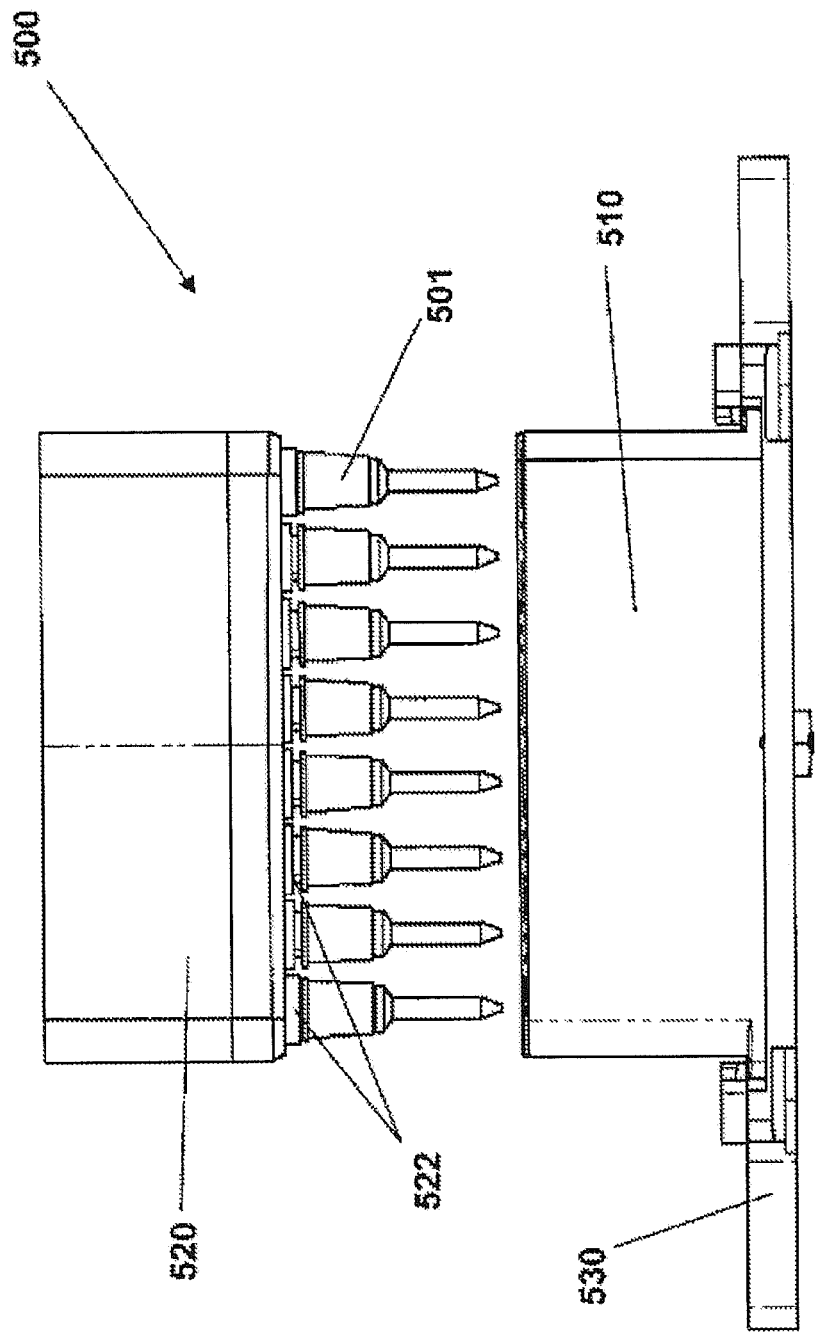

FIG. 10 demonstrates an example of a system comprising a device and a fluid transfer device.

Figure 11:
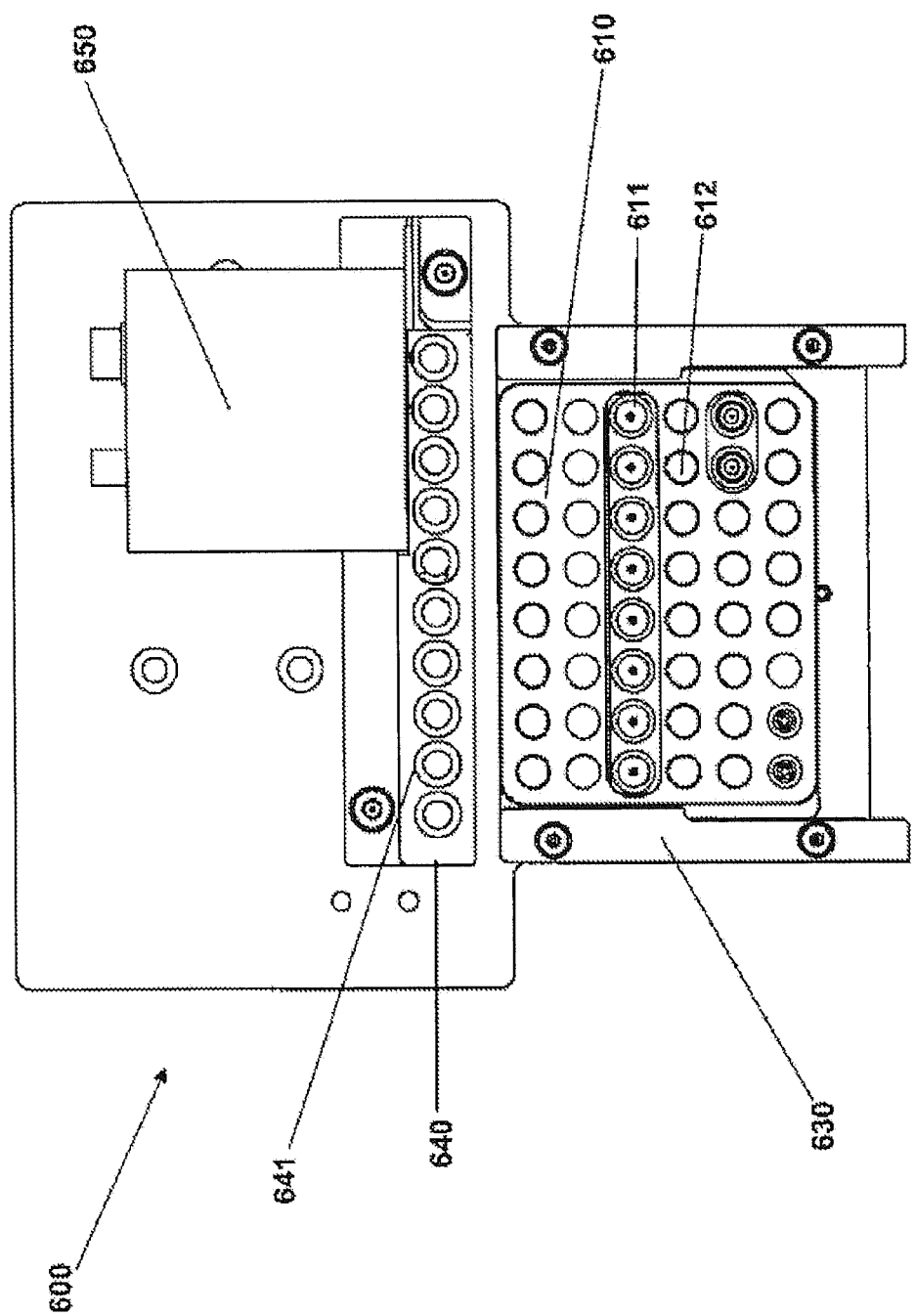

FIG. 11 illustrates an exemplary system of the invention comprising a heating block for temperature control and a detector.

Figure 12:
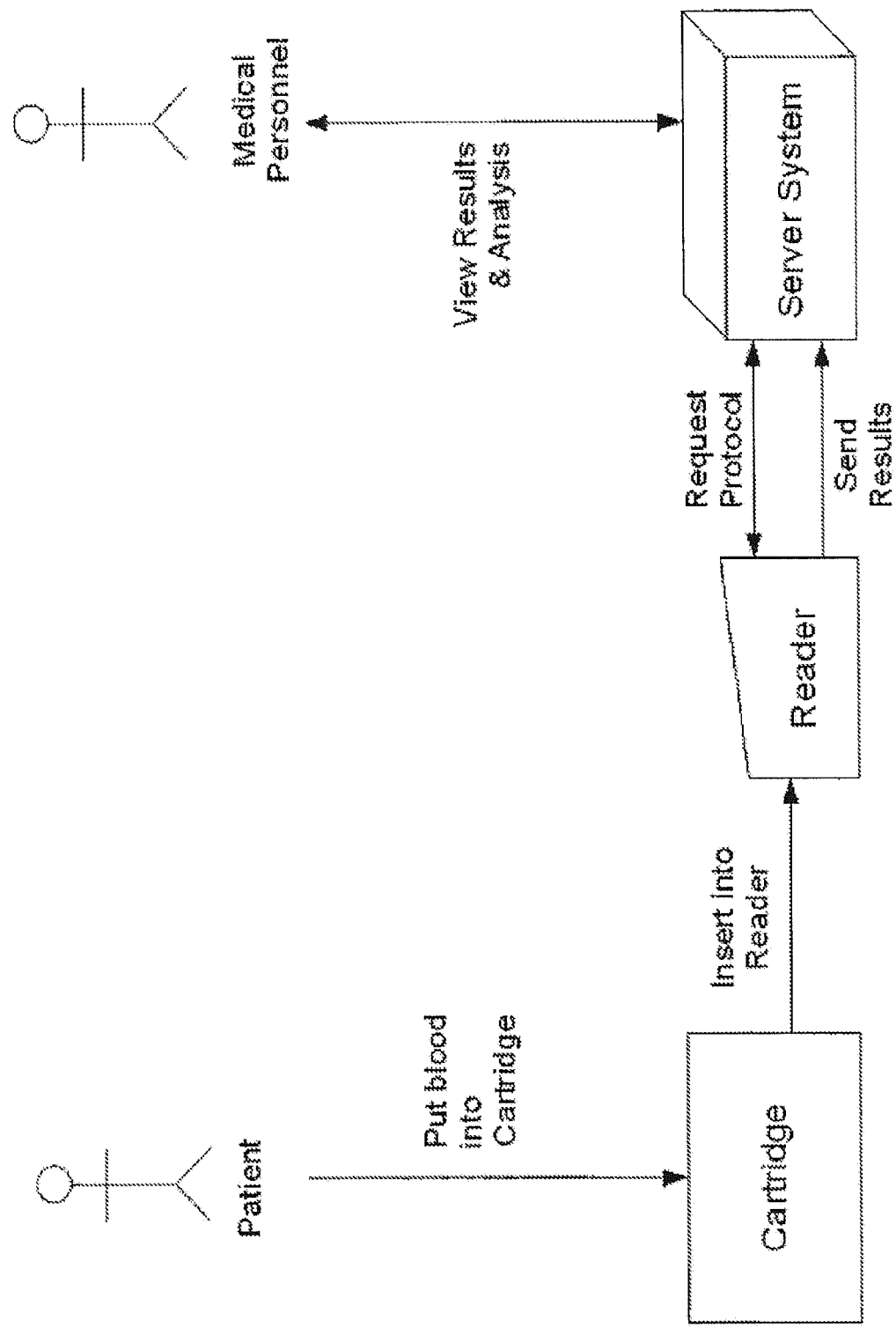

FIG. 12 demonstrates an exemplary a system wherein a patient delivers blood to a device and then the device is inserted into a reader.

Figure 13:
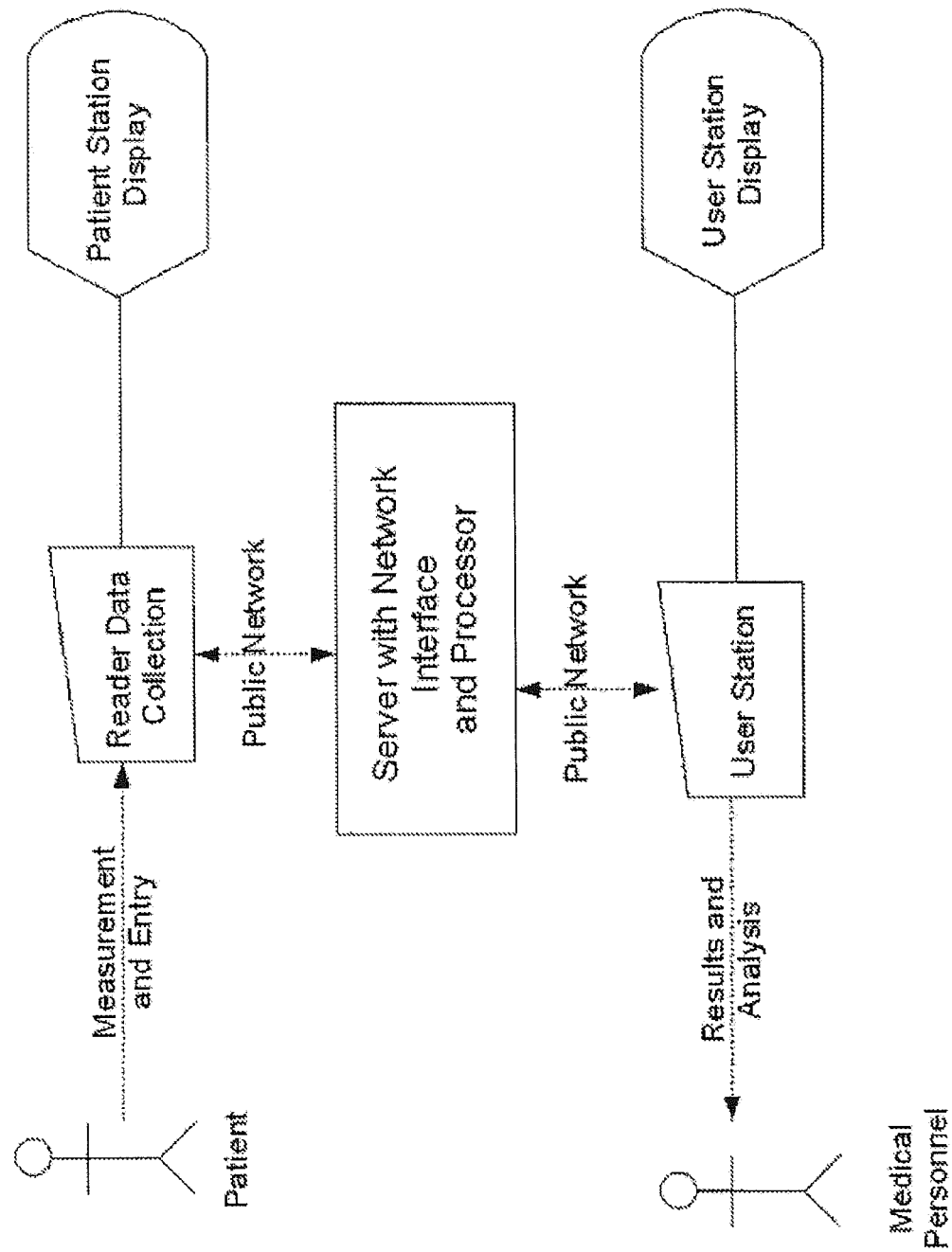

FIG. 13 illustrates the process flow of building a system for assessing the medical condition of a patient.

FIGS. 14A through 14E demonstrate an example of a plasma separation method wherein a whole blood sample has been aspirated into a sample tip and a magnetic reagent is mixed and suspended with the sample, then a magnetic field is applied to the whole blood sample and magnetic reagent mixture. Separated blood plasma sample can then be distributed into a well of a device.

Figure 15:
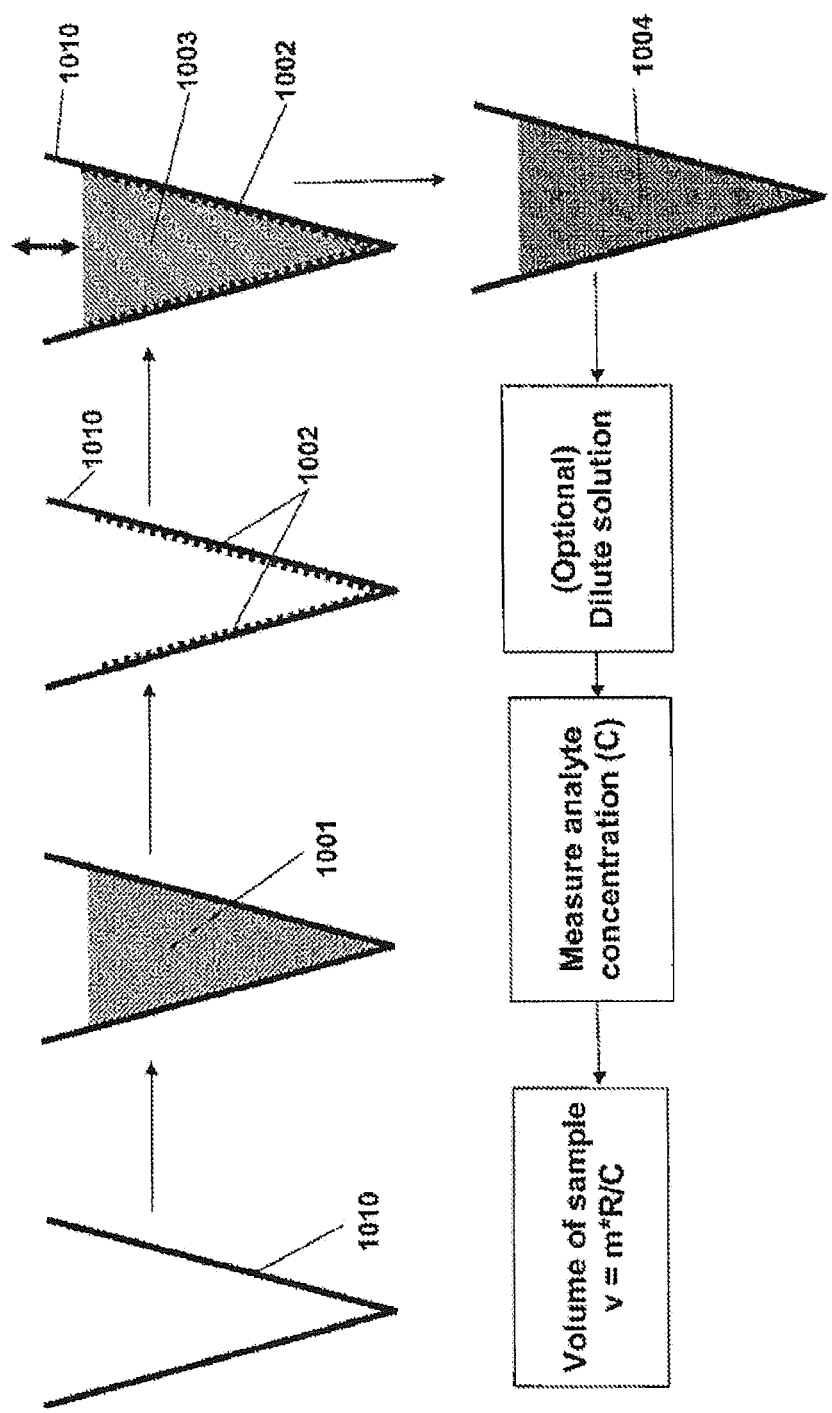

FIG. 15 demonstrates an exemplary method of a control assay as described herein comprising a known quantity of control analyte.

Figure 16:
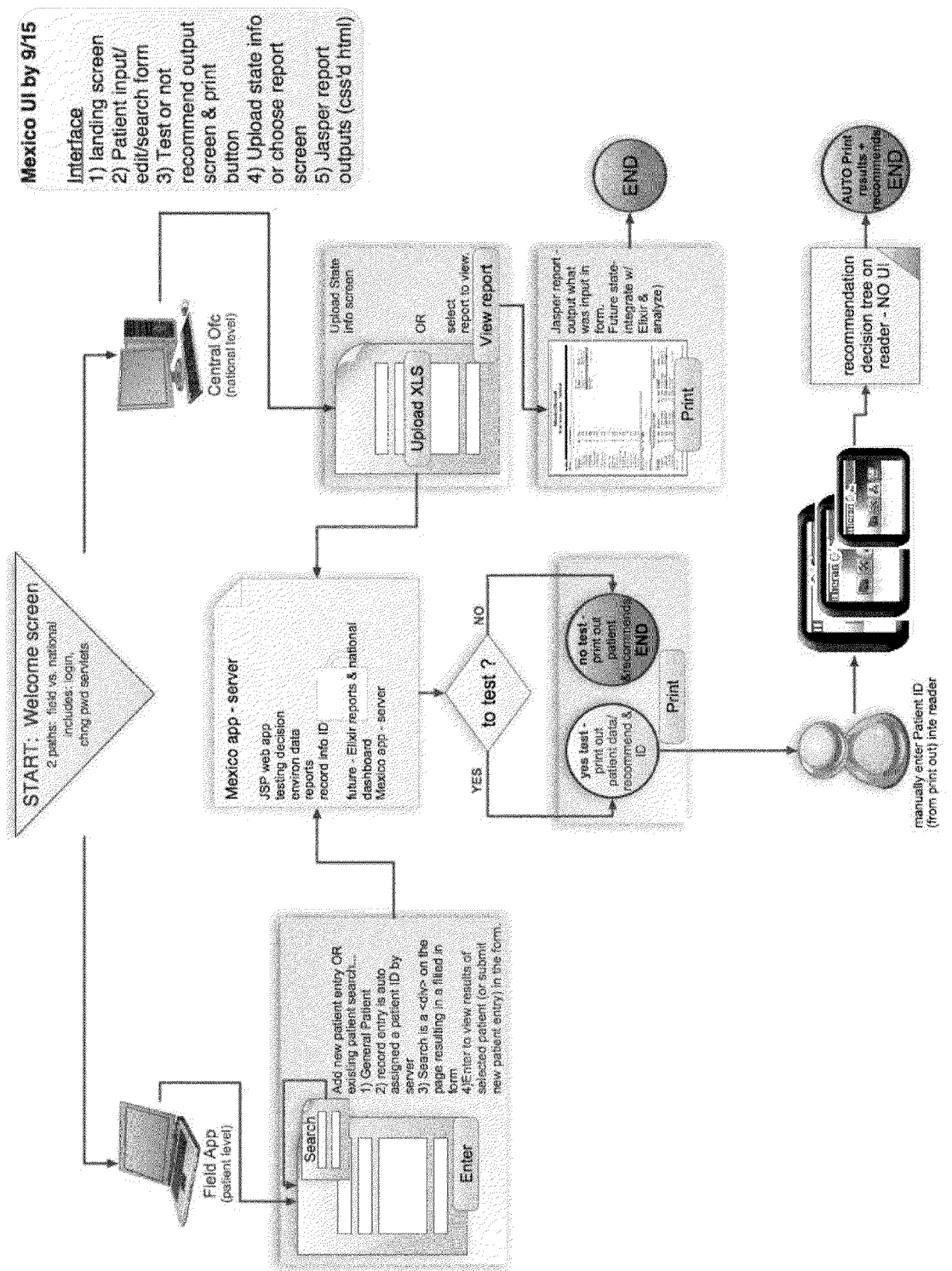

FIG. 16 illustrates an exemplary embodiment of a Health Shield user interface.

Figure 17:
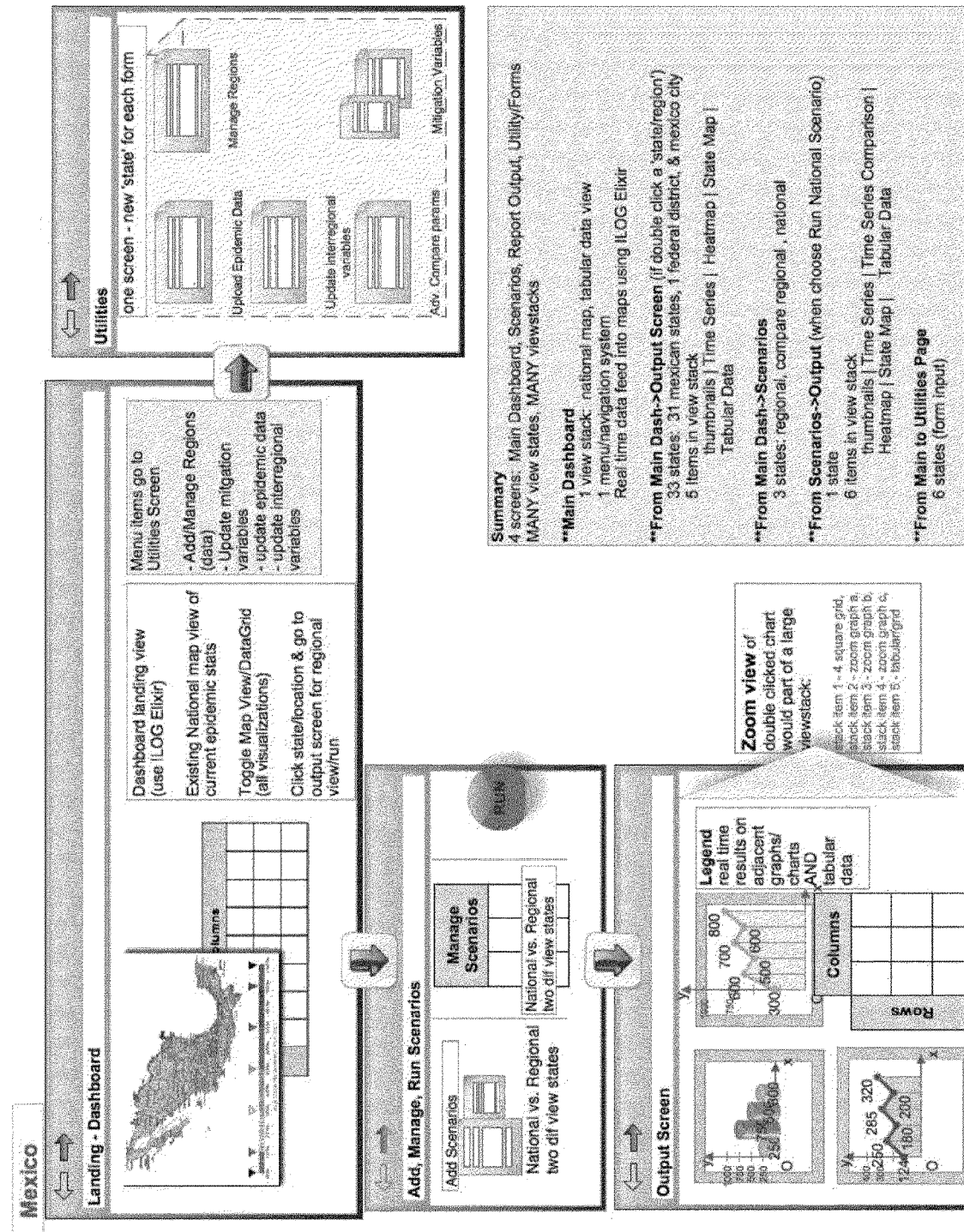

FIG. 17 illustrates another exemplary embodiment of a Health Shield use interface.

Figure 18:
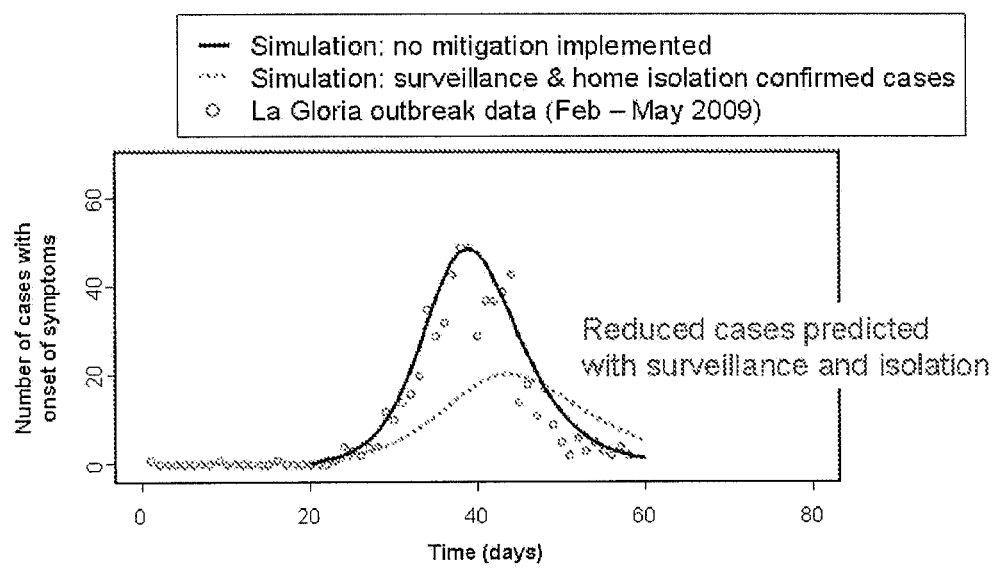

FIG. 18 illustrates simulation of the 2009 La Gloria outbreak with and without Health Shield mitigation policies.

Figure 19:
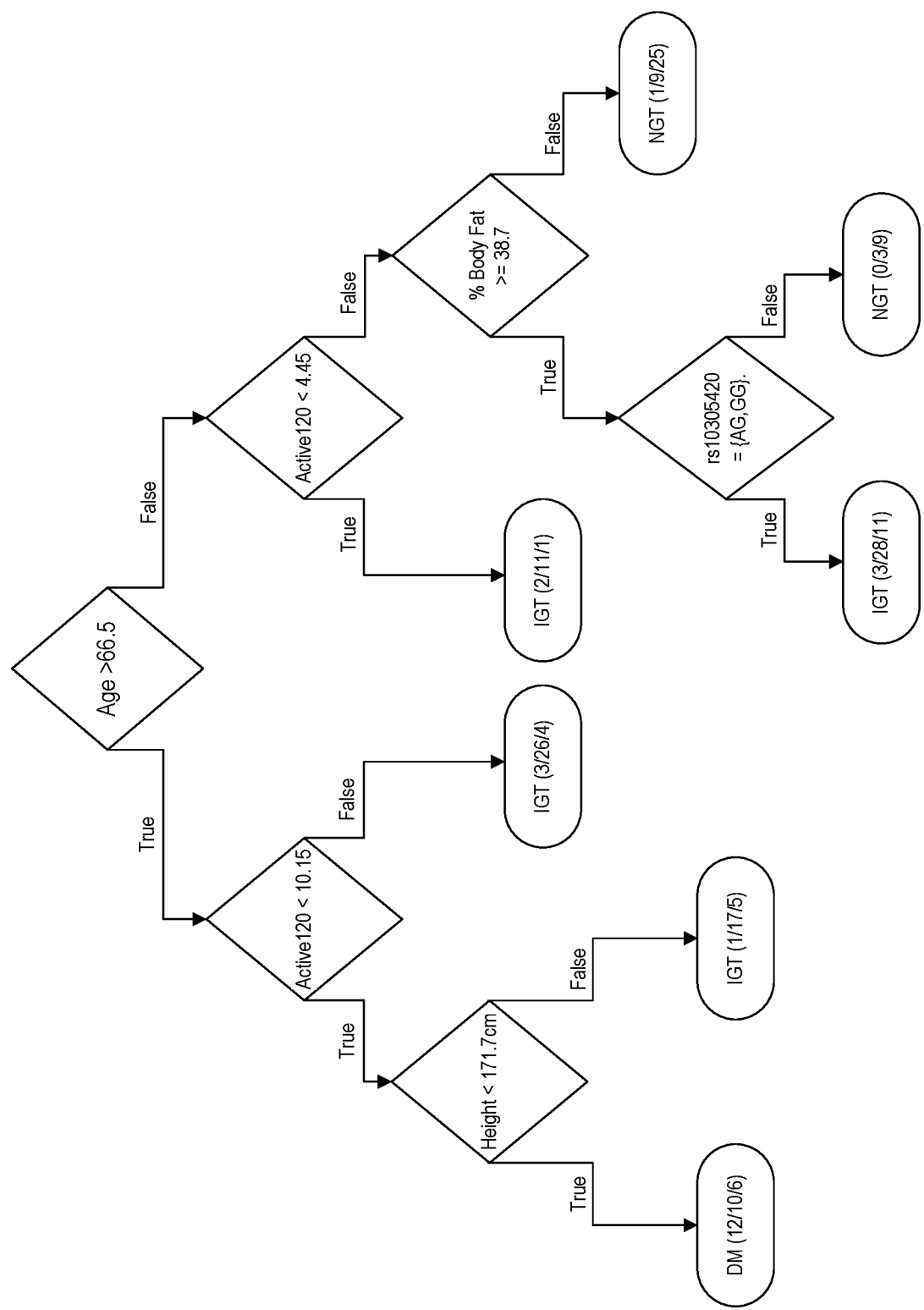

FIG. 19 illustrates diabetes risk prediction visualization.

Figure 20A:
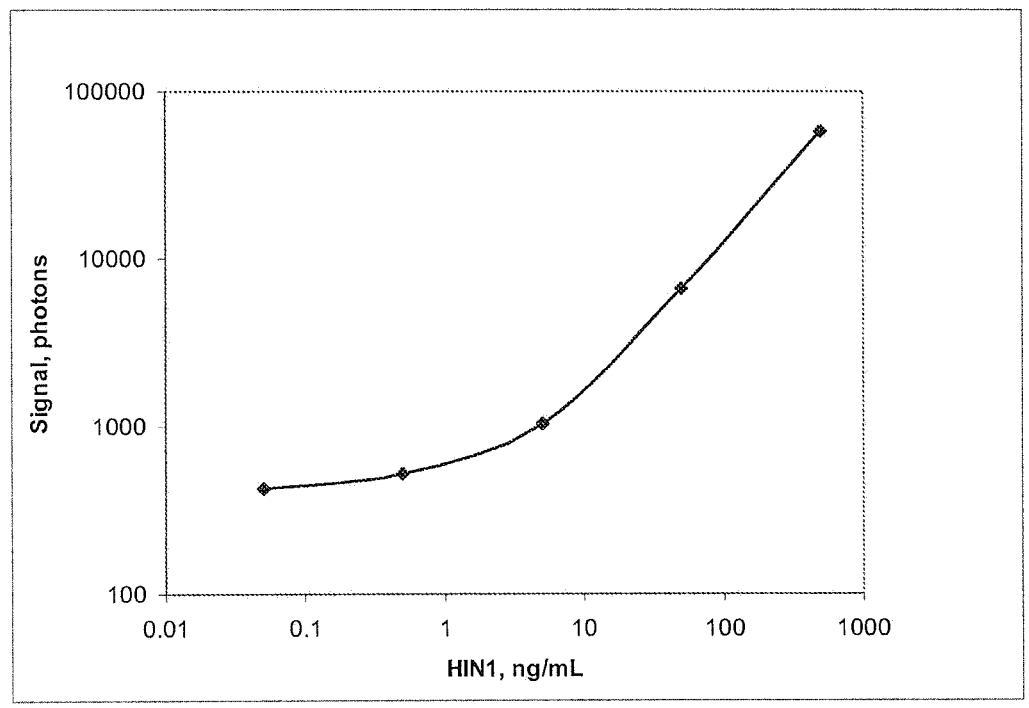
Figure 20B:
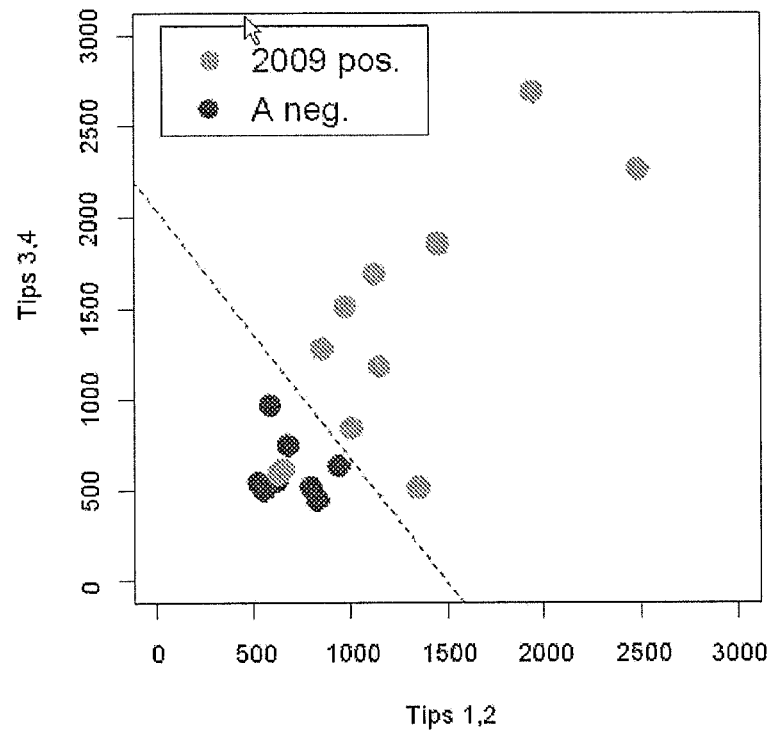

FIG. 20A illustrates the detection of H1N1 viral particles using a point of care device. FIG. 20B illustrates the detection of H1N1 viral particles using a point of care device in clinical samples.

Figure 21:
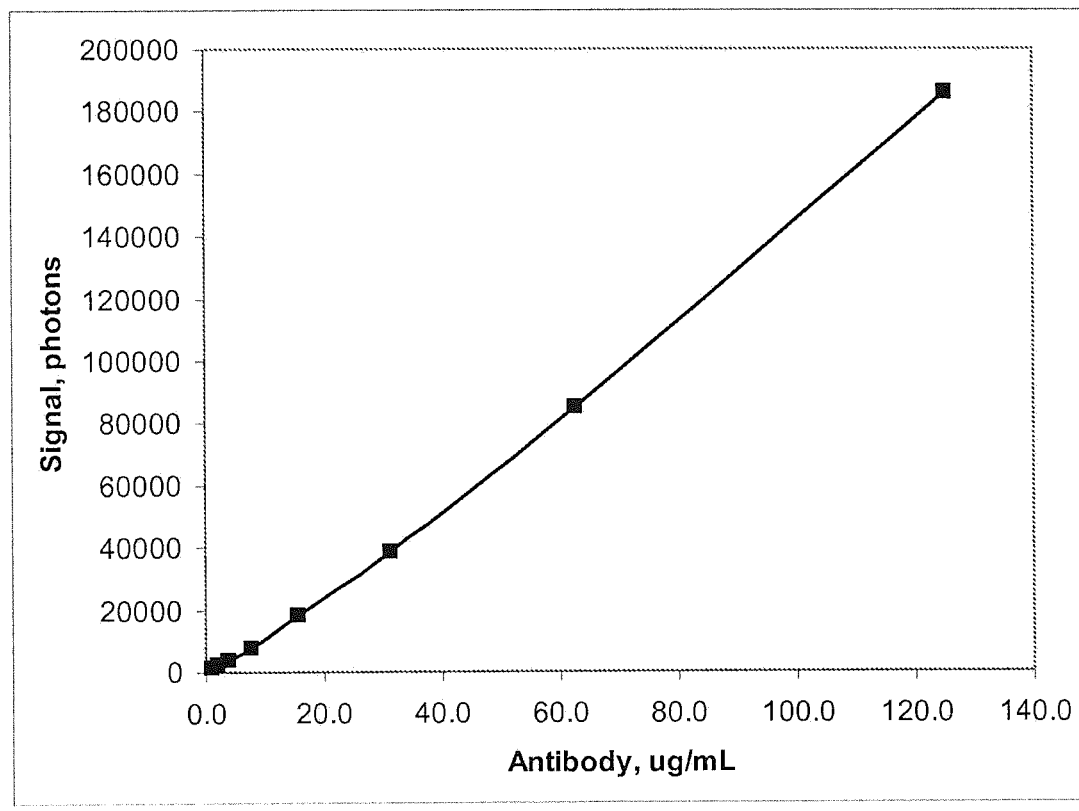

FIG. 21 illustrates the detection of host antibodies using a point of care device.

Figure 22A:
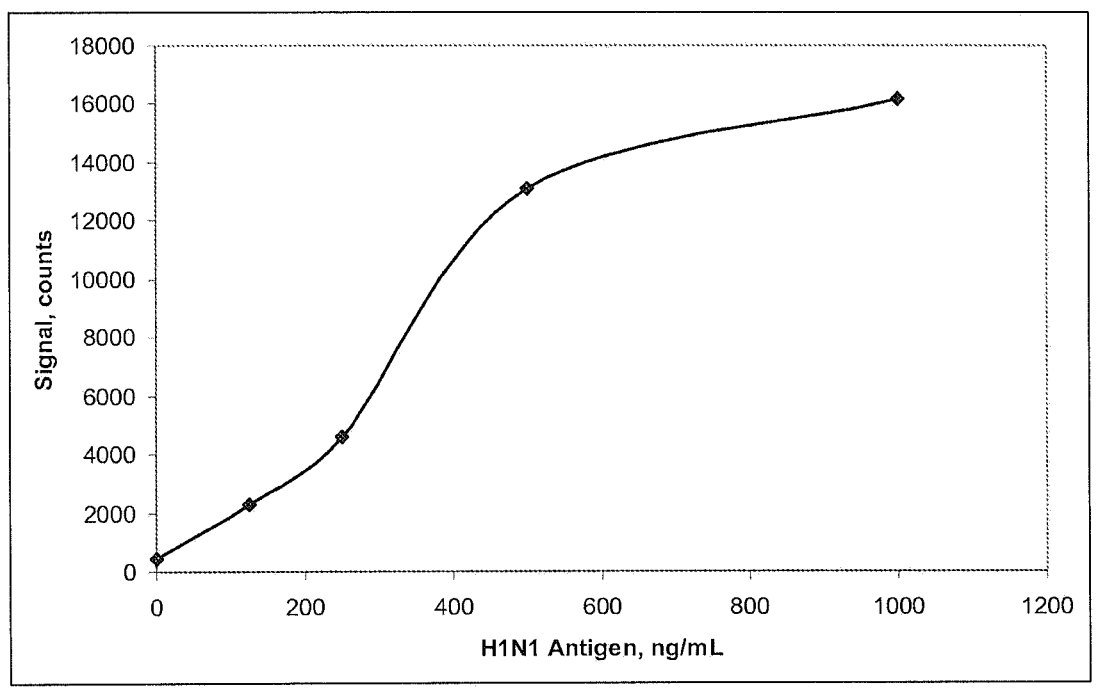

FIG. 22A illustrates the detection of host antibodies using a point of care device.

Figure 22B:
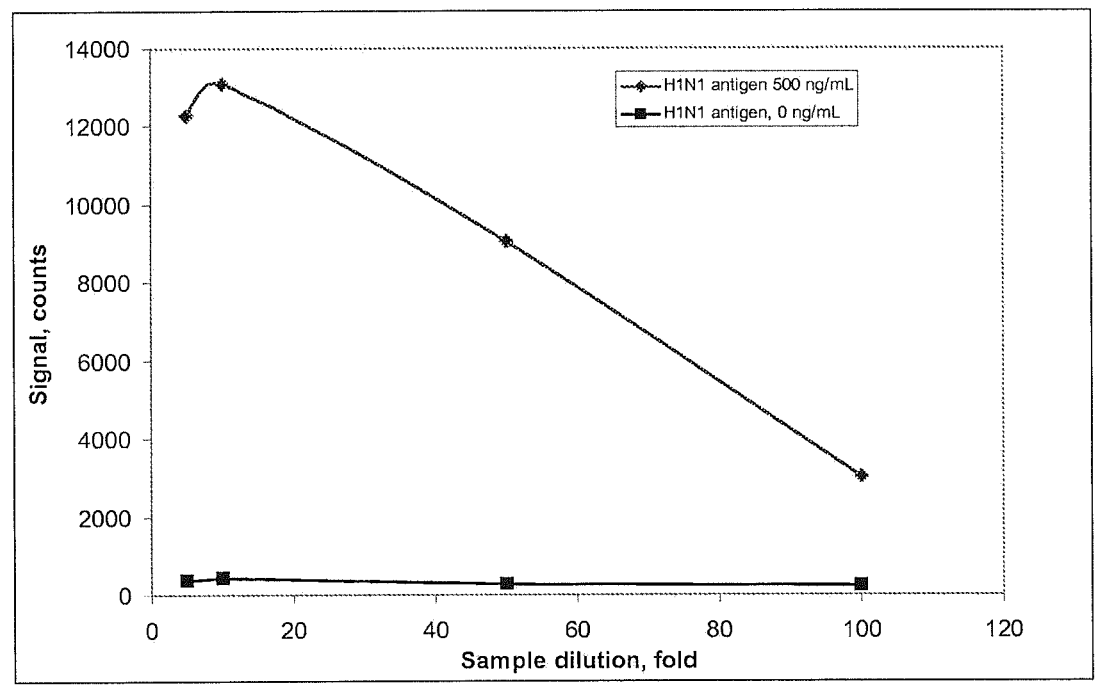

FIG. 22B illustrates the dynamic range of host antibody detection using a point of care device.

Figure 23:
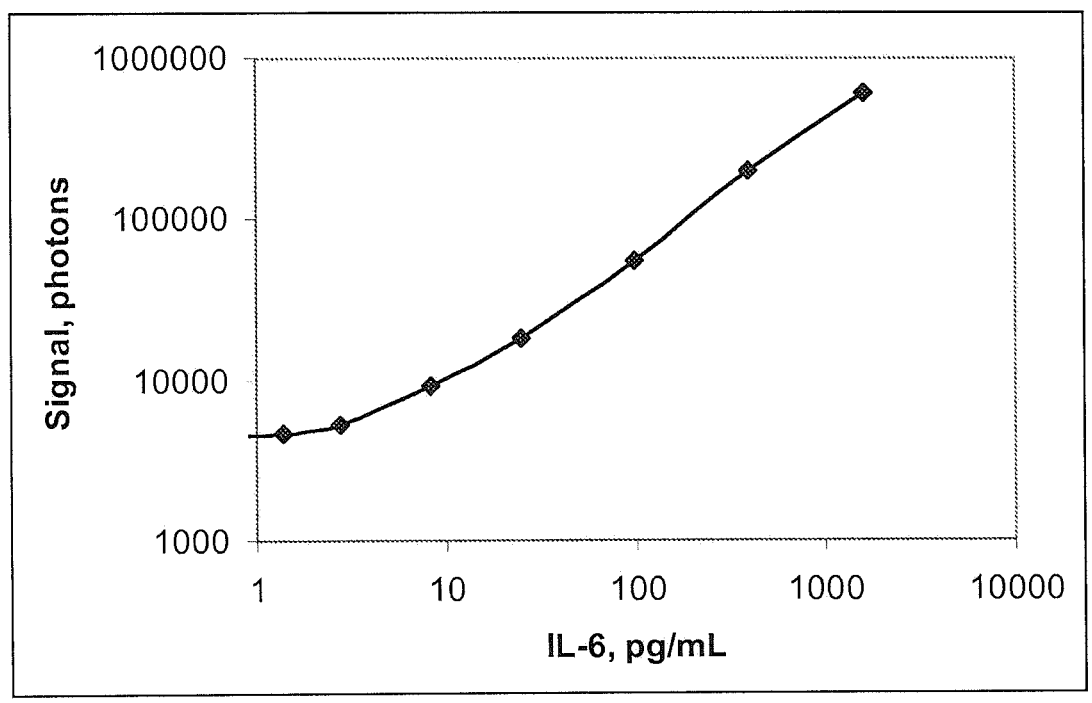

FIG. 23 illustrates the detection of human cytokine IL-6 using a point of care device.

Figure 24:
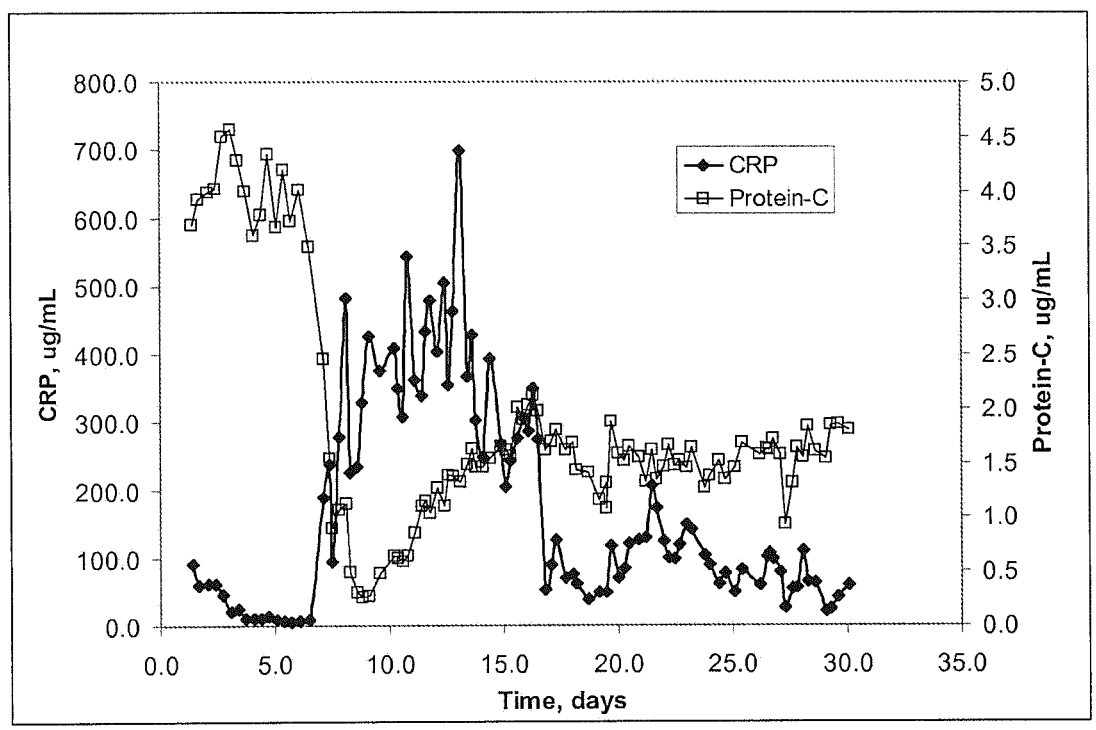

FIG. 24 illustrates the detection of protein-C and C-reactive protein (CRP) using a point of care device in a patient undergoing chemotherapy.

Figure 25:
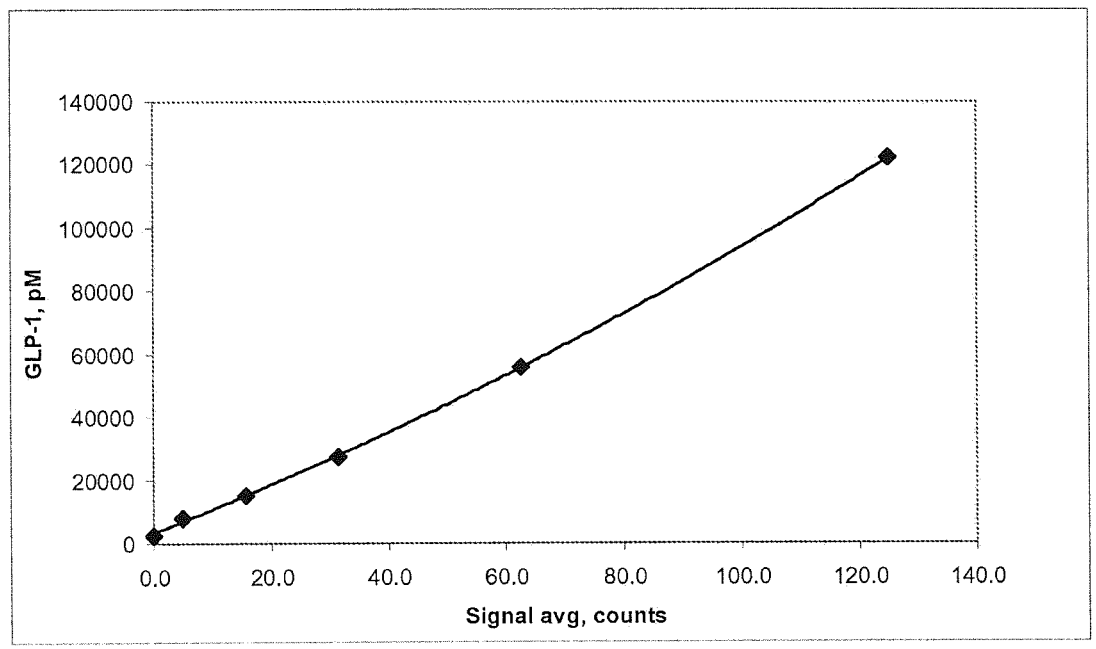

FIG. 25 illustrates the detection of glucagon-like peptide 1 (GLP-1) using a point of care device.

Figure 26:
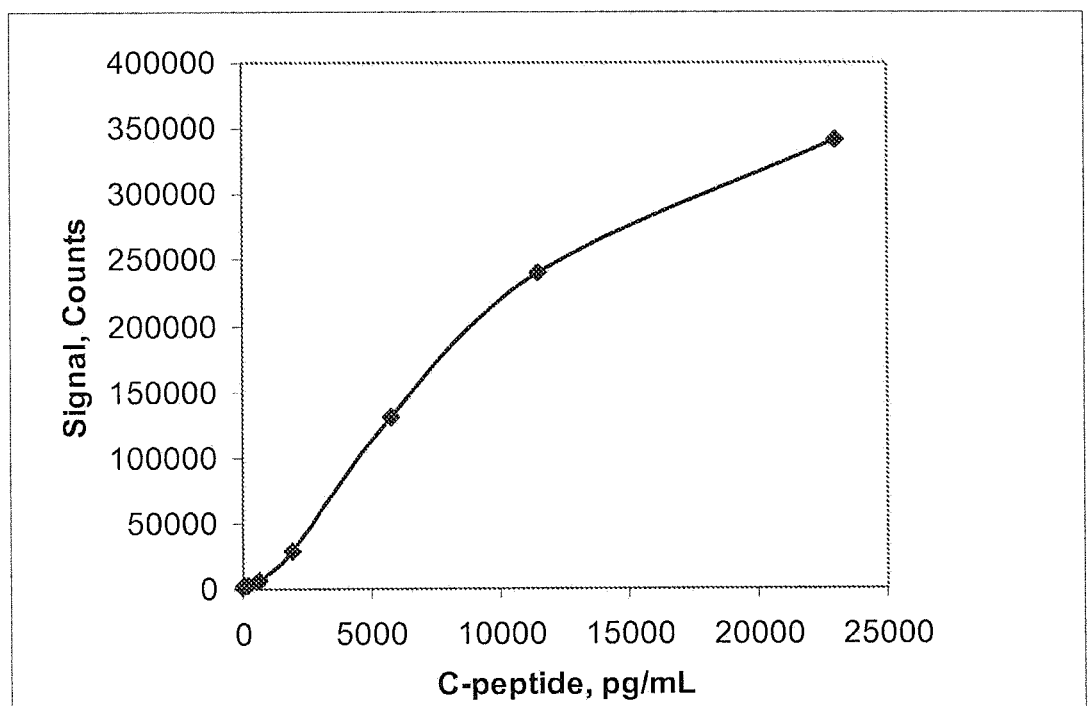

FIG. 26 illustrates the detection of C-peptide, an insulin precursor, using a point of care device.

Figure 27:
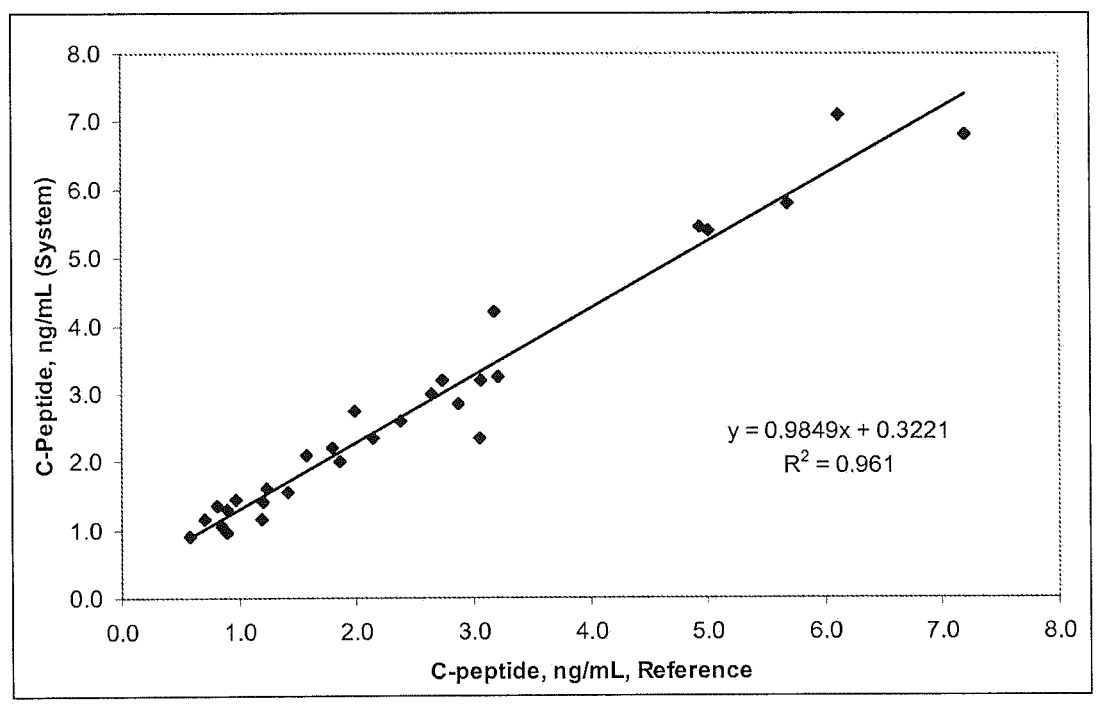

FIG. 27 illustrates the detection of C-peptide using a cartridge point of care device compared to a reference detection system (Linco).

Figure 28A:
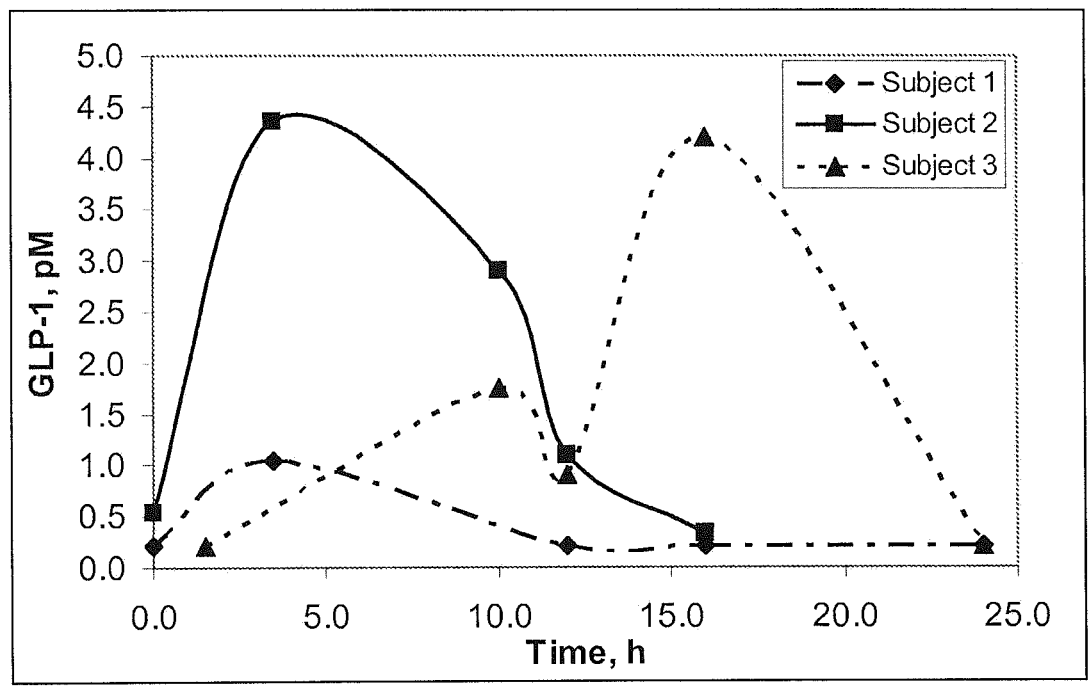
Figure 28B:
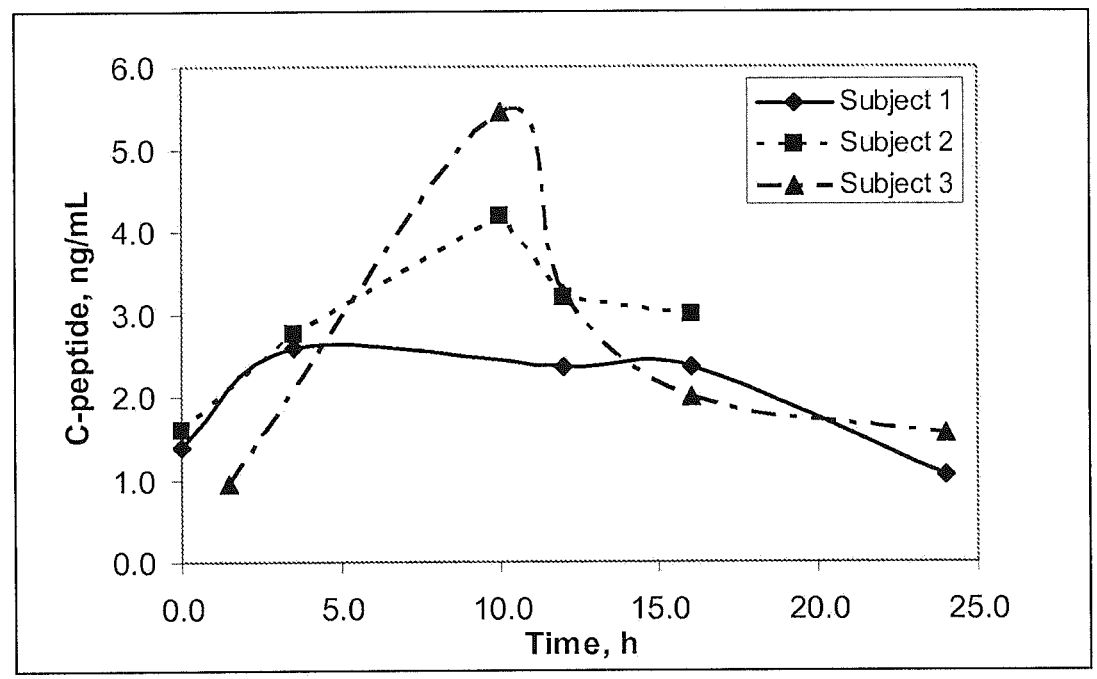

FIG. 28A illustrates the measurement of GLP-1 in three human subjects after feeding. FIG. 28B illustrates the measurement of C-peptide over the course of the same experiment.

Figure 29:
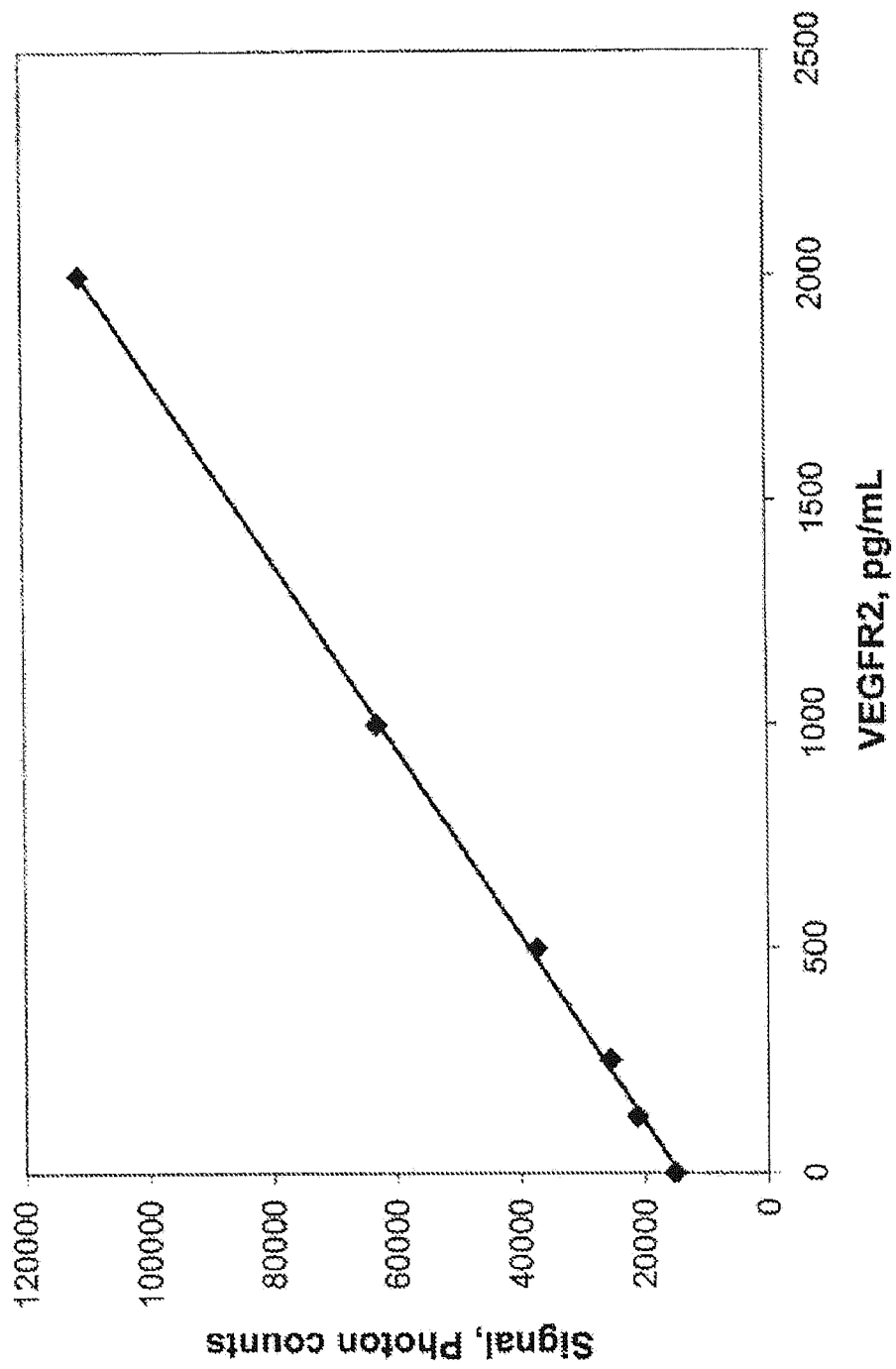

FIG. 29 illustrates a calibration curve correlating an assay unit and a reagent unit for conducting an assay for VEGFR2.

Figure 30:
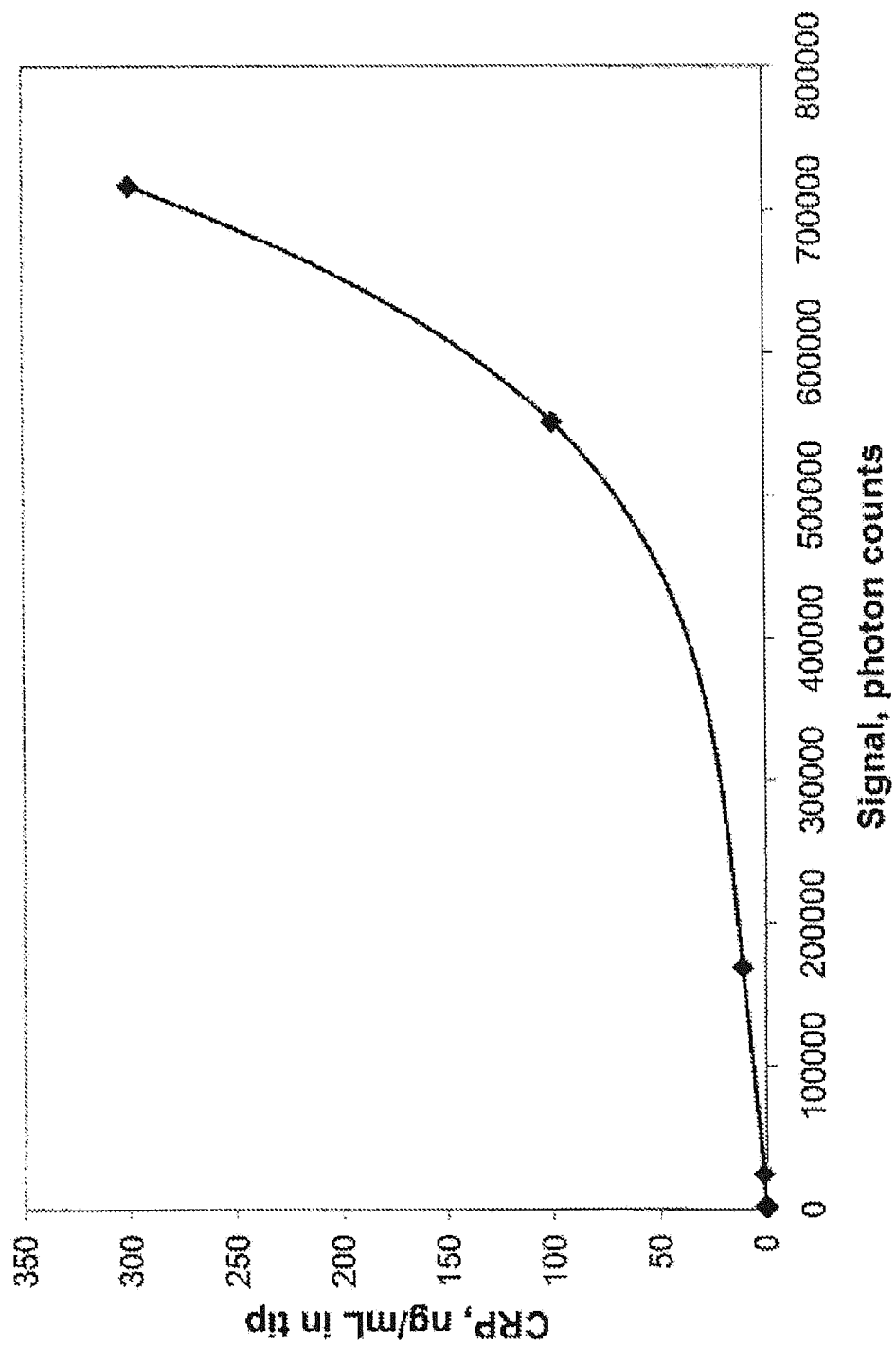

FIG. 30 illustrates CRP concentration plotted against the assay signal (photon counts) and the data fitted to a 5-term polynomial function to generate a calibration function.

Figure 31:
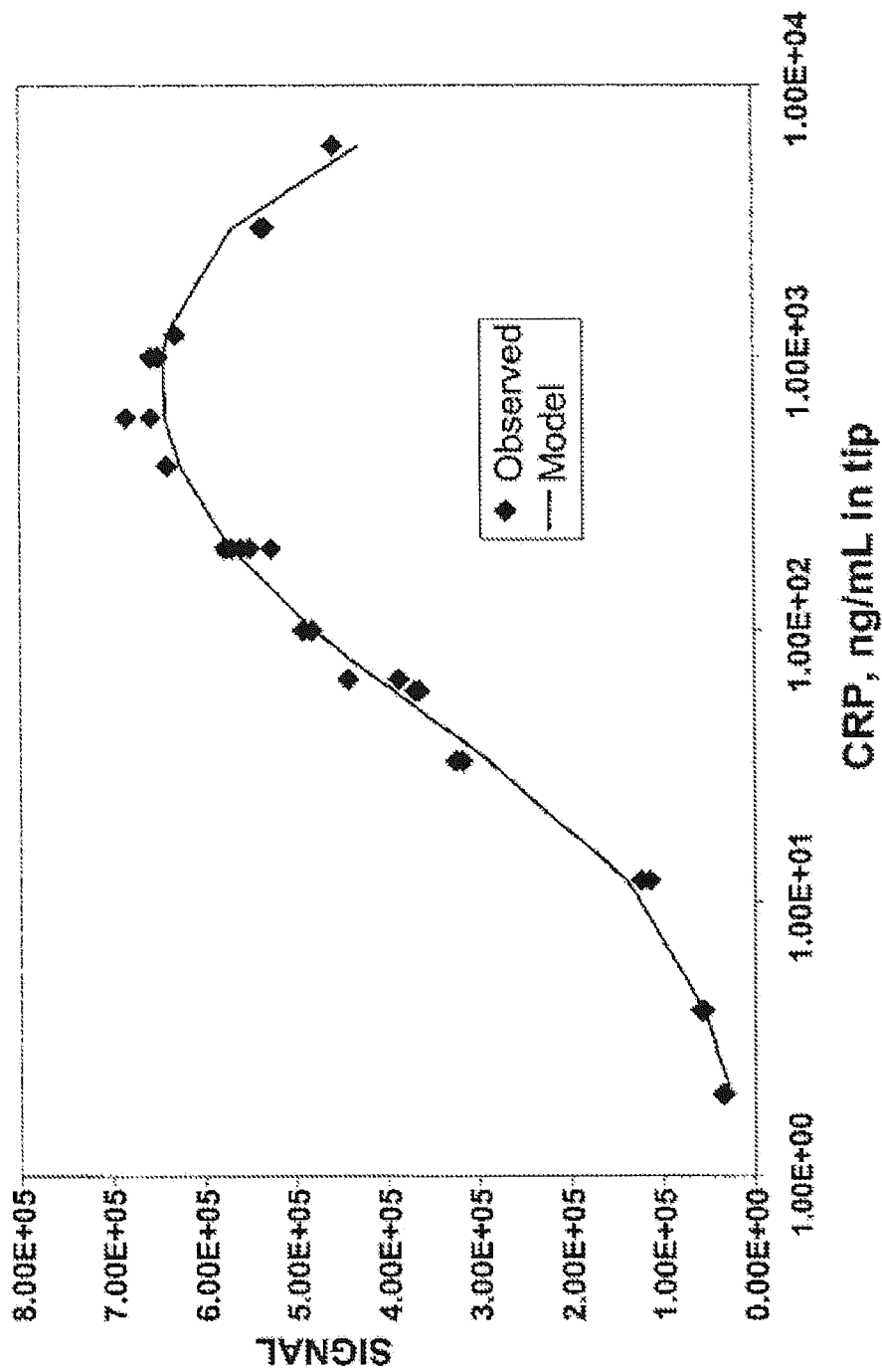

FIG. 31 shows a fit was achieved between a model and the values of the parameters Smax, C0.5 and D as described herein.

Figure 32:
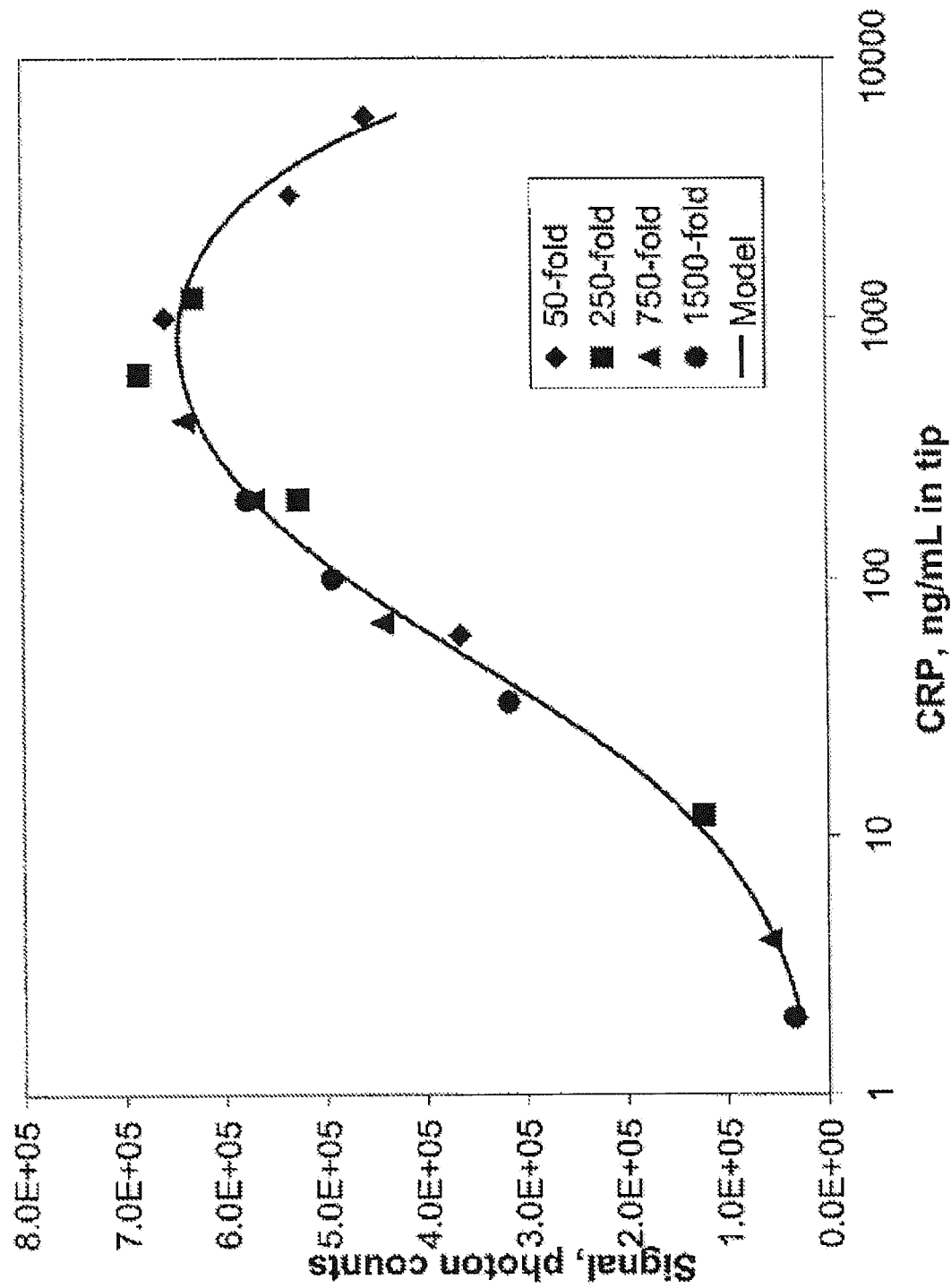

FIG. 32 displays data according to the dilution used to achieve the final concentration in an assay tip.

Figure 33:
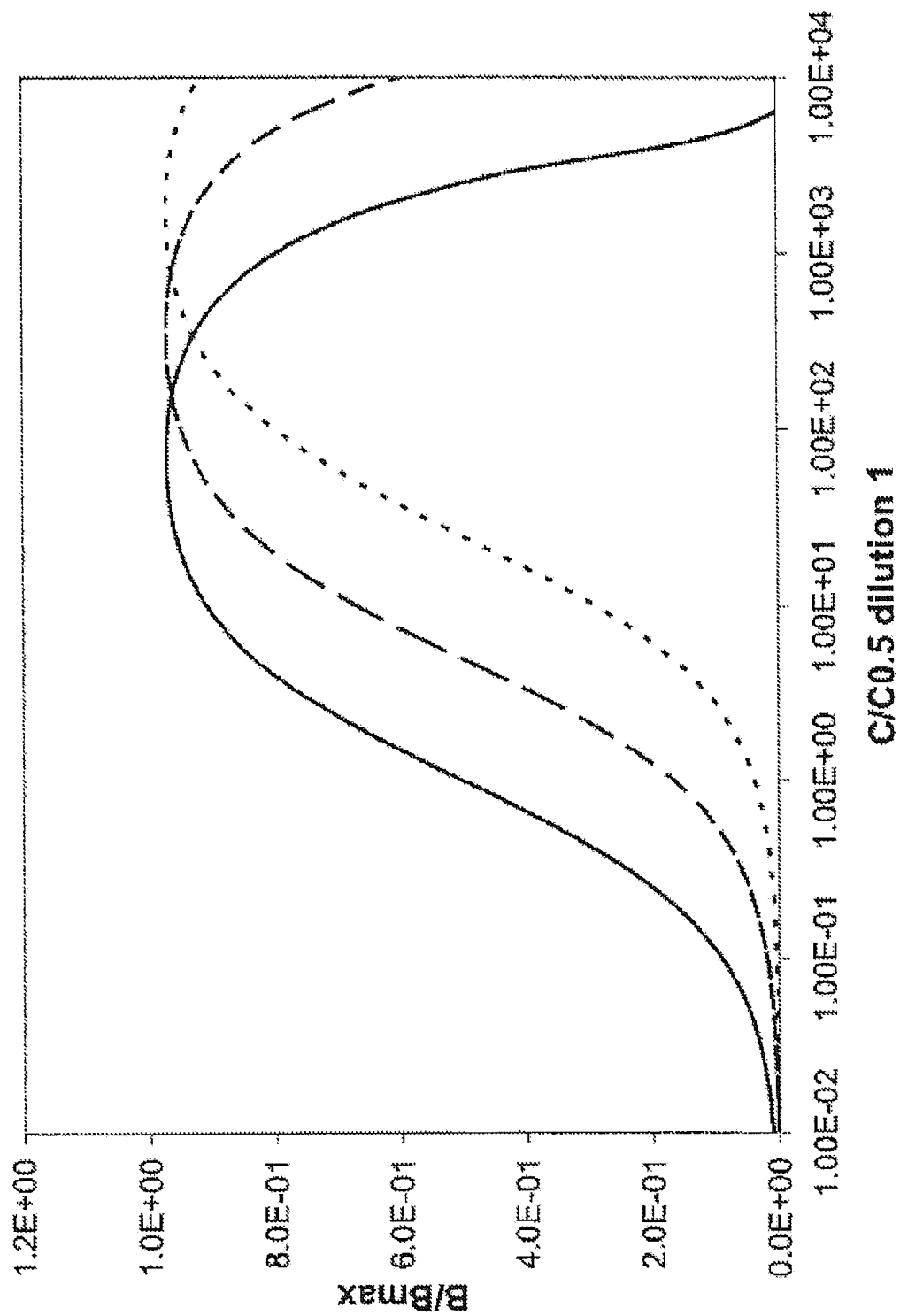

FIG. 33 illustrates the normalized assay response (B/Bmax) is plotted against the log normalized concentration (C/C0.5) for relative dilutions: 1:1 (solid line), 5:1 (dashed line), and 25:1 (dotted line).

Figure 34:
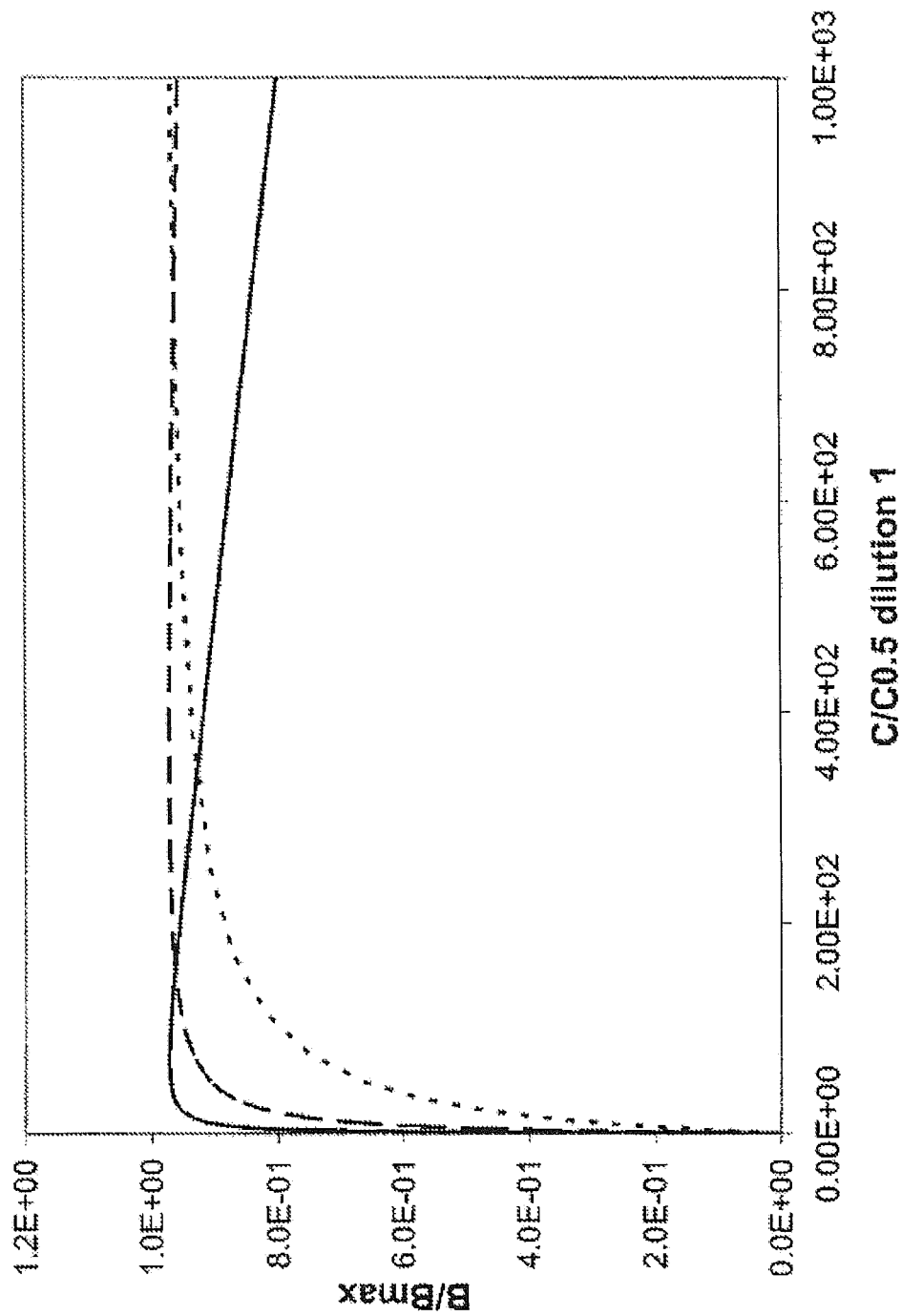
Figure 35:
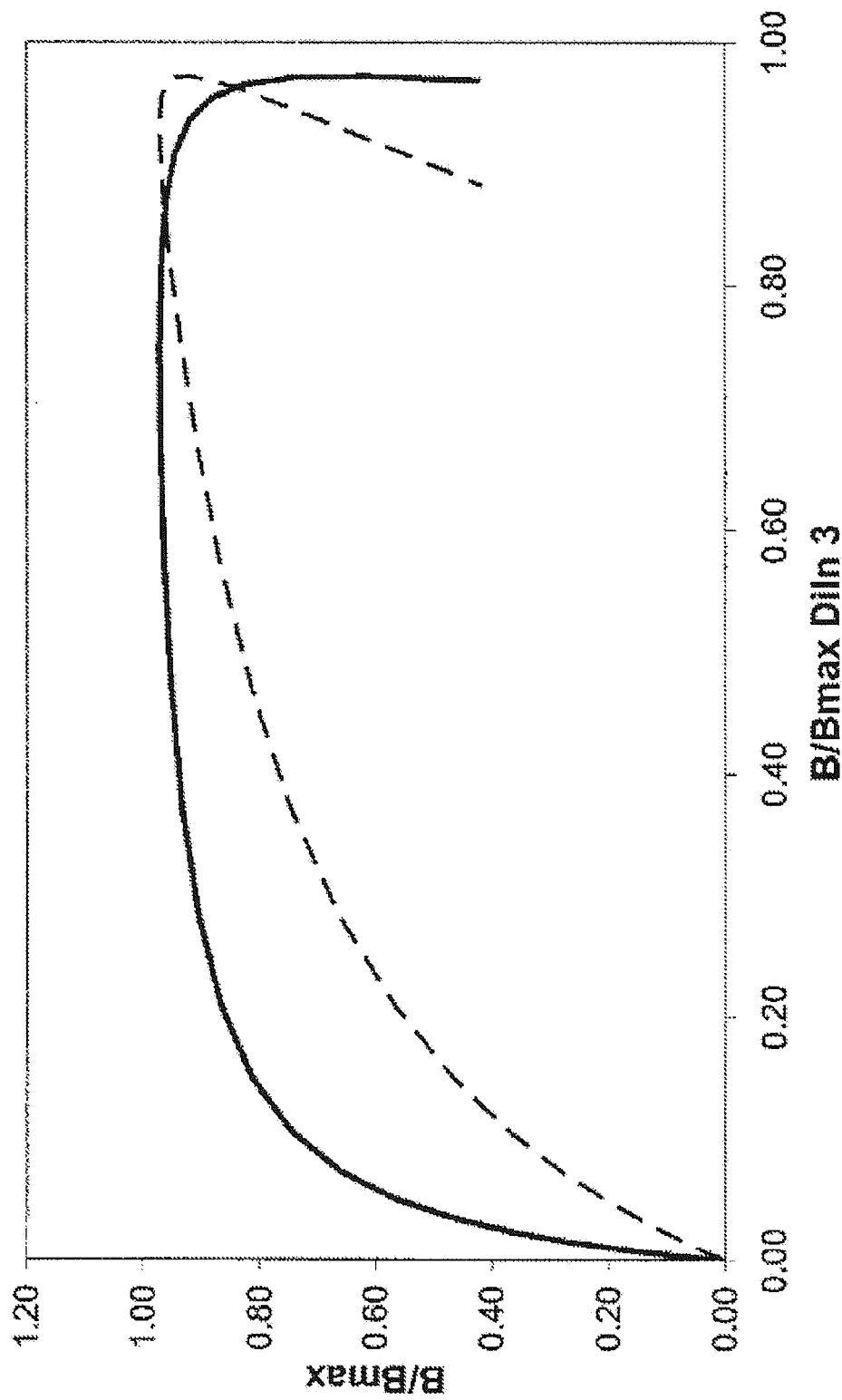

FIGS. 34 and 35 illustrate a similar example as FIG. 33 at different normalized concentrations.

Figure 36A:
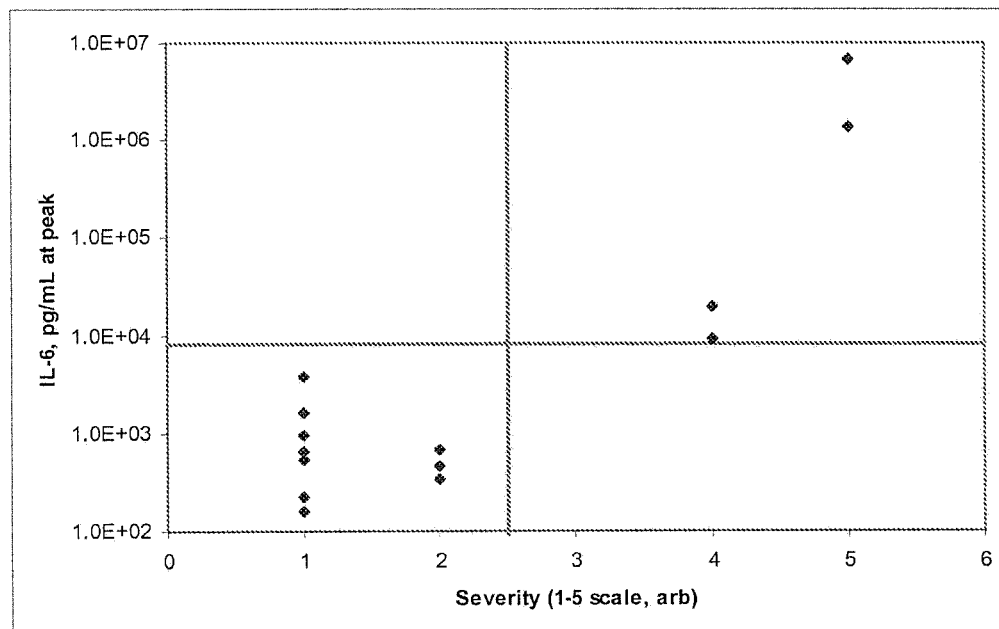
Figure 36B:
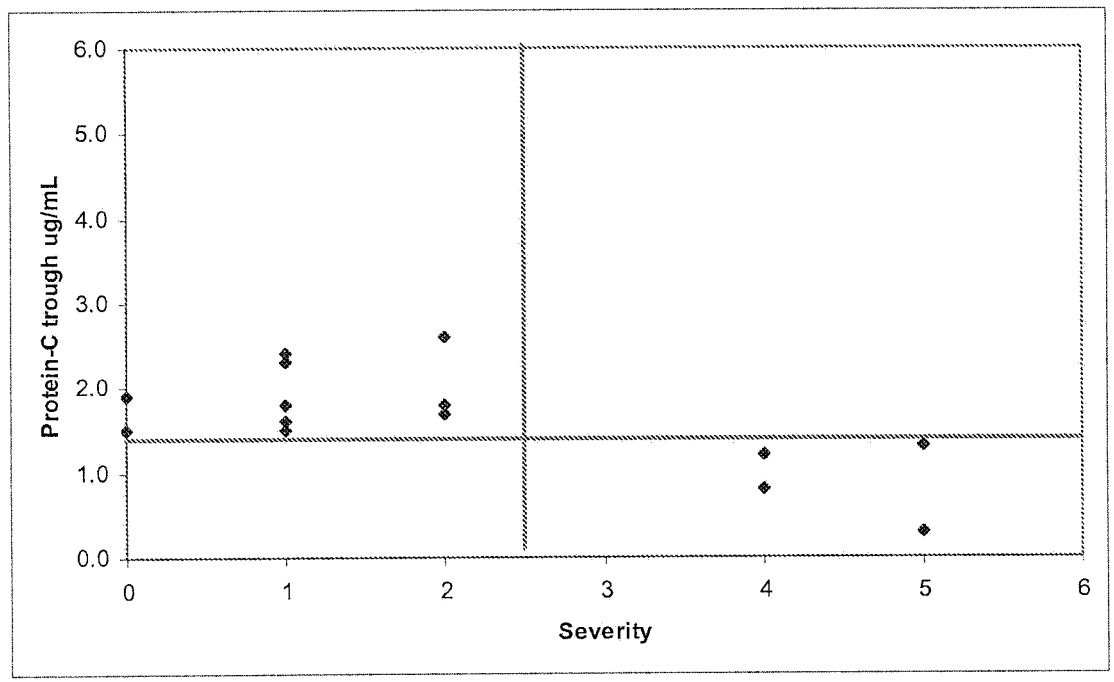

FIG. 36A shows a spike in IL-6 in septic individuals. FIG. 36B shows a decline in Protein C in septic individuals.

Figure 37:
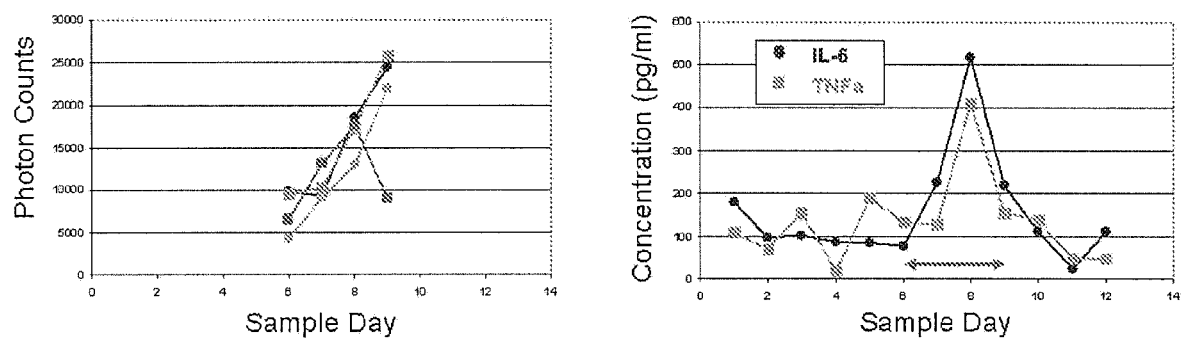

FIG. 37 shows an increase in Il-6 and TNF-α (right panel) in an individual as the load of H1N1 influenza increased in the patient (left panel).

DETAILED DESCRIPTION OF THE INVENTION

In one embodiment, the present invention provides an integrated health data capture, analysis and pandemic mitigation solution, referred to herein as the Health Shield (HS). HS can be used for infection caused by the influenza virus and other pathogenic agents prone to endemic or pandemic spread. Flu outbreaks cost billions of dollars and cannot presently be completely contained by vaccination. Economic losses can be minimized if the flu can be contained through proactive screening that allows for administration of effective anti-viral agents and narrowly targeted quarantines. Based on epidemic models, activating the HS of the invention can reduce spread of the virus, e.g., by at least 50%, through proactive sampling and containment. The HS can also reduce unnecessary avoidance behavior by tracking the virus's spread in real time. Where desired, test results can be wirelessly relayed to a server operating HS software. Accordingly, appropriate entities (e.g., local, regional and national governments) can be notified with alerts when an event is detected, thereby allowing for proactive management of a possible outbreak.

In further embodiments, the Health Shield infrastructure provides strategic industrial and commercial parks as "safe zones," which allow economically important activities to continue. As a result, fewer workers will be infected with the virus, and schools and businesses will be less disrupted.

Pandemic mitigation strategies will maintain productivity to drive economic growth and preclude actions prompted by panic.

The system can comprise an integrated sampling and modeling technology suite embedded in a real-time informatics infrastructure. The ability to sample, model, and learn from data as it is acquired longitudinally, enables the development of an optimal strategy for the care and management of disease both on an individual and population basis. Custom applications can be built for numerous diseases and therapeutic areas. The HS infrastructure can also be used to protect a region from a wide spectrum of threats beyond infectious disease, including chronic disease and bioterrorism threats.

I. Health Shield Infrastructure

The Health Shield provides a system to contain the spread of infectious diseases through integrated, automated, and real-time sampling, modeling, analysis, and recommended interventions. For example, the HS can identify active cases in an outbreak (through pro-active sampling in high risk locations, such as schools or crowded commercial areas) and direct the sampling and defensive measures, e.g., quarantine, of surrounding cases to mitigate or eradicate the outbreak. HS algorithms characterize spread of the epidemic similarly to the case of a forest fire, where the THS models' mitigation policy aims to eradicate "hot spots" before a "fire" can take hold and spread and/or can create a fire-break around a disease hot spot.

In some embodiments, the HS comprises two technological components—a Field System (FS) and an Operating System (OS)—that can be adapted for management of chronic diseases to improve health outcomes and decrease healthcare costs.

(a) Field System (FS)

The Field System components of the HS can be deployed at various points of care, including without limitation a clinic, a community site (e.g., school, community center), a hospital, a doctor's office or an individual's home. The FS can also use any number of platforms to monitor disease, e.g., immunoassays, PCR assays, real-time PCR, microorganism plating, etc. The FS also includes standard medical equipment, e.g., scales to determine weight, blood pressure devices, thermometers to measure temperature, ruler to measure height, etc. In some embodiments, the FS devices comprise customized portable, single-use cartridges, as described herein. The FS collects relevant data in the field, and transmits the data to the OS.

In some embodiments, the Field System comprises a measurement device intended to be deployed in an area to be monitored. In some embodiments, the FS analyzes bodily fluid samples, e.g., blood from a finger stick, in real-time. The system analyzes the bodily fluids for evidence of infection or disease by detecting, e.g., markers of a pathogen, nucleic acids, proteins, glycoproteins, lipids, or a combination thereof indicative of a disease condition. In some embodiments, the FS simultaneously measures multiple markers including one or more of selected antigens or the pathogen, antibodies directed to the pathogen, intracellular or cell surface proteins or glycoproteins, and cytokines indicative of the response of an infected subject to a given pathogen, (e.g., a viral strain or other microorganism). The system can also collect environmental, demographic, personal and physiological (e.g. temperature, blood pressure) information. In some embodiments, such information is collected through a graphical touchscreen interface. Individualized content can be analyzed by a remote system to facilitate mitigation strategies in real-time.

In some embodiments, the FS includes cartridges that perform assays on the bodily fluids. The devices include without limitation non-significant risk devices, and the assays can be validated under appropriate guidelines, e.g., those provided by the U.S. Federal Drug Administration (FDA) and/or International Conference on Harmonization (ICH). Cartridges used by the present invention are described in U.S. patent application Ser. No. 11/389,409 entitled "POINT-OF-CARE-FLUIDIC SYSTEMS AND USES THEREOF," U.S. patent application Ser. No. 11/746,535 entitled "REAL-TIME DETECTION OF INFLUENZA VIRUS," and U.S. patent application Ser. No. 12/244,723 entitled "MODULAR POINT-OF-CARE DEVICES, SYSTEMS, AND USES THEREOF" and are described in further detail below. The measurement systems can be self-contained and few if any extra materials are required to operate them. In some embodiments, the only requirement for an FS system is a power source for the instruments. In other embodiments, the power source is provided with the FS in form of a battery, generator, solar or other portable power source. The cartridges can be pre-loaded with the desired assays and require little or no preparation prior to use. For example, some or all assay components can be stored in a refrigerator (e.g., at about 4 degrees C.) prior to deployment.

The FS platform can run any appropriate assay that is currently performed in the conventional laboratory infrastructure. New assays can be rapidly transferred and fully validated. In some embodiments, assays that are entirely new to the HS system can be customized and validated within less than about three months, two months, one month, 3 weeks, 2 weeks or less than about 1 week. In some embodiments, the assays run on HS Systems are validated under FDA ICH guidelines.

The Field Systems can be placed at any desired point of care, e.g., an area suspected or known to be at risk of infection or disease. Point of care testing (POCT) is defined by a near-patient testing system. Exemplary points-of-care include but are not limited to the home, clinic, schools, or commercial centers. In some embodiments, the FS is deployed in mobile units. Thus, it should be understood that medical experts are not necessarily required for the testing. To enable this, the FS can be engineered to be simple to use and provides all directions for use in a simple user interface with a touch screen. In some embodiments, the systems are designed for non-computer literate individuals to test themselves in their own homes. In such a setting, the data can be sent to a remote system, e.g., the Operating System as described below, where officials or others monitoring the assays can learn of positive test results. In some embodiments, the testing and data upload/analysis are performed in real-time so that containment measures can be initiated immediately.

In some embodiments, the systems are deployed in public locations. If desired, standard public health employees can be trained to do the testing. In some embodiments, the systems are designed so that total training time is minimized at a given site. For example, current deployment demonstrates that training should require no longer than half an hour per site, although supplemental and advanced training can be performed as appropriate. In some embodiments, trained individuals can in turn train others on using the systems. The FS can be successfully used in the home by patients who have no medical training—as the testing is designed to be fully automated and uses a graphical touchscreen interface on the instrument to walk users through the test process. In some embodiments, the only steps required from a user are to: 1) place a sample into the cartridge, e.g., sputum or a finger-stick which can be performed by the user themselves using a disposable single-use lancet just as used in diabetes management for glucose monitoring; and 2) insert the cartridge into the accompanying instrument, as described in more detail below.

Non-limiting customized cartridge devices for use with the FS of the invention are described in U.S. patent application Ser. No. 11/389,409 entitled "POINT-OF-CARE-FLUIDIC SYSTEMS AND USES THEREOF," U.S. patent application Ser. No. 11/746,535 entitled "REAL-TIME DETECTION OF INFLUENZA VIRUS," and U.S. patent application Ser. No. 12/244,723 entitled "MODULAR POINT-OF-CARE DEVICES, SYSTEMS, AND USES THEREOF." Such devices are further detailed below.

(b) Operating System (OS)

The data collected from each FS device can be securely transmitted to the Operating System in real-time through network connection, e.g., over a broadband, wireless, satellite or cellular network. One of skill in the art will appreciate that network communications often comprise multiple hops, e.g., an FS device can connect to a wireless local area network (WLAN) that is securely connected to the World Wide Web through broadband landlines.

In some embodiments, the Operating System includes one or more servers as are known in the art and commercially available. Such servers can provide load balancing, task management, and backup capacity in the event of failure of one or more of the servers or other components of the system, to improve the availability of the OS. A server can also be implemented on a distributed network of storage and processor units, as known in the art, wherein the data processing according to the present invention reside on workstations such as computers. A server of the OS component can include a database and system processer. A database can reside within the server, or it can reside on another server system that is accessible to the server. As the information in a database may contains sensitive information, a security system can be implemented that prevents unauthorized users from gaining access to the database.

In some embodiments, the Operating System comprises a data engine that imports data from a desired source to provide direction for epidemic or pandemic mitigation. The OS can translate the source data into a standardized format to be analyzed. In some embodiments, the data engine is self-learning and dynamically models a plurality of integrated data sets in real-time. This OS modeling approach provides several benefits. For example, the models can be trained to perform a variety of calculations, including but not limited to: 1) predicting outcomes for individuals and populations; 2) considering the efficacy of proposed intervention strategies for individuals and populations; and 2) quantifying the socioeconomic effect of the recommended interventions. In some embodiments, the OS is made available to remote users via a remote interface. For example, the users can access the OS through a secure online web-portal or the like.

The OS software portal incorporates automatic modeling in a system that is constantly learning from each new data point that is transmitted to the software portal. The system thereby becomes increasingly more predictive over time. In some embodiments, Monte Carlo modeling approaches are used. Monte Carlo approaches rely on repeated random sampling to compute results. Monte Carlo simulation considers random sampling of probability distribution functions as model inputs to produce hundreds or thousands of possible outcomes instead of a few discrete scenarios. The results provide probabilities of different outcomes occurring.

In some embodiments, the solution and refitting/refining of model parameters sets is achieved by using reverse search and integrated parameter estimation techniques. See, e.g., Sheela, 1979-COMPUTER METHODS IN APPLIED MECHANICS AND ENGINEERING 19 (1979) 99-106; Moles, et al. 2003—Genome Res. 2003 13: 2467-2474; Rodriguez-Fernandez, et al. BMC Bioinformatics 2006, 7:483-500; Barthelmann, et al. 2000—Advances in Computational Mathematics 12: 273-288.

There is a rich literature surrounding the modeling and simulation of epidemiological data. The basis of the McKendrick model is a stochastic process (Birth Process) that yields a series of differential equations that can be parameterized, explored, and, eventually, optimized regarding the control and spread of the disease. A reasonably straightforward analysis of the process is given by Chiang, C. L. 1978. An Introduction to Stochastic Processes and Their Applications. Robert E. Kreiger Publishing Co, Inc. Huntington, N.Y. p 517. Once the process is established in a stochastic space, and appropriately parameterized, explicit expressions for population moments and or extinction probabilities can be derived. If the process is straightforward these expressions can be modeled and estimated either in closed form or numerically.

If the populations are large enough that stochastic variation is small compared to overall population sizes and system dynamics one can model the spread and growth of a disease state using differential equations systems. For example, a simple SIR model (Susceptible, Infected, Removed) of SARS was explored by Choi and Pak, J Epidemiol Community Health. 2003 October; 57(10):831-5. More complex models accounting for exposure, the SEIR model, have been explored by d'Onofrio, Mathematical Biosciences 179 (2002) 57-72, especially with respect to the optimization of vaccination strategies. For influenza in particular, Stilianakis, et al., J Infect Dis. 1998 April; 177(4): 863-73, looked at particular aspects of drug resistance in the growth and spread of disease. Other aspects of disease modeling including spread and diffusion kinetics (FitzGibbon, et al., MATHEMATICAL BIOSCIENCES 128:131-155 (1995)), mathematical and numerical stability (Dwyer, et al., The American Naturalist, 150(6): 685-707; Inaba, J. Math. Biol. (1990) 28:411-434).

Simulation is a valuable tool in the solution of these complex systems. There are many models that lend themselves to simulation solution. See, e.g., Longini, et al., 1984, Int J. Epidemiology. 13:496-501; O'Neill, 2002. A Tutorial Introduction to Bayesian Inference for Stochastic Models Using Markov Chain Monte Carlo Methods. *Math Biosci.* 180:103-114; Gibson, G. J. 1997. Investigating mechanisms of Spatiotemporal Epidemic Spread Using Stochastic Models. *Am Phytopathological* Society. 87:139-146. In particular, see Timpka, et al. (2005) *AMIA* 2005 Symposium Proceedings. 729-733, with regards to simulating influenza. In some embodiments, the model of epidemic growth and spread and the incumbent screening and containment strategies are embedded into a health economics model of cost effectiveness. See, e.g., Brandeau, et al. Journal of Health Economics 22 (2003) 575-598.

Figure 1:
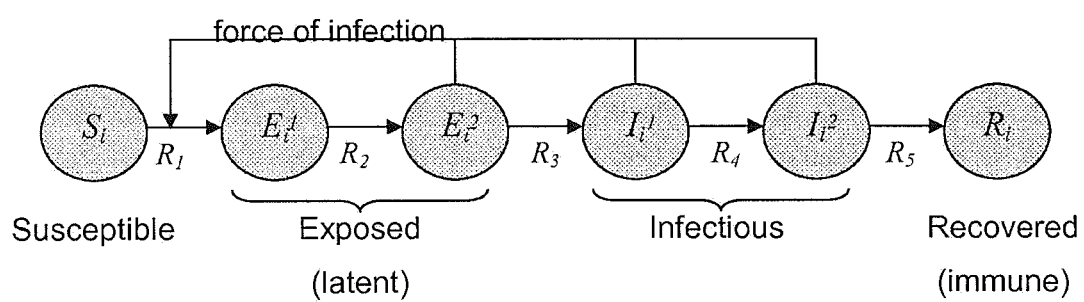
FIG. 1 illustrates a simplified model representation.

A simplified exemplary model representation according to the invention is shown in FIG. 1. The model can be configured to describe the spread, surveillance, and mitigation with its attendant cost effectiveness for epidemic/pandemic policy management. Briefly, an at risk population is segmented into various states or conditions (represented by the circles in the Figure), with flux components between each state modified by a variety of configurable parameters, including but not limited to the rate of infection, the means and granularity of the surveillance mechanism, and the policy decision at hand. To aid the policy maker in the decision process, both the out-of-pocket and societal costs, e.g., QALYs, can be calculated by the model and displayed to the policy maker.

The model illustrated in FIG. 1 comprises a system of deterministic nonlinear ordinary differential equations. Each node (or state) represents a population of individuals having similar phenotypic and disease characteristics, such as their state of infectiousness. Various states can also represent individuals in different locations, such as in schools, workplaces, during hospitalization, isolated quarantine, or home isolation. A plurality of age groups, e.g., 2, 3, 4, 5, 6, 7, 8, 9, 10, 11, 12, 13, 14, 15, 20, 25, 30, 35, 40, 45, 50 or more age groups, are represented by modular structure, thus allowing specification of age-specific characteristics. In some embodiments, the model takes age into account in a continuum as opposed to within discrete groups. The arrows shown connecting the nodes in the figure indicate flux from one state to another. As described herein, the model parameters come from a variety of sources, e.g., literature reports, patient data, prior outbreaks, and can be estimated based on data as desired. The model projections capture a range of possibilities based on the quantified uncertainties. As the model predictions are implemented, the parameters can be continuously adjusted in real time according to the actual results in the field. For example, the effectiveness of various mitigation policies might be reassessed and adjusted given real world results applied to the current, specific affected populations.

Figure 2:
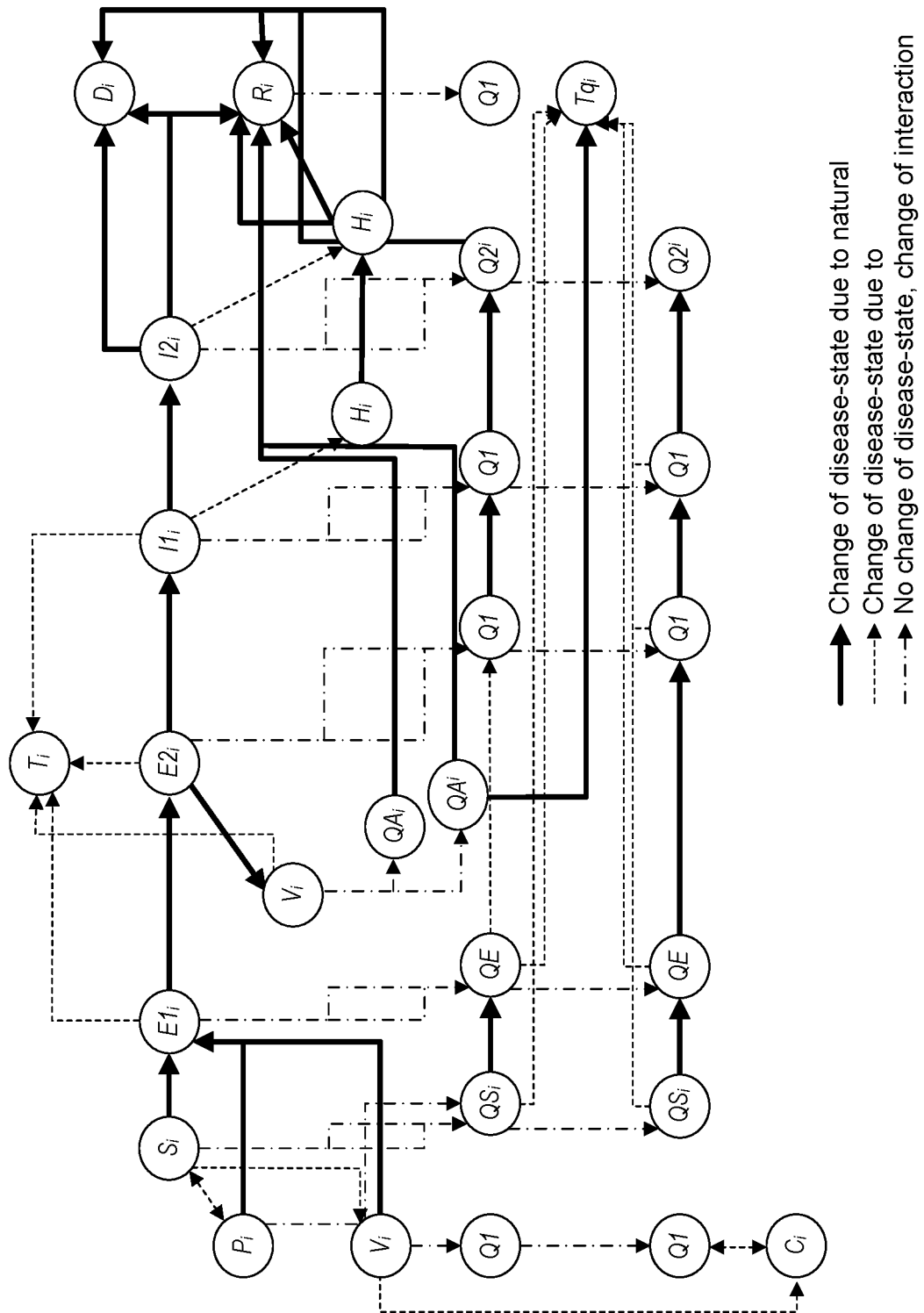
FIG. 2 illustrates a model representation taking into account various states and transitions between states.

Those skilled in the art will appreciate that the model shown in FIG. 1 can be expanded to take into account any number of relevant states and parameters. FIG. 2 shows a larger model representation. Each circle represents a class of individual and each arrow represents a transition from one stated to another. Transitions from one state to another can take into account changes from natural causes, or from interventions, e.g., therapeutic treatment. The model can also take into account transitions that don't involve disease state, e.g., change of social interaction with various groups. For example, a quarantined individual may transition from community involvement to involvement with a limited number of individuals, e.g., contact being limited to health care workers or other care-takers. The model parameters at the outset of an epidemic can be derived from data from the closest applicable previous disease outbreak with the closest demographics and type of location (e.g., a city, a rural area). The model can be continuously refined by application of data gathered within the present epidemic to become progressively better.

Near the top of FIG. 2, a flux from left to right is highlighted by the row $P_i$, $S_i$, $E1_i$, $E2_i$, $I1_i$, $I2_i$, $R_i$, and $D_i$. These states represent a disease spread model comprising states of prophylactically treated, e.g., with anti-virals ($P_i$), susceptible individuals ($S_i$), early exposed individuals ($E1_i$), late exposed individuals ($E2_i$), early symptomatic infected individuals ($I1_i$), late symptomatic infected individuals ($I2_i$), recovered—and thus potentially immune—individuals ($R_i$), and the deceased ($D_i$). An individual can transition from state $E2_i$ to state $A_i$, which represents the asymptomatic infectious subpopulation in the community at hand. An individual can also transition to state $V_i$, which represents vaccination. From the vaccinated state, an individual can transition to either a cleared and immune state, $C_i$, or to the ineffective and exposed state, $E1_i$. By taking into account any number of individuals, i, the model can capture a population representation of epidemic spread. The delay criteria, $E2_i$ and $I2_i$, accommodate the time dependent spread of the disease. The segment above the disease spread model represents the impact of a policy of treatment and its effects on population wellness and disease spread, while the segment below the disease specific spread represents a mitigation strategy of quarantine. The model integrates an active, user-defined surveillance strategy and user defined mitigation strategy with a cost effectiveness matrix to aid in decision making. In some embodiments, the model accounts for sub-optimal disease mitigation. For example, even when a developing disease hot spot has been located, there can be logistic delays in getting therapeutic agents to the area and in implementing quarantine. These delays can permit further progression of the epidemic without mitigation. The model can take such sub-optimal mitigation into account.

The model equations form an Ordinary Differential Equation System (ODEs) with appropriately parameterized flux coefficients as defined by the arrows in FIG. 2. The basic form of the model is given by the vector ODE:

$$dX/dt = f(X,t)$$

where X is a dimensionalized vector and the function f(X,t) is represented by a matrix of mixing parameters and functional interactions as defined in the Figure. In the model in the figure, there are more than 80 dimensions to the dimensionalized vector. One of skilled in the art will appreciate that the format and components of the matrix for the function f is derivable from FIG. 2 and the explanation herein.

The equation sets represented above are duplicated for each of a variety of age groups, as described herein. Consider an example with seven age groups. In the example, the conglomerate model of seven sets is replicated for each geopolitical region in a given geographical region. The model then can be generalized to account for more wide spread of the disease in a larger region. For example, by parameterizing the mixing matrices and resource/cost tables, one can account for interregional travel and nationwide surveillance and mitigation strategies.

A variety of states modeled by the OS and presented in FIGS. 1 and 2 are shown in Table 1:

TABLE 1

Description and nomenclature for the states used to describe the outbreak

| Variable Name | Description |
| --- | --- |
| S | Susceptible individuals |
| E1 | Early exposed individuals |
| E2 | Late exposed individuals |
| I1 | Early infected individuals |
| I2 | Late infected individuals |
| R | Recovered individuals |

TABLE 1-continued

Description and nomenclature for the states used to describe the outbreak

| Variable Name | Description |
|---|---|
| D | Individuals who have died due to the infection and associated complications |
| A | Asymptomatic individuals |
| T | Individuals treated with antivirals |
| Tq | Individuals treated with antivirals & quarantined |
| P | Individuals prophylaxtically treated with antivirals |
| V | Vaccinated individuals |
| C | Individuals protected due to vaccination |
| H1 | Early infected individuals who are hospitalized |
| H2 | Late infected individuals who are hospitalized |
| QS | Susceptible individuals who are home quarantined |
| QE1 | Early exposed individuals who are home quarantined |
| QE2 | Late exposed individuals who are home quarantined |
| QI1 | Early infected individuals who are home quarantined |
| QI2 | Late infected individuals who are home quarantined |
| QA | Asyptomatics who are home quarantined |
| QS_iso | Susceptibles quarantined in the whole neighborhood |
| QE1_iso | Early exposed individuals quarantined in the whole neighborhood |
| QE2_iso | Late exposed individuals quarantined in the whole neighborhood |
| QI1_iso | Early infected individuals quarantined in the whole neighborhood |
| QI2_iso | Late infected individuals quarantined in the whole neighborhood |
| QA_iso | Asymptomatics quarantined in the whole neighborhood |
| Dv | Amount of drug doses available |
| Da | Amount of antivirals available |
| Q1v | Home quarantined individuals that are vaccinated |
| Q1c | Home quarantined individuals that are protected due to vaccination |
| Qr | Home quarantined individuals that recovered |
| Sm | Susceptibles earmarked by mitigation policies for action |
| E1m | Early exposed individuals earmarked by mitigation policies for action |
| E2m | Late exposed individuals earmarked by mitigation policies for action |
| Am | Asymptomatics earmarked by mitigation policies for action |
| I1m | Early infected individuals earmarked by mitigation policies for action |
| I2m | Late infected individuals earmarked by mitigation policies for action |
| Pm | Prophylactic-treated individuals earmarked by mitigation policies for action |
| Vm | Vaccinated individuals earmarked by mitigation policies for action |
| Cm | Protected individuals earmarked by mitigation policies for action |
| Rm | Recovered individuals earmarked by mitigation policies for action |
| St | Susceptibles earmarked for treatment with antivirals |
| E1t | Early exposed individuals earmarked for treatment with antivirals |
| E2t | Late exposed individuals earmarked for treatment with antivirals |
| At | Asymptomatics earmarked for treatment with antivirals |
| I1t | Early infected individuals earmarked for treatment with antivirals |
| I2t | Late infected individuals earmarked for treatment with antivirals |
| Ss | Susceptibles earmarked for surveillance |
| E1s | Early exposed individuals earmarked for surveillance |
| E2s | Late exposed individuals earmarked for surveillance |
| As | Asymptomatics earmarked for surveillance |
| I1s | Early infected individuals earmarked for surveillance |
| I2s | Late infected individuals earmarked for surveillance |
| Ps | Prophylactic individuals earmarked for surveillance |
| Vs | Vaccinated individuals earmarked for surveillance |
| Cs | Protected individuals earmarked for surveillance |
| Sm_iso | Susceptibles in whole neighborhood quarantine earmarked by mitigation policies for action |
| E1m_iso | Early exposed individuals in whole neighborhood quarantine earmarked by mitigation policies for action |
| E2m_iso | Late exposed individuals in whole neighborhood quarantine earmarked by mitigation policies for action |
| Am_iso | Asymptomatics in whole neighborhood quarantine earmarked by mitigation policies for action |
| I1m_iso | Early infected individuals in whole neighborhood quarantine earmarked by mitigation policies for action |
| I2m_iso | Late infected individuals in whole neighborhood quarantine earmarked by mitigation policies for action |
| Pm_iso | Prophylactic-treated individuals in whole neighborhood quarantine individuals earmarked by mitigation policies for action |
| N_Dv | Cumulative number of Drug doses administered |
| N_Da | Cumulative number of Antivirals administered |
| N_QA | Cumulative number of home quarantined asymptomatics |
| N_QS | Cumulative number of home quarantined symptomatics |
| N_TI | Cumultative number of total infected individuals |
| N_I | Cumulative number of Infected individuals who are not quarantined |

TABLE 1-continued

Description and nomenclature for the states used to describe the outbreak

| Variable Name | Description |
|---|---|
| N_Idet | Cumulative number of Infected individuals with some action taken |
| N_H | Cumulative number of hospitalized individuals |
| N_D | Cumulative number of deaths |

The model of the invention can be configured to take into account many characteristics of the individuals, populations and disease being monitored. In some embodiment, the force of infection is taken into account in the model. The force of infection, also termed the transmission rate, refers to the rate at which existing infectious individuals transmit the disease to susceptible individuals. In some embodiments, each infectious individual is given two attributes: an age-group j, based on the individual's age, and a mixing group k, based on the individual's mixing pattern in the society. Mixing patterns include without limitations mixing freely with others in society, e.g., at school or work, reduced mixing from taking days-off from work due to illness, etc. The force of infection exerted on population age-group i by all populations of age-groups j can be computed as follows:

$$\Lambda_j = \rho_i \beta \sum_k \sum_j \varphi_j \left( \Delta_{ij}^k \theta \frac{I_j^k}{N_j^k} + (1-\theta) \frac{I_j^k}{N_t} \right)$$

where,
- $\beta$ is rate of transmission (per day per infectious individual per susceptible individual)
- $\theta$ is parameter defining randomness of mixing between different age-groups: if $\theta=1$ the interactions are perfectly assortative, if $\theta=0$, the interactions are perfectly random
- $\rho_i$ is relative susceptibility of individuals in age group i
- $\varphi_j$ is relative infectiousness of infectious individuals of age group j
- $\Delta_{ij}^k$ is a weight factor that accounts for the differences in the relative extent of potentially transmission-causing interactions between individuals of age-group i and those of age-groups j and mixing-groups k
- $I_j^k$ is the number of infectious individuals of age-group j
- $N_j^k$ is total number of individuals of age-group j and mixing group k in the population
- $N_t$ is total number of individuals of all-age-groups in the population In the force of infection equation, the interaction weights $\Delta_{ij}^k$ are calculated based upon
1. the time spent by an individual of age-group i in company of individuals of age-group j and mixing-group k in different locations such as work, school, home etc
2. the number of individuals of age-group j and mixing-group k that come in potentially transmission-causing contact with an individual of age-group i Of the above parameters, $\rho_j$, $\varphi_j$, $\Delta_{ij}^k$, $I_j^k$, $N_j^k$ can change dynamically with time as a result of evolution of the epidemic, imposition of mitigation policies or both.

The OS model can include a number of mitigation policies that direct medical decision making policy when faced with an outbreak. These policies can be modeled for each particular setting, e.g., geographical location and disease or infectious agent, to best take advantage of the available resources. Each policy can be imposed with a realistic efficacy/compliance which can be estimated from historical data. The model can predict the results of implementing various mitigation policies, thereby providing the appropriate individuals with a suggested response. Exemplary non-limiting mitigation policies are listed in Table 2:

TABLE 2

Mitigation Policies Represented in the Model

| | |
|---|---|
| Community/Public Health Measures | 1. Individual hygiene: hand sanitizer, face masks, etc;<br>2. Social distancing;<br>3. Hospital hygiene;<br>4. School/daycare closure;<br>5. Workplace closure;<br>6. Public transportation closure;<br>7. Household quarantine;<br>8. Geographical area quarantine: e.g., neighborhood, village, town, city;<br>9. Individual quarantine; or<br>10. Travel restrictions |
| Pharmaceutical Prophylaxis | 1. Targeted prophylaxis, e.g., anti-viral<br>  (a) Household of an infected individual;<br>  (b) Workplace of an infected individual;<br>  (c) Condition-targeted: individuals with primary conditions; or<br>  (d) Health care workers treating infected individuals<br>2. Blanket prophylaxis, e.g., anti-viral;<br>3. Targeted vaccination: single or multiple doses:<br>  (a) Children between 1-4 years of age;<br>  (b) Children between 5-14 years of age;<br>  (c) Pregnant women;<br>  (d) Young adults between 15-30 years of age;<br>  (e) First-line medical response personnel;<br>  (f) Individuals identified at high risk of mortality; |

TABLE 2-continued

| Mitigation Policies Represented in the Model | |
|---|---|
| | (g) Geriatrics; or |
| | (h) Middle aged individuals between 30-60 years of age. |
| | or |
| | 4. Blanket vaccination: single or multiple doses |
| Treatment | 1. Therapeutic administration, e.g., anti-viral; |
| | 2. Hospitalization (antibiotic, anti-pyretic, saline, etc); or |
| | 3. Antibiotics treatment of quarantined individuals |

In addition to mitigation policies, the OS model can incorporate results obtained in the field when performing surveillance with a variety of different technologies. These include the cartridge systems described herein, rapid antigen test, immunofluorescence, immunoassays, real time PCR, viral culture test, physiological measures, urine and blood workup, etc. The model includes the representation of the sensitivity and specificity of each test for samples from both asymptomatic individuals and symptomatic individuals. In addition, the turn around time for the different tests can be included in the model.

Depending on each particular system, various forms of surveillance strategies can be included in the model. In one embodiment, surveillance comprises the testing of individuals reporting for testing voluntarily. The surveillance can also be performed for population-groups which include, but are not limited to, the following:
   Children between 1-4 yrs of age
   Children between 5-14 yrs of age
   Pregnant women
   Young-adults between 15-30 yrs of age
   First-line medical response workers
   Individuals identified to at high risk of mortality
   Geriatrics
   Middle-aged individuals between 30-60 yrs of age Each of these population-groups can be tested using any of the testing methods or combinations thereof. Different proportions of asymptomatic individuals and symptomatic individuals reporting for voluntary testing can also be accounted for in the model.

In another embodiment, surveillance includes the testing based on implementation of any surveillance policy as defined by the end user. The catalog of surveillance policies captured by the model includes without limitation the following:
   Household surveillance: testing of entire household based on index confirmed case
   School surveillance: testing of school children based on index confirmed case
   Work place surveillance: testing of employees based on index confirmed case For confirmed cases identified as a result of the surveillance tests, appropriate action of quarantine, prophylaxis or hospitalization can be taken. In some embodiments, the HS allows for an automated analysis to be performed using these methodologies for the selection, parameterization, and/or exploration of an appropriate epidemic model to implement the optimal screening and containment strategy. The model can be modified according to a cost effectiveness health economics model. In some embodiments, the model is configured to predict spread of an infectious pathogen in a heterogeneous human population. The models can take into account regional demographics and individual risk factors. As described in more detail below, in one embodiment, the model enables evaluation of healthcare mitigation policies, including without limitation: a) surveillance/testing strategies; b) hospitalization, home isolation, and quarantine policies; c) prophylactic vaccination and treatment policies, e.g., anti-viral therapy; and d) social distancing measures such as school and workplace closures.

In addition to infectious outbreak dynamics, the model can provide cost assessment as well as evaluation of the quality adjusted life years (QALY) saved by comparing alternative mitigation approaches. The model can be configured to take into account non-economic cost measures. The model can be configured to adjust for the cost associated with different errors, based on economic cost, temporal costs, or other factors, in order to minimize the cost of the errors made by a model. For example, the model may assign a high cost to misdiagnosing an infected individual so that mitigation strategies are not put into place. The model could then adjust to favor avoidance of such errors. Similarly, a misdiagnosis for a chronic condition may have a lesser cost as the individual may be tested again before the disease has progressed very far. In the case of an epidemic, predictions may not only relate to an individual's case, but to populations of people in different regions. Based on large sets of demographic data, the HS analytic system can be configured to predict risk and costs optimized for both treatment and assay delivery. For example, locations with lower expected risk may be sampled less than locations with greater expected risk.

The OS has actions built in that are triggered when certain events are detected. For example, alerts can be sent to government officials when an infected individual is detected. Rules can be set to notify a clinician automatically by phone, email or fax when a case is detected. The detected individual and contacts, e.g., family members, co-workers, or anyone who has had contact with the individual in the past few days, weeks, months, or years, can also be notified. The rules that trigger the action can be customized prior to deployment or during a period of monitoring depending on the needs of the situation.

The OS models also perform sanity and outlier checks on the data received from the FS. In some embodiments, actions are taken when variability or noise is identified in the data. In some embodiments, an assay for an individual is repeated when outliers are detected.

In some embodiments, the OS models can predict outcomes for individuals and populations. In some embodiments, the models match predictions—such as response to infection, optimal treatment regimen for an individual or population, and projected spread of the virus—to actual historical data, e.g., data from the spring flu season. In some embodiments, the models consider the efficacy of proposed intervention strategies for individuals and populations, including use of pre-emptive antiviral therapies, reactive anti-viral therapies, quarantine, hospitalization, targeted closures and establishment of "safe zones" in key hotels, restaurants, schools, manufacturing plants and other locations. The models can also quantify the socioeconomic effect (in out-of-pocket expenditures, lives saved, lost days of productivity, etc.) that the recommended interventions would have had at the time of each case.

In some embodiments, the Field Systems and OS are also customized to provide solutions for various settings wherein the systems can improve outcomes and reduce the cost of care. For example, the FS and OS can provide health monitoring solutions for pharmaceutical and biotechnology companies and for consumers.

II. Deployment of the Health Shield

In some embodiments, the Health Shield comprises a fully integrated diagnostic/Patient Health Record/Electronic Medical Record platform. The deployed Field System devices can be configured to be portable, and thus can be deployed in a variety of points-of-care, including without limitation a clinic, a community site (e.g., school, community center), a hospital, a doctor's office or an individual's home. As described herein, portable FS devices can be configured to wirelessly connect to a network, requiring only an optional cable for power. In some embodiments, the network connection is made to a web-portal where assay data is sent in real-time. The FS systems can be deployed in urban environments near care centers and the same devices can by deployed in remote settings, e.g., even where patients live long distances from the nearest medical clinics.

The performance of the FS assays will vary from assay to assay but all tests are developed with a goal of high accuracy, e.g., via high specificity and sensitivity. In some embodiments, the specificity is greater than about 50%, 55%, 60%, 65%, 70%, 75%, 80%, 85%, 90%, 91%, 92%, 93%, 94%, 95%, 96%, 97%, 98% or greater than about 99%. In some embodiments, the specificity approaches 100%. In some embodiments, the sensitivity is greater than about 50%, 55%, 60%, 65%, 70%, 75%, 80%, 85%, 90%, 91%, 92%, 93%, 94%, 95%, 96%, 97%, 98% or greater than about 99%. In some embodiments, the sensitivity approaches 100%. The exact performance of an assay can depend on a number of factors, including but not limited to the performance of the marker being detected, the skill of the user and assay performance inherent in the device. In some embodiments, the FS systems are designed to be highly user friendly and require minimal skill to effectively operate. The time required for assay performance will also vary based on the use case for deployment. Each system is fully customized to best achieve the goals of deployment so all specifications are set accordingly. In some embodiments, the assays are run in a matter of minutes, e.g., less than about 30 min, 25 min, 20 min, 15 min, 10 min, 9 min, 8 min, 7 min, 6 min, 5 min, 4 min, 3 min, 2 min, or less than about 1 minute. In some embodiments, the HS out-performs current centralized laboratory test analyses across broad ranges of tests.

The assays of the present invention advantageously can examine a set of markers. In some embodiments, the assays will measure both antibodies and viral load to provide enhanced evaluation of the status of an individual subject. The assays can also be designed to measure other markers for infection and response to infection, e.g., cytokine production levels, and will therefore provide additional information about the severity of illness, suggest individualized treatments, and can also indicate when confirmatory tests are appropriate for a negative initial screen.

The system can also be configured to detect infection with mutant or other strains that are as yet uncharacterized. Before those strains are identified, spikes in inflammatory markers can indicate that an individual is infected with a strain that has not yet been identified, thereby allowing for potential rapid containment and identification of the fact the virus is mutating. Defensive measures (such as investments in vaccinations) can then be updated accordingly.

The HS technology is configurable to be simple to use and eliminates the multiple steps for data sampling analysis that would otherwise occur under existing situations (e.g., sample collection, shipping, remote analysis, decision making). As a result, the HS can provide greater accuracy and faster decision by providing real-time field data to a central monitoring site, e.g., that of a governmental agency. The system thereby provides the opportunity for optimal healthcare support and direction. For example, the FS systems can be located at community friendly sites, such as pharmacies, schools, clinics, or recreation centers, so that citizens could easily be tested and/or treated on a desirable basis, e.g., to monitor infectious diseases such as flu. In addition, because the device can be portable, community workers can visit the elderly and others incapable of traveling, or make home visits when infection, e.g., by flu, is suspected. In some embodiments, the data collected is analyzed on both an individual and population based circumstance. This assay data collected by the deployed FS devices can be made available to providers, government officials, hospitals, or the like.

When deployed in a region of interest, e.g., a school, community center, commercial center, locally, regionally, or nationally, the HS can be used to develop safety systems for monitoring potential adverse events and healthcare pandemics. The FS device can also be used in high screening strategies where a large number of individuals, e.g., everyone at-risk or suspected to be at-risk, can be tested on a routine basis in a preventive manner or in reaction to an outbreak. The data collected by the FS is accumulated at the OS, which then aggregates and manages the collective data. In some embodiments, the system requires only a small sample of bodily fluid, e.g., a finger stick of blood, saliva or sputum, typical safety issues that arise from blood draws are greatly reduced or eliminated. In some embodiments, the real time data is used to help select the optimal biomarker assays for a given situation. In some embodiments, the analyte set is chosen prospectively as a sub-set from a large assay menu. Thus, the ideal assay set appropriate for the early stage of an epidemic (which might emphasize antigen detection) can be changed later in the epidemic, e.g., to look for antibodies that provide information as to the likely stage of community immunity that may be relevant to management of subsequent epidemics.

When monitoring infectious disease, the Health Shield deployment strategy can provide screening and sampling for the at-risk population derived from the minimum number of expected initial outbreaks. In some embodiments, the system assumes the same range of cases that had occurred to provide real world empirical data for modeling disease spread.

An index case can potentially infect any number of secondary individuals. The number of secondary individuals can depend on any number of factors of the index case, including but not limited to age, mobility, living situation, work environment, socialization, and geographical location. The HS can model these factors and others to estimate the potential spread of a given outbreak. In a non-limiting example, real world data suggests that a typical index case is likely to infect 50 other individuals. An exemplary infection pattern may comprise 4 or 5 family members and 45 or 46 co-workers, friends, and other people with whom the infected person has come in contact. In the HS rapid response model, each index case would require 25 to 50 secondary screens (regardless of age group) to prevent the people in contact with the index case from becoming infected and spreading the virus. Depending on characteristics of the index case and infective agent, 5, 10, 15, 20, 25, 30, 35, 40, 45, 50, 55, 60, 65, 70, 75, 80, 85, 90, 95 or 100 secondary screens might be required. In some embodiments, more than 100 secondary screens may be necessary for an index case.

In some embodiments, the HS is equipped with an initial quantity of FS device cartridges, e.g., about 1, 2, 3, 4, 5, 6, 7, 8, 9, 10, 20, 30, 40, 50, 60, 70, 80, 90, or 100 times the expected number of index cases. In some embodiments, the system provides about 50 times the cartridges per expected number of index cases. Each cartridge can be used to test a bodily fluid sample, as described herein. The abundance of cartridges provides on-demand, proactive containment for pandemic mitigation. Once the infrastructure is activated, the HS provides additional on-demand shipments as required. This scheme provides screening and sampling sufficient to cover the at-risk population surrounding the index cases.

Individuals may be provided with a device when procuring a prescription of drugs by any common methods, for example, at a pharmacy. The individual may be given a device in a school, a work place, or other area of interest. The devices may also be distributed manually by healthcare workers. When the device is distributed to an individual, the individual's contact information, including without limitation cell phone, email address, text messaging address, or other means of wireless communication, may at that time be entered into the databases of the OS component and associated with the individual therein. The OS system may include a script or other program that can detect when a signal generated from a detection device has not yet been sent to the OS system, for example at a given time, and the OS system can then send an alert notifying the individual to test a bodily fluid sample.

Because of the portability and size of the FS components of the Health Shield, the HS can become a part of everyday lifestyle for managing disease and potential health hazards. In some embodiments, the systems are placed in homes and at easily available locations. The real-time data collection and data analysis provide a rapid pro-active healthcare system to respond to sudden outbreaks.

The HS systems can predict the optimal surveillance measures for disease management. The HS system can identify outbreaks as early as possible to track and contain spread to enable appropriate, rapid mitigation strategies to be put into place. The model for a given setting can be optimized to take into account various factors to provide optimal surveillance and mitigation strategy. One factor includes prioritizing testing based on risk factors and symptoms, including prioritizing testing of infants, children, pregnant women, medical personnel, high risk individual and geriatrics. Another factor includes testing close contacts of index cases, such as targeting testing at household, schools, and workplaces where there are confirmed or suspected cases. In addition, the system as assess the impact of alternate diagnostic tests based on various factors, such as sensitivity, specificity, turn around (i.e., time to get results from an assay). In some embodiments, the assays performed comprise one or more of cartridge assays, real time PCR, rapid antigen tests, viral culture, and immunoassays. In some embodiments, a less expensive assay may be used for a large number of secondary assays to minimize expense. Based on these data, a smaller number of more expensive, but more sensitive and specific assays can be used to test selected individuals.

When suspected infected individuals are detected by the HS, whether the individual is symptomatic or asymptomatic, assays can be performed in the field with the FS and the results and location of the subject can be relayed to the OS, e.g., at a central server at a central monitoring site. At the monitoring site, the results can be displayed and alerts registered if appropriate so that containment efforts, including further deployment and testing of FS components, can be initiated. In some embodiments, the model contained in the software will automatically suggest where the disease is likely to spread and where resources will need to be deployed to contain the disease and do further in-field monitoring. The system can contact individuals involved in surveillance, e.g., government or healthcare workers, e.g., by phone, pager, fax, email, text message, or other rapid form of communication. In some embodiments, the data and analysis provided by the HS is provided to officials and health care professionals, not to individual users. This helps ensure that medical decision making is made appropriately.

An advantage of the Health Shield as described herein is that assay results from the field systems can be substantially immediately communicated to any third party that may benefit from obtaining the results. For example, once results of a measurement taken by an FS device are communicated to the OS, an analyte concentration can be determined at the Operating System component and transmitted to an individual or to medical personnel who may need to take further action. This might include identification of an index case. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

The systems of the invention can be designed to interface with any combination of different Electronic Health Record (EHR) systems and any other relevant databases. Moreover, the system can be configured to automatically translate data that currently exists in different formats into one standard format. Once the system imports and translates the data, it can centralize the information into one or more repositories and pass the imported data through predictive models. In this manner, the system can compile and take advantage of multiple data sources to best model the outbreak and predict appropriate containment responses. Those models learn from every new data point, becoming increasingly predictive over time. In some embodiments, the models recognize patterns that predict how a given individual's disease is likely to progress.

A pilot program can be used to help refine the system parameters. In some embodiment, an initial screening and containment strategy is developed. The HS is then deployed to pilot that model in a region of interest, e.g., a township, neighborhood, hospital or commercial area. With this pilot the robustness of the assumptions underlying the modeling effort can be tested, and the containment strategy can be fine tuned. In some embodiments, the fine tuning is performed automatically by the learning algorithms of the OS. For example, the modeling software contains pattern recognition technologies that allow the algorithms forecasting the spread of the disease to be continually refined with every new data-point sent to the software portal. As such, the system becomes increasingly predictive over time. In some embodiments, these refinements continue even after the system is deployed after the pilot stages.

After a system is developed using historical data, archived samples and even the pilot phase, the systems can be placed in strategic locations to begin preventing the spread of any outbreak. Because each instrument can process different cartridges that can be customized for a given disease of interest, e.g., with a specific strain of influenza that presents concern, the same systems can be used to contain and prevent the spread of a virus even if it mutates. In some embodiments, the cartridges contain protein-based tests which measure inflammation and response to infection allowing officials to recognize severe infection even if the virus mutates, and specific tests for new viral trains can immediately be developed and deployed through the existing infrastructure and instruments. In addition, the same instruments deployed to monitor infectious disease are available to then monitor other health-related issues such as diabetes, obesity, cardiovascular disease and oncology concerns, e.g., cancer therapy. Different cartridges and additional models for the software can be customized around the HS systems already in place. Validation data for each application can be performed prior to deployment and adjusted prospectively by learning from the incoming data.

Noncompliance with the recommended treatment can undermine the efficacy of the containment strategy of the present invention. As such, in some embodiments the system of the present invention can be used to monitor patient compliance and notify the patient or other medical personnel of such noncompliance. For example, a patient taking a pharmaceutical agent as part of medical treatment plan can take a bodily fluid sample which is assayed as described herein, but a metabolite concentration, for example, detected by the system may be at an elevated level compared to a known profile that will indicate multiple doses of the pharmaceutical agent have been taken. The patient or medical personnel may be notified of such noncompliance via any method discussed herein, including without limitation notification via a handheld device such a PDA or cell phone, or through a third party such as a healthcare worker who also receives communication of the noncompliance. Such a known profile may be located or stored on an external device described herein.

In an embodiment, the system can be used to identify sub-populations of patients which are benefited or harmed by a therapy. In this way, drugs with potential toxicity can be administered to only to those who will benefit.

In terms of pharmaceutical-related adverse events, the Health Shield systems can be placed in an individual's residence. In some embodiments, the HS is used to monitor safety and efficacy of treatments for acute conditions, e.g., debilitating or life threatening illnesses, or for chronic conditions. The FS components can also be placed in central locations such as pharmacies such that individuals can be tested when filling prescriptions.

Case studies have been performed for diabetes, infection, and oncology considering the needs of governmental disease management systems as well as healthcare corporations. One such study was aimed at a model for preventing and reversing diabetes. The modeled data demonstrated dramatic cost savings associated with eliminating the centralized infrastructure for blood and data analysis of health information and instead using the systems of the present invention with FS systems placed at various points of care, including the home environment. The system provided savings in part by limitation of shipping costs, reduction of personnel costs associated with running analysis, reduction of costs associated with false positives, reduction of time associated with waiting for results. In various modeling environments, the HS system would reduce the costs associated with conventional testing by greater than an estimated 50%, in addition to the value of time-saved in acquiring the relevant data.

5. Monitoring Influenza Outbreaks

In one aspect, the systems of the invention are deployed to monitor and contain disease outbreaks. The HS is particularly beneficial in the influenza setting because containment strategies that initially rely on mass vaccination programs may not be sufficiently effective to contain an outbreak. Influenza A virus strains are categorized according to two proteins found on the surface of the virus: hemagglutinin (H) and neuraminidase (N). All influenza A viruses contain these two surface proteins, but the structures of these proteins differ between virus strains, due to rapid genetic mutation in the viral genome. There are 16 H and 9 N subtypes known in birds, but only a subset, e.g., H 1, 2 and 3, and N 1 and 2, are commonly found in humans. The pathogenicity of a strain varies among subtype. For example, the H5N1 strain, commonly referred as "avian flu" or "bird flu," most commonly affects birds but a recent outbreak of the strain in humans in Asia killed up to 60% of those infected.

Although flu vaccines can help prevent spread, the changing subtypes and mutations of the flu makes vaccination only a partial solution. For example, the H1N1 influenza virus, commonly referred to as the Swine Flu, is responsible for the 2009 pandemic. Like H5N1, H1N1 can be virulent in humans. The United States Center for Disease Control and Prevention (CDC) maintains information about the 2009 H1N1 pandemic at www.cdc.gov/H1N1FLU/. The CDC is concerned that the new H1N1 flu virus could result in a particularly severe flu season in 2009, e.g., through widespread illness, doctor's visits, hospitalizations and deaths. The first H1N1 vaccine will not be available before mid-October at the earliest, and vaccine supplies will not be sufficient to treat even the most at-risk populations until later in the fall. As a result, the best way to prevent a widespread epidemic and public panic will be to control the virus by preventing its spread, particularly to those who are at highest risk.

Some governments have been trying flu containment methods that were effective with Severe Acute Respiratory Syndrome (SARS), including screening for fever or respiratory symptoms. However, those methods are not sufficiently targeted to contain H1N1. One problem is the flu victims can be contagious at least a day before a fever or other symptoms present. In some embodiments, the Health Shield of the invention systematically tests not only those who are symptomatic but also family members and close work associates. Accordingly, infected individuals can be treated and isolated before they have an opportunity to spread the infection widely, reducing the flu's real and psychological impact.

The spread and the death rate from flu in the fall of 2009 would be mitigating by keeping patients from flooding emergency rooms for testing and treatment. Potentially hundreds of millions of dollars can be saved by reducing costly emergency room and hospital visits, by proper use of medication, and by reducing virus spread in hospitals. The HS models of the invention can identify optimal intervention strategies and timing for administration of appropriate medication, such as Tamiflu. These steps can reduce hospital and emergency room visits and allow people to resume work more quickly. Eliminating such unnecessary emergency room visits can help prevent the spread of the virus and reduce hospitalization and emergency room spending.

Influenza, e.g., H1N1 and H5N1, can be detected from a bodily fluid, e.g., a finger-stick of blood, sputum, saliva, or a combination thereof, using FS point-of-care instruments. These instruments can be placed in appropriate locations (e.g., home, schools, restaurants, primary care units, livestock facilities etc.) and can be deployed in many cases without local supporting infrastructure other than a power source. The testing can be done rapidly, e.g., in less than about 1, 2, 3, 4, 5, 10, 15, 20, 25, 30, 35, 40, 45, 50, 55 or 60 minutes. In some embodiments, the results from the FS are reported back to an OS central monitoring site in real-time. The blood or saliva based assays can detect influenza by several methods, including immunodetection by sensitive antibodies of specific epitopes of the virus itself, e.g., hemagglutinin and/or neuraminidase. The assays can distinguish between the various types of identified influenza strains, e.g., influenza A, influenza B, H5N1, H1N1, etc. The assays can detect individual particles of a particular virus strain, even in a background of differing strains or genetic variants. The assays can detect biomarkers, viral proteins, coat proteins, and the like.

In some embodiments, the assays measure inflammatory markers and immune response markers, e.g., cytokines, which allow for clinicians to identify the severity of infection, the extent of the acute phase and/or inflammatory reactions of the subject. This can, e.g., assist in determining the proper treatment regimen for an individual. The ability to measure response to infection allows for characterization of infection even to strains of viruses that have not yet been characterized. As those strains are characterized, specific tests can be customized and added to the cartridges. Depending on the assay required, the new tests can be deployed immediately, within days, within weeks, or within a matter of months.

There are currently over 100 cytokines/chemokines whose coordinate or discordant regulation is of clinical interest. Exemplary cytokines that can be used in systems and methods of the invention include, but are not limited to, BDNF, CREB pS133, CREB Total, DR-5, EGF, ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene-keratinocytes (GRO-KC), HGF, ICAM-1, IFN-alpha, IFN-gamma, the interleukins IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotacin, M-CSF, monocyte chemoattractant protein-1 (MCP-1), MCP-1 (MCAF), MCP-3, MCP-5, MDC, MIG, macrophage inflammatory (MIP-1 alpha), MIP-1 beta, MIP-1 gamma, MIP-2, MIP-3 beta, OSM, PDGF-BB, regulated upon activation, normal T cell expressed and secreted (RANTES), Rb (pT821), Rb (total), Rb pSpT249/252, Tau (pS214), Tau (pS396), Tau (total), Tissue Factor, tumor necrosis factor-alpha (TNF-alpha), TNF-beta, TNF-RI, TNF-RII, VCAM-1, and VEGF. In some embodiments, the cytokine is IL-12p70, IL-10, IL-1 alpha, IL-3, IL-12 p40, IL-1ra, IL-12, IL-6, IL-4, IL-18, IL-10, IL-5, eotaxin, IL-16, MIG, IL-8, IL-17, IL-7, IL-15, IL-1β, IL-2R (soluble), IL-2, LIF/HILDA, IL-1 beta, Fas/CD95/Apo-1, and MCP-1.

Markers of inflammation that can be used with the systems and methods of the invention include ICAM-1, RANTES, MIP-2, MIP-1-beta, MIP-1-alpha, and MMP-3. Further markers of inflammation include adhesion molecules such as the integrins $\alpha1\beta1$, $\alpha2\beta1$, $\alpha3\beta1$, $\alpha4\beta1$, $\alpha5\beta1$, $\alpha6\beta1$, $\alpha7\beta1$, $\alpha8\beta1$, $\alpha9\beta1$, $\alpha V\beta7$, $\alpha4\beta7$, $\alpha6\beta4$, $\alpha D\beta2$, $\alpha L\beta2$, $\alpha M\beta2$, $\alpha V\beta3$, $\alpha V\beta5$, $\alpha V\beta6$, $\alpha V\beta8$, $\alpha X\beta2$, $\alpha IIb\beta3$, $\alpha IELb\beta7$, beta-2 integrin, beta-3 integrin, beta-2 integrin, beta-4 integrin, beta-5 integrin, beta-6 integrin, beta-7 integrin, beta-8 integrin, alpha-1 integrin, alpha-2 integrin, alpha-3 integrin, alpha-4 integrin, alpha-5 integrin, alpha-6 integrin, alpha-7 integrin, alpha-8 integrin, alpha-9 integrin, alpha-D integrin, alpha-L integrin, alpha-M integrin, alpha-V integrin, alpha-X integrin, alpha-IIb integrin, alphaIELb integrin; Integrin-associated Molecules such as Beta IG-H3, Melusin, CD47, MEPE, CD151, Osteopontin, IBSP/Sialoprotein IL, RAGE, IGSF8; Selectins such as E-Selectin, P-Selectin, L-Selectin; and Ligands such as CD34, GIyCAM-1, MadCAM-1, PSGL-1, vitronectic, vitronectin receptor, fibronectin, vitronectin, collagen, laminin, ICAM-1, ICAM-3, BL-CAM, LFA-2, VCAM-1, NCAM, and PECAM. Further markers of inflammation include cytokines such as IFN-α, IFN-β, IFN-ε, -κ, -τ, and -ζ, IFN-ω, IFN-γ, IL29, IL28A and IL28B, IL-1, IL-1α and β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, and TCCR/WSX-1. Further markers of inflammation include cytokine receptors such as Common beta chain, IL-3 R alpha, IL-3 R beta, GM-CSF R, IL-5 R alpha, Common gamma Chain/IL-2 R gamma, IL-2 R alpha, IL-9 R, IL-2 R beta, IL-4 R, IL-21 R, IL-15 R alpha, IL-7 R alpha/CD127, IL-1ra/IL-1F3, IL-1 R8, IL-1 RI, IL-1 R9, IL-1 RII, IL-18 R alpha/IL-1 R5, IL-1 R3/IL-1 RAcP, IL-18 R beta/IL-1 R7, IL-1 R4/ST2 SIGIRR, IL-1 R6/IL-1 R rp2, IL-11 R alpha, IL-31 RA, CNTF R alpha, Leptin R, G-CSF R, LIF R alpha, IL-6 R, OSM R beta, IFN-alpha/beta R1, IFN-alpha/beta R2, IFN-gamma R1, IFN-gamma R2, IL-10 R alpha, IL-10 R beta, IL-20 R alpha, IL-20 R beta, IL-22 R, IL-17 R, IL-17 RD, IL-17 RC, IL-17B R, IL-13 R alpha 2, IL-23 R, IL-12 R beta 1, IL-12 R beta 2, TCCR/WSX-1, and IL-13 R alpha 1. Further markers of inflammation include chemokines such as CCL-1, CCL-2, CCL-3, CCL-4, CCL-5, CCL-6, CCL-7, CCL-8, CCL-9, CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27, CCL-28, MCK-2, MIP-2, CINC-1, CINC-2, KC, CINC-3, LIX, GRO, Thymus Chemokine-1, CXCL-1, CXCL-2, CXCL-3, CXCL-4, CXCL-5, CXCL-6, CXCL-7, CXCL-8, CXCL-9, CXCL-10, CXCL-11, CXCL-12, CXCL-13, CXCL-14, CXCL-15, CXCL-16, CXCL-17, XCL1, XCL2, and Chemerin. Further markers of inflammation include chemokine receptors such as CCR-1, CCR-2, CCR-3, CCR-4, CCR-5, CCR-6, CCR-7, CCR-8, CCR-9, CCR-10, CXCR3, CXCR6, CXCR4, CXCR1, CXCR5, CXCR2, Chem R23. Further markers of inflammation include Tumor necrosis factors (TNFs), such as TNFα, 4-1BB Ligand/TNFSF9, LIGHT/TNFSF14, APRIL/TNFSF13, Lymphotoxin, BAFF/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA, TNF-beta/TNFSF1B, EDA-A2, TRAIL/TNFSF10, Fas Ligand/TNFSF6, TRANCE/TNFSF11, GITR Ligand/TNFSF18, and TWEAK/TNFSF12. Further markers of inflammation include TNF Superfamily Receptors such as 4-1BB/TNFRSF9, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/

TNFRSF13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF10D, Fas/TNFRSF6, TROY/TNFRSF19, GITR/TNFRSF18, TWEAK R/TNFRSF12, HVEM/TNFRSF14, and XEDAR. Further markers of inflammation include TNF Superfamily Regulators such as FADD, TRAF-2, RIPI, TRAF-3, TRADD, TRAF-4, TRAF-1, and TRAF-6. Further markers of inflammation include acute-phase reactants and acute phase proteins. Further markers of inflammation include TGF-beta superfamily ligands such as Activins, Activin A, Activin B, Activin AB, Activin C, BMPs (Bone Morphogenetic Proteins), BMP-2, BMP-7, BMP-3, BMP-8, BMP-3b/GDF-10, BMP-9, BMP-4, BMP-10, BMP-5, BMP-15/GDF-9B, BMP-6, Decapentaplegic, Growth/Differentiation Factors (GDFs), GDF-1, GDF-8, GDF-3, GDF-9 GDF-5, GDF-11, GDF-6, GDF-15, GDF-7, GDNF Family Ligands, Artemin, Neurturin, GDNF, Persephin, TGF-beta, TGF-beta, TGF-beta 3, TGF-beta 1, TGF-beta 5, LAP (TGF-beta 1), Latent TGF-beta bp1, Latent TGF-beta 1, Latent TGF-beta bp2, TGF-beta 1.2, Latent TGF-beta bp4, TGF-beta 2, Lefty, MIS/AMH, Lefty-1, Nodal, Lefty-A, Activin RIA/ALK-2, GFR alpha-1/GDNF R alpha-1, Activin RIB/ALK-4, GFR alpha-2/GDNF R alpha-2, Activin RIIA, GFR alpha-3/GDNF R alpha-3, Activin RIIB, GFR alpha-4/GDNF R alpha-4, ALK-1, MIS RII, ALK-7, Ret, BMPR-IA/ALK-3, TGF-beta RI/ALK-5, BMPR-IB/ALK-6, TGF-beta RII, BMPR-II, TGF-beta RIIb, Endoglin/CD105, and TGF-beta RIII. Further markers of inflammation include TGF-beta superfamily Modulators such as Amnionless, NCAM-1/CD56, BAMBI/NMA, Noggin, BMP-1/PCP, NOMO, Caronte, PRDC, Cerberus 1, SKI, Chordin, Smad1, Chordin-Like 1, Smad2, Chordin-Like 2, Smad3, COCO, Smad4, CRIMI, Smad5, Cripto, Smad7, Crossveinless-2, Smad8, Cryptic, SOST, DAN, Latent TGF-beta bp1, Decorin, Latent TGF-beta bp2, FLRG, Latent TGF-beta bp4, Follistatin, TMEFF1/Tomoregulin-1, Follistatin-like 1, TMEFF2, GASP-1/WFIKKNRP, TSG, GASP-2/WFIKKN, TSK, Gremlin, and Vasorin. Further markers of inflammation include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, and LRIG. Further markers of inflammation include EGF R/ErbB Receptor Family, such as EGF R, ErbB3, ErbB2, and ErbB4. Further markers of inflammation include Fibrinogen. Further markers of inflammation include SAA. Further markers of inflammation include glial markers, such as alpha. 1-antitrypsin, C-reactive protein (CRP), α2-macroglobulin, glial fibrillary acidic protein (GFAP), Mac-1, and F4/80. Further markers of inflammation include myeloperoxidase. Further markers of inflammation include Complement markers such as C3d, C1q, C5, C4d, C4 bp, and C5a-C9. Further markers of inflammation include Major histocompatibility complex (MHC) glycoproteins, such as HLA-DR and HLA-A,D,C. Further markers of inflammation include Microglial markers, such as CR3 receptor, MHC I, MHC II, CD 31, CD1 a, CD11b, CD1 c, CD68, CD45RO, CD45RD, CD18, CD59, CR4, CD45, CD64, and CD44. Further markers of inflammation include alpha.2 macroglobulin receptor, Fibroblast growth factor, Fc gamma RI, Fc gamma RII, CD8, LCA (CD45), CD18, CD59, Apo J, clusterin, type 2 plasminogen activator inhibitor, CD44, Macrophage colony stimulating factor receptor, MRP14, 27E10, 4-hydroxynonenal-protein conjugates, IκB, NFκB, cPLA$_2$, COX-2, Matrix metalloproteinases, Membrane lipid peroxidation, and ATPase activity. HSPC228, EMP1, CDC42, TLE3, SPRY2, p40BBP, HSPC060 and NAB2, or a down-regulation of HSPA1A, HSPA1B, MAPRE2 and OAS1 expression, TACE/ADAM17, alpha-1-Acid Glycoprotein, Angiopoietin-1, MIF, Angiopoietin-2, CD 14, beta-Defensin 2, MMP-2, ECF-L/CHI3L3, MMP-7, EGF, MMP-9, EMAP-II, MSP, EN-RAGE, Nitric Oxide, Endothelin-1, Osteoactivin/GPNMB, FPR1, PDGF, FPRL1, Pentraxin 3/TSG-14, FPRL2, Gas6, PLUNC, GM-CSF, RAGE, S100A10, S100A8, S100A9, HIF-1 alpha, Substance P, TFPI, TGF-beta 1, TIMP-1, TIMP-2, TIMP-3, TIMP-4, TLR4, LBP, TREM-1, Leukotriene A4, Hydrolase TSG-6, Lipocalin-1, uPA, M-CSF, and VEGF.

Physiological data for each individual can also be measured and communicated from the FS instruments or points-of-care to the OS. Such data can include without limitation temperature, heart rate/pulse, blood pressure, oximetric signals, weight, water retention, plethysmographic signals, respiratory rate, fat content, water content, blood perfusion, mobility, posture, bioelectric impedance, electrocardiogram (ECG), or galvanic skin response.

In some embodiments, the assays are used to detect host antibodies against a particular pathogen or marker. One potential problem when measuring such antibodies is interference which can occur in individuals who had flu vaccinations in the past. In such situations, high influenza antibody titers in the blood may interfere with the assay. Flu virus mainly replicates in lungs and therefore may be detected in, e.g., sputum, nasal lavage and saliva. Therefore, a saliva based sample can also be processed in the point-of-care for verification. The hemagglutinin (H antigen) antigen on the surface of influenza particles is believed to be instrumental in the entry of the virus into target cells. Hemagglutinin can bind red cells and in appropriate conditions causes the cells to agglutinate. Accordingly, red cells in blood can act as concentrating agents for the virus. This phenomenon can be exploited in assays for the virus since red cells can be concentrated before a blood sample is analyzed. Furthermore red cells can be collected (and concentrated) on an appropriate surface in an assay cartridge, thereby presenting large amounts of virus for analysis and detection.

Two key evaluative measures of any medical screening or diagnostic test are its sensitivity and specificity, which measure how well the test performs to accurately detect all affected individuals without exception, and without falsely including individuals who do not have the target disease (predictive value).

A true positive (TP) result is where the test is positive and the condition is present. A false positive (FP) result is where the test is positive but the condition is not present. A true negative (TN) result is where the test is negative and the condition is not present. A false negative (FN) result is where the test is negative but the condition is not present. In this context: Sensitivity=TP/(TP+FN); Specificity=TN/(FP+TN); and Predictive value of a positive=TP/(TP+FP).

Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical treatments with their attendant risks, emotional and financial stresses, and which could have adverse effects on the patient's health. Specificity is important when the cost or risk associated with further diagnostic procedures or further medical intervention is very high.

In some embodiments, the HS performs multiple assays to improve assay sensitivity and/or specificity. For example, the sensitivity and specificity of disease monitoring can be enhanced. In some embodiments, multiple bodily samples are assayed for an individual. For example, saliva and blood based (finger-stick) tests can be run simultaneously for persons who have previously been vaccinated for the flu. Testing multiple samples can increase the chance of identifying the infection. In addition, it can be important to control for false negatives to maximize containment. In some embodiments, the present invention address false negatives by including tests for both inflammation and infection markers on each test cartridge. Where the flu test is negative but these other markers are strongly suggestive of flu, confirmatory tests can be included for that specific subset of patients. A variety of exemplary marker panels, also referred to as test menus, are disclosed herein for various disease settings. One of skill will appreciate that the use of multiple assays and/or physiological parameters to improve sensitivity and/or specificity is not limited to these exemplary embodiments but rather can be an effective technique when monitoring many diseases and disorders.

In some embodiments, the HS decentralized detection capability provided by the FS units can provide early identification of persons with a confirmed case of flu, i.e., an "index case," and then query all close contacts that those individuals so identified. Given such a network of contacts, containing epidemic spread ideally requires rapid deployment, identification, and preemptive action in an exposed and/or asymptomatically infected population. The HS provides a system to carry out these operations and prevent the spread of disease.

The Health Shield system can be deployed for the surveillance and containment of an influenza outbreak. The HS can be deployed in a variety of settings, e.g., at a local, regional or national level. The OS for a given setting can use in silico modeling to simulate various deployment strategies to best contain the flu or other condition and can be optimized for each setting. In some embodiments, the model comprises an epidemiological model that includes a variety of appropriate parameters to model the expected and/or contained outbreak. In some embodiments, the system uses Monte Carlo simulations to test a spectrum of screening and containment strategies which will, in turn, be analyzed as to cost/benefit ratios, etc. For example, the system can project where and how to deploy limited resources, e.g., medical personnel, therapeutic treatments and vaccines. The OS model can be preloaded with population and individual specific information for the setting to be monitored. These factors include but are not limited to incubation time, connectivity of the susceptible population, manner of infection, virulence of the virus, death rates and hospitalization rates, disease incidence, transmission mode, infection rate, therapeutic intervention outcomes, vaccine efficacy, and resistance to or effectiveness of anti-viral therapies, e.g., Tamiflu. Parameters for the individuals being monitored include without limitation age, sex, social contacts (living arrangements, family, co-workers, etc.), prior history of disease, general health (e.g., other pre-existing conditions), etc. Model parameters can be continuously updated once the system is deployed.

The FS instruments are deployed to operate in conjunction with the configured OS. In some embodiments, the data from the FS are provided to an OS through a software portal. The remote OS can then perform the desired calculations. In general, the FS systems are deployed to selected hotspots. In some embodiments, the OS model is used to direct the optimal deployment of the FS instruments. Optimal and hotspot locations include without limitation areas where people gather, e.g., shopping areas, schools and work places. Locations where sick people gather are also targeted, including without limitation clinics, pharmacies and hospitals. In some embodiments, FS devices are deployed to homes, as described herein.

Once deployed, the FS systems are used to test the subjects. In some embodiments, this includes testing for disease antigens, e.g., viral coat proteins. The analytes also include host proteins as markers of disease, e.g., immune markers including cytokines, and inflammatory markers that indicate an ongoing infection. In detecting infectious disease agents and evaluating the status and prognosis of patients, it can be desirable to be able to measure multiple analytes simultaneously. For example, this increases the chance of detecting disease as any one single analyte may not be found at abnormal levels. Multiple analyte measurements also reduce noise and can make the system more accurate in disease monitoring.

The following table presents an example menu for detection of H1N1 virus, also known as swine flu:

TABLE 3

| Marker | Sample | Indication |
|---|---|---|
| H1 | Blood/Sputum/Saliva/Nasal lavage | Infection |
| N1 | Blood/Sputum/Saliva/Nasal lavage | Infection |
| H1:N1 | Blood/Sputum/Saliva/Nasal lavage | Infection |
| IgM anti-H1 | Blood | Primary response to infection |
| IgM anti-N1 | Blood | Primary response to infection |
| IgG anti-H1 | Blood | Prior infection |
| IgG anti-N1 | Blood | Prior infection |
| IgA anti-H1 | Sputum/Saliva/Nasal lavage | Prior infection |
| IgA anti-N1 | Sputum/Saliva/Nasal lavage | Prior infection |
| IgG anti-H1:H1 | Blood | Prior + current infection |
| IgG anti-N1:N1 | Blood | Prior + current infection |
| Cytokines | Blood | Acute process |
| C-Reactive Protein | Blood | Acute process |

In the table, "Ab:Ag" represents the complex formed between an antibody (Ab) and an antigen (Ag). For example, "IgG anti-H1:H1" represents a complex between host IgG anti-H1 antibodies and influenza hemagluttinin H1 antigens.

As different influenza strains are monitored, the menu will be adjusted accordingly. For example, a menu for monitoring H1N5 virus would comprise detection of N5 antigen and anti N5 antibodies.

Detection of IgM versus IgG or IgA antibodies can be used to determine whether an individual had a prior exposure to the influenza particles of interest. IgM antibodies are made rapidly in the days following infection on the first exposure to an immunogen. When previously exposed individuals encounter a second infectious agent having similar or identical antigenic character, IgG and IgA antibodies are produced very rapidly. This secondary response is typically much stronger and more specific than the original IgM response. In primary infections and in very severe infections, active virus is more likely to be present in blood and to be detectable directly. In secondary infections, where antibody is present, it will generally be in excess over the antigen and antigen may be masked to immunoassay methods. In some embodiments, the complex formed by antigen and antibody is detected using a sandwich immunoassay in which one reagent is directed to the antigen and the other to IgG. Once a subject produces IgG and IgA antibodies, such may be found in the blood well after the infection has resolved.

As shown in Table 3, the menu can also include one or more cytokines as a marker of immune response and/or inflammation. Cytokines of interest include without limitation IL-1β, IL-6, IL-8, IL-10 and TNFα. Cytokines such as these may be produced in large amounts during the early part of a viral infection. In some cases, the level of these markers will rise and fall rapidly. Valuable information as to patient status and prognosis can be obtained by making serial measurements of one or more cytokines. For example, fevers of viral and bacterial origin may be distinguished by measuring changes in cytokine levels. A recent study found that "CRP velocity" (CRPv), defined as the ratio between blood C-reactive protein on admission to an Emergency Room and the number of hours since the onset of fever, can differentiate acute bacterial and non-bacterial febrile illnesses. Paran et al., C-reactive protein velocity to distinguish febrile bacterial infections from non-bacterial febrile illnesses in the emergency department, Crit Care. 2009; 13(2):R50. The study also found that blood levels of other acute-phase proteins, such as IL-1, IL-6, and TNF-α, correlated with CRPv.

The detection levels of influenza markers is shown in Table 4:

TABLE 4

Threshold or action levels for influenza bio-markers

| Marker | Sample | Level |
| --- | --- | --- |
| H1 | Blood/Sputum/Saliva/Nasal lavage | ng/mL |
| N1 | Blood/Sputum/Saliva/Nasal lavage | ng/mL |
| H1:N1 | Blood/Sputum/Saliva/Nasal lavage | ng/mL |
| IgM anti-H1 | Blood | ug/mL |
| IgM anti-N1 | Blood | ug/mL |
| IgG anti-H1 | Blood | ug/mL |
| IgG anti-N1 | Blood | ug/mL |
| IgA anti-H1 | Sputum/Saliva/Nasal lavage | ug/mL |
| IgA anti-N1 | Sputum/Saliva/Nasal lavage | ug/mL |
| IgG anti-H1:H1 | Blood | ug/mL |
| IgG anti-N1:N1 | Blood | ug/mL |
| Cytokines | Blood | 10× increase |
| C-Reactive Protein | Blood | 10× increase |

The exemplary markers in Tables 3 and 4 correspond to a menu for detection of H1N1. The threshold levels for detecting a certain marker are shown in Table 4. When the measurements are made over a time course, the fold increase in a marker, e.g., cytokines or C-reactive protein, can be detected. Here, a 10× change is considered indicative of an event. When time course data for an individual is not available, the fold-change can be determined by comparing to a reference threshold. For example, the detected level of a given marker can be compared to the mean level of the marker in the general healthy population. It will be appreciated that different flu strains, e.g., H5N1, H3N2, etc, can be detected using appropriate analytical methods.

An OS recommended course action for influenza when detecting a given marker is shown in Table 5.

TABLE 5

Suspected swine flu action matrix

| Marker | Sample | Indication | Action |
| --- | --- | --- | --- |
| H1 | Blood/Sputum/Saliva/Nasal lavage | Infection | Quarantine |
| N1 | Blood/Sputum/Saliva/Nasal lavage | Infection | Quarantine |
| H1:N1 | Blood/Sputum/Saliva/Nasal lavage | Infection | Quarantine |
| IgM anti-H1 | Blood | 1o response to infection | Quarantine |
| IgM anti-N1 | Blood | 1o response to infection | Quarantine |
| IgG anti-H1 | Blood | Prior infection | None |
| IgG anti-N1 | Blood | Prior infection | None |
| IgA anti-H1 | Sputum/Saliva/Nasal lavage | Prior infection | None |
| IgA anti-N1 | Sputum/Saliva/Nasal lavage | Prior infection | None |
| IgG anti-H1:H1 | Blood | Prior + current infection | Quarantine |
| IgG anti-N1:N1 | Blood | Prior + current infection | Quarantine |
| Cytokines | Blood | Acute process | Quarantine |
| C-Reactive Protein | Blood | Acute process | Quarantine |
| Drug resistance | Any | Viral mutation | Special |
| Virulence gene(s) | Any | Dangerous viral strain | Special |
| Temperature rise | NA | Infection | Quarantine |

As above, the example in Table 5 highlights H1N1 swine flu. It will be appreciated that different flu strains, e.g., H5N1, H3N2, etc, can be detected using appropriate analytical methods. Further, the action will depend on a number of factors, including but not limited to expected virulence, transmission, cost of treatment, etc. For example, a quarantine may be required for a virulent strain but not for a less severe outbreak. The recommended course of action for drug resistance can depend on the drug. In the influenza setting, resistance to oseltamivir (Tamiflu®) can be especially important. Oseltamivir is an orally active antiviral drug that acts as a neuraminidase inhibitor. The drug slows the spread of influenza (flu) virus between cells in the body by stopping the new virus from chemically cutting ties with its host cell. It can be used for both influenza A and B. Resistance can be determined by a number of methods, e.g., a functional assay (culture) or identification of a genetic marker. Zanamivir is also used to treat flu infection.

Figure 3:
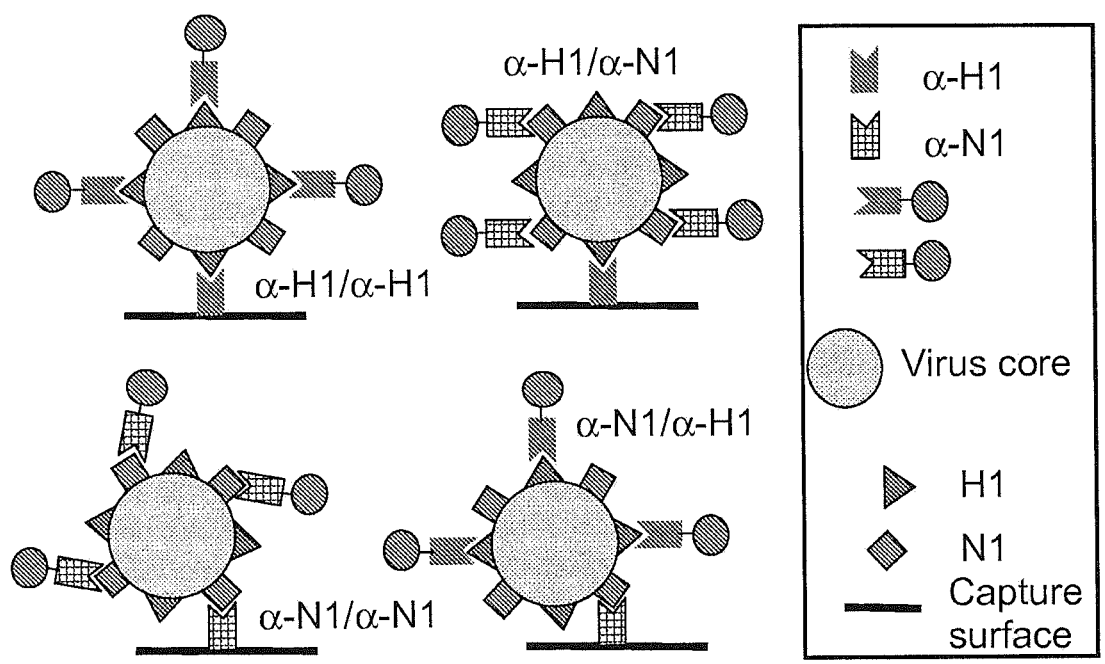
FIG. 3 illustrates an assay for H1N1 antigen using sandwich complexes in four different configurations.

Specific strains of influenza virus can be detected using a sandwich assay format. A number of assay configurations can be used. FIG. 3 illustrates assays for H1N1 antigen illustrating sandwich complexes in four different assay types. One of skill will understand that a similar arrangement can be used to detect other virus strains, e.g., H5N1, H2N3, etc. Shown are the final reaction products for four assay configurations for measurement of H1N1 virus (having several copies of each on the viral particle). The assays involve: 1) adding sample, e.g., blood, serum, saliva or nasal lavage, to a capture surface having an antibody to one of the viral surface antigens (H1, N1); 2) adding enzyme-labeled antibody to one of the surface antigens; and 3) washing the surface to remove unbound viral particles. The different assay configurations can detect various particles. Configurations α-H1/α-N1 and α-N1/α-H1 will measure H1N1 virus, configuration α-H1/α-H1 detects any virus having H1 antigen, and configuration α-N1/α-N1 detects any virus having the N1 antigen. A cartridge system to detect the assays is described in U.S. patent application Ser. No. 11/746,535, filed May 9, 2007 and entitled "REAL-TIME DETECTION OF INFLUENZA VIRUS."

Sandwich assays can also be used to detect host antibodies to influenza strains, e.g., human antibodies to H1N1 swine flu. A first embodiment of such assay is shown in FIG. 4A. In the figure, the assay capture phase has antibody to viral antigen attached to a solid phase. The viral particle (antigen) can be captured by the solid phase and a detection-reagent, e.g., Alkaline-phosphatase labeled antibody to viral antigen, can be used to detect the host antibodies. This assay is configured as an antigen assay. Antibody is detected by spiking viral antigen to the sample, e.g., bodily fluid such as blood or plasma, and comparing the assay response with and without added antigen. Anti-viral antibodies can be measured by adding (spiking) a known, fixed amount of virus or viral antigen to the patient sample. Following incubation, the spiked sample is used in an assay for viral antigen. If antibodies are present, the assay will exhibit reduction in measured antigen (low spike recovery). The sample dilution or the level of the spiked antigen can be titrated to give a quantitative value for the antibody. When antibody to viral antigen is present, there is little or no signal generated in the absence of added antigen. There is a reduced (or zero) response when antigen is added compared with the response to antigen-negative control samples which were spiked with antigen. In other words, the antigen "spike recovery" is low or zero. The amount of antibody can be deduced from the spike recovery if it is more than zero. Antibody in the sample can also be titered by using increasing antigen spikes until an assay response is obtained. One of skill will appreciate that the assays can be adapted to detect host antibody to other virus strains, e.g., H5N1. The method can also be adapted to detect host antibodies to any appropriate antigen, e.g., to other microbial insults.

Another configuration to detect host antibodies to influenza viral particles is shown schematically in FIG. 4B. This is a direct detection method. In this embodiment, the assay capture phase has viral antigen attached to a solid phase and uses a detection-reagent comprised of Alkaline-phosphatase labeled antibody to human immunoglobulin. As described herein, the ideotype of the host antibodies can determine whether the host is naive to the antigen (IgM antibodies are found) or has had prior exposure (IgG or IgA antibodies are found). By use of antibodies specific to immunoglobulin species, e.g., IgM, IgG, IgA, etc.), the type of antibody can be determined. The assay involves: 1) incubating sample with a capture surface to which is bound virus and/or viral antigen; 2) washing the surface to remove unbound IgG, then 3) incubating with an enzyme-labeled anti-human immunoglobulin specific for either IgG of IgM; 4) washing to remove unbound enzyme-labeled antibody; and 4), incubating with substrate. FIG. 4B shows the assay status after the fourth step.

The FS systems are used to monitor the analytes and other individual parameters (blood pressure, temperature, weight, etc.) over time. In some embodiments, tests are performed on an individual on a set schedule, e.g., one or more assays might be performed at least every 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 2 days, 3 days, 4 days, 5 days, 6 days, 1 week, 10 days, 2 weeks, 3 weeks, 4 weeks, 1 month, 5 weeks, 6 weeks, 7 weeks, 8 weeks, 2 months, 9 weeks, 10 weeks, 11 weeks, 12 weeks, 3 months, 4 months, 5 months, 6 months, 7 months, 8 months, 9 months, 10 months, 11 months, or at least every year. The frequency of testing can vary between individuals and between different diseases. For example, those considered to be at risk, e.g., school children, the elderly, health care workers and physicians, can be tested more frequently. In some embodiments, the OS directs the frequency of assays. For example, the OS may identify those at risk at schedule more frequent testing. Testing can also be scheduled in real-time or semi-real time. For example, once an index case is identified, other individuals in social contact with the index case might be tested immediately and more frequently thereafter. In some embodiments, test frequency in increased in a hotspot with increased risk. In some embodiments, test frequency is reduced as risk is abated, thereby conserving resources.

As noted, a variety of field devices can be used with the systems and methods of the invention. The OS can direct an optimal deployment of the FS devices. In some embodiments, the types of assays are adjusted over time as the threat changes, e.g., to monitor different analytes. In some embodiments, the sample type or types are adjusted over time as the threat changes. In addition, viral nucleic acid has been detected in blood using PCR techniques, e.g., real-time PCR. In some embodiments, multi-sample type cartridges as described herein are used. These cartridges enable sample processing and analysis of a limited number of analytes in more than one sample type, e.g., using one or more of blood, concentrated red cells, sputum, saliva, nasal lavage, or other bodily fluid. In some embodiments, multi-analyte cartridges as described herein are used. These cartridges can perform analysis of many analytes on a single sample type. Both types of cartridges can be used in a given setting as deemed optimal in a given setting.

The deployed FS systems are used to test the selected sample types using the selected assays, and the results are reported back to the OS system, as described herein. In evaluating individuals for possible flu infection, it is advantageous to make a series of measurements over time. Based on early measurements, the ideal analyte set may be changed to optimize the information gathered by the assay system. Use of such longitudinal measurements permits computation of trends in analyte levels indicating trends in the disease processes. In some embodiments, the longitudinal measurements of the invention take account of dynamic data from particular individuals along with population information gathered in previous epidemics. In some embodiments, the models also adjust for data from cohorts of subjects exposed to a current epidemic.

The OS monitors the incoming data for incidence of infection, and provides assessment and containment recommendations when an infection is encountered. When an infection is observed, appropriate parties are notified, e.g., individuals, social contacts thereof, health-care workers, and government officials. In some embodiments, the course of action recommended by the OS is used to contain the spread of the virus. In some embodiments, the course of action includes providing therapeutic treatment to an infected individual. In some embodiments, prophylactic treatment is administered to those in contact with the infected individual. This might include vaccination. In some embodiments, depending on the severity of the outbreak, infected individuals may be quarantined. Those having contact with the infected individual can be quarantined as well.

The FS and OS continue to monitor throughout, and continuously updates the OS database with the incoming information. In some embodiments, the OS adjusts the recommended course of action in response to the real world measurements. In this manner, the Health Shield of the present invention provides dynamic response to the detected outbreak. Once an outbreak has been contained, the FS components of the system can be relocated to alternate hotspots, etc.

6. Monitoring Infectious Disease

It will be appreciated that the systems of the invention as described above can be employed to monitor the incidence of a number of infectious diseases in addition to influenza. For example, the HS can be deployed to monitor and prevent spread of infectious diseases in areas where resources are limited, e.g., rural or remote areas, or developing countries. In some embodiments, the HS is used to monitor Acquired Immune Deficiency Syndrome (AIDS), tuberculosis (TB), and/or malaria. AIDS is a disease of the human immune system caused by the human immunodeficiency virus (HIV). HIV is transmitted through direct contact of a mucous membrane or the bloodstream with a bodily fluid containing HIV, such as blood, semen, vaginal fluid, preseminal fluid, and breast milk. The disease is also spread due to sharing of infected syringes used to inject illicit drugs. AIDS progressively reduces the effectiveness of the immune system and leaves individuals susceptible to opportunistic infections and tumors. This weakening of the immune system exacerbates the risks of TB and malaria. Tuberculosis is a common and often deadly infectious disease caused by mycobacteria, e.g., *Mycobacterium tuberculosis*. Tuberculosis resides mostly in the lungs, and is spread through the air, when infected individuals cough, sneeze, or spit. Malaria is a vector-borne infectious disease caused by protozoan parasites, and is spread by the bite of an infective female *Anopheles* mosquito. AIDS, TB and malaria each kill over a million people a year, mostly in developing countries. Treatments are available for these infectious agents, but the cost of treatment varies widely. TB and malaria treatments are relatively inexpensive but AIDS treatments can be costly. Drug-resistance can be an issue for all of these pathogens.

In some embodiments, the HS system is deployed to monitor and limit the spread of infectious diseases including AIDS, TB and malaria. In some embodiments, this configuration of the Health Shield is deployed in developing countries. The general infrastructure can be manner similar to that described above for influenza. The data entered into the model can include pharmacokinetic and pharmacodynamic (PK/PD) data for the various drugs and drug combination administered for the diseases. Assays for drug resistance can also be included in the FS systems. The system may also gather information about the drug therapy compliance of the individuals. The system can thereby estimate the optimal treatment regimen for each individual. Given an individual's profile, one person may be treated with drug regimen aimed at aggressively curing or halting disease progression. Another individual may be assigned a treatment that is less optimal for achieving rapid cure, but will have a higher compliance rate (e.g., fewer treatments, e.g., fewer pills per day) and ultimately achieve better long term results for that individual.

The FS systems can be located in developing hot spots. Hot spots can include, e.g., areas with a greater amount of infective mosquitoes, or areas wherein the individuals have lesser ability to protect themselves from mosquito bites. In some embodiments, central testing zones may be constructed within the hotspots. In some embodiments, individuals without access to power may have blood samples taken and/or analyzed in a central lab setting that has the necessary resources. These labs can be located at or near the hotspots. In some embodiments, the central labs are contained in mobile units that can be moved to the location of the individuals.

The HS systems of the invention can be configured to provide strategies and recommendations for controlling the spread of the disease. Individuals and organizations in a hotspot or monitored area can be educated about the disease, e.g., causes, treatments, and methods to avoid spread. In some embodiments, the OS models suggest active protective measures. For example, if the system identifies an emerging hotspot for TB, extra mosquito nets, bug sprays, insecticides, or anti-pesticides can be deployed to that area. Vaccinations or prophylactic treatments can also be administered. In some embodiments, the model predicts areas where the infection is most likely to spread, thus allowing early or preemptive vaccination in those areas to prevent disease. Infected individuals or groups of individuals can be placed under supervision or quarantined. In some embodiments, individuals are quarantined within their home, a hospital or other care facility. Additionally, the contacts of an infected individual, e.g., friends, family and co-workers, can be quarantined or placed under close monitoring or surveillance. In some embodiments, the HS system identifies carriers, i.e., individuals who carry a disease but are not symptomatic. For example, about 80% of the population of Africa tests positive for tuberculosis. In some embodiments, steps are taken to reduce spread by carriers. For example, the carriers can be treated, educated about methods to reduce spread, e.g., avoiding exchange of bodily fluids or hygienic methods, or quarantined as appropriate. The OS system can provide estimates of the overall benefits and cost-benefit analysis of various actions to be taken.

The assays of the FS systems can be designed to measure analytes specific to the disease or disease being monitored. Non-limiting examples of analytes measured when monitoring AIDS, TB and malaria include HIV virus, HIV viral RNA, IgM antibodies to HIV, IgG antibodies to HIV, CD4, CD8, and/or drug treatments. Non-limiting examples of analytes measured when monitoring TB include TB antigens, anti-TB antibodies, *mycobacterium* antibodies and interferon gamma, which can rise upon infection. Non-limiting examples of analytes measured when monitoring malaria include malarial antigens and anti-malaria antibodies. Various actions that can be taken when detecting AIDS analytes include without limitation those actions listed in Table 6.

TABLE 6

Analyte and action matrix for AIDS

| Analyte or analytical indication | Interpretation | Action | Community action |
|---|---|---|---|
| Viral RNA | Current infection | Treat | Council contacts |
| Low helper T-cell [CD4] (#) | Current infection | Treat | Council contacts |
| Low CD4/CD8 ratio | Current infection | Treat | Council contacts |
| IgM Antibody to virus | Recent infection | Initiate treatment | Contact tracing |
| IgG Antibody to virus | Established infection | Treat | Council contacts |
| Protective antibody | Subject for research | | None |
| Antibody to CMV | Risk of blindness | Monitor/Treat | None |
| Antibody to Herpes Virus | Risk of severe herpes | Monitor/Treat | None |
| Viral resistance to drug | Mutation of virus | Change drug | Council contacts |
| Viral resistance to drug combinations | Mutation of virus | Change combination | Council contacts |
| Drug level not optimal | | Adjust | None |
| Increase in viral RNA level | Viral breakout | Treat aggressively | None |
| Decrease in CD4 | Viral breakout | Treat aggressively | None |
| Decrease in CD4/CD8 | Viral breakout | Treat aggressively | None |

In some embodiments, the systems of the invention are used to monitor chronic, incurable infectious diseases. Such diseases are over spread by contact with infected blood and other bodily fluids. AIDS is currently incurable but individuals with HIV can sometimes live for decades through the use of antiviral treatments. Transmission can be reduced by over 80% through the proper use of condoms, restriction of sexual partners and abstinence. Hepatitis B and C are chronic liver diseases caused by infection with hepatitis B and C virus, respectively. The Health Shield of the present invention can be used to monitor the health status of those with hepatitis, in a similar manner to other infectious disease as described herein. For example, containment methods at hot spots can be implemented, e.g., education and distribution of condoms can be used to halt the spread of Hepatitis C, which can be spread through sexual contact. At the individual level, infected individuals can be assigned appropriate education and therapy or interventions if the condition worsens. For example, liver damage in the late stages of hepatitis can be made worse by alcohol abuse. Infected individuals can be educated about such adverse effects of alcohol. Non-limiting examples of analytes measured when monitoring hepatitis include hepatitis B viral antigens, hepatitis C viral antigens, hepatitis B viral DNA, hepatitis C viral DNA, anti-hepatitis B surface antigen antibodies, anti-hepatitis C surface antigen antibodies, anti-hepatitis B core protein antibodies, anti-hepatitis C core protein antigen antibodies. Non-limiting examples of analytes measured when monitoring liver function include aspartate transaminase (AST) or alanine transaminase (ALT). The AST/ALT ratio is sometimes useful in differentiating between causes of liver damage when liver enzymes are elevated. For example, a ratio greater than 2.0 is more likely to be associated with alcoholic hepatitis whereas a ratio less than 1.0 is more likely to be associated with viral hepatitis.

Those of skill in the art will appreciate that the Health Shield system can be configured and adapted for the monitoring and containment of any number of infectious agents using similar approaches as described herein. The present invention includes monitoring of the following non-limiting infectious agents and analytes thereof: Adenovirus, *Bordella pertussis, Chlamydia pneumoiea, Chlamydia trachomatis*, Cholera Toxin, Cholera Toxin β, *Campylobacter jejuni*, Cytomegalovirus, Diptheria Toxin, Epstein-Barr NA, Epstein-Barr EA, Epstein-Barr VCA, *Helicobacter Pylori*, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3 KD, Hepatitis E virus (HEV) orf2 6 KD, Hepatitis E virus (HEV) orf3 3KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, *Leishmania donovani*, Lyme disease, Mumps, *M. pneumoniae, M. tuberculosis*, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15 kd, *T. pallidum* p47, *T. cruzi, Toxoplasma*, and *Varicella Zoster.*

7. Monitoring Chronic Disease and Treatment Efficacy

In addition to monitoring infectious disease, the Health Shield makes it possible to understand an individual's disease trajectory and his/her response to therapy. Given both the inherent genetic variance embedded in the human species and variability of an individual's environment, the ability to monitor and track the most informative pathophysiologic factors in a disease process allows us to determine whether a therapy is effective. Such monitoring can help make sure that health care dollars are spent on treatments and drugs that work. With traditional laboratory systems, up to 50% of individuals fail to comply with prescriptions for laboratory testing and as many as 60% of therapeutic prescriptions do not have the intended effects. The HS provides greater compliance via home deployment and greater drug effectiveness by real-time monitoring of efficacy. Because the HS provides for point-of-care testing, it helps facilitate compliance with lab testing orders.

In some embodiments, the integrated technologies of the invention are used to manage chronic diseases like congestive heart failure. Such monitoring can help improve quality of life and avoid costly hospitalizations through pre-emptive action. For diabetic individuals, the systems can provide automated counseling that help coordinate and manage life style changes and reverses the progression of the disease and prevents (and predicts) complications. By improving outcomes and allowing for earlier interventions, significant healthcare savings can be achieved. In some embodiments, the same systems can be used to monitor the interactions between drugs for chronic disease patients taking multiple therapies. This ability not only prevents adverse drug reactions and reduces the costs of the associated complications but also allows potentially life saving drugs to be used more widely in chronic disease populations.

Diabetes mellitus (diabetes) is a condition in which the body either fails to properly produce or respond to insulin, a hormone produced in the pancreas that enables cells to absorb glucose in order to turn it into energy. In diabetes, the body either fails to properly respond to insulin, does not make enough insulin, or both. This causes glucose to accumulate in the blood, leading to various complications. Acute complications including hypoglycemia, diabetic ketoacidosis, or nonketotic hyperosmolar coma may occur if the disease is not adequately controlled. Serious long-term complications include cardiovascular disease, chronic renal failure, retinal damage and blindness, several types of nerve damage, and microvascular damage, which may cause erectile dysfunction and poor wound healing. Poor healing of wounds, particularly of the feet, can lead to gangrene, and possibly amputation. In type 1 diabetes, or juvenile diabetes, the body fails to produce insulin. Presently almost all persons with type 1 diabetes must take insulin injections. Type 2 diabetes, also known as adult-onset or late-onset diabetes, results from insulin resistance, a condition in which cells fail to use insulin properly, sometimes combined with relative insulin deficiency. About 90% of Americans who are diagnosed with diabetes have type 2 diabetes. Many people destined to develop type 2 diabetes spend many years in a state of pre-diabetes, a condition that occurs when a person's blood glucose levels are higher than normal but not high enough for a diagnosis of type 2 diabetes. As of 2009 there are 57 million Americans who have pre-diabetes.

Pre-diabetes has been termed "America's largest healthcare epidemic." Handelsman, Yehuda, Md. A Doctor's Diagnosis: Prediabetes. Power of Prevention, Vol 1, Issue 2, 2009. High sugar and high fat diets are causing earlier onset of obesity and diabetes, especially in wealthy countries. Young people consume a diet high in sugar and fat and become obese, which can in turn progress to serious diseases and disorders, including but not limited to prediabetes, diabetes, heart disease. In many environments, easy access to carbonated beverages containing high levels of sugar and to fat-rich fast foods promotes this process.

The HS system of the invention can be used to aid response to the spread of diabetes. In some embodiments, the system is used to identify individuals at high risk. In some embodiments, the system can identify locations, e.g., geographic locations, communities, school systems or schools, where the risk of progression to disease is highest. In a non-limiting example, consider the HS deployed within a school. The FS system would be deployed to the school in a manner similar to that described above for infectious diseases. In some embodiments, school employees, e.g., a school nurse, could administer assays to all students or to a subset of students, e.g., at risk students. The testing could be performed at regular intervals, e.g., at least once a school year, at least once a semester, at least once a quarter, at least monthly, at least every three weeks, at least every two weeks, or at least weekly. In some embodiments, subsets of students could be tested at different intervals. For example, the entire student body might be tested at a first frequency, and a subset of the student body, e.g., those identified at risk from various factors, e.g., obesity or previous test results, could be monitored at a second frequency. In a non-limiting example, the first frequency might be at least once a school year and the second frequency might be at least once a semester, at least once a quarter, or at least monthly. Any similar scheme where those at risk are tested more frequently can be used.

The FS systems deployed in the schools can be used to monitor a variety of analytes which are indicative of risk or disease, e.g., hormone levels and glucose levels. In some embodiments, such analytes are measured in blood. Non-limiting examples of appropriate analytes that can be measured by the FS systems include glucose, hemoglobin A1c, insulin, glucagon, glucagon-like peptide 1 (GLP-1), the insulin precursor peptide-C, leptin, adiponectin, cholesterol, HDL cholesterol, LDL cholesterol and triglycerides. Other physiological data, e.g., body mass, can also be entered into the system for the OS component of the HS to calculate individual and group risks. The system can also monitor drug therapy, by entering a regimen into an individual's health profile, or by directly detecting drug levels with the FS. In some embodiments, the system monitors the progression of any or all of these variables over time.

When the HS identifies an individual, e.g., a student, or a population, e.g., a student body, having or at risk of developing prediabetes or diabetes, the system can recommend a course of action. In the case of a population, the system may issue a warning and/or recommend action if the population incidence or risk increases above a threshold level. In some embodiments, the course of action comprises counseling to individuals, care takers, or other individuals who can influence an individual's lifestyle to mitigate disease or risk thereof. For example, parents or school officials may be notified. The system can also recommend therapies or interventions, including exercise, weight loss, altered eating habits, etc. For a population, a recommendation might include population control measures, including without limitation removal of sugary soft drinks from a school's premises, healthier cafeteria menus, and improved physical education.

Susceptibility to Type II diabetes is not only is this due to poor lifestyle choices but is affected by other factors, e.g., genetic factors. In the United States, such variation, e.g. in the Native American population and those with significant indigenous ancestry, such as the Hispanic population, are potentially at elevated risk. Environmental factors are also potential factors. The OS model can be extended to take into account additional factors, including without limitation genetic and environmental factors. For example, the model can be configured to include adaptive sampling based on non-assay risk measures. Such risk measures include without limitation body weight, medical history, blood pressure, family history, activity level, genetic variability, and alcohol use. The model can also be configured to adaptive sampling based on FS assay data in conjunction with geographic, family, demographic, employment, health care provider, and other data. Similarly, the system can model adaptive therapeutic treatment based on outcomes for the individual and for a population that the analytics system determines to be similar for the variables that best indicate risk. The system can also incorporate visualization that assists a doctor in explaining and clarifying to the user their risk factors, and appropriate actions to mitigate risk, e.g., therapeutic and/or prophylactic treatments and/or interventions, weight loss, dietary changes, exercise and other lifestyle changes. Such visualization might include, e.g., a decision tree or heat map. In some embodiments, the visualization shows cumulative risk from additive factors. An exemplary use of a decision tree for diabetes is presented in Example 4. Each of these approaches can be applied to the model for diabetes and other chronic or infectious diseases.

In another embodiment, the point-of-care and real-time monitoring capabilities of the HS can be used to improve the efficiency of clinical trials. The time-savings impact of the Health Shield has been quantified next to conventional testing and data analytics by pharmaceutical companies. Modeling studies show that the HS can reduce the clinical trials process by potentially a number of years and save $100 Ms per program. In addition, the data generated can provide better success and outcomes for the drugs monitored by defining patient populations and identifying possible adverse events in a predictive manner.

In a separate embodiment, a method of monitoring more than one pharmacological parameter useful for assessing efficacy and/or toxicity of a therapeutic agent is provided. For example, a therapeutic agent can include any substance that has therapeutic utility and/or potential. Such substances include but are not limited to biological or chemical compounds such as simple or complex organic or inorganic molecules, peptides, proteins (e.g. antibodies) or a polynucleotides (e.g. anti-sense). A vast array of compounds can be synthesized, for example polymers, such as polypeptides and polynucleotides, and synthetic organic compounds based on various core structures, and these can also be included as therapeutic agents. In addition, various natural sources can provide compounds for therapeutic use, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. For example, small molecule drugs are often measured by mass-spectrometry which can be imprecise. ELISA (antibody-based) assays can be much more accurate and precise.

Physiological parameters according to the present invention include without limitation parameters such as temperature, heart rate/pulse, blood pressure, and respiratory rate. Pharmacodynamic parameters include concentrations of biomarkers such as proteins, nucleic acids, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

Being able to monitor the rate of change of an analyte concentration or PD or PK parameters over a period of time in a single subject, or performing trend analysis on the concentration, PD, or PK parameters, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

A number of other diseases and conditions can be monitored using the HS system and methods described herein. For example, the system can be used to monitor and control spread of a microorganism, virus, or Chlamydiaceae. Exemplary microorganisms include but are not limited to bacteria, viruses, fungi and protozoa. Analytes that can be detected by the subject method also include blood-born pathogens selected from a non-limiting group that consists of *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*.

Other microorganisms that can be detected by the subject method also encompass a variety of sexually transmitted diseases selected from the following: gonorrhea (*Neisseria gorrhoeae*), syphilis (*Treponena pallidum*), clamydia (*Clamyda tracomitis*), nongonococcal urethritis (*Ureaplasm urealyticum*), yeast infection (*Candida albicans*), chancroid (*Haemophilus ducreyi*), trichomoniasis (*Trichomonas vaginalis*), genital herpes (HSV type I & II), HIV I, HIV II and hepatitis A, B, C, G, as well as hepatitis caused by TTV.

Additional microorganisms that can be detected by the subject methods encompass a diversity of respiratory pathogens including but not limited to *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*.

Any number of biomarkers can be detected in a deployed Health Shield. Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alpha-fetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreatic markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx) Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone gla-protein), Alkaline phosphatase, Cathepsin K, COMP (Cartilage Oligimeric Matrix Protein), Osteocrin, Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF-2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, CAA pancreatic, Neuron-specific enolase, Angiostatin DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c-kit/KDR, KDR, and Midkine.

Exemplary infectious disease conditions include without limitation: Viremia, Bacteremia, Sepsis, and markers: PMN Elastase, PMN elastase/α1-PI complex, Surfactant Protein D (SP-D), HBVc antigen, HBVs antigen, Anti-HBVc, Anti-HIV, T-supressor cell antigen, T-cell antigen ratio, T-helper cell antigen, Anti-HCV, Pyrogens, p24 antigen, Muramyldipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation TNF-α, IL-6, IL1β, Rheumatoid factor (RF), Antinuclear Antibody (ANA), acute phase markers including C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, amd sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII, Anti-hemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High-molecular-weight kininogen, Protein C, Protein S, D-dimer, Tissue plasminogen activator, Plasminogen, a2-Antiplasmin, Plasminogen activator inhibitor 1 (PAI1).

Exemplary monoclonal antibodies include those for EGFR, ErbB2, and IGF1R.

Exemplary tyrosine kinase inhibitors include without limitation Ab, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threoline Kinas Inhibitors include without limitation AKT, Aurora A/B/B, CDK, CDK (pan), CDK1-2, VEGFR2, PDGFRb, CDK4/6, MEK1-2, mTOR, and PKC-beta.

GPCR targets include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

Because the HS comprises a series of integrated technologies that can be quickly adapted to perform additional assays, the system offers a customizable technology package distinct from other systems presently available. For example, systems that focus on a specific technology/application will have difficulty being broadly applied to improve outcomes and reduce healthcare expenditures across all diseases.

8. Field System Cartridge Systems (a) Field System Devices

Customized cartridge devices for use with the FS of the invention are described in U.S. patent application Ser. No. 11/389,409, filed Mar. 24, 2006 and entitled "POINT-OF-CARE-FLUIDIC SYSTEMS AND USES THEREOF," U.S. patent application Ser. No. 11/746,535, filed May 9, 2007 and entitled "REAL-TIME DETECTION OF INFLUENZA VIRUS," and U.S. patent application Ser. No. 12/244,723, filed Oct. 2, 2008 and entitled "MODULAR POINT-OF-CARE DEVICES, SYSTEMS, AND USES THEREOF." Further details are provided herein.

In one embodiment, a FS device for use with the invention comprises a device for automated detection of an analyte in a bodily fluid sample comprises an array of addressable assay units configured to run a chemical reaction that yields a detectable signal indicative of the presence or absence of the analyte. In some embodiments, the device further an array of addressable reagent units, each of which is addressed to correspond to one or more addressable assay units in said device, such that individual reagent units can be calibrated in reference to the corresponding assay unit(s) before the arrays are assembled on the device. In some embodiments, at least one of the assay units and at least one of the reagent units are movable relative to each other within the device such that reagents for running the chemical reaction are automatically brought to contact with the bodily fluid sample in the assay unit. The array of assay units or reagent units can be addressed according to the chemical reaction to be run by the configured assay unit.

In one embodiment, the device is self-contained and comprises all reagents, liquid- and solid-phase reagents, required to perform a plurality of assays in parallel. Where desired, the device is configured to perform at least 2, 3, 4, 5, 6, 7, 8, 9, 10, 20, 30, 40, 50, 100, 200, 500, 1000 or more assays. One or more control assays can also be incorporated into the device to be performed in parallel if desired.

The assays can be quantitative immunoassays and can be conducted in a short period of time. Other assay type can be performed with a device of the invention including, but not limited to, measurements of nucleic acid sequences and measurements of metabolites, such as cholesterol and enzymes such as alanine aminotransferase. In some embodiments, the assay is completed in no more than one hour, preferably less than 30, 15, 10, or 5 minutes. In other embodiments, the assay is performed in less than 5 minutes. The duration of assay detection can be adjusted accordingly to the type of assay that is to be carried out with a device of the invention. For example, if needed for higher sensitivity, an assay can be incubated for more than one hour or up to more than one day. In some examples, assays that require a long duration may be more practical in other POC applications, such as home use, than in a clinical POC setting.

Any bodily fluids suspected to contain an analyte of interest can be used in conjunction with the system or devices of the invention. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid.

A bodily fluid may be drawn from a patient and provided to a device in a variety of ways, including but not limited to, lancing, injection, or pipetting. As used herein, the terms subject and patient are used interchangeably herein, and refer to a vertebrate, preferably a mammal, more preferably a human. Mammals include, but are not limited to, murines, simians, humans, farm animals, sport animals, and pets. In one embodiment, a lancet punctures the skin and a sample is collected using, e.g., gravity, capillary action, aspiration, or vacuum force. The lancet may be part of the device, or part of a system, or a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the device, as for example, could occur with a saliva sample. The collected fluid can be placed in the sample collection unit within the device. In yet another embodiment, the device comprises at least one microneedle which punctures the skin.

The volume of bodily fluid to be used with a device is generally less than about 500 microliters, typically between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the device.

In an embodiment, the volume of bodily fluid used for detecting an analyte using the subject devices or systems is one drop of fluid. For example, one drop of blood from a pricked finger can provide the sample of bodily fluid to be analyzed with a device, system or method described herein.

A sample of bodily fluid can be collected from a subject and delivered to a device of the invention as described hereinafter.

In an embodiment, the arrays of assay and reagent units are configured to be a set of mix-and-match components. The assay units can comprise at least one capture surface capable of reacting with an analyte from the sample of bodily fluid. The assay unit may be a tubular tip with a capture surface within the tip. Examples of tips of the invention are described herein. A reagent unit typically stores liquid or solid reagents necessary for conducting an assay that detect a give analyte. Each individual assay and reagent unit can be configured for assay function independently. To assemble a device, the units can be assembled in a just-in-time fashion for use in integrated cartridges.

Separate components, both liquid and solid phase, can be made and then be tested for performance and stored. In an embodiment, the assembly of the device is carried out in on-demand fashion at a manufacturing location. The device can be modular and include components such as a housing that is generic for all assays, assay units, such as tips, and reagent units, such as a variety of frangible or instrument operable containers that encapsulate liquid reagents. In some instances, an assembled device is then tested to define and/or verify calibration (the relation of the system response to known analyte levels). Assay devices can be assembled from a library of pre-manufactured and calibrated elements on demand. In some embodiments, fluidic pathways within a device can be simple and obviate any chance of trapping bubbles and providing an efficient way to wash away excess labeled reagents in reagent excess assays such as ELISAs.

A housing for a FS device of the invention can be made of polystyrene or another moldable or machinable plastic and can have defined locations to place assay units and reagent units. In an embodiment, the housing has means for blotting tips or assay units to remove excess liquid. The means for blotting can be a porous membrane, such as cellulose acetate, or a piece bibulous material such as filter paper.

In some embodiments, at least one of the components of the device may be constructed of polymeric materials. Non-limiting examples of polymeric materials include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass.

The device or the subcomponents of the device may be manufactured by variety of methods including, without limitation, stamping, injection molding, embossing, casting, blow molding, machining, welding, ultrasonic welding, and thermal bonding. In an embodiment, a device in manufactured by injection molding, thermal bonding, and ultrasonic welding. The subcomponents of the device can be affixed to each other by thermal bonding, ultrasonic welding, friction fitting (press fitting), adhesives or, in the case of certain substrates, for example, glass, or semi-rigid and non-rigid polymeric substrates, a natural adhesion between the two components.

An exemplary device as described herein is illustrated in FIG. 5. The device 100 is also sometimes referred to herein as a cartridge 100. The device 100 comprises a housing 130 with locations to accommodate assay units 121 and reagent units 103, 122, 124, 125. In the exemplary embodiment of FIG. 5, assay units 121 occupy a center row of the housing 130 of the device 100. The assay units 121 can optionally include at least one calibration unit 126. In an example, the assay units 121 are similar to pipette tips and are referred to as assay tips 121 and the calibration units 126 are referred to as calibration tips 126 herein, however, the assay units 121 can be of any shape and size as are accommodated broadly by a device 100 as described herein. The assay units 121 and calibration units 126 are exemplary assay units 121 and are described in more detail herein. The assay units 121 in FIG. 5 can comprise a capture surface and are capable, for example, of performing a chemical reaction such as nucleic acid assays and immunoassays. The assay units 121 can be assembled into the housing according to instructions or the assays that a user wishes to perform on a sample.

As shown in FIG. 5, the housing of the device 100 can comprise a sample collection unit 110 configured to contain a sample. A sample, such as a blood sample, can be placed into the sample collection unit 110. A sample tip 111 (for example, a pipette tip that couples to a fluid transfer device as described in more detail herein) can occupy another portion of the housing 130. When an assay is to be run the sample tip 111 can distribute the sample to pretreatment reagent units or pretreatment units 103, 104, 105, 106, 107, or assay units 121. Exemplary pretreatment units 103, 104, 105, 106, 107 include but are not limited to: mixing units 107, diluent or dilution units 103, 104, and, if the sample is a blood sample, plasma removal or retrieval units 105, 106. The pretreatment units 103, 104, 105, 106, 107 can be the same type of unit or different types of units. Other pretreatment units 103, 104, 105, 106, 107 as are necessary to run a chemical reaction can be incorporated into device 100 as would be obvious to one skilled in the art with knowledge of this disclosure. The units 103, 104, 105, 106, 107 can contain various amounts of reagents or diluents, flexible to whatever is needed to run the assay on the current cartridge 100.

Often, the assay units 121 can be manufactured separately from the housing 130 and then inserted into the housing 130 with pick-and-place methods. The assay units 121 can fit snugly into the housing 130 or can fit loosely into the housing 130. In some embodiments, the housing 130 is manufactured such that it holds the reagent units 103, 122, 124, 125 and/or assay units 121 snugly in place, for example during shipping or manipulation a cartridge 100. Reagents units 103, 122, 124, 125 are shown in FIG. 5 that contain a conjugate reagent 122 (for example, for use with an immunoassay), a wash reagent 125 (for example, to wash said conjugate from capture surfaces), and a substrate 124 (for example, an enzyme substrate). Other embodiments of the device 100 and the components in the example in FIG. 5 are described herein. Reagent units 103, 122, 124, 125 can be manufactured and filled separately from the housing 130 and then placed into the housing 130. In this way, a cartridge 100 can be built in a modular manner, therefore increasing the flexibility of the cartridge 100 to be used for a variety of assays. Reagents in a reagent unit 103, 122, 124, 125 can be chosen according to the assay to be run. Exemplary reagents and assays are described herein.

A device, such as the example shown in FIG. 5, can also comprise other features as may be needed to run a chemical reaction. For example, if the assay units 121 are assay tips 121 as described herein, the device can comprise tip touch-off pads 112 to remove excess sample or reagent from an assay tip 121 or a sample tip 111 after fluid transfer, for example, by a system as described herein. The housing 130 can also comprise units or areas 101, 102 within the device 100 for placing a used tip or unit, for example, in order to avoid cross-contamination of a sample tip 111 or assay unit 121. In FIG. 5, the device 100 comprises a sample tip 111 for transferring a sample between units of the device 100. The device 100 as illustrated in FIG. 5 also comprises a pretreatment tip 113 for transferring a sample that has been pretreated in a unit of the device 100 to other units of a device 100 to perform a chemical reaction. For example, the sample tip 111 can be used to remove a blood sample from the sample collection unit 110 and transfer the blood sample to pretreatment units 103, 104, 105, 106, 107 as described. Red cells can be removed from the blood sample in the pretreatment units 103, 104, 105, 106, 107 and the pretreatment tip 113 can then be used to collect the blood plasma from the pretreatment units 103, 104, 105, 106, 107 and transfer the blood plasma to another pretreatment unit (for example, a diluent unit) 103, 104, 105, 106, 107 and/or to at least one assay unit 121. In an embodiment, a sample tip 111 is the sample collection unit 110. In another embodiment, the sample collection unit 110 is similar to a well and is configured to contain a sample as received by a user.

Assay units 121 and reagent units 103, 122, 124, 125 as shown in FIG. 5 can be addressable to indicate the location of the units on the cartridge 100. For example, a column of the cartridge 100 as shown in FIG. 5 can contain an assay unit 121 to run an assay configured to detect C-reactive protein, and the column can contain corresponding reagent units 103, 122, 124, 125 for that assay in the same column, wherein the units are addressed to correspond to each other. For example, the addresses can be entered and stored in a computer system, and the cartridge 100 can be given a label, such as a bar code. When the bar code of the cartridge 100 is scanned for use, the computer system can send the addresses of the units to a system, such as those described herein, to transfer the fluids and run a reaction according to the addresses entered into the computer. The addresses can be part of a protocol sent to operate the system. The addresses can be in any configuration and can be altered if need be to change the protocol of running an assay, which in turn can offer a change in assay protocol or steps to a user of the cartridge that has not been typically available in prior art POC devices. In some embodiments, the housing 130 and units are configured in a 6 by 8 array of units as shown in FIG. 5. The layout of the units can be of any format, for example, rectangular arrays or random layouts. A cartridge 100 can comprise any number of units, for example between 1 and about 500. In some embodiments, a cartridge 100 has between 5-100 units. As an example as shown in FIG. 5, the cartridge 100 has 48 units.

Two side cut-away views of the exemplary device 200 of FIG. 5 are illustrated in FIG. 6. A cavity can be shaped in a housing 220 of a device to accommodate assay units (for example, assay tips) 201 in a vertical orientation (housing horizontal) with their bosses toward the top of the device 200. As shown in FIG. 6, a cavity can also be shaped to accommodate a reagent unit 210, 212 or a sample collection unit or tip 202. There may be features in the housing 220 to capture the units precisely and hold them securely. Such features can also be designed to operate with a mechanism for moving the tips, such as tip pick-up and drop-off. In another embodiment, the sample collection unit comprises a bendable or breakable element that serves to protect a small collection tube during shipment and to hold a plunger device in place within a capillary. Also shown in FIG. 6 are two exemplary embodiments of reagent units 210, 212 as are described herein. The bottom of the housing 220 can be configured to collect waste liquids, for example, wash reagents after use that are transferred back through a hole in the housing 220 to the bottom. The housing 220 can comprise an absorbent pad to collect waste fluids. The assay units 201 and sample units 202 can be positioned to fit through a cavity of the housing 220 of the device 200 and extend beyond an inner support structure. The reagent units 210, 212 fit snugly into the housing as is shown in FIG. 6 and do not extend beyond the inner support structure. The housing 220 and the areas in which the assay units 201 and reagents units 210, 212 can be held and positioned may adapt a variety of patterns.

In some embodiments, each tip provides for a single assay and can be paired with or corresponded to an appropriate reagent, such as required reagents for running the designated assay. Some tips provide for control assay units and have known amounts of analyte bound to their capture surfaces either in the manufacturing process or during the performance of an assay. In case of a control assay unit, the unit is configured to run a control assay for comparison. The control assay unit may comprise, for example, a capture surface and analyte that are in a solid or liquid state.

In many embodiments, the device holds all reagents and liquids required by the assay. For example, for a luminogenic ELISA assay the reagents within the device may include a sample diluent, capture surfaces (e.g., three capture antibodies), a detector conjugate (for example, three enzyme-labeled antibodies), a wash solution, and an enzyme substrate. Additional reagents can be provided as needed.

In some embodiments, reagents can be incorporated into a device to provide for sample pretreatment. Examples of pretreatment reagents include, without limitation, white cell lysis reagents, red cell lysis reagents, red cell removal reagents, reagents for liberating analytes from binding factors in the sample, enzymes, and detergents. The pretreatment reagents can also be added to a diluent contained within the device.

An individual reagent unit can be configured to receive a movable assay unit. In some embodiments, the individual assay unit comprises an open ended hollow cylindrical element comprising a capture surface and a reaction cuvette. A cylindrical assay unit can be referred to as an assay tip herein. In some embodiments, the individual assay unit is configured to run an immunoassay. An assay unit 301 that comprises a small tip or tubular formation is shown in FIG. 7A. In some instances, the tip 301 is configured to provide an interior cylindrical capture surface 311 and a boss 321 capable of engaging with the housing of device. In some instances, the boss 321 and the tip 301 is configured to engage with a mechanism of moving the tip 301 such as a system as described herein or for example, a fluid transfer device. An assay tip 301 as shown in FIG. 7A can comprise an opening 331 at the bottom of the tip. The opening 331 can be utilized for transferring fluids or reagents in and out of an assay unit 301. In an embodiment, an assay unit 301 as described is or is similar to a pipette tip with the improvement that the assay unit 301 comprises a capture surface 311 configured to detect an analyte in a sample.

The tip 301 can be manufactured by an injection-molded process. In an embodiment, the tip 301 is made of a clear polystyrene for use with chemiluminescence assays. As shown in FIG. 7A, an exemplary tip 301 comprises a boss (shown as the larger top half of the tip 301), which can engage with a housing and can engage, for example, with tapered elements of a fluid transfer device and/or pipetting devices so as to form a pressure-tight seal. Also shown in FIG. 7A, the exemplary tip 301 comprises a smaller cylindrical part. In many embodiments, an assay capture surface is contained within the smaller cylindrical part. The assay capture surface can be anywhere within the tip 301 or on the outside of the tip 301. The surface of the tip 301 can be of many geometries including, but not limited to, tubular, cubic, or pyramidal. In chemiluminescence and fluorescence-based assays, the tip 301 can serve as a convenient means to present the assay product to the assay optics.

FIG. 7B demonstrates an exemplary sample collection unit 302 comprising a sample tip 302. The sample tip 302 as shown in FIG. 7B can also be separate from a sample collection unit 302 and used to transfer sample from the sample collection units to other units on a device as described herein. The sample tip as shown in FIG. 7B comprises a boss 322 as described herein to couple the tip 302 with a housing of a device and a fluid transfer device. The sample tip 302 also comprises an opening 332 to allow the transfer of fluids or samples in and out of the sample tip. In some embodiments, the sample tip 302 is of the same shape as an assay tip 301. In other embodiments (such as those shown in FIGS. 7A and 7B), the sample tip 302 is a different shape than the assay tip 301.

In an embodiment, one function of a tip is to enable samples and liquid reagents to be brought into contact with the capture surface of the assay unit. The movement can occur by a variety of means including, but not limited to, capillary action, aspiration, and controlled pumping. The small size of the tips enables rapid control of the required temperature for a chemical reaction. Heat transfer and/or maintenance can be carried out by simply placing the tip in a temperature controlled block or chamber.

In some embodiments, the tip is able to contain about 1 to 40 microliters of fluid. In a further embodiment, the tip is able to contain about 5 to 25 microliters of fluid. In an embodiment, the tip contains 20 microliters of fluid. In some instances, a tip can contain 1 microliter of fluid or less. In other instances, a tip can contain up to 100 microliters.

Where desired, the end of the tip can be blotted onto an absorbent material (for example incorporated into a disposable cartridge) prior to introduction of the next assay component to avoid contamination with a small amount of sample and/or reagent. Due to physical forces, any liquid drawn into a subject tip can be held at any desired location with minimal risk of the liquid draining out, even when held in a vertical orientation.

The assay unit (for example, an assay tip) can be coated with assay capture reagents prior to use, using similar fluidics as in the assay (for example, controlled capillary or mechanical aspiration).

A capture surface (also referred to herein as a reaction site) can be formed by a binding antibody or other capture reagents bound covalently or by adsorption to the assay unit. The surface can then dried and maintained in dry condition until used in an assay. In an embodiment, there is a reaction site for each analyte to be measured.

In an embodiment, the assay unit can be moved into fluid communication with the reagent unit and/or a sample collection unit, such that a reagent or sample can interact with a reaction site where bound probes can detect an analyte of interest in the bodily fluid sample. A reaction site can then provide a signal indicative of the presence or concentration of the analyte of interest, which can then be detected by a detection device described herein.

In some embodiments, the location and configuration of a reaction site is an important element in an assay device. Most, if not all, disposable immunoassay devices have been configured with their capture surface as an integral part of the device.

In one embodiment, a molded plastic assay unit is either commercially available or can be made by injection molding with precise shapes and sizes. For example, the characteristic dimension can be a diameter of 0.05-3 mm or can be a length of 3 to 30 mm. The units can be coated with capture reagents using method similar to those used to coat microtiter plates but with the advantage that they can be processed in bulk by placing them in a large vessel, adding coating reagents and processing using sieves, holders, and the like to recover the pieces and wash them as needed.

The assay unit can offer a rigid support on which a reactant can be immobilized. The assay unit is also chosen to provide appropriate characteristics with respect to interactions with light. For example, the assay unit can be made of a material, such as functionalized glass, Si, Ge, GaAs, GaP, SiOz, $SiN_4$, modified silicon, or any one of a wide variety of gels or polymers such as (poly)tetrafluoroethylene, (poly)vinylidenedifluoride, polystyrene, polycarbonate, polypropylene, PMMA, ABS, or combinations thereof. In an embodiment, an assay unit comprises polystyrene. Other appropriate materials may be used in accordance with the present invention. A transparent reaction site may be advantageous. In addition, in the case where there is an optically transmissive window permitting light to reach an optical detector, the surface may be advantageously opaque and/or preferentially light scattering.

A reactant immobilized at the capture surface can be anything useful for detecting an analyte of interest in a sample of bodily fluid. For instance, such reactants include, without limitation, nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art. Surface immobilization can also be achieved via a Poly-L Lysine tether, which provides a charge-charge coupling to the surface.

The assay units can be dried following the last step of incorporating a capture surface. For example, drying can be performed by passive exposure to a dry atmosphere or via the use of a vacuum manifold and/or application of clean dry air through a manifold.

In many embodiments, an assay unit is designed to enable the unit to be manufactured in a high volume, rapid manufacturing processes. For example, tips can be mounted in large-scale arrays for batch coating of the capture surface into or onto the tip. In another example, tips can be placed into a moving belt or rotating table for serial processing. In yet another example, a large array of tips can be connected to vacuum and/or pressure manifolds for simple processing.

In an embodiment, an assay unit can be operably coupled with a fluid transfer device. The fluid transfer device can be operated under automatic control without human interaction. In assay units comprising tips, the control of the installed height of a disposable liquid tip relies on the tapered interference attachment of the tip to the liquid dispenser. A fluid transfer device can engage the tip. In some instances, the immersion length of a tip in liquid to be transferred must be known to minimize the liquid contact with the outside of the tip which may be uncontrolled. In order to couple or adhere a tip to the fluid transfer device a hard stop can be molded at the bottom of the tapered connector which engages the nozzle of the dispenser. An air tight seal can be made by an o-ring that is half way up the taper or in the flat bottom of the nozzle. By separating the seal function of the tip from the controlled height of the tip both can be separately adjusted. The modular device and fluid transfer device can enable many assays to be performed in parallel.

The reagent units of a device can store reagents that are required to perform a give chemical reaction for detecting a given analyte of interest. Liquid reagents can be dispensed into small capsules that can be manufactured from a variety of materials including, without limitation, plastic such as polystyrene, polyethylene, or polypropylene. In some embodiments, the reagent units are cylindrical cups. Two examples of a reagent unit 401, 402 comprising a cup are shown in FIGS. 8A and 8B. Where desired, the units 401, 402 fit snugly into cavities in a housing of a device. The units 401, 402 can be sealed on the open surface to avoid spilling the reagents 411, 412 onboard. In some embodiments, the seal is an aluminized plastic and can be sealed to the cup by thermal bonding. A unit can be of any shape as is necessary to contain a reagent. For example, a cylindrical shaped reagent unit 401 is shown in FIG. 8A, and the reagent unit contains a liquid reagent 411. A different shaped reagent unit 402 is illustrated in FIG. 8B also contain a liquid reagent 412. Both exemplary reagent units 401, 402 comprise optional slight modifications near the top surface that allow the units 401, 402 to fit snugly into a housing of a device as described herein.

In many embodiments of the invention the reagent units are modular. The reagent unit can be designed to enable the unit to be manufactured in a high volume, rapid manufacturing processes. For example, many reagent units can be filled and sealed in a large-scale process simultaneously. The reagent units can be filled according to the type of assay or assays to be run by the device. For example, if one user desires different assays than another user, the reagent units can be manufactured accordingly to the preference of each user, without the need to manufacture an entire device. In another example, reagent units can be placed into a moving belt or rotating table for serial processing.

In another embodiment, the reagent units are accommodated directly into cavities in the housing of a device. In this embodiment, a seal can be made onto areas of housing surrounding the units.

Reagents according to the present invention include without limitation wash buffers, enzyme substrates, dilution buffers, conjugates, enzyme-labeled conjugates, DNA amplifiers, sample diluents, wash solutions, sample pretreatment reagents including additives such as detergents, polymers, chelating agents, albumin-binding reagents, enzyme inhibitors, enzymes, anticoagulants, red-cell agglutinating agents, antibodies, or other materials necessary to run an assay on a device. An enzyme-labeled conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments, the reagents comprise immunoassay reagents. In general, reagents, especially those that are relatively unstable when mixed with liquid, are confined separately in a defined region (for example, a reagent unit) within the device.

In some embodiments, a reagent unit contains approximately about 5 microliters to about 1 milliliter of liquid. In some embodiments, the unit may contain about 20-200 microliters of liquid. In a further embodiment, the reagent unit contains 100 microliters of fluid. In an embodiment, a reagent unit contains about 40 microliters of fluid. The volume of liquid in a reagent unit may vary depending on the type of assay being run or the sample of bodily fluid provided. In an embodiment, the volumes of the reagents do not have to predetermined, but must be more than a known minimum. In some embodiments, the reagents are initially stored dry and dissolved upon initiation of the assay being run on the device.

In an embodiment, the reagent units can be filled using a siphon, a funnel, a pipette, a syringe, a needle, or a combination thereof. The reagent units may be filled with liquid using a fill channel and a vacuum draw channel. The reagent units can be filled individually or as part of a bulk manufacturing process.

In an embodiment, an individual reagent unit comprises a different reagent as a means of isolating reagents from each other. The reagent units may also be used to contain a wash solution or a substrate. In addition, the reagent units may be used to contain a luminogenic substrate. In another embodiment, a plurality of reagents are contained within a reagent unit.

In some instances, the setup of the device enables the capability of pre-calibration of assay units and the reagent units prior to assembly of disposables of the subject device.

In an aspect, an FS system of the invention comprises a device comprising assay units and reagent units comprising reagents (both liquid and solid phase reagents). In some embodiments, at least one of the whole device, an assay unit, a reagent unit, or a combination thereof is disposable. In a system of the invention, the detection of an analyte with a device is operated by an instrument. In most embodiments, the instrument, device, and method offer an automated detection system. The automated detection system can be automated based upon a defined protocol or a protocol provided to the system by a user.

In an aspect, a system for automated detection an analyte in a bodily fluid sample comprises a device or cartridge, and a detection assembly or detector for detecting the detectable signal indicative of the presence or absence of the analyte.

In an embodiment, the user applies a sample (for example, a measured or an unmeasured blood sample) to the device and inserts the device into the instrument. All subsequent steps are automatic, programmed either by the instrument (hard wired), the user, a remote user or system, or modification of the instrument operation according to an identifier (for example, a bar code or RFID on the device).

Examples of different functions of that can be carried out using a system of the invention include, but are not limited to, dilution of a sample, removal of parts of a sample (for example, red blood cells (RBCs)), reacting a sample in an assay unit, adding liquid reagents to the sample and assay unit, washing the reagents from the sample and assay unit, and containing liquids during and following use of the device. Reagents can be onboard the device in a reagent unit or in a reagent unit to assembled onto the device.

An automated system can detect a particular analyte in a biological sample (for example, blood) by an enzyme-linked immunosorbent assay (ELISA). The system is amenable to multiplexing and is particularly suited for detecting an analyte of interest present in a small volume of a whole blood sample (for example, 20 microliters or less). The system can also detect analytes in different dilutions of a single sample, allowing different sensitivities to be tested on the same device, when desired. All reagents, supplies, and wastes can be contained on the device of the system.

In use, a sample from a subject is applied to the assembled device and the device is inserted into an instrument. In an embodiment, an instrument can begin processing the sample by some combination of removal of red cells (blood sample), dilution of the sample, and movement the sample to the assay unit. In an embodiment with multiplexed assays, a plurality of assay units is used and a portion of the sample is moved to individual assay units in sequence or in parallel. Assays can then be performed by a controlled sequence of incubations and applications of reagents to the capture surfaces.

An exemplary fluid transfer device is comprised of any component capable of performing precise and accurate fluid movements. Example of components include, but are not limited to, pumps to aspirate and eject accurately known fluid volumes from wells or units of the device, at least one translational stage for improving the precision and accuracy of the movement within the system. The system also comprises a detector to detect a signal generated by a signal generator (such as an enzyme in contact with its substrate) in an assay unit. Detectors include PMTs, Diodes, CCD and the like. In the case of absorbance or fluorescence based assays, a light source is used. For luminescence-based assays, no light source is needed in the system instrument and a PMT or an Avalanche photodiode detector can be employed. Where desired, the instrument has temperature regulation to provide a regulated temperature environment for incubation of assays. In an embodiment of the invention, the instrument controls the temperature of the device. In a further embodiment, the temperature is in the range of about 30-40 degrees Celsius. In some embodiments, the temperature control by the system can comprise active cooling. In some instances, the range of temperature is about 0-100 degrees Celsius. For example, for nucleic acid assays, temperatures up to 100 degrees Celsius can be achieved. In an embodiment, the temperature range is about 15-50 degrees Celsius. A temperature control unit of the system can comprise a thermoelectric device, such as a Peltier device.

Cartridges, devices, and systems as described herein can offer many features that are not available in existing POC systems or integrated analysis systems. For example, many POC cartridges rely on a closed fluidic system or loop to handle small volumes of liquid in an efficient manner. The cartridges and fluidic devices described herein can have open fluid movement between units of the cartridge. For example, a reagent can be stored in a unit, a sample in a sample collection unit, a diluent in a diluent unit, and the capture surface can be in an assay unit, wherein in one state of cartridge, none of the units are in fluid communication with any of the other units. Using a fluid transfer device or system as described herein, the assay units do not have to be in fluid communication with each other. This can be advantageous in some settings because each assay chemistry does not interact physically or chemically with others to avoid interference due to assay cross talk. The units can be movable relative to each other in order to bring some units into fluid communication. For example, a fluid transfer device can comprise a head that engages an assay unit and moves the assay unit into fluidic communication with a reagent unit.

The devices and systems herein can provide an effective means for high throughput and real-time detection of analytes present in a bodily fluid from a subject. The detection methods may be used in a wide variety of circumstances including identification and quantification of analytes that are associated with specific biological processes, physiological conditions, disorders or stages of disorders. As such, the systems have a broad spectrum of utility in, for example, drug screening, disease diagnosis, phylogenetic classification, parental and forensic identification, disease onset and recurrence, individual response to treatment versus population bases, and monitoring of therapy. The subject devices and systems are also particularly useful for advancing preclinical and clinical stage of development of therapeutics, improving patient compliance, monitoring ADRs associated with a prescribed drug, developing individualized medicine, outsourcing blood testing from the central laboratory to the home or on a prescription basis, and monitoring therapeutic agents following regulatory approval or during clinical trials. The devices and systems can provide a flexible system for personalized medicine. Using the same system, a device can be changed or interchanged along with a protocol or instructions to a programmable processor of the systems to perform a wide variety of assays as described. The systems and devices herein offer many features of a laboratory setting in a desk-top or smaller size automated instrument. Because of these features, the devices are particularly well suited for deployment as FS devices for the HS systems of the invention.

In some embodiments, an individual be monitored by the HS is provided with a plurality of devices to be used for detecting a variety of analytes. An individual may, for example, use different fluidic devices on different days of the week. In some embodiments the software on the external device associating the identifier with a protocol may include a process to compare the current day with the day the fluidic device is to be used based on a clinical trial for example. In another embodiment, the individual is provided different reagent units and assay units that can be fit into a housing of a device interchangeably. In yet another embodiment, as described the individual does not need a new device for each day of testing, but rather, the system can be programmed or reprogrammed by downloading new instructions from, e.g. an external device such as a server. If for example, the two days of the week are not identical, the external device can wirelessly send notification to the individual using any of the methods described herein or known in the art to notify them of the proper device and/or proper instructions for the system. This example is only illustrative and can easily be extended to, for example, notifying a subject that a fluidic device is not being used at the correct time of day. Using these methods, the FS devices can be rapidly adjusted as the disease being monitored. For example, the OS may direct the FS to immediately assay individuals in contact with an index case.

In one embodiment, a cartridge as illustrated in FIG. 5 comprises a variety of assay units and reagent units. The assay units can comprise a capture surface according to an analyte to be detected. The assay units can then be assembled with the rest of the device in a just-in-time fashion. In many prior art POC devices, the capture surface is integral to the device and if the capture surface is incorrect or not properly formed, the whole device may function improperly. Using a device as described herein, the capture surface and/or assay unit can be individually quality controlled and customized independently of the reagent units and the housing of the device.

Reagent units can be filled with a variety of reagents in a similar just-in-time fashion. This provides flexibility of the device being customizable. In addition, the reagent units can be filled with different volumes of reagents without affecting the stability of a device or the chemical reactions to be run within the device. Coupled with a system as described with a fluid transfer device, the devices and units described herein offer flexibility in the methods and protocols of the assays to be run. For example, a batch of similar devices containing the same reagents can be given to a community being monitored by the HS. After a period of monitoring, the OS identifies that the assay could be optimized by changing the dilution of the sample and the amount of reagent provided to the assay unit. As provided herein, the assay can be changed or optimized by only changing the instructions to a programmable processor of the fluid transfer device. For example, the batch of cartridges in the patient pool had excess diluent loaded on the cartridge. The new protocol demands four times as much diluent as the previous protocol. Due to the methods and systems provided herein, the protocol can be changed at the central OS server and sent to all the systems for executing the methods with the devices without having to provide new devices to the patient pool. In other words, a POC device and system as described herein can offer much of the flexibility of a standard laboratory practice where excess reagents and often excess sample are often available. Such flexibility can be achieved without compromising the advantages of the POC testing scenario or the capability to assay small sample volumes.

In some instances, wherein the units of the cartridge are separate, devices and systems provide flexibility in construction of the systems described herein. For example, a cartridge can be configured to run 8 assays using an array of assay units and an array of reagent units. Due to the features of the cartridge as described herein, the same housing, or a housing of the same design can be used to manufacture a cartridge with up to 8 different assays than the previous cartridge. This flexibility is difficult to achieve in many other POC device designs because of the closed systems and fluid channels, and therefore the devices may not be modular or as easy to assemble as described.

Currently, a need exists for detecting more than one analyte where the analytes are present in widely varying concentration range, for example, one analyte is in the pg/ml concentration range and another is in the ug/ml concentration range. In a non-limiting example, a viral antigen may be detected in pg/ml range whereas a host antibody to that antigen is detected in the ug/ml range. See Table 4. The system as described herein has the ability to simultaneously assay analytes that are present in the same sample in a wide concentration range. Another advantage for being able to detect concentrations of different analytes present in a wide concentration range is the ability to relate the ratios of the concentration of these analytes to safety and efficacy of multiple drugs administered to a patient. For example, unexpected drug-drug interactions can be a common cause of adverse drug reactions. A real-time, concurrent measurement technique for measuring different analytes would help avoid the potentially disastrous consequence of adverse drug-drug interactions. This can be useful when rapidly deploying drugs to control an outbreak.

Being able to monitor the rate of change of an analyte concentration and/or or concentration of pharmacodynamic (PD) or pharmacokinetic (PK) markers over a period of time in a single subject, or performing trend analysis on the concentration, or markers of PD, or PK, whether they are concentrations of drugs or their metabolites, can help prevent potentially dangerous situations. For example, if the HS is being used to monitor diabetes and glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

Accordingly, the data generated with the use of the subject fluidic devices and systems can be utilized for performing a trend analysis on the concentration of an analyte in a subject.

Often, multiple assays on the same cartridge may require different dilutions or pre-treatments. The range of dilution can be substantial between assays. Many current POC devices offer a limited range of dilution and therefore a limited number of assays that can be potentially carried out on the POC device. However, a system and/or cartridge as described herein can offer a large range of dilutions, e.g., 1:2-1:10,000 due to the ability of the system to serially dilute a sample. Therefore, a large number of potential assays can be performed on a single cartridge or a plurality of cartridges without modifying the detector or reading instrument for the assays.

In an example, a system as provided herein is configured to run multiple (e.g., five or more) different target analyte detection assays. In order to bring the expected analyte concentration within the range of detection of an immunoassay as described herein and commonly used in the POC field, a sample must be diluted e.g., 3:1, 8:1, 10:1, 100:1, and 2200:1, to run each of the five assays. Because the fluid transfer device is able to hold and move fluid within the device, serial dilutions can be performed with a system as described herein to achieve these five different dilutions and detect all five different target analytes. As described above, the protocol for performing the assays is also capable of being adjusted without modifying the device or the system.

In a laboratory setting with traditional pipetting, typically larger volumes of sample are used than in a POC setting. For example, a laboratory may analyze a blood sample withdrawn from the arm of a patient in a volume in the milliliter range. In a POC setting, many devices and users demand that the process is fast, easy and/or minimally invasive, therefore, small samples (on the order of a volume in the microliter range) such as one obtained by a fingerstick) are typically analyzed by a POC device. Because of the difference in sample, current POC devices can lose flexibility in running an assay that is afforded in a laboratory setting. For example, to run multiple assays from a sample, a certain minimum volume can be required for each assay to allow for accurate detection of an analyte, therefore putting some limits on a device in a POC setting.

In another example, a system and/or fluid transfer device as described herein provides a great deal of flexibility. For example, the fluid transfer device can be automated to move an assay unit, an assay tip, or an empty pipette from one unit of the device to a separate unit of the device, not in fluid communication with each other. In some instances, this can avoid cross-contamination of the units of a device as described. In other instances, it allows for the flexibility of moving several fluids within a device as described into contact with each other according to a protocol or instructions. For example, a cartridge comprising 8 different reagent sets in 8 different reagent units can be addressed and engaged by a fluid transfer device in any order or combination as is instructed by a protocol. Therefore, many different sequences can be run for any chemical reaction to run on the device. Without changing the volume of the reagents in the cartridge or the type of reagents in the cartridge, the assay protocol can be different or modified without the need for a second cartridge or a second system.

For example, an FS worker orders a cartridge with a specific type of capture surface and specific reagents to run an assay to detect an analyte (for example, C-reactive protein (CRP)) in a sample. The protocol the FS worker originally planned for may require 2 washing steps and 3 dilution steps. After the FS worker has received the device and system, those at the OS site responsible for the deployed FS devices determines that the protocol should have 5 washing steps and only 1 dilution step. The devices and systems herein can allow the flexibility for this change in protocol without having to reconfigure the device or the system. In this example, only a new protocol or set of instructions are needed to be sent from the OS component to the programmable processor of the FS system or the fluid transfer device.

In another example, a system as provided herein is configured to run five different target analyte detection assays, wherein each assay needs to be incubated at a different temperature. In many prior art POC devices, incubation of multiple assays at different temperatures is a difficult task because the multiple assays are not modular and the capture surfaces cannot be moved relative to the heating device. In a system as described herein, wherein an individual assay unit is configured to run a chemical reaction, an individual assay unit can be place in an individual heating unit. In some embodiments, a system comprises a plurality of heating units. In some instances, a system comprises at least as many heating units as assay units. Therefore, a plurality of assays can be run as a plurality of temperatures.

Systems and devices as described herein can also provide a variety of quality control measures not previously available with many prior art POC devices. For example, because of the modularity of a device, the assay units and reagents units can be quality controlled separately from each other and/or separately from the housing and/or separately from a system or fluid transfer device. Exemplary methods and systems of quality control offered by the systems and devices herein are described.

An FS system as described for use with the invention can run a variety of assays, regardless of the analyte being detected from a bodily fluid sample. A protocol dependent on the identity of the device may be transferred from the external OS component where it can be stored to a reader assembly to enable the reader assembly to carry out the specific protocol on the device. In some embodiments, the device has an identifier (ID) that is detected or read by an identifier detector described herein. The identifier detector can communicate with a communication assembly via a controller which transmits the identifier to an external device. Where desired, the external device sends a protocol stored on the external device to the communication assembly based on the identifier. The protocol to be run on the system may comprise instructions to the controller of the system to perform the protocol, including but not limited to a particular assay to be run and a detection method to be performed. Once the assay is performed by the system, a signal indicative of an analyte in the bodily fluid sample is generated and detected by a detection assembly of the system. The detected signal may then be communicated to the communications assembly, where it can be transmitted to the external device for processing, including without limitation, calculation of the analyte concentration in the sample.

In some embodiments, the identifier may be a bar code identifier with a series of black and white or reflective lines or blocks, which can be read by an identifier detector such as a bar code reader, which are well known or an Radio-frequency identification (RFID) tag with an appropriate detector. Other identifiers could be a series of alphanumerical values, colors, raised bumps, or any other identifier which can be located on a device and be detected or read by an identifier detector. The identifier detector may also be an LED that emits light which can interact with an identifier which reflects light and is measured by the identifier detector to determine the identity of a device. In some embodiments the identifier may comprise a storage or memory device and can transmit information to an identification detector. In some embodiments a combination of techniques may be used. In some embodiments, the detector is calibrated by use of an optical source, such as an LED.

In an example, a bodily fluid sample can be provided to a device, and the device can be inserted into a system. In some embodiments the device is partially inserted manually, and then a mechanical switch in the reader assembly automatically properly positions the device inside the system. Any other mechanism known in the art for inserting a disk or cartridge into a system may be used. In some embodiments, manual insertion may be required.

In some embodiments a method of automatically selecting a protocol to be run on a system comprises providing a device comprising an identifier detector and an identifier; detecting the identifier; transferring said identifier to the external OS component of the systems of the invention; and selecting a protocol to be run on the system from a plurality of protocols on external OS component associated with said identifier.

In one embodiment, an FS system of the invention for automated detection of a plurality of analytes in a bodily fluid sample comprises: a fluidic device (such as those described herein) comprising: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent. The system further comprises a fluid transfer device comprising a plurality of heads, wherein an individual head of the plurality of heads is configured to engage the individual assay unit, and wherein said fluid transfer device comprises a programmable processor configured to direct fluid transfer of the bodily fluid sample from the sample collection unit and the reagent from the individual reagent unit into the individual assay unit. For example, an individual assay unit comprises a reagent and is configured is to run a chemical reaction with that reagent.

In some instances, the configuration of the processor to direct fluid transfer effects a degree of dilution of the bodily fluid sample in the array of assay units to bring signals indicative of the plurality of analytes being detected within a detectable range, such that said plurality of analytes are detectable with said system. In an example, the bodily fluid sample comprises at least two analytes that are present at concentrations that differ by at least 1, 2, 3, 4, 5, 6, 7, 8, 9, 10, 15, 50, or 100 orders of magnitude. In an example the bodily fluid sample is a single drop of blood. In an embodiment, the concentrations of at least two analytes present in a sample differs by up to 10 orders of magnitude (for example, a first analyte is present at 0.1 pg/mL and a second analyte is present at 500 ug/mL. In another example, some protein analytes are found at concentrations of greater than 100 mg/mL, which can extend the range of interest to about twelve orders of magnitude.

A degree of dilution of the bodily fluid sample can bring the signals indicative of the at least two analytes within the detectable range. In many instances, a system further comprises a detector, such as a photomultiplier (PMT). With a photomultiplier, for example, a detectable range of the detector can be about 10 to about 10 million counts per second. Each count corresponds to a single photon. In some instances, PMTs are not 100% efficient and the observed count rate may be slightly lower than, but still close to, the actual number of photons reaching the detector per unit time. In some instances, counts are measured in about ten intervals of about one second and the results are averaged. In some embodiments, ranges for assays are 1000-1,000,000 counts per second when using a PMT as a detector. In some instances, count rates as low as 100 per second and count rates as high as 10,000,000 are measurable. The linear response range of PMTs (for example, the range where count rate is directly proportional to number of photons per unit time) can be about 1000-3,000,000 counts per second. In an example, an assay has a detectable signal on the low end of about 200-1000 counts per second and on the high end of about 10,000-2,000,000 counts per second. In some instances for protein biomarkers, the count rate is directly proportional to alkaline phosphatase bound to the capture surface and also directly proportional to the analyte concentration. Other exemplary detectors include avalanche photodiodes, avalanche photodiode arrays, CCD arrays, super-cooled CCD arrays. Many other detectors have an output that is digital and generally proportional to photons reaching the detector. The detectable range for exemplary detectors can be suitable to the detector being used.

An individual head of a fluid transfer device can be configured to adhere to the individual assay unit. The fluid transfer device can be a pipette, such as an air-displacement pipette. The fluid transfer device can be automated. For example, a fluid transfer device can further comprise a motor in communication with a programmable processor and the motor can move the plurality of heads based on a protocol from the programmable processor. As described, an individual assay unit can be a pipette tip, for example, a pipette tip with a capture surface or reaction site.

Often times, in a POC device, such as the systems and devices described herein, the dilution factor must be estimated and reasonably precise. For example, in environments where non-expert users operate the system there needs to be ways of ensuring accurate dilution of a sample.

As described herein, a fluid transfer device can affect a degree of dilution of a sample to provide accurate assay results. For example, a programmable fluid transfer device can be multi-headed to dilute or serially dilute samples as well as provide mixing of a sample and diluent. A fluid transfer device can also provide fluid movement in POC devices.

As described, the systems and devices herein can enable many features of the flexibility of laboratory setting in a POC environment. For example, samples can be collected and manipulated automatically in a table top size or smaller device or system. A common issue in POC devices is achieving different dilution ranges when conducting a plurality of assays, wherein the assays may have significantly different sensitivity or specificity. For example, there may be two analytes in a sample, but one analyte has a high concentration in the sample and the other analyte has a very low concentration. As provided, the systems and devices herein can dilute the sample to significantly different levels in order to detect both analytes. For example, if the analyte is in a high concentration, a sample can be serially diluted to the appropriate detection range and provided to a capture surface for detection. In the same system or device, a sample with an analyte in a low concentration may not need to be diluted. In this manner, the assay range of the POC devices and systems provided herein can be expanded from many of the current POC devices.

A fluid transfer device can be part of a system that is a bench-top instrument. The fluid transfer device can comprise a plurality of heads. Any number of heads as is necessary to detect a plurality of analytes in a sample is envisioned for a fluid transfer device of the invention. In an example, a fluid transfer device has about eight heads mounted in a line and separated by a distance. In an embodiment, the heads have a tapered nozzle that engages by press fitting with a variety of tips, such as assay unit or sample collection units as described herein. The tips can have a feature that enables them to be removed automatically by the instrument and disposed into in a housing of a device as described after use. In an embodiment, the assay tips are clear and transparent and can be similar to a cuvette within which an assay is run that can be detected by an optical detector such as a photomultiplier tube.

In an example, the programmable processor of an FS system can comprise instructions or commands and can operate a fluid transfer device according to the instructions to transfer liquid samples by either withdrawing (for drawing liquid in) or extending (for expelling liquid) a piston into a closed air space. Both the volume of air moved and the speed of movement can be precisely controlled, for example, by the programmable processor.

Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be performed in a similar fashion. Incubation of liquid samples and reagents with a capture surface on which is bound a capture reagent (for example an antibody) can be achieved by drawing the appropriate liquid into the tip and holding it there for a predetermined time. Removal of samples and reagents can be achieved by expelling the liquid into a reservoir or an absorbent pad in a device as described. Another reagent can then be drawn into the tip according to instructions or protocol from the programmable processor.

In an example as illustrated in FIG. 9, a liquid 1111 previously in a tip 1101 can leave a thin film 1113 within the tip 1101 when expelled. Therefore, a system can use the action of the leading (for example uppermost) portion of the next liquid 1112 to scour the previously present liquid 1111 from the tip 1101. The portion of the subsequent liquid contaminated with the liquid previously present 1113 can be held within the top of the tip 1101 where it does not continue to interact with the capture surface 1102. The capture surface 1102 can be in a defined area of the tip 1101 such that the previous liquid 1111 does not react with the capture surface 1102, for example as shown in FIG. 9, the capture surface 1102 occupies a defined portion of the cylindrical part of the tip 1101 not extending all the way up to the boss of the tip. In many instances, incubation time is short (for example 10 minutes) and separation of the contaminated zone of liquid is relatively large (>1 mm) so diffusion or the active components of the contaminated portion of liquid 1113 does not occur rapidly enough react with the capture surface 1102 during the incubation. For many high sensitivity assays, there is a requirement to remove one reagent or wash the capture surface (for example, a detector antibody which is labeled with the assay signal generator). In an example, a fluid transfer device of a system described herein can provide washing by adding further removal and aspiration cycles of fluid transfer, for example, using a wash reagent. In an example, four wash steps demonstrated that the unbound detector antibody in contact with the capture surface is reduced by a factor of better than $10^6$-fold. Any detector antibody non-specifically bound to the capture surface (highly undesirable) can also be removed during this wash process.

Extension of the range of an assay can be accomplished by dilution of the sample. In POC assay systems using disposable cartridges containing the diluent there is often a practical limit to the extent of dilution. For example, if a small blood sample is obtained by fingerstick (for example, about 20 microliters) is to be diluted and the maximum volume of diluent that can be placed in a tube is 250 microliters, the practical limit of dilution of the whole sample is about 10-fold. In an example herein, a system can aspirate a smaller volume of the sample (for example about 2 microliters) making the maximum dilution factor about 100-fold. For many assays, such dilution factors are acceptable but for an assay like that of CRP (as described in the examples herein) there is a need to dilute the sample much more. Separation-based ELISA assays can have an intrinsic limitation in the capacity of the capture surface to bind the analyte (for example equivalent to about a few hundred ng/ml in the diluted sample for a typical protein analyte). Some analytes are present in blood at hundreds of micrograms/ml. Even when diluted by 100-fold, the analyte concentration may be outside the range of calibration. In an exemplary embodiment of a system, device, and fluid transfer device herein, multiple dilutions can be achieved by performing multiple fluid transfers of the diluent into an individual assay unit or sample collection unit. For example, if the concentration of an analyte is very high in a sample as described above, the sample can be diluted multiple times until the concentration of the analyte is within an acceptable detection range. The systems and methods herein can provide accurate measurements or estimations of the dilutions in order to calculate the original concentration of the analyte.

In an embodiment, an FS system as described herein can move a liquid sample and move an assay unit. A system can comprise a heating block and a detector. In order to move a liquid sample, a system may provide aspiration-, syringe-, or pipette-type action. In an exemplary embodiment, a fluid transfer device for moving a liquid sample is a pipette and pipette head system. The number of pipette devices required by the system can be adjusted according to the type of analyte to be detected and the number of assays being run. The actions performed by the pipette system can be automated or operated manually by a user.

FIG. 10 demonstrates an example of a fluid transfer device 520 and system 500 as described herein. The fluid transfer device system can move eight different or identical volumes of liquid simultaneously using the eight different heads 522. For example, the cartridge (or device as described herein) 510 comprises eight assay units 501. Individual assay units 501 are configured according to the type of assay to be run within the unit 501. Individual assay units 501 may require a certain volume of sample. An individual head 522 can be used to distribute a proper amount of sample to an individual assay unit 501. In this example, each head 522 corresponds to an addressed individual assay unit 501.

The fluid transfer device mechanism 520 can also be used to distribute reagents from the reagent units. Different types of reagents include a conjugate solution, a wash solution, and a substrate solution. In an automated system, the stage 530 on which the device 510 sits can be moved to move the device 510 relative to the positioning of the assay units 501 and heads 522 and according to the steps necessary to complete an assay as demonstrated in FIG. 10. Alternatively, the heads 522 and tips 501 or the fluid transfer device 520 can be moved relative to the position of the device 510.

In some embodiments, a reagent is provided in dry form and rehydrated and/or dissolved during the assay. Dry forms include lyophilized materials and films coated on and adherent to surfaces.

A FS system can comprise a holder or engager for moving the assay units or tips. An engager may comprise a vacuum assembly or an assembly designed to fit snugly into a boss of an assay unit tip. For example, a means for moving the tips can be moved in a manner similar to the fluid transfer device heads. The device can also be moved on a stage according to the position of an engager or holder.

In an embodiment, an instrument for moving the tips is the same as an instrument for moving a volume of sample, such as a fluid transfer device as described herein. For example, a sample collection tip can be fit onto a pipette head according to the boss on the collection tip. The collection tip can then be used to distribute the liquid throughout the device and system. After the liquid has been distributed, the collection dip can be disposed, and the pipette head can be fit onto an assay unit according to the boss on the assay unit. The assay unit tip can then be moved from reagent unit to reagent unit, and reagents can be distributed to the assay unit according to the aspiration- or pipette-type action provided by the pipette head. The pipette head can also perform mixing within a collection tip, assay unit, or reagent unit by aspiration- or syringe-type action.

An FS system can comprise a heating block for heating the assay or assay unit and/or for control of the assay temperature. Heat can be used in the incubation step of an assay reaction to promote the reaction and shorten the duration necessary for the incubation step. A system can comprise a heating block configured to receive an assay unit. The heating block can be configured to receive a plurality of assay units from a device as described herein. For example, if 8 assays are desired to be run on a device, the heating block can be configured to receive 8 assay units. In some embodiments, assay units can be moved into thermal contact with a heating block using the means for moving the assay units. The heating can be performed by a heating means known in the art.

An exemplary FS system 600 as described herein is demonstrated in FIG. 11. The system 600 comprises a translational stage 630 onto which a device 610 (or cartridge in this example) is placed either manually or automatically or a combination of both. The system 600 also comprises a heating block 640 that can be aligned with the assay units 611 of the device 610. As shown in FIG. 11, the device 610 comprises a series of 8 assay units 611 and multiple corresponding reagent units 612, and the heating block 640 also comprises an area 641 for at least 8 units to be heated simultaneously. Each of the heating areas 641 can provide the same or different temperatures to each individual assay unit 611 according to the type of assay being run or the type of analyte being detected. The system 600 also comprises a detector (such as a photomultiplier tube) 650 for detection of a signal from an assay unit 611 representative of the detection of an analyte in a sample.

In an embodiment, a sensor is provided to locate an assay unit relative to a detector when an assay is detected.

In an embodiment, the detector is a reader assembly housing a detection assembly for detecting a signal produced by at least one assay on the device. The detection assembly may be above the device or at a different orientation in relation to the device based on, for example, the type of assay being performed and the detection mechanism being employed. The detection assembly can be moved into communication with the assay unit or the assay unit can be moved into communication with the detection assembly.

In many instances, an optical detector is provided and used as the detection device. Non-limiting examples include a photodiode, photomultiplier tube (PMT), photon counting detector, avalanche photo diode, or charge-coupled device (CCD). In some embodiments a pin diode may be used. In some embodiments a pin diode can be coupled to an amplifier to create a detection device with sensitivity comparable to a PMT. Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

A detector can also comprise a light source, such as a bulb or light emitting diode (LED). The light source can illuminate an assay in order to detect the results. For example, the assay can be a fluorescence assay or an absorbance assay, as are commonly used with nucleic acid assays. The detector can also comprise optics to deliver the light source to the assay, such as a lens or fiber optics.

In some embodiments, the detection system may comprise non-optical detectors or sensors for detecting a particular parameter of a subject. Such sensors may include temperature, conductivity, potentiometric signals, and amperometric signals, for compounds that are oxidized or reduced, for example, $O_2$, $H_2O_2$, and $I_2$, or oxidizable/reducible organic compounds.

A device and system may, after manufacturing, be shipped to the end user, together or individually. The device or system of the invention can be packaged with a user manual or instructions for use. In an embodiment, the system of the invention is generic to the type of assays run on different devices. Because components of the device can be modular, a user may only need one system and a variety of devices or assay units or reagent units to run a multitude of assays in a point-of-care environment. In this context, a system can be repeatedly used with multiple devices, and it may be necessary to have sensors on both the device and the system to detect such changes during shipping, for example. During shipping, pressure or temperature changes can impact the performance of a number of components of the present system, and as such a sensor located on either the device or system can relay these changes to, for example, the external device so that adjustments can be made during calibration or during data processing on the external device. For example, if the temperature of a fluidic device is changed to a certain level during shipping, a sensor located on the device could detect this change and convey this information to the system when the device is inserted into the system by the user. There may be an additional detection device in the system to perform these tasks, or such a device may be incorporated into another system component. In some embodiments information may be transmitted to either the system or the external device, such as the OS component of the invention, or a personal computer at a local installation. The transmission may comprise wired and/or wireless connections. Likewise, a sensor in the system can detect similar changes. In some embodiments, it may be desirable to have a sensor in the shipping packaging as well, either instead of in the system components or in addition thereto. For example, adverse conditions that would render an assay cartridge or system invalid that can be sensed can include exposure to a temperature higher than the maximum tolerable or breach of the cartridge integrity such as moisture penetration.

In an embodiment, the system comprises a communication assembly capable of transmitting and receiving information wirelessly from an external device, e.g., the OS component of the present invention. Such wireless communication can use, without limitation, Wifi, Bluetooth, Zigbee, satellite, cellular or RTM technology. Various communication methods can be used, such as a dial-up wired connection with a modem, a direct link such as a T1, ISDN, or cable line. In some embodiments, a wireless connection is established using exemplary wireless networks such as cellular, satellite, or pager networks, GPRS, or a local data transport system such as Ethernet or token ring over a local area network. In some embodiments the information is encrypted before it is transmitted. In some embodiments the communication assembly may contain a wireless infrared communication component for sending and receiving information. The system may include integrated graphic cards to facilitate display of information.

In some embodiments the communication assembly can have a memory or storage device, for example localized RAM, in which the information collected can be stored. A storage device may be required if information can not be transmitted at a given time due to, for example, a temporary inability to wirelessly connect to a network. The information can be associated with the device identifier in the storage device. In some embodiments the communication assembly can retry sending the stored information after a certain amount of time.

In some embodiments an external device, e.g., the OS portal component of the invention, communicates with the communication assembly within the reader assembly. An external device can wirelessly or physically communicate with the FS system, but can also communicate with a third party, including without limitation an individual, medical personnel, clinicians, laboratory personnel, or others in the health care industry.

An exemplary method and system is demonstrated in FIG. 12. In the example of FIG. 12, a patient delivers a blood sample to a device as described herein and then the device is inserted into a reader, wherein the reader can be desktop system capable of reading an analyte in the blood sample. The reader can be a system as described herein. The reader can be a bench-top or desk-top system and can be capable of reading a plurality of different devices as described herein. The reader or system is capable of carrying out a chemical reaction and detecting or reading the results of the chemical reaction. In the example in FIG. 12, a reader is automated according to a protocol sent from an external device (for example, a server comprising a user interface). A reader can also send the results of the detection of the chemical reaction to the server and user interface. In an exemplary system, the user (for example, medical personnel such as a physician or researcher) can view and analyze the results as well as decide or develop the protocol used to automate the system. Results can also be stored locally (on the reader) or on the server system. The server can also host patient records, a patient diary, and patient population databases.

FIG. 13 illustrates the process flow of building a system for assessing the medical condition of an individual according to an embodiment of the HS system disclosed herein. The patient inputs personal data and or measurements from a device, reader, and/or system as described herein into a database as may be present on a server, e.g., the OS component. The FS system can configured to display the personal data on a patient station display. In some embodiments, the FS station display is interactive and the individual can modify inputted data. The OS database contains data from other individuals being monitored by the Health Shield. The HS database can also include data from the other individuals collected historically from public or private institutions. In some embodiments, data from other individuals is internal data from a clinical study.

FIG. 13 also illustrates the flow of data from reader collection data that includes the data from the subject to a server that is connected over a public network. The server can manipulate the data or can just provide the data to a user station. The patient data may also be input to the server separately from the data pertaining to a medical condition that is stored in a database. FIG. 13 also demonstrates a user station display and the flow of information to medical personnel or a user. For example, using the exemplary process flow of FIG. 13, a patient at home can input a bodily fluid sample into a cartridge of the invention as described herein and place it in a system or reader as described herein. The patient can view the data from the system at a patient station display and/or modify or input new data into the process flow. The data from the patient can then travel over a public network, such as the internet, for example, in an encrypted format, to a server comprising a network interface and a processor, wherein the server is located at a central computing hub or in a clinical trial center. The server can use medical condition data to manipulate and understand the data from the user and then send the results over a public network as described to a user station. The user station can be in a medical office or laboratory and have a user station display to display the results of the assay and manipulation of the patient data to the medical personnel. In this example, the medical personnel can receive results and analysis of a sample from a patient from a test that the patient administered in an alternate location such as the patient's home. Other embodiments and example of systems and components of systems are described herein.

The OS component of the HS system can store protocols to be run on an FS system. The protocol can be transmitted to the communication assembly of a FS system after the OS has received an identifier indicating which device has been inserted in the FS system. In some embodiments a protocol can be dependent on a device identifier. In some embodiments the OS component stores more than one protocol for each field device. In other embodiments patient information on the external device includes more than one protocol. In some instances, the OS component stores mathematical algorithms to process a photon count sent from a communication assembly and in some embodiments to calculate the analyte concentration in a bodily fluid sample.

Having the FS and OS components of the systems integrated over a network connection provides a number of advantages. For example, the information can be transmitted from the Operating System back to not only the FS reader assembly, but to other parties or other external devices, for example without limitation, a PDA or cell phone. Such communication can be accomplished via a wireless network as disclosed herein. In some embodiments a calculated analyte concentration or other patient information can be sent to, for example but not limited to, medical personnel or the patient. In a non-limiting example, a quarantine notice can be sent to both the infected individual and to medical personnel who can put into place the quarantine.

In some embodiments, the data generated with the use of the subject devices and systems can be utilized for performing a trend analysis on the concentration of an analyte in a subject.

Another advantage as described herein is that assay results can be substantially immediately communicated to any third party who may benefit from obtaining the results. For example, once the analyte concentration is determined at the Operating System component, it can be transmitted to a patient or medical personnel who may need to take further action. This might include identification of an index case. The communication step to a third party can be performed wirelessly as described herein, and by transmitting the data to a third party's hand held device, the third party can be notified of the assay results virtually anytime and anywhere. Thus, in a time-sensitive scenario, a patient may be contacted immediately anywhere if urgent medical action may be required.

By detecting a device based on an identifier associated with a fluidic device after it is inserted in the FS system, the system allows for fluidic device-specific protocols to be downloaded from an external device, e.g., the OS component, and run. In some embodiments the OS component can store a plurality of protocols associated with the system or associated with a particular individual or group of individuals. For example, when the identifier is transmitted to the OS component, software on the OS component, such as a database, can use the identifier to identify protocols stored in the database associated with the identifier. If only one protocol is associated with the identifier, for example, the database can select the protocol and software on the external device can then transmit the protocol to the communication assembly of the system. The ability to use protocols specifically associated with a device allows for any component of a device of the invention to be used with a single system, and thus virtually any analyte of interest can be detected with a single system.

In some embodiments multiple protocols may be associated with a single identifier. For example, if it is beneficial to detect from the same individual an analyte once a week, and another analyte twice a week, protocols on the external device associated with the identifier can also each be associated with a different day of the week, so that when the identifier is detected, the software on the external device can select a specific protocol that is associated with the day of the week. Such optimized testing can reduce the cost of the HS system by only performing assays according to an optimized schedule.

In some embodiments, an individual is provided with a plurality of devices to use to detect a variety of analytes. The individual may, for example, use different devices on different days of the week. In some embodiments the software on the Operating System associating the identifier with a protocol may include a process to compare the current day with the day the device is to be used based on a clinical trial for example. If for example, the two days of the week are not identical, the Operating System can wirelessly send notification to the subject using any of the methods described herein or known in the art to notify them that an incorrect device is in the system and also of the correct device to use that day. This example is only illustrative and can easily be extended to, for example, notifying a subject that a device is not being used at the correct time of day.

The system can also use a networking method of assessing the medical condition of a subject. A system of communicating information may or may not include a reader for reading subject data. For example, if biomarker data is acquired by a microfluidic point-of-care device, the values assigned to different individual biomarkers may be read by the device itself or a separate device. Another example of a reader would be a bar code system to scan in subject data that has been entered in an electronic medical record or a physician chart. A further example of a reader would consist of an electronic patient record database from which subject data could be directly obtained via the communications network. In this way, the efficacy of particular drugs can be determined in real-time, thereby helping to determine whether a different mitigation strategy should be put into place.

(b) Field System Methods

The FS devices described herein provide an effective means for real-time detection of analytes present in a bodily fluid from a subject. Accordingly, in an embodiment, the present invention makes use of a method of detecting an analyte in a bodily fluid sample comprising providing a blood sample to a FS device, allowing the sample to react within at least one assay unit of the device, and detecting the detectable signal generated from the analyte in the blood sample.

FIG. 5 demonstrates an exemplary embodiment of a FS device comprising at least one assay unit and at least one reagent unit. The assay units (for example, designated as sample tips and calibrator tips in FIG. 5) can contain a capture surface and the reagent units can contain items such as conjugates, washes, and substrates. The device exemplified in FIG. 5 also comprises a whole blood sample collection tip, a plasma sample collection tip, a blood input well, a beads well or plasma separation well, a tip touch-off or blotting pad, a dilution well, a diluted plasma sample well or plasma diluent well, collection tip disposal areas.

In an embodiment, a method comprises performing an Enzyme-linked Immunosorbent Assay (ELISA). In an example, a sample is provided to a sample collection unit of a device as described herein. The device is then inserted into a reader system, wherein reader system detects the type of cartridge or device that is inserted. The reader system can then communicate with an external device, e.g., the OS component of the HS system, to receive a set of instructions or protocol that allows the reader system to perform the desired assay or assays of the cartridge. The protocol can be sent to the programmable processor of a fluid transfer device of the reader system. In an example, the fluid transfer device engages a sample tip of the cartridge and picks up a certain volume of the sample from the sample collection unit and moves it to a pretreatment unit where red blood cells are removed. The plasma of the sample can then be aspirated into a plasma tip or any assay tip by the fluid transfer device according to the protocol. The tip containing the plasma can then pick up a diluent to dilute the sample as is necessary for the assays to be run. Many different dilutions can be carried by using serial dilutions of the sample. For example, each assay tip or assay unit can contain a sample of a different dilution. After the sample is aspirated into an assay unit by the fluid transfer device, the assay unit can then be incubated with the sample to allow any target analyte present to attach to the capture surface. Incubations as described in this example can be at the system or room temperature for any period of time, for example 10 minutes, or can be in a heating device of the system as described herein. The assay unit can engage a reagent unit addressed with a reagent corresponding to the assay to be run in each individual assay unit that have a capture surface for that assay. In this example, the first reagent is a detector solution of an ELISA, for example, comprising a detector antibody such as a labeled anti-protein antibody different from that of the capture surface. The detector solution is then aspirated out of the assay unit and then a wash solution can be aspirated into the assay unit to remove any excess detector solution. Multiple wash steps can be used. The final reagent to be added is an enzymatic substrate which causes the bound detector solution to chemiluminesce. In some embodiments, the results of the assay are read by a detector of the system while the tip still contains the assay product. In other embodiments, the enzymatic substrate is expelled from the assay unit and the results of the assay are read by a detector of the system. At each step as described, incubations can occur as necessary as described herein. In this example, the entire process after putting the cartridge into the system is automated and carried out by a protocol or set of instructions to the programmable system.

One exemplary method proceeds with delivering a blood sample into the blood input well. The sample can then be picked up by a collection tip and inserted into the plasma separation well. Alternatively, the blood can be deposited directly into a well containing a blood separator. For example, plasma separation can be carried out by a variety of methods as described herein. In this example, plasma separation proceeds using magnetizable beads and antibodies to remove the components of the blood that are not plasma. The plasma can then be carried by a plasma collection tip as to not contaminate the sample with the whole blood collection tip. In this example, the plasma collection tip can pick-up a predetermined amount of diluent and dilute the plasma sample. The diluted plasma sample is then distributed to the assay units (sample tips) to bind to a capture surface. The assay units can be incubated to allow for a capture reaction to be carried out. The assay unit then can be used to collect a conjugate to bind with the reaction in the assay unit. The conjugate can comprise an entity that allows for the detection of an analyte of interest by a detector, such as an optical detector. Once conjugate has been added to the assay unit, the reaction can be incubated. In an exemplary method using an exemplary device of FIG. 5, a reagent unit containing a wash for the conjugate is then accessed by the assay unit (sample tip) to remove any excess conjugate that can interfere with any analyte detection. After washing away excess conjugate, a substrate can be added to the assay unit for detection. In addition, in the example of FIG. 5 and this method, a calibrator tip assay unit can be used to carry out all of the methods described in this paragraph except the collection and distribution of the sample. Detection and measurements using the calibrator tip assay unit can be used to calibrate the detection and measurements of the analyte from the sample. Other processes and methods similar to those used in this example are described hereinafter.

Any bodily fluids suspected to contain an analyte of interest can be used in conjunction with the system or devices of the invention. For example, the input well or sample collection unit in the example of FIG. 5 can collect of contain any type of commonly employed bodily fluids that include, but are not limited to blood, serum, saliva, urine, gastric and digestive fluid, tears, stool, semen, vaginal fluid, interstitial fluids derived from tumorous tissue liquids extracted from tissue samples, and cerebrospinal fluid. In an embodiment, the bodily fluid is blood and can be obtained by a fingerstick. In an embodiment, the bodily fluid sample is a blood plasma sample. In another embodiment, the bodily fluid sample is an unmodified blood sample.

A bodily fluid may be drawn from a patient and distributed to the device in a variety of ways including, but not limited to, lancing, injection, or pipetting. In one embodiment, a lancet punctures the skin and delivers the sample into the device using, for example, gravity, capillary action, aspiration, or vacuum force. The lancet may be onboard the device, or part of a reader assembly, or a stand alone component. Where needed, the lancet may be activated by a variety of mechanical, electrical, electromechanical, or any other known activation mechanism or any combination of such methods. In another embodiment where no active mechanism is required, an individual can simply provide a bodily fluid to the device, as could occur, for example, with a saliva sample. The collected fluid can be placed into a collection well or unit of the device. In some embodiments, there is a user activated lancet and sample collecting capillary within the device.

The volume of bodily fluid to be used with a method or device described herein is generally less than about 500 microliters, further can be between about 1 to 100 microliters. Where desired, a sample of 1 to 50 microliters, 1 to 40 microliters, 1 to 30 microliters, 1 to 10 microliters or even 1 to 3 microliters can be used for detecting an analyte using the subject fluidic device. In an embodiment, the sample is 20 microliters. A slight excess of sample may be collected over that required for the assay, e.g., 1%, 2%, 3%, 4%, 5%, 6%, 7%, 8%, 9%, 10%, 12%, 15%, 20%, 25%, 30%, 35%, 40%, 45%, 50%, 55%, 60%, 65%, 70%, 75%, 80%, 85%, 95%, or 100% extra. In some embodiments, more than 100% extra sample volume is collected. For example, when the sample volume required for the assays is, for example, 15 uL, the system may use a volume in the range 16-50 uL.

In an embodiment, the volume of bodily fluid used for detecting an analyte in the field is one drop of fluid. For example, one drop of blood from a pricked finger can provide the sample of bodily fluid to be analyzed according to the invention.

In some embodiments, the bodily fluids are used directly for detecting the analytes present in the bodily fluid without further processing. Where desired, however, the bodily fluids can be pre-treated before performing the analysis with a device. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions or using nucleic acid binding resins following the accompanying instructions provided by manufacturers. For blood or plasma samples, the sample may be mixed with an anticoagulant such as EDTA or heparin. These agents may conveniently be added from dried form. Where the analyte is a molecule present on or within a cell, extraction can be performed using lysing agents including but not limited to anticoagulants such as EDTA or heparin, a denaturing detergent such as SDS or non-denaturing detergent such as Thesit®, sodium deoxycholate, triton X-100, and tween-20.

In an embodiment, a user collects a sample of bodily fluid with a syringe. The sample can enter the syringe through a capillary tube. In an embodiment measuring an analyte in a blood sample, the subject performs a fingerstick and touches the outer end of the glass capillary to the blood so that blood is drawn by capillary action and fills the capillary with a volume. In some instances, the sample volume is known. In some embodiments, the sample volume is in the range of about 5-20 microliters or other volume ranges as described herein.

In another embodiment, a method and system is provided to obtain a plasma sample substantially free of red blood cells from a blood sample. When conducting an assay, the analytes are often contained in the blood plasma, and the red blood cells can interfere with a reaction.

Often, when measuring a blood sample, the analytes of interest are in the serum or plasma. For clinical purposes, the final reported concentration of multiple blood tests often needs to relate to the concentration of blood serum or blood plasma in a diluted sample. In many cases, blood serum or blood plasma is the test medium of choice in the lab. Two operations may be necessary prior to running an assay, dilution and red blood cell removal. Blood samples vary significantly in the proportion of the sample volume occupied by red cells (the hematocrit which varies from about 20-60%). Furthermore, in a point-of-care environment when assay systems are operated by non-expert personnel, e.g., a device deployed in the home of an individual being monitored by the Health Shield, the volume of sample obtained may not be that which is intended. If a change in volume is not recognized, it can lead to error in the reported analyte concentrations.

In related but separate embodiment, the present invention uses a method of retrieving plasma from a blood sample comprising mixing a blood sample in the presence of magnetizable particles in a sample collection unit, wherein the magnetizable particles comprise an antibody capture surface for binding to non-plasma portions of the blood sample, and applying a magnetic field above a plasma collection area to the mixed blood sample to effect suspension of the non-plasma portions of the blood sample on top of the plasma collection area, thereby retrieving the plasma from a blood sample.

In order to process blood samples, the device or system of the invention may include a magnetic reagent or object which binds to red cells and enables magnetic removal of red cells from plasma. The reagent can be provided in lyophilized form but also can be present as a liquid dispersion. A reagent comprised of magnetizable particles (for example, about 1 micrometer in size) can be coated with an antibody to a red cell antigen or to some adaptor molecule. In some embodiments, the reagent also contains unbound antibodies to red cell surface antigens, which may be unlabeled or labeled with an adaptor moiety (such as biotin, digoxigenin, or fluorescein). In an embodiment analyzing a blood sample, the red blood cells in a diluted sample co-agglutinate with the magnetizable particles aided by a solution phase antibody. Alternatively, a lectin that recognizes a red cell surface carbohydrate can be used as a co-agglutination agent. Sometimes, combinations of red cell agglutinating agents are used. Alternatively, a device of the invention can comprise a blood filter, such as a pad of glass fiber, to aid in the separation of red blood cells from a sample.

When blood is mixed with a magnetic reagent, a co-agglutination can occur in which many, if not all, of the red cells form a mixed agglutinate with the magnetizable particles. The reagent dissolution and mixing process is driven by repeated aspiration using a tip or collection tip of the invention or a pipette-like tip. After the magnetizable mass has formed, the mass can be separated from the blood plasma by use of a magnet to hold the mass in place as plasma is allowed to exit the tip. In an embodiment, the plasma exits the tip by gravity in a vertical orientation, while the magnet holds the mass in place. In another embodiment, the plasma exits the tip by vacuum or pressure means, while the mass is held within the tip. The plasma can be deposited into a well, another collection tip, or assay unit as described herein.

An example of a plasma separation method of the invention is demonstrated in FIGS. 14A through 14E. In FIG. 14A, a whole blood sample 901 has been aspirated into a sample tip 910 as described herein, for example in the amount of about 20 microliters. The whole blood sample 901 is then deposited into a separation well 920 (for example, a well containing magnetic beads or particles) of an example device. FIG. 14B illustrates a method of suspending and mixing a magnetic reagent in the whole blood sample 902 in a separation well (for example, magnetic bead particles and free binding molecules). FIG. 14C demonstrates a 10 microliter air slug 930 that can be used to prevent loss from the tip 910. The mixed whole blood sample and magnetic reagent 902 are incubated for several seconds (for example, 60 to 180 seconds) to allow an agglutination reaction to occur.

FIG. 14D demonstrates the application of a magnetic field 940 to the whole blood cell and magnetic reagent mixture 902. The magnetic field 940 can be applied by a magnetic collar 942 that is incorporated with a system or with any magnetic means known in the art. The magnetic field 940 attracts any particles that have adhered to the magnetic reagent. In this way, the plasma 903, which does not adhere with the magnetic reagent, can be separated from non-plasma portions of a whole blood sample.

FIG. 14E demonstrates a method of distributing a blood plasma sample 903, as separated by the magnetic reagent described herein, into a well or unit 950 of a device as described herein. The blood plasma sample 903 can also be distributed to a collection tip or assay unit, as well as any other sort of assay device as obvious to one skilled in the art. In FIG. 14E, the magnetic field 940 is shown to move with the tip 910 distributing the blood plasma sample 903. In this example, 5 to 8 microliters of plasma have been removed from a 20 microliter whole blood sample. 1 to 99% of a whole blood sample can be plasma separated using a method described herein. In an embodiment, 25 to 60% of the volume of the whole blood sample is plasma that can be separated.

Other exemplary steps of a method as described can be completed. In order to move the blood plasma sample to another well or unit, a capillary plasma collection tip (which can be operated by a robotic system or any other system of the invention) collects the blood plasma sample by capillary and aspiration force. Another step can comprise distributing the plasma sample in a diluent, and the sample can then be diluted by the diluent. The diluted blood plasma sample can then be collected by the collection tip in a predetermined volume. The diluted blood plasma sample can then be mixed and distributed into a well or unit of a device to be distributed to one or a plurality of assay units of a device of the invention. The sample can also be distributed into any other type of device, such as a microtiter plate, as would be obvious to those skilled in the art.

The example process demonstrated in FIGS. 14A through 14E can be used with other devices and systems, such as any of the FS devices described herein. For example, a fluid transfer tip can contain the agglutinated mass and the plasma could be deposited into a microtiter plate. Other devices and systems as would be obvious to those skilled in the art could be utilized to execute the example blood plasma separation as disclosed herein.

The sample of bodily fluid can also be diluted in a variety of other manners, such as using a sample collection device capable of dilution. The housing of the sample collection device can comprise a tube. In the tube, two moveable seals can contain a volume of a diluent. In a preferable embodiment, the volume of the diluent is predetermined, e.g., in about the range of 50 microliters to 1 milliliter, preferably in the range of about 100 microliters to 500 microliters.

In one embodiment, the FS devices of the invention are used in a method for automated detection of a plurality of analytes in a bodily fluid sample comprising: providing the bodily fluid sample to a fluidic device, wherein the fluidic device comprises: a sample collection unit configured to contain the bodily fluid sample; an array of assay units, wherein an individual assay unit of said array of assay units is configured to run a chemical reaction that yields a signal indicative of an individual analyte of said plurality of analytes being detected; and an array of reagent units, wherein an individual reagent unit of said array of reagent units contains a reagent. The method can also comprise engaging the individual assay unit using a fluid transfer device. Continuing the method, the bodily fluid sample can be transferred from the sample collection unit to the individual assay unit using the fluid transfer device and the reagent from the individual reagent unit can be transferred to the individual assay unit, thereby reacting the reagent with the bodily fluid sample to yield the signal indicative of the individual analyte of the plurality of analytes being detected. In some embodiments, the fluid transfer device comprises a plurality of heads, wherein an individual head of the plurality of heads is configured to engage the individual assay unit; and wherein said fluid transfer device comprises a programmable processor configured to direct fluid transfer of the bodily fluid sample from the sample collection unit and the reagent from the individual reagent unit into the individual assay unit.

In some instances, instructions are provided to the programmable processor, for example, by a user, an individual, or the manufacturer. Instructions can be provided from an external device, such as a personal electronic device or, preferably, from the OS component of the Health Shield system. The instructions can direct the step of transferring the bodily fluid sample to the individual assay unit. For example, the step of transferring the bodily fluid sample can affect a degree of dilution of the bodily fluid sample in the individual assay unit to bring the signal indicative the individual analyte of the plurality of analytes being detected within a detectable range. In some examples, the degree of dilution of the bodily fluid sample brings the signals indicative of the at least two individual analytes within a detectable range as described herein.

Pattern recognition techniques can be used to determine if the detection of an analyte or a plurality of analytes by a method as described herein is within or outside a certain range. For example, detectable signals outside the reportable range can be rejected. The certain range can be established during calibration of a fluidic device the reagent and assay units. For example, the range is established when a device is assembled in a just-in-time fashion.

In some instances, if the detectable signal of an analyte as detected with a lower dilution factor or degree of dilution exceeds that for a higher dilution factor, the lower dilution result can be identified as insufficient for computing a quantitative result. In most instances, concentrations of an analyte in a sample as derived from signals from samples with different degrees of dilution get lower as the degree of dilution becomes greater. If this does happen, an assay result can be verified. The FS devices described herein provide the flexibility of quality control rules such as those described that many POC devices cannot offer. The FS devices described provide many of the quality control features as would be expected in a laboratory setting.

In an embodiment, a sample is diluted in a ratio that is satisfactory for both high sensitivity and low sensitivity assays. For example, a dilution ratio of sample to diluent can be in the range of about 1:10,000-1:1. The device can enable a sample to be diluted into separate locations or extents. The device can also enable the sample to be subject to serial dilutions. Combining the use of serial dilution with the wide dynamic range of detection of luminescence with a PMT provides for quantitation of analytes in a range of about 1000,000,000 fold. For example, for protein biomarkers the range can be from about 1 pg/mL to 1000 ug/mL.

In embodiments, a sample containing an analyte for detection can be moved from a first location to a second location by aspiration-, syringe-, or pipette-type action. The sample can be drawn into the reaction tip by capillary action or reduced atmospheric pressure. In some embodiments, the sample is moved to many locations, including an array of assay units of a device of the invention and different wells in the housing of a device of the invention. The process of moving the sample can be automated by a system of the invention, as described herein.

The assay units and/or collection tips containing the sample can also be moved from a first location to a second location. The process of moving an assay unit or a collection tip can be automated and carried out by a user-defined protocol.

In an embodiment, the assay units are moved to collect reagent from a reagent unit of the invention. In many embodiments, movement of an assay unit is automated. Aspiration-, syringe-, or pipette-type action can be used to collect reagent from a reagent unit into an assay unit.

Once a sample has been added to an assay unit that comprises a capture surface, the entire unit can be incubated for a period of time to allow for a reaction between the sample and the capture surface of the assay unit. The amount of time needed to incubate the reaction is often dependent on the type of assay being run. The process can be automated by a system of the invention. In an embodiment, the incubation time is between 30 seconds and 60 minutes. In another embodiment, the incubation time is 10 minutes.

An assay unit can also be incubated at an elevated temperature. In an embodiment, the assay unit is incubated at temperature in a range of about 20 to 70 degrees Celsius. The assay unit can be inserted into a heating block to elevate the temperature of the assay unit and/or the contents of the assay unit.

In an embodiment of a FS method of the invention, a conjugate is added to the assay unit after a sample has been added to the unit. The conjugate can contain a molecule for labeling an analyte captured by a capture surface in the assay unit. Examples of conjugates and capture surface are described hereinafter. The conjugate can be a reagent contained within a reagent unit. The conjugate can be distributed to the assay unit by aspiration-, syringe-, or pipette-type action. Once a conjugate has been distributed to an assay unit, the assay unit can be incubated to allow the conjugate to react with an analyte within the assay unit. The incubation time can be determined by the type of assay or the analyte to be detected. The incubation temperature can be any temperature appropriate for the reaction.

In another embodiment, a method of calibrating a device for automated detection of an analyte in a bodily fluid sample is used with the FS device of the invention. A device can comprise an array of addressable assay units configured to run a chemical reaction that yields a detectable signal indicative of the presence or absence of the analyte, and an array of addressable reagent units, each of which is addressed to correspond to one or more addressable assay units in said device, such that individual reagent units are calibrated in reference to the corresponding assay unit(s) incorporated into a complete assay device. The final multiplexed device can then be assembled using the calibrated components, making the device, and a method and system that utilize the device, modular components. In some embodiments, calibration for multiplexed assays is performed as above using all the assays simultaneously in a multiplexed assay device.

Calibration can be pre-established by measuring the performance of assay reagents, such as conjugates, before the assay units and reagent unit are assembled in a device of the invention. Calibration information and algorithms can be stored on a server linked wirelessly to the assay system. Calibration can be performed in advance or retrospectively by assays performed in replicate systems at a separate location or by using information obtained when the assay system is used.

In an aspect, a control material can be used in a device or system to measure or verify the extent of dilution of a bodily fluid sample. For example, another issue of solid-phase based assays such as ELISA is that an assay uses a solid-phase reagent that is difficult to quality control without destruction of its function. The systems and methods herein provide methods to determine the dilution achieved in a POC system using a disposable device with automated mixing and/or dilution.

In an embodiment, a method provides retrospective analysis, for example, by use of the OS component to analyze data in real time prior to reporting results. For example, an assay can be performed and a control assay can be run in parallel to the assay. The control assay provides a measurement of an expected dilution of the sample. In some examples, the control assay can verify the dilution of the sample and thus, dilution of a sample for the assay or plurality of assays run within the system can be considered accurate.

A method of measuring a volume of a liquid sample can comprise: reacting a known quantity of a control analyte in a liquid sample with a reagent to yield a detectable signal indicative of the control analyte; and comparing an intensity of said detectable signal with an expected intensity of said detectable signal, wherein the expected intensity of said signal is indicative of an expected volume of the liquid sample, and wherein said comparison provides a measurement of said volume of said liquid sample being measured. In many instances, the control analyte is not present in said liquid sample in a detectable amount.

In an embodiment, a method can further comprise verifying the volume of said liquid sample when the measurement of the volume of the sample is within about 50% of the expected volume of the liquid sample.

For example, a method utilized an FS device described herein can further comprise: reacting a bodily fluid sample containing a target analyte with a reagent to yield a detectable signal indicative of the target analyte; and measuring the quantity of the target analyte in the bodily fluid sample using an intensity of said detectable signal indicative of the target analyte and the measurement of said volume of said liquid sample. The liquid sample and the bodily fluid sample can be the same sample. In some embodiments, the control analyte does not react with the target analyte in the bodily fluid sample, therefore providing not interacting with detection of the target analyte.

In some instances, the liquid sample (to be used as a control) and the bodily fluid sample are different liquid samples containing the analyte of interest. For example, a control liquid, such as a control solution containing a known control analyte level. This type of control verifies that the assay chemistry is operating properly.

A control analyte used to verify correct dilution of a sample can be, without limitation, fluorescein-labeled albumin, fluorescein labeled IgG, anti-fluorescein, anti-digoxigenin, digoxigenin-labeled albumin, digoxigenin-labeled IgG, biotinylated proteins, non-human IgG. Other exemplary control analytes can be obvious to one skilled in the art. In an embodiment, the control analyte does not occur in a human bodily fluid sample. In some embodiments, the control analyte is added as a liquid or in dried form to the sample.

In a POC system as described herein configured to detect a plurality of analytes within a sample, the system can have capabilities to dilute and mix liquids. In many instances, an automated system or user can use a control assay to measure the dilution actually achieved and factor that dilution into the system calibration. For example, a control analyte can be never found in the sample of interest and dried into a reagent unit. The quantity of the dried control analyte can be known and mixed with a sample in the reagent unit. The concentration of analyte can be measured to indicate the volume of sample and any dilution performed on the sample.

Examples of control analytes for an immunoassay include, but are not limited to: fluorescein-labeled protein, biotinylated protein, fluorescein-labeled, Axlexa™-labeled, Rhodamine-labeled, Texas Red-labeled, immunoglobulin.

For example the labeling can be achieved by having at least two haptens linked per molecule of protein. In some embodiments, 1-20 haptens are linked per molecule of protein. In a further embodiment, 4-10 haptens are linked per molecule of protein. Many proteins have large numbers of free amino groups to which the haptens can be attached. In many instances, hapten-modified proteins are stable and soluble. Also, haptens such as fluorescein and Texas Red are sufficiently large and rigid that antibodies with high affinity can be made (for example, a hapten is large enough to fill the antibody binding site). In some embodiments, haptens can be attached to proteins using reagents, such as fluorescein isothocyanate, and fluorescein carboxylic acid NHS ester to create control analytes in which the part recognized by the assay system is the hapten.

In some embodiments, a method utilizes dried control analyte. In some examples, a dried control analyte avoids dilution of the sample and can make the control analyte more stable. Dried control analyte can be formulated so it dissolves rapidly and/or completely on exposure to a liquid sample. In some embodiments, a control analyte can be an analyte for which antibodies with high affinity. In some instances, a control analyte can be an analyte that has no cross reaction with any endogenous sample component. Additionally, for example, the analyte can be inexpensive and/or easy to make. In some embodiments, the control analyte is stable over the lifetime of the device or system described herein. Exemplary carriers used to create analytes with covalently linked haptens include proteins such as, but not limited to: albumin, IgG, and casein. Exemplary polymer carriers used to create novel analytes with covalently linked haptens include, but are not limited to: Dextran, Poly-vinylpyrolidone. Exemplary excipients used to formulate and stabilize control analytes include, but are not limited to: sucrose, salts, and buffers (such as sodium phosphate and tris chloride).

A control analyte and method as described herein can be used in a variety of ways including the examples described herein. For example, a method can measure a volume of a sample. In some embodiments, a method measures dilution or a dilution factor or a degree of dilution of a sample. In some instances, a method provides a concentration of the control analyte in a sample. In a system or device described herein to detect a plurality of analytes, measurements from a method herein using a control analyte can be used to verify or describe measurements of target analytes. For example, a fluid transfer device with multiple heads may be used to distribute liquid into a plurality of assay units, including a control unit. In some instances, it can be assumed that liquid amount distributed into the plurality of units is the same or similar between the individual units. In some embodiments, a method described herein with a control analyte can be used to verify that the correct volume of sample has been collected or utilized within a device or system. In another embodiment, a method verifies the correct volume of diluent has been provided to the sample. Also, the dilution factor or degree of dilution can also be verified. In yet another embodiment, a method with a control analyte verifies the correct volume of diluted sample has been distributed to the plurality of units.

FIG. 15 demonstrates an exemplary method of a control assay as described herein comprising a known quantity of control analyte. A unit 1010 before assembly into a cartridge can be filled with a solution 1001 comprising a known mass of control analyte 1002. The liquid of the solution can be dried to leave the control analyte 1002 in the unit 1010. The unit 1010 can then be inserted into a device and transported for use. When the unit 1010 is used and receives a sample or diluent 1003, the sample 1003 can be delivered in an expected volume and mixed with the dried control analyte 1002 within the unit 1010 to create a control solution 1004 with an expected concentration. The control solution 1004 can be optionally diluted. In an embodiment, the control analyte 1002 can be detected in the same manner as a target analyte in the device. The control analyte concentration in the control solution 1004 is measured. The measurement of the concentration can be used to calculate the volume of the sample 1003 added to create the control solution 1004. In this manner, a user can compare the measured volume of the sample 1003 with the expected volume of the sample 1003.

In an example, red blood cells can be removed from a blood sample. However, if some red blood cells remain, or red blood cells are not removed from a blood sample, a method with a control analyte can be used to correct for effects from red blood cells in the blood sample. Because hematocrit can vary significantly (for example, from 20-60% of the total volume of a sample), the quantity of an analyte in a fixed or expected volume (v) of blood can be a function of the hematocrit (H expressed here as a decimal fraction). For example, the quantity of analyte with a concentration C in plasma is $C*v*(1-H)$. Thus the quantity for a sample with hematocrit 0.3 is 1.4 times that for a sample with hematocrit 0.5. In an exemplary embodiment, undiluted blood can be dispensed into a device as described and red cells can be removed. A control analyte concentration in the plasma fraction can then be measured to estimate the volume of sample plasma and determine the hematocrit.

In some embodiments, unbound conjugate may need to be washed from a reaction site to prevent unbound conjugates from producing inaccurate detection. The limiting step of many immunoassays is a washing step. The compromise of minimum carryover and high sensitivity is dependent on the wash removal of unbound conjugate. The wash step can be severely limited in a microtiter plate format due to the difficulty of removing the wash liquid from a well (for example, by automatic means). An assay unit device can have a number of advantages in the way liquids are handled. An advantage may be an improvement in the signal to noise ratio of an assay.

Removal of the conjugate can be difficult to if conjugates are sticking to the edges of the assay units of a device if, for example, there is not an excess of a wash solution. A wash of the conjugate can occur by either pushing the wash solution from above or drawing the wash solution up and expelling the liquid similar to the loading of the sample. The washing can be repeated as many times as necessary.

When using a wash buffer in an assay, the device can store the wash buffer in reagent units and the assay unit can be brought into fluid communication with the wash. In an embodiment, the wash reagent is able to remove unbound reagent from the assay units by about 99, 99.9, or 99.999% by washing. In general, a high washing efficiency resulting in a high degree of reduction of undesired background signals is preferred. Washing efficiency is typically defined by the ratio of signal from a given assay to the total amount of signal generated by an assay with no wash step and can be readily determined by routine experimentation. It can be generally preferred to increase the volume of washing solution and time of incubation but without sacrificing the signals from a given assay. In some embodiments, washing is performed with about 50 ul to about 5000 ul of washing buffer, preferably between about 50 ul to about 500 ul washing buffer, for about 10 to about 300 seconds.

Additionally, it can be advantageous to use several cycles of small volumes of wash solution which are separated by periods of time where no wash solution is used. This sequence allows for diffusive washing, where labeled antibodies diffuse over time into the bulk wash solution from protected parts of the assay unit such as the edges or surfaces where it is loosely bound and can then be removed when the wash solution is moved from the reaction site.

In many embodiments, the last step is to distribute an enzymatic substrate to detect the conjugate by optical or electrical means. Examples of substrates are described hereinafter.

For example, the reagent in the individual reagent unit of a device herein can be an enzyme substrate for an immunoassay. In another embodiment, the step of transferring the substrate reagent from the individual reagent unit can be repeated after a reaction at the capture site. For example, enzymatic substrate is transferred to a reaction site and incubated. After measuring the assay signal produced, used substrate can be removed and replaced with fresh substrate and the assay signal remeasured. A signal indicative of the individual analyte being can be detected using a system as described herein from both the first and the second application of substrate. The second substrate is usually the same as the original substrate. In an embodiment, the second substrate is transferred to a reaction site from a second reagent unit of a device herein. In another embodiment, the second substrate is transferred to a reaction site from the same reagent unit as the original substrate. Transferring a second substrate thereby creates a second reaction to yield a second signal indicative of the individual analyte. The intensity of the original signal and a second intensity of the second signal can be compared to calculate the final intensity of the signal indicative of the individual analyte and whether the assay was properly conducted.

In an embodiment, the intensities of the multiple signals can be used for quality control of an assay. For example, if the signals differ by 20%, 30%, 40%, 50%, 60%, 70%, 80%, 90%, 100% or more, the assay results may be disregarded.

In an embodiment, a method as described herein comprises re-loading sample and or detector-conjugate (enzyme-labeled antibody) and or the enzyme substrate and sample to rectify or confirm an assay signal or to use as an internal control. For example, re-use of an assay tip or unit as described can be provided to verify function and/or to add further sample or control materials obtain a second signal.

In some instances, a method of re-loading a substrate to an enzyme unit is enabled by the ability of a system as described herein to automatically to transfer liquid samples and reagents into the assay units. Some assays do not require the system to deliver a result immediately or on a schedule, therefore, a control method as described offers an opportunity to possibly enhance the reliability of the results. A response observed following iterations of adding an enzyme substrate can be used to verify the initial response or to calculate spike recovery.

Experiments have shown that by adding a second aliquot of enzyme substrate to an assay unit, the reproducibility of results can be maintained. In some embodiments, a control method provides replicate analyses using an assay unit gave a response significantly lower than that expected.

With any control methods described herein, there are numerous possible errors that can be accounted for or postulated from executing a control method. Exemplary assay errors include, but are not limited to, improper manufacturing of an assay unit or device, improper aspiration of a sample and/or one or more reagents, an assay unit is not positioned properly relative to the photomultiplier during detection, and a missing assay unit in the device or system.

In some embodiments a method of automatically monitoring an individual's compliance with a medical treatment using the subject devices or systems is provided using the FS devices. The method comprises the steps of allowing a sample of bodily fluid to react with assay reagents in a device to yield a detectable signal indicative of the presence of an analyte in said sample; detecting said signal with said device; comparing said signal with a known profile associated with said medical treatment to determine if the individual is compliant or noncompliant with said medical treatment; and notifying the individual or associated individuals, e.g., local health care agents, of said compliance or noncompliance. This can be important for the HS systems of the invention because the mitigation policies will not be as effective if the recommended treatments are not followed. In some embodiments, noncompliance events are reported to the OS systems. The model can be updated to account for noncompliance. The officials monitoring the OS modeling results can also contact local officials to take action.

In another embodiment, the system and methods of the invention can identify trends in biomarker levels and daily patient diary information over time that can be used to adjust a drug dose to an optimal level for particular patients (for example, adaptive dose-ranging).

In some embodiments noncompliance may include taking an improper dose of a pharmaceutical agent including without limitation multiple doses or no dose, or may include inappropriately mixing pharmaceutical agents. In preferred embodiments a patient is notified substantially immediately after the signal is compared with a known profile.

An individual monitored by the Health Shield may forget to take a bodily fluid sample for analysis as described herein. In some embodiments a method of alerting an individual to test a sample of bodily fluid using a device as described herein comprises providing a protocol to be run on said device, said protocol communicated from the OS component, associated with said individual, and comprising a time and date to test said sample of bodily fluid; and notifying individual to test said bodily fluid on said date and time if said sample has not been tested. In some embodiments an individual can be notified as described herein, e.g., over a wireless connection. Compliance with therapeutic regimes can be improved by use of prompts on a display and obtaining responses from patients (for example, by way of a touch-screen).

In one embodiment, the system includes a convenient way to package the FS elements required for multiple complex assays in a secure form for shipping. For example, assay elements click fit into a housing.

(c) Field System Assays

A variety of assays may be performed on a fluidic device described herein to detect an analyte of interest in a sample. A wide diversity of labels is available in the art that can be employed for conducting the subject assays. In some embodiments labels are detectable by spectroscopic, photochemical, biochemical, electrochemical, immunochemical, or other chemical means. For example, useful nucleic acid labels include the radioisotopes $32P$, $35S$, C14, H3, I125, and I131, fluorescent dyes, electron-dense reagents, and enzymes. A wide variety of labels suitable for labeling biological components are known and are reported extensively in both the scientific and patent literature, and are generally applicable to the present invention for the labeling of biological components. Suitable labels include radionucleotides, enzymes, substrates, cofactors, inhibitors, fluorescent moieties, chemiluminescent moieties, bioluminescent labels, colorimetric labels or redox labels. Reagents defining assay specificity optionally include, for example, monoclonal antibodies, polyclonal antibodies, proteins, nucleic acid probes or other polymers such as affinity matrices, carbohydrates or lipids. Detection can proceed by any of a variety of known methods, including spectrophotometric or optical tracking of radioactive, fluorescent, or luminescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Thus, a label includes without limitation any composition detectable by spectroscopic, photochemical, biochemical, immunochemical, nucleic acid probe-based, electrical, optical thermal, or other chemical means.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non-radioactive labels are often attached by indirect means. Generally, a receptor specific to the analyte is linked to a signal generating moiety. Sometimes the analyte receptor is linked to an adaptor molecule (such as biotin or avidin) and the assay reagent set includes a binding moiety (such as a biotinylated reagent or avidin) that binds to the adaptor and to the analyte. The analyte binds to a specific receptor on the reaction site. A labeled reagent can form a sandwich complex in which the analyte is in the center. The reagent can also compete with the analyte for receptors on the reaction site or bind to vacant receptors on the reaction site not occupied by analyte. The label is either inherently detectable or bound to a signal system, such as a detectable enzyme, a fluorescent compound, a chemiluminescent compound, or a chemiluminogenic entity such as an enzyme with a luminogenic substrate. A number of ligands and anti-ligands can be used. Where a ligand has a natural anti-ligand, it can be used in conjunction with labeled, anti-ligands. Exemplary ligand—anti-ligands pairs include without limitation biotin—avidin, thyroxine—anti-t4, digoxigenin—anti-digoxin, and cortisol—anti-cortisol, Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl groups, and umbelliferone. Chemiluminescent compounds include dioxetanes, acridinium esters, luciferin, and 2,3-dihydrophthalazinediones, such as luminol.

Methods of detecting labels are well known to those of skilled in the art. Thus, for example, where the label is radioactive, means for detection include scintillation counting or photographic films as in autoradiography. Where the label is fluorescent, it may be detected by exciting the fluorochrome with light of an appropriate wavelength and detecting the resulting fluorescence by, for example, microscopy, visual inspection, via photographic film, by the use of electronic detectors such as digital cameras, charge coupled devices (CCDs) or photomultipliers and phototubes, or other detection device. Similarly, enzymatic labels are detected by providing appropriate substrates for the enzyme and detecting the resulting reaction product. Finally, simple colorimetric labels are often detected simply by observing the color, i.e., the absorbance, associated with the label. For example, conjugated gold often appears pink, while various conjugated beads appear the color of the bead.

In some embodiments the detectable signal may be provided by luminescence sources. Luminescence is the term commonly used to refer to the emission of light from a substance for any reason other than a rise in its temperature. In general, atoms or molecules emit photons of electromagnetic energy (e.g., light) when then move from an excited state to a lower energy state (usually the ground state). If exciting cause is a photon, the luminescence process is referred to as photoluminescence. If the exciting cause is an electron, the luminescence process can be referred to as electroluminescence. More specifically, electroluminescence results from the direct injection and removal of electrons to form an electron-hole pair, and subsequent recombination of the electron-hole pair to emit a photon. Luminescence which results from a chemical reaction is usually referred to as chemiluminescence. Luminescence produced by a living organism is usually referred to as bioluminescence. If photoluminescence is the result of a spin-allowed transition (e.g., a single-singlet transition, triplet-triplet transition), the photoluminescence process is usually referred to as fluorescence. Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as phosphorescence. Typically, phosphorescence emissions persist long after the exciting cause is removed as a result of long-lived excited states which may relax only through such spin-forbidden transitions. A luminescent label may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca] benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

The term analytes as used herein includes without limitation drugs, prodrugs, pharmaceutical agents, drug metabolites, biomarkers such as expressed proteins and cell markers, antibodies, serum proteins, cholesterol and other metabolites, polysaccharides, nucleic acids, biological analytes, biomarkers, genes, proteins, or hormones, or any combination thereof. Analytes can be combinations of polypeptides, glycoproteins, polysaccharides, lipids, and nucleic acids.

Of particular interest are biomarkers are associated with a particular disease or with a specific disease stage. Such analytes include but are not limited to those associated with infectious diseases, autoimmune diseases, obesity, hypertension, diabetes, neuronal and/or muscular degenerative diseases, cardiac diseases, endocrine disorders, metabolic disorders, inflammation, cardiovascular diseases, sepsis, angiogenesis, cancers, Alzheimer's disease, athletic complications, and any combinations thereof.

Of also interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

REFERENCES

Brandeau, M. L., G. S. Zaric, and A. Richter. 2003. Resource Allocation for Control of Infectious Disease in Multiple Independent Populations: Beyond Cost-Effectiveness Analysis. *J. Health Econ* 22:575-598

Chiang, C. L. 1978. *An Introduction to Stochastic Processes and Their Applications*. Kreiger. 517 pgs.

Choi, B C K and A W P Pak. 2003. A simple approximate mathematical model to predict the number of severe acute respiratory syndrome cases and deaths. *J Epidemiol Community Health*. 57(10):831-5

D'Onofrio, A. 2002. Stability Properties of Pulse Vaccination Strategy in SEIR Epidemic Model. *Math. Biosci.* 179:52-72.

Dwyer, G. J. S. Elkinton, and J. P. Buonaccorsi. 1997. Host heterogeneity in Susceptibility and Disease Dynamics: Tests of a mathematical Model. *Am Naturalist*. 150:685-707

FitzGibbon, W. E., M. E. Parrot, and G. F. Webb. 1995. Diffusion Epidemic Models with Incubation and Criss-cross Dynamics. *Math. Biosci.* 128:131-155.

Gibson, G. J. 1997. Investigating mechanisms of Spatiotemporal Epidemic Spread Using Stochastic Models. *Am Phytopathological Society*. 87:139-146

Inaba, H. 1990. Threshold and Stability Results for an Age-structured Epidemic Model. *J Math Biol*. 28:411-434.

Longini, I. M., S. K. Seaholm, E Ackerman, J. S. Koopman, and A. S. Monto. 1984.

Simulation Studies of Influenza Epidemics: Assessment of Parameter Estimation and Sensitivity. *Int J Epidemiology*. 13: 496-501

McKendrick, A. 1926. Applications of Mathematics to Medical Problems. *Proc Edin. Math. Soc.* 44:98-130.

O'Neill, P. D. 2002. A Tutorial Introduction to Bayesian Inference for Stochastic Models Using Markov Chain Monte Carlo Methods. *Math Biosci*. 180:103-114.

Stilianakis, A. I, A. S. Perelson, and F. G. Hayden. Emergence of Drug resistance During an Influenza Epidemic: Insights From a Mathematical Model. *J. Infect Dis*. 177: 863-873.

Timpka, T., M. Morin, J. Jenvald, H. Eriksson, and E. A. Gursky. 2005. Towards a Simulation Environment for Modeling Local Influenza Outbreaks. *AMIA* 2005 *Symposium Proc*. 729-733

EXAMPLES

Example 1. National Influenza Healthcare Monitoring System

In this example, the Health Shield system is customized for the national disease control agency and deployed as a national health shield. The primary objective of the program is to customize a system for containment and pro-active management of diseases such as influenza that can cause epidemics. The system is designed to identify, track, and contain the spread of flu outbreak and significant 'mutant' strains (such as those with resistance to antiviral drugs or those with more virulence) at the earliest stages of infection, thereby improving disease prevention and response. Inputs to the Operating System (OS) modeling efforts are used to determine an optimal sampling and containment strategy for influenza.

A second objective of a subject system is to improve outcomes and reduce healthcare costs by better managing and preventing the progression of chronic diseases, starting with diabetes. The ability to improve outcomes and dramatically reduce healthcare costs by preventing and reversing diabetes alone may reduce annual health expenditure by billions of dollars. HS systems deployed for influenza and diabetes can also be customized to apply to prevention and better management of other chronic diseases such as congestive heart failure (CHF).

The Field System components are deployed nationally, with initial deployment focused on geographic locations and/or populations considered to be at risk. FS systems are deployed in part as robotically automated assays run in central laboratories. The systems have automated on-board controls to improve the reliability of the results. Mobile Field Systems are also deployed in multiple points-of-care, including hospitals, clinics, doctors' offices, and public locations such as schools, pharmacies, airports, etc. The FS components are also deployed for family home use in rural areas where limited health-care infrastructure exists, allowing individuals in those areas to be tested remotely and as needed communicate with health experts wirelessly without having to travel to a clinic or hospital.

For H1N1 influenza ("swine-flu") monitoring, the FS measures antigens and antibodies to H1N1 in blood samples and saliva. The blood and saliva samples are tested on two separate cartridges. The blood tests are multiplexed with tests for a combination of cytokines which measure the body's response to infection.

For H1N1, the FS cartridges are customized to run six assays and two controls, including assays for H1N1 antibody and antigen and four cytokines measuring the body's response to infection. Assay multiplexes are run in less than 90 minutes or less than 30 minutes depending on specific FS configuration. The cartridges for blood and saliva are processed separately or together depending on specific FS configuration. As new virus strains emerge, additional assays are added to the existing panels. For example, the H1N1 assays are further multiplexed with assays for H5N1

(avian or bird flu) antibodies and antigens. High volume reader systems are provided in addition to the single sample readers. The high volume readers are configurable to run tens of samples simultaneously.

The test results are transferred to the centralized government Operating System over secure high speed networks in real-time along with other clinically relevant patient data collected through the instrument touch-screens or through the OS web-portal software extracting information from patient records. The integrated data sets are passed through pattern recognition algorithms to assess an individual's disease status and to check for other abnormalities. The integrated analytical system has controls built in to check for and identify sources of variability in the data. The actions taken when variability or noise in the data is identified are built into the alerting capability of the system based on customized rules set for the governmental organization prior to deployment. The rules specify when and how to notify a clinician, patient and/or patient contacts automatically by phone, email or similar electronic communications when an actionable event is detected.

In implementing a containment strategy for influenza, the parameters of the system are set to control against false negatives. The deployment strategy is weighed against that uncertainty. Monte Carlo modeling is used to estimate the robustness of the strategy by quantifying the uncertainty.

Table 7 below details the configuration and pilot plan for implementing the rollout of the influenza monitoring phase. The Tasks in the table can be completed in parallel to accommodate a faster timeline.

TABLE 7

| Rollout of influenza monitoring phase | |
|---|---|
| Configuration and Deployment Tasks | Motivation/Notes |
| (1) A. Validate assays on test samples and calibrate to establish gold standard levels of performance | (2) |
| (3) A.1 Gain Access to extant archived blood/serum samples for assay development | (4) Validate a high fidelity methodology for detection of key measures of viral load/exposure |
| (5) | (6) Develop insights into extent of the systemic inflammatory response in the presence of the observed viral exposure |
| (7) | (8) Develop a statistical model and insight of the inflammatory measures involved in disease spread |
| (9) B. Establish appropriate regulatory credentials and validations | (10) |
| (11) C. Establish an optimal containment strategy | (12) |
| (13) C.1 Develop a mathematical model and simulation system of epidemic spread | (14) |
| (15) C.1.1 Using extant models of disease spread estimate contract rates, connectivities, incubation periods, infectious potential (i.e., communicability), etc | (16) |
| (17) C.1.2 Build a Monte Carlo simulation system for unperturbed epidemic spread | (18) |
| (19) C.1.3 Identify candidate sampling strategies (e.g., screening in schools or workplaces, rapid follow-up of close relatives/friends upon presentation at the hospital or clinic, etc.) and select the most strategic locations for deployment | (20) |
| (21) C.1.4 Identify candidate containment strategies (e.g., physical quarantine, pre-emptive antiviral treatment of close contacts, etc.) | (22) |
| (23) C.1.5 Work with health economists to evaluate each screening strategy in the context of each containment strategy | (24) |
| (25) C.1.6 Stress model assumptions and explore quantitative impact of these assumptions on ultimate deployment strategy | (26) |
| (27) D. Deploy and pilot system in a government designated test site for system validation | (28) |

TABLE 7-continued

Rollout of influenza monitoring phase

| Configuration and Deployment Tasks | Motivation/Notes |
| --- | --- |
| (29) D.1 Based on the library of containment approaches generated above, adapt the sampling/containment strategy to real world observations | (30) As data emerges, remodel and continuously update to assess whether the containment strategy is still optimal |
| (31) D.2 Adapt sampling and containment strategy to extant logistical constraints in each region/state | (32) |
| (33) D.3. Identify and evaluate cost/benefits of each alternative adaptational strategy | (34) |

Two deployment scenarios for this program are as follows:

Scenario A:

Small pilot program to deploy Health Shield with many measurements at several locations (100,000 assay measurements in people and/or animals monitored across 5-7 centers/high risk locations in a contained area). The program lasts six months. Steps:

a. Customization of the Health Shield per government requirements b. Pilot program run with 100,000 measurements and 100 readers c. Training of 5-7 centers/high risk locations d. Modeling and simulation to identify the most effective containment and prevention strategy in terms of outcomes and health costs e. Modeling and simulation to identify the most effective alerts and recommended actions to be taken based on the various test results Scenario B:

Equip a contained region and surrounding high risk locations for containment and prevention of the spread of influenza while improving treatment of those infected. Demonstrate that the Health Shield effectively contains flu outbreak and prevents the spread of a virus through a comprehensive program in and around the local area using a larger number of measurements and locations than required by scenario A (500,000 measurements in people and/or animals across 25-30 centers/high risk locations). The program lasts six months. Steps:

a. Customization of the Health Shield per government requirements b. Pilot program with 500,000 measurements and 500 readers c. Training of 25-30 centers in and around the contained region d. Modeling and simulation to identify the most effective containment and prevention strategy in terms of outcomes and health costs e. Modeling and simulation to identify the most effective alerts and recommended actions to be taken based on the various test results f. Activate readers to function for disease containment for any influenza outbreak and for the management of other chronic diseases An integrated software component is developed for the FS systems and OS systems, the user interface of which is shown in FIGS. 16 and 17. The integrated software component consists of two applications. One application shown in FIG. 16 is primarily used at regional and local triage centers to collect individual patient data and to make specific recommendations for treatment based on information collected from the patient and assay data collected by the FS. There is a central office component wherein data in loaded to supply the OS model with national and regional data describing the current state of the epidemic. This data updated periodically is used to refine the model to enhance accuracy of prediction. Reports are generated of the data collected and actions taken at local centers.

The application shown in FIG. 17 is used in the central or national office. This application is the user interface for running the model and producing reports generated as outputs of the model. It is here that the user may engage in "what if" scenarios to determine appropriate actions and mitigations to the epidemic.

The ability to detect and proactively contain the spread of mutating flu strains provides a life-saving and economic protection capability that has not been met using existing methodology. These benefits are especially important in decentralized and remote locations where optimal healthcare is not readily available. The proactive health management strategy for chronic diseases is estimated to reduce current healthcare costs by a third to one half of today's spending and ensure that all individuals obtain a consistent and uniform high level of healthcare.

Example 2. Simulation of La Gloria Outbreak with and without Mitigation Policies FIG. 18 illustrates the real world versus simulated results from an outbreak of influenza in La Gloria, Mexico that occurred between February and May of 2009. La Gloria is a town of about 3,000 in Mexico's Velacruz state. Hundreds of townspeople were diagnosed with respiratory problems, including positive tests for swine flu (H1N1) and the more common H2N3 flu variant. FIG. 18 shows a comparison of the actual outbreak data (circles) compared to a model without HS mitigation (solid line). The model with no mitigation agrees closely with actual data. A model with HS surveillance and mitigation policies is shown in the dashed line. The model is determined by iterative fitting of the actual outbreak to the model of FIG. 2 until an optimal fit is achieved. With the HS in place, both the severity and rapidity of the outbreak are projected to be dramatically reduced. The projected improvement is based on the model parameters as determined for the unmitigated outbreak and using the model to predict the outcome assuming surveillance using the HS system and home isolation of those found to be infected.

| Critical model parameters: |
| --- |
| basic reproduction number R0 = 2.2
mean generation time in days Tg = 2.0
fraction of the generation time that is latent (uninfectious) fL = 1/3;
For the unmitigated outbreak
    no surveillance was performed
    no action was taken on the infected population.
For the mitigation illustrated
    60% of the symptomatics (suspected infected) reported for voluntary testing
    Subjects with positive result (based on assay sensitivity of 0.8 (80%) were home quarantined. |

Example 3. Preventing and Reversing Diabetes

For diabetes and its complications (e.g., renal and cardiovascular disease), the cost-benefit relationship of the Health Shield is being quantified both through government and private programs. The programs are designed to dramatically reduce the cost of Type 2 Diabetes Mellitus (T2DM) by preventing, delaying and reversing the progression of the disease through individualized and remotely delivered life style modification therapy using the HS system.

T2DM and often-associated obesity (coined the "diobesity epidemic") lead to frequent cardiovascular, metabolic, ocular, neurologic and renal complications as well as increased cardiovascular morbidity and mortality. T2DM results in a heavy economic burden on the health care system. In the U.S. thirteen percent of adults have diabetes, and 1.6 million new cases are diagnosed each year. The total estimated cost of diabetes in 2007 in the USA was $174 billion and 284,000 deaths in 2007 were attributed to diabetes. See American Diabetes Association, *Diabetes Care* 31, 596 (Mar. 1, 2008).

The United States Armed Forces Services are not immune from the diobesity epidemic. For instance, there are 140,000 diabetic patients cared for by the USAF. On average, diabetes is responsible for $6,649 in excess expenditures per year per person with diabetes. So if just 20% of those with diabetes have their disease delayed or reversed, the savings come to $186,172,000 annually. In just five years the savings is anticipated to reach $1 billion. The costs of delaying the onset of costly micro- and macro-vascular complications are expected to produce an even larger return. Id.

There is evidence that lifestyle interventions reduce the risk of developing diabetes by up to 58%. J. Tuomilehto et al., *N Engl J Med* 344, 1343 (May 3, 2001); W. C. Knowler et al., *N Engl J Med* 346, 393 (Feb. 7, 2002). Large epidemiologic population studies have demonstrated that insulin resistance and the presence of metabolic syndrome parameters identify subjects at higher risk of developing T2DM and cardiovascular and cerebral events. P. W. Wilson, R. B. D'Agostino, H. Parise, L. Sullivan, J. B. Meigs, *Circulation* 112, 3066 (Nov. 15, 2005); C. Lorenzo, M. Okoloise, K. Williams, M. P. Stern, S. M. Haffner, *Diabetes Care* 26, 3153 (November, 2003). The Cardiovascular Health Study just demonstrated that 9 out of 10 new cases of diabetes in subjects 65 years and older are attributable to 5 lifestyle factors whose improvement can drastically reduce the risk of diabetes up to 89%. D. Mozaffarian et al., *Arch Intern Med* 169, 798 (Apr. 27, 2009). These factors include physical activity, diet, smoking, alcohol use, and adiposity. In the Diabetes Prevention Program (DPP), the lifestyle intervention was estimated to delay the development of T2DM by 11 years and to reduce the absolute incidence of diabetes by 20%. P. Lindgren et al., *Int J Technol Assess Health Care* 23, 177 (Spring, 2007).

Accordingly, a promising preemptive strategy to improve national health includes early intervention with individuals at high risk of developing T2DM. The pre-diabetic population, as defined by impaired fasting glucose (IFG) levels and/or impaired glucose tolerance (IGT), is at a greater risk of developing T2DM than their normoglycemic counterparts. However, the rate and time of conversion are difficult to predict at the level of individual subjects. To build on these significant epidemiologic findings, the Health Shield provides a novel diagnostic and treatment paradigm that can focus on the individual subject using dynamic collection and analyses of physiological measures. This approach detects and predicts earlier a subject's risk and trajectory towards the development of T2DM and subsequent cardiovascular, metabolic, ocular, neurologic and renal events. At the same time, the Health Shield delivers to each patient individualized tools and strategies to make necessary life-style changes. The HS reinforces the relevant health messages sent to users by providing physiologically relevant information about the effect of these life-style changes on each individual/family basis.

Management of subjects with T2DM is performed by a comprehensive health care team (HCT) including physicians, nurse practitioners, physician's assistants, nurses, dieticians, pharmacists, and mental health professionals. Additionally, individuals with diabetes assume an active role in their care and receive a comprehensive diabetes self-management education to act upon. The Health Shield aids in that education and management through the flexible point of care testing (POCT) and feedback technology.

For diabetes and its complications, 6 tests are run for each time-point with a run-time of less than 30 minutes. Additional cartridges are provided for renal and cardiovascular disease, each with an additional 6 tests, which are processed in 15 minutes or less to detect the risk of onset of a cardiovascular event or renal failure and assess the need for a hospital visit. This allows for patients to be treated before their diseases progress to the point that they need to visit costly Emergency Rooms.

POCT is defined as a near-patient testing system and has been available for many years, relying on bench top and hand held devices. POCTs as diagnostic tools and clinical decision aids are now an integral part of health care delivery in ambulatory care, primary care, emergency care, and operating rooms. A compelling example is the monitoring of blood glucose during gestational diabetes mellitus that reduces the rate of complications to the mother and the baby.

The Health Shield extends POCT resources to the pre-diabetic population by delivering, e.g.:

1. A Point of Care system which serially and conveniently assesses, in real-time, a variety of circulating blood markers that best quantify, in a dynamic way, insulin resistance, metabolic syndrome, inflammation, and cardiovascular risk. The device is also used as an interface to the Mobile Healthcare System (item 3 below).

2 A mathematical/statistical learning engine that, early-on, characterizes and quantifies the risk of a given subject to develop T2DM and associated complications. The work product of the learning engine will be the set of biological markers that best predict the onset of diabetes and the model that incorporates that predictive power. This type of analysis is typically developed during a statistical model building exercise around competing survival curves as defined by a Kaplan-Meier statistic and in the context of a Cox proportional hazards analysis. The learning engine described herein takes advantage of this probability landscape by sampling at high enough frequencies so as to establish the most informative marker patterns in the most parsimonious markers subset, and from it derives a dynamic hazard/risk space for each individual subject in a cohort. Complementary covariates that are accounted for in the model include age, smoking status, alcohol use, body mass index (BMI), dietary habits, exercise levels, glucose, blood pressure and lipid levels. As additional data are made available to the models, the system improves the probability patterns so as to more completely learn about each subject cohort and adjust itself appropriately.

3. A Mobile Healthcare System that uses the integrated data, algorithms, and models described above in concert with interactions with the subject to assist with behavior modification and increase adherence to diet, exercise and therapy. By interfacing with a subject via either a device touch screen or a network-integrated mobile device such as a cell phone or PDA, the system performs the following:

Assesses the situation and mood behind the subject inquiry

Obtain key indicators by asking questions

Transmit truly individualized and context-specific content to the device touch-screen or to the mobile device/phones to assist users in modifying behavior The individualized content is determined by applying artificial intelligence techniques such as Rule-Based Inference to the subject's measured data from the device, as well as other provided data, the answers to the questions posed to the subject and, if available, the geographic location of the originating call as provided by the on-board GPS.

By integrating and analyzing the response data, the learning engine will provide subject-specific feedback by selecting from a library a particular item that is relevant to the subject's mood, circumstance and location. Items presented include nutritional advice, exercise advice, general lifestyle advice, psychological counseling, restaurant selection in the vicinity of the subject, as well as recommended menu items within that restaurant, electronic coupons for food and lifestyle products, collection of nutritional or exercise data, and reinforcement/encouragement on progress toward achieving health goals.

The use of these tools and the data sent back to the clinicians help the HCT offer each individual subject tailored early therapeutic lifestyle modifications preventing the development of T2DM and its deadly complications.

Example 4. Diabetes Risk Prediction Visualization and Model

In a study of 187 people not known to be diabetic, subjects were subjected to an Oral Glucose Tolerance Test (OGTT). When performing an OGTT, the individual fasts for up to fourteen hours beforehand, and only ingests water. At initiation of the test, the individual is given a blood sugar test to determine a baseline number. Then a sugar solution is given orally. Blood is then retested over a time course. For diabetes, the important numbers will come two hours into the test. For a hypoglycemic individual, blood sugar may not drop for four to six hours.

More information is available online at diabetes-diagnosis.suite101.com/article.cfm/the_glucose_tolerance_test#ixzz0SWaqWbQr A series of measurements of glucose and the hormone GLP-1 were made starting with a fasting glucose level then at several time points following the ingestion of glucose. Measured variable included:

Active GLP and Total GLP at 5 minutes before, and 10, 20, 30, 60, 90, and 120 minutes after the consumption of glucose solution.

Basic profile data: age, height, weight, gender, % body fat.

Creatinine concentration.

Genetic markers: identification of single-nucleotide polymorphism variations (SNPs) for 12 different SNP locations.

Fasting and post-test glucotolerance diagnoses (Normal or Impaired Fasting Glucose; Normal or Impaired Glucotolerance or Diabetes Mellitus)

The glucose tolerance test shows that many subjects either have diabetes or impaired glucose tolerance (IGT). The remainder have normal glucose tolerance (NGT). The GLP-1 results together with demographic information (age, sex, height) and determinations of the 12 SNPs are evaluated by recursive partitioning using Classification and Regression Trees (CART) and generated the recursive partitioning tree shown in FIG. 19. The tree is designed to correlate with and/or predict glucose tolerance. CART is described by Breiman, Friedman, Olshen, and Stone in Classification and Regression Trees, Chapman & Hall/CRC; 1st edition (Jan. 1, 1984). This and similar techniques develop a model through recursively dividing the data according to indicators that will most accurate separate the data. For instance, in this example, the problem is to classify the patient's glucotolerance state. Among the many predictors, the variable "age" with the test criterion of 66.5 years (i.e., is a person 67 years old or older?) gives the split with the fewest classification errors in the model describing the study. For each resulting sub-population in each partition, the next most effective split is identified. By using only part of the data for fitting the model and the remainder for testing, the algorithm avoids overfitting the "training" data.

The analysis revealed that in the population studied, five factors produced an optimal categorization of the subjects: (1) age; (2) GLP-1 (active) levels determined at 120 minutes following administration of glucose; (3) height; (4) body fat (computed from height and weight); and (5), one SNP: rs10305420.

The visualization has multiple purposes. For example, a doctor can use the tree to explain to a patient their risk factors for diabetes. For instance, counting the leaf (terminal) nodes from left to right, a doctor may explain to a patient that they are currently in leaf node #4 ("IGT (2/11/1)"), and that as they age, they will end up in either leaf node #1 or #2, depending on their height. For a shorter patient, this can indicate a very severe risk of developing diabetes, and they may be advised to take a therapeutic intervention, such as lifestyle changes and/or therapeutic treatment.

The tree can also be used to investigate different populations at risk for diabetes. Each of the split criteria indicates a different type of risk and a different mechanism for separating the larger population into subpopulations. As a result, the effect of each splitting criterion could be examined for a causal relationship. In addition, patients who are misclassified as diabetic are classified as such due to significant risk factors that could contribute to their disease. As a result, it would be worth studying this group to determine what other factors may mitigate their risk. For long-term longitudinal study development, the tree can be used to research disease progression. By selecting patients whose condition is still NGT or IGT, but who are at elevated risk (e.g. misclassified as IGT or DM, respectively), a researcher may follow them over time to see which members of the sub-population worsen, and which do not, in order to understand the effects and causes of impaired glucotolerance risk factors. Similarly, the tree can be used for comparative analyses for sub-populations of patients.

Weights (or population counts) may be assigned for a larger sample of a population in order to assess risk that may vary due to different sampling strategies. For such recursive partitioning models, risk may be assessed in different geographic regions, and SIR parameters may be calculated with such trees or with ensembles of CART (classification and regression trees) and other methods, such as kernel methods and other methods involving similarity measures, generalized linear models, various non-parametric and parametric Bayesian methods, and more.

Example 5. Cost-Matrix Adjusted Confusion Matrices

The model of the invention can be adjusted for the cost associated with different errors, based on economic cost, temporal costs, or other factors, in order to minimize the cost of the errors made by a model. This Example present a cost analysis using the data presented in the Example above. Results are shown in Table 8.

TABLE 8

| Predict | True - OGTT DM(22) | IGT (104) | NGT (61) |
|---|---|---|---|
| DM | 12 | 10 | 6 |
| IGT | 9 | 82 | 21 |
| NGT | 1 | 12 | 34 |

In the table, the predicted patient category is compared with the diagnosis based on OGTT. The table was constructed without regard to costs of errors.

A similar matrix of predictions is present below when the model is developed incorporating a weighting based on misclassification costs advised by an expert in the field. Here, the rule states that it is more costly to predict NGT when DM is the correct state for the patient. The rationale is that certain types of error are far worse than others, such as the eventual cost of sending a diabetic patient home with a clean bill of health, versus the cost of follow-up testing for a patient misclassified as diabetic.

TABLE 9

| Predict | True - OGTT DM(22) | IGT (104) | NGT (61) |
|---|---|---|---|
| DM | 19 | 11 | 14 |
| IGT | 3 | 90 | 32 |
| NGT | 0 | 3 | 15 |

Examples of such weights are given below in Table 10 using the costs imposed to generate Table 9. If a diabetic patient is predicted to be NGT, a penalty of 100 is assessed, while a prediction that an IGT patient is diabetic is assessed a much lower penalty of 10: the cost of secondary testing and lifestyle changes would not be as significant as the cost of medical care for the diabetic. These costs can be changed in order to optimize the prediction model for other contexts.

TABLE 10

| Predict | Correct DM | IGT | NGT |
|---|---|---|---|
| DM | 0 | 10 | 30 |
| IGT | 50 | 0 | 20 |
| NGT | 100 | 75 | 0 |

Example 6. Predicting the Onset of Infection and Sepsis and Enabling Earlier Treatment For infection, one focus of Health Shield programs in civilian and military populations has been targeted on improving outcomes in the wounded/burned/seriously ill populations and quantifying the impact of earlier intervention/treatment (~36-24 hours) on survival of those persons.

Through more frequent sampling made possible by the small volume requirement), and a wirelessly integrated analytical modeling engine, Health Shield Systems can be used to anticipate the onset of sepsis up to 36 hours prior to clinical diagnosis.

In this example, hospitalized patients undergoing chemotherapy for Acute Myeloid Leukemia are monitored for the inflammatory markers IL-6, IL-1β, and Protein-C, a protein involved in coagulation control. In patients who become septic (N=4), a combination of events occurred that do not occur in patients who do not progress to sepsis (N=1 1). The events include: 1) Temperature spike to >=38C; 2) IL-6 elevated to >5 ng/mL during a rapid spike (occurring over an interval of <12 hours); 3) Protein-C decline to <1 ug/mL; and 4) IL-1β elevated to >100 pg/mL. Individual events are indicative of occurrence of sepsis. 11-6 peaks at greater than about 10,000 pg/mL in all subjects who become septic (FIG. 36A). Protein-C declines to a minimum of about 1.3 ug/mL in all subjects who become septic (FIG. 36B).

However, fever spike is not predictive of sepsis. Combining information (temperature, IL-6, Protein-C and IL-1β) is effective in prediction of sepsis.

The combination of events was: IF the Temperature>38 OR decline in Protein-C>30%, AND subsequently IL-6 was >5 ng/mL OR IL-1β was >100 pg/mL, the patient progressed to sepsis.

Table 11 shows the time elapsing from an indication of progression to sepsis as defined above to diagnosis for those patients who progress to sepsis. The event combination provides a significant window prior to diagnosis in which therapy can be initiated.

TABLE 11

| Patient | Criterion | Time elapsing (Days) between Marker recognition and Diagnosis |
|---|---|---|
| 1 | IL-6 | 2.2 |
| 1 | Protein-C decline | 0.8 |
| 1 | Fever | 0.0 |
| 4 | IL-6 | 0.2 |
| 4 | Protein-C | 1.1 |
| 4 | IL-1 □ | 0.9 |
| 4 | Fever | 0.0 |
| 12 | Protein-C + Fever | 2.0 |
| 12 | Fever | 2.0 |
| 15 | IL-6 | 0.5 |
| 15 | Fever | 0.1 |

Sepsis is a whole-body inflammatory state comprising a blood infection. Sepsis can lead to septic shock, which is fatal in about 50% of cases. Sepsis and septic shock represent a challenging problem in critical care medicine and are a major cause of mortality in the intensive care unit. In the United States, sepsis develops in 750,000 subjects and septic shock results in about 215,000 deaths per year. The incremental cost of bloodstream infections (BSI) has been calculated to be close to $20,000. M. Kilgore, S. Brossette, *Am J Infect Control* 36, S172 e1 (December, 2008). Patients with intensive care unit (ICU)-acquired BSIs have a significantly increased mean length of ICU stay (15.5 vs. 12 days)

and median costs of hospital care ($85,137 vs. $67,879) compared with patients without ICU-acquired BSI. Id.

Initiating therapy early reduces septic shock-related mortality. The flexible, convenient and intelligent set of tools provided by the HS enables better and earlier care at a lower cost. A salient feature of the system is its ease of use and the direct and active participation of the individual patients and the HCT. A 25% improvement in the number of lives saved correlates with a 25% decrease in the cost of care of those patients who would otherwise have died. In addition to those cost savings is a decrease in the cost of care of those who survive but require lengthy expensive treatment which with the HS system can be treated more rapidly and thus bear less cost on the health center. The total cost reduction associated with HS in managing infection is estimated to be greater than 50% or over $7.5 Bn per year in the United States.

The HS can identify a predictive signature of the onset of infection and sepsis in patients. A similar signature can be used in detecting the presence of infection and the body's response to infection in persons infected by various strains of influenza so that treatments can likewise be customized and made earlier.

Example 7. Influenza Surveillance: Disease Detection Assays

Viral Particle Detection.

FIG. 20A shows detection of an H1 antigen in response to H1:N1 particles. The assays for H1 antigen are performed as described in PCT Patent Publication WO/2009/046227, filed Oct. 2, 2008 and entitled "MODULAR POINT-OF-CARE DEVICES AND USES THEREOF." Samples containing known concentrations of H1N1 antigen are mixed with detector antibody and the mixture is incubated for 30 min. in 384 well microtiter plate wells coated with capture antibody. The wells are washed by repeated aspiration of buffer and then enzyme substrate is added. After 10 min, the microtiter plate is read in an M5 luminometer. The capture antibody is a monoclonal anti-H1 antibody tethered to a substrate. The detector antibody is a polyclonal anti-H1 antibody labeled with APase. The analyte is a particulate preparation displaying both H1 and N1 antigens. Varying amounts of analyte spiked into buffer are shown in FIG. 20 on the X-axis.

Assay for H1N1 in Nasal Sample.

A nasal sample obtained using a swab is extracted using the reagents and protocol of a kit commercially available kit (Quickvue). A buffer solution and the nasal extract with and without added H1N1 antigen are assayed (four replicate measurements/sample) according to the protocol described above with the following results:

TABLE 12

| Analyte | Added Analyte ng/mL | Signal Avg. Counts | Signal CV % |
|---|---|---|---|
| Assay buffer | 0 | 611 | 14 |
| Nasal swab extract | 0 | 324 | 72 |
| Assay buffer | 500 | 29602 | 5 |
| Nasal swab extract | 500 | 18595 | 7 |

The response of the assay to samples with no added antigen is essentially negative and a clear distinction between samples with added antigen and no added antigen is observed.

In a similar example using clinical samples, two assays are run on each multiplexed cartridge with duplicate "tips" for each assay for H1. Results are shown in FIG. 20B. In the figure, "Tips 1, 2" gives an average signal (counts) for one antibody pair and "Tips 3, 4" gives a count for a different assay pair. Nasal swab samples from eight Influenza A-negative samples and 11 2009 Flu positive (H1N1) samples are assayed using the PCR method. Good discrimination between positive and negative samples are found for the samples presented by using the data from both assays using the dotted line as a discriminator (cut-off). Using this threshold, there are eight true negatives, two false negatives, nine true positives and no false positives. The sensitivity (TP/TP+FN) is 81% and the specificity (TN/TN+FP) is 100%. Discrimination using either assay alone is less effective than combining results of both assays.

Host Antibodies.

Host antibodies against influenza particles can be detected according to the invention. The presence of such antibodies can indicate that an individual has a decreased likelihood of active infection leading to disease. FIG. 21 show an assay designed to detect host antibodies in an FS cartridge. In this example, the capture reagent is a surrogate antigen comprising an anti-ideotope of the antibody to be measured bound to the solid phase. The detection reagent is an anti-Human IgG antibody labeled with alkaline phosphatase. Purified humanized monoclonal antibody (analyte) is added in known concentrations to human serum as shown on the X axis. Microtiter plate wells coated with antibody to viral antigen H1 are incubated with diluted sample (human blood, plasma or serum) mixed with alkaline phosphatase-labeled antibody to H1 for 30 min at RT. The wells are washed with buffer and exposed to chemilumiogenic alkaline phosphatase substrate for 10 min before reading the rate of production of photons an M5 luminometer (Molecular Devices). Influenza antibodies can be measured by the same method using influenza antigen bound to the solid phase.

In another set of experiments, host antibodies to H1N1 are detected directly. Capture surfaces are coated with viral antigen. An antibody positive serum sample is diluted 10-fold and incubated with the capture surface for 10 min, followed by incubation with APase-labeled anti-Human IgG for 10 min. After washing the capture surface, an enzyme substrate is added and the assay signal (photon production) is measured after 10 minutes. The results are shown in FIG. 22A. As seen in the figure, the signal increases with antigen load on the surface and reaches a plateau level at about 1000 ng/mL of antigen.

FIG. 22B shows the results of an assay performed as above using an antibody positive sample diluted to different extents. As seen in the figure, the assay response is titrated to a maximum level at about a 10-fold dilution. As a specificity control, measurements are performed in parallel at 0, and 500 ng/mL coating viral antigen coating concentration. There is essentially no response at any sample dilution without antigen present.

Inflammatory Markers.

Spikes in inflammatory markers, e.g., immune markers such as cytokines, can indicate that an individual is infected with an influenza strain that is not identified by the current antigen assays or is undergoing another acute process requiring medical support. FIG. 23 shows the results of an assay for human cytokine IL-6 using an FS cartridge device according to the invention. In this example, the capture reagent is a monoclonal antibody to human 1L-6, and the detection reagent is a polyclonal anti-Human IL-6 antibody labeled with alkaline phosphatase. Purified IL-6 is added to human plasma initially containing essentially no IL-6 in varying amounts as shown on the X-axis of FIG. 23. The plasma samples are assayed in the FS system with the results shown.

In another example, a hospitalized human subject suspected of having swine flu is monitored with the HS system. Two different cartridge types are used on serial nasal samples collected from the subject. One cartridge type has three different multiplexed assays for H1N1 antigen (using different pairs of antibodies), the other type has assays for the inflammatory markers Il-6 and TNF-α. As seen in FIG. 37, the antigen level (as measured by the count rate of the assays) increases by several-fold over days 6-10 of the monitoring period. Over the same time interval, both cytokine levels spike, thereby indicating an acute inflammatory process.

Example 8. Sepsis Marker Assays

Sepsis is a serious medical condition characterized by a whole-body inflammatory state and the presence of a known or suspected infection. Sepsis can lead to septic shock, multiple organ dysfunction syndrome, and death. Protein C is a major physiological anticoagulant. The protein C pathway's key enzyme, activated protein C, provides physiologic antithrombotic activity and exhibits both anti-inflammatory and anti-apoptotic activities. Drotrecogin alpha (activated) is recombinant activated protein C used in the treatment of severe sepsis and septic shock. C-reactive protein (CRP) is a protein found in the blood, the levels of which rise in acute inflammation. CRP is used mainly as a marker of inflammation, and can be used to measure disease progress or treatment efficacy.

FIG. 24 shows the results of monitoring sepsis over time. Reagents for protein-C and C-reactive protein (CRP) were assembled into multiplexed Field System cartridges. The assay system was used to measure these analytes in blood samples obtained from a human patient undergoing chemotherapy. Results are plotted below against the time from beginning therapy. The patient was diagnosed as septic at about day 6 and given intensive care. After making a recovery and being released from the ICU, the patient again became septic at about day 18. The decline in Protein-C preceded recognition of sepsis by about a day. The severity of the inflammatory response to sepsis is indicated by the massive increase in CRP.

Example 9. Diabetes Surveillance: GLP-1 and C-Peptide Assays

FIG. 25 shows an assay performed using an FS cartridge system according to the invention for GLP-1, a hormone involved in regulating glucose metabolism. In this example, the capture reagent is a monoclonal antibody to GLP-1 and the detection reagent is a monoclonal anti Human GLP-1 antibody labeled with alkaline phosphatase. The samples are GLP-1 free human plasma spiked with various concentrations of GLP-1, as indicated on the Y-axis in FIG. 25.

FIG. 26 shows an assay for C-Peptide, a peptide that is made when proinsulin is split into insulin and C-peptide. There is a 1:1 ratio between the amount of insulin and C-peptide created. In this example, the capture reagent is a monoclonal antibody to C-peptide and the detection reagent is a monoclonal anti-Human C-Peptide antibody labeled with alkaline phosphatase. The samples comprise C-peptide spiked into buffer at various concentrations, as indicated on the X-axis in FIG. 26.

FIG. 27 illustrates a correlation using an FS cartridge system according to the invention for measuring C-Peptide compared to the results obtained by measuring C-Peptide with a reference method. In this example, plasma samples are analyzed using an FS cartridge system and a reference method (Linco). Results from the two assays are compared and correlate well over the entire reportable range of the assay.

The concentrations of GLP-1 and C-Peptide change in the blood in response to caloric intake. FIG. 28 presents the results of a clinical study of response of these analytes to a food challenge. In the study, human subjects are monitored for about a day. Three subjects consume a meal following time point 0. Blood samples are collected into collection tubes supplemented with inhibitors of GLP-1 proteolysis at the time points indicated on the graph. Plasma from these samples is analyzed in the system in multiplexed assay cartridges configured to measure GLP-1 (FIG. 28A) and C-peptide (FIG. 28B) simultaneously. As shown in FIG. 28, subjects exhibit very different responses with respect to both the kinetics and magnitude of the hormonal responses for both GLP-1 and C-peptide.

Example 10. Cost Savings During Clinical Trials

The demands of a clinical trial are exceptionally challenging because of the tremendous cost of analysis and the strict regulatory requirements. Feedback from our clinical trial experiences, where many of the practices are even more rigorous in actual clinical practice (e.g., higher costs for equivalent tests), suggests great cost savings using the Health Shield according to the invention.

The referenced savings are accumulated over a series of steps, including:
1) Sample collection.
2) Sample shipping.
3) Sample analysis.
4) Data collection.
5) Data integration.
6) Transmission of results.
7) Follow up testing and passing through the cycle again.

Steps 1 through 4 are all performed by the HS systems, thereby eliminating many potential human error phases. Further cost reductions are realized through reduced infrastructure. The cost of reagents on Health Shield Systems scales with volume and as higher volumes of a given test are produced, the cost of reagents decreases significantly. The costs presented below are based on known costs of the HS system and typical costs of conventional testing.

| Conventional Infrastructure Health Shield Per Assay Cost Using Theranos | | | vs. | Per Assay Cost Using Conventional Infrastructure | | |
|---|---|---|---|---|---|---|
| (35) Blood draw | (36) | $0 | (37) (38) | Blood draw | (39) | $5 |
| (40) Sample prep | (41) | $0 | (42) (43) | Sample prep | (44) | $10 |
| (45) Shipping/Storage | (46) | $0 | (47) (48) | Shipping/Storage | (49) | $7 |

-continued

| | Conventional Infrastructure Health Shield Per Assay Cost Using Theranos | | | vs. | | Per Assay Cost Using Conventional Infrastructure | | |
|---|---|---|---|---|---|---|---|---|
| (50) | Assay Reagents | (51) | $59 | (52) | (53) | Assay Reagents | (54) | $10 |
| (55) | Lab Tech | (56) | $0 | (57) | (58) | Lab Tech | (59) | $25 |
| (60) | Data Analysis | (61) | $0 | (62) | (63) | Data Analysis | (64) | $10 |
| (65) | Subject Compensation | (66) | $0 | (67) | (68) | Subject Compensation | (69) | $10 |
| (70) | Overhead | (71) | 0% | (72) | (73) | Overhead | (74) | 25% |
| (75) | Total | (76) | $59 | (77) | (78) | Total | (79) | $96 |

Example 11. Data Communications

This example shows the efficiency and reliability of data communications of a deployed Health Shield system. As described herein, the Health Shield system of the invention comprises two components, the Field Systems (FS) and Operating System (OS). The FS units are deployed in the field and can communicate with the centrally located OS system using wireless communication, among others. The communication channels can provide two-way communications. For example, assay protocols can be sent from the OS to the FS instruments, and assay results sent from the FS instruments to the OS for (1) interpretation using calibration algorithms and (2) routing of analyte values and further analysis to designated persons including drug company staff, doctors, patients. To evaluate the reliability of the communication system, FS instruments are deployed to several locations and data transmission from FS instruments to an OS server were recorded. Instruments were located in four different countries and in laboratories and homes of patients. Several hundred samples are analyzed with 100% successful communication of results. In some cases, the instrument does not communicate on the first try (overall 92% success), but communication occurs after the instrument tried to communicate again. Attempts continue until communication is successful.

at the point of care for monitoring cancer therapy. One significant new class of anti-cancer drugs are inhibitors of angiogenesis that interfere with the action of VEGF on cell surface VEGFR2. Assays for VEGF and its receptor VEGFR2 are therefore of interest. The capture surface of an assay unit is coated with capture reagent as follows. The inner surface of the assay unit made from injection molded polystyrene is exposed to a succession of coating reagents by aspiration and pneumatic ejection. Twenty microliters of each coating reagents are drawn into assay units and incubated at room temperature for 10 minutes. The coating reagents used in this example are, as used in succession, Neutravidin (20 ug/mL) in Carbonate-Bicarbonate buffer (pH 9), biotinylated "capture antibody" (a monoclonal antibody directed to VEGFR2 at 20 ug/mL) in Tris buffered saline, (pH 8), and a "fixative" reagent containing 3% bovine serum albumin in Tris-buffered saline. After the succession of coatings, the assay units are dried by exposure to dry air and stored desiccated. Assay units and other reagents are assembled in a housing and used for sample analysis in the instrument of the system.

Samples for analysis are distributed to the assay unit diluted in a solution of 50 mM tris-buffer (pH 8) containing bovine serum albumin and isotonic sucrose for 20 minutes. In a reagent unit comprising a conjugate, a solution of Alkaline phosphatase (bovine intestine)—labeled monoclo-

TABLE 13

Efficiency and Reliability of Data Communications

| Trial | Site type and location | Samples assayed | Data transmitted GSM[1] bytes | Communication attempts | Retries | % first time successful |
|---|---|---|---|---|---|---|
| 1 | Homes (N = 22) + Laboratory #1, USA | 121 | 3.5E+08 | 471 | 22 | 95.3 |
| 2 | Laboratory #2, UK | 38 | 4.6E+07 | 158 | 3 | 98.1 |
| 3 | Laboratory #3, UK | 435 | 3.8E+09 | 29,274 | 2,449 | 91.6 |
| 4 | Laboratory #4, UK | 79 | 3.5E+08 | 344 | 1 | 99.7 |
| 5 | Laboratories #5-7 NL, IT | 32 | 3.7E+07 | 120 | 3 | 97.5 |
| All | | 705 | 4.5E+09 | 30,367 | 2,478 | 91.8 |

[1]Global System for Mobile Communications

Example 12. VEGFR2 Assay

In this example, a Field System cartridge device is used to perform an assay for human soluble VEGFR2. The example demonstrates a type of assay that can be performed nal antibody directed to VEGFR2 (binding to a distinct epitope to the antibody of the capture surface) at 250 ng/mL in a stabilizer reagent from Biostab is provided to the assay unit for 10 minutes. After the conjugate is allowed to bind with the complex of the analyte bound to the capture surface, the assay unit is washed with a solution contained in a reagent unit (commercially available wash buffer from Assay Designs). The assay unit is washed 5 times. Then the assay unit is moved to collect and mix with another reagent contained in a different reagent, a solution of a commercially available luminogenic substrate for alkaline phosphatase (KPL Phosphaglo), and incubated for 10 minutes. The reaction of the assay in the assay unit is detected by a detector assembly of the invention.

FIG. 29 demonstrates the VEGFR2 assay response using the method of the example. The x axis scale is VEGFR2 concentration (pg/mL); the y scale is relative luminescence (counts). The curve is used to calibrate the modular assay unit and reagent units.

Example 13. Analyte Detection in Plasma

Magnetizable beads are 1.3 um diameter BioMag magnetic particles from Bangs Laboratories. Beads are coated (by the manufacturer) with anti-Rabbit IgG. Beads are dispersed at 14 mg/mL in tris-buffered sucrose (or, alternatively, tris buffered saline) containing 3% bovine serum albumin and rabbit anti-human red blood cell IgG, from CedarLane at >=1.15 mg/mL. Aliquots (10 uL of this dispersion were dispensed into conical tubes and lyophilized (frozen in liquid N2 and lyophilized for approximately 24 hrs. at −70 C) prior to insertion into a slot in the cartridge housing. The rabbit antibody binds both to the red cells and to the anti-rabbit IgG-coated beads and forms a co-agglutinate of beads and red cells.

The lyophilized magnetizable bead pellet is re-suspended by adding 20 uL of whole blood then aspirating and dispensing eight times (over 1.5 min) into a conical tube.

Blood is separated by placing the tip (in a vertical orientation) in a strong, horizontally oriented magnetic field. Typically 8 uL of essentially red cell free plasma with no observable hemolysis is recovered from a 20 ul blood sample (70% yield of plasma). Recovery of analytes (compared to plasma not exposed to the magnetic separation) is close to 100% for Protein-C, VEGF, PlGF, Insulin, GIP and GIP-1.

Example 14. C-Reactive Protein

Serial dilution of a sample for analyses of an analyte can be carried out in a system as described herein. C-reactive protein (CRP) is an acute-phase marker. Normal levels are in the high ng/mL to low ug/ml range. In any acute disease process, the human liver produces CRP and levels in blood can increase to hundreds of ug/ml. CRP has presented issues for prior art POC analytic systems because of the wide dynamic range of analyte to be measured (>$10^5$-fold).

An FS cartridge system as described herein comprising a fluid transfer device and a cartridge or device with arrays of assay and reagent units is developed. Assay tips having monoclonal anti-CRP bound to their inner surface are mounted in cartridge together with a detector-antibody solution (alkaline-phosphatase labeled monoclonal anti-CRP (having a different epitope specificity than that on the tips), a wash solution and a chemiluminogenic alkaline phosphatase (PhosphaGLO™) substrate from KPL.

To assay CRP, the cartridges are loaded with pre-diluted solutions of CRP used without further dilution. The cartridges are processed by a FS device. Successively the CRP solution (10 uL), detector antibody (12 uL) are drawn into the tips incubated for 10 min at 34° C. then discarded. The tips are washed by four aspirations of 20 uL wash solution before 15 uL of substrate is aspirated into the tips. After 10 min at 37° C., light emission is measured by the instrument for 5 s. CRP concentration is plotted against the assay signal (photon counts) and the data is fitted to a 5-term polynomial function as shown below to generate a calibration function as shown in FIG. 30.

An experiment is executed using serial dilutions of a sample containing highly concentrated analyte to obtain an unambiguous assay response in a system and device as described herein. Solutions of CRP (20 uL) are loaded into cartridges and serially diluted by the instrument (to dilutions of 1: 50, 250, 750 and 1500-fold respectively). The diluted solutions are processed as above. When the diluted CRP concentration exceeds the upper end of the calibration range of the assay (300 ng/mL), a downward response is seen (as shown below; data from two instruments).

The response as shown in FIG. 31 can be modeled using a modification of the Scatchard binding isotherm ($S/S_{max}=C/(C+C0.5)$). The modification assumes that the response of the assay is linearly proportional to the concentration of the detector antibody, as is the case in this example (data not shown). Any carry-over of CRP in the diluted sample into the next reagent (detector antibody) will react rapidly with the reagent rendering it incapable of binding to antigen bound to the solid phase antibody. The reduction in effective concentration is reduced in proportion to the CRP carried-over and can be accounted for with a factor $(D-C*f)/D$.

Therefore, $S=S_{max}*(C/(C+C0.5))*(D-C*f)/D$, wherein S is the assay signal, Smax is the maximum signal (corresponding to zero carry-over), C is the concentration of analyte, C0.5 is the concentration for half-maximal signal (no carry-over), D is the detector antibody concentration, and f is the fractional carryover.

Values used to fit the data, is derived by optimizing each of the four parameters below using the technique of minimization of least square differences between the data and the model fit. As can be seen in FIG. 31, an excellent fit is achieved and the values of the parameters Smax, C0.5 and D (see Table 14) are close to the values that can be estimated from the maximum signal reached, the observed C0.5 and the known detector antibody concentration. This model estimated the extent of carry-over as 0.034% (decimal 3.83E-04).

TABLE 14

Best fit parameters to model describing biphasic CRP assay response

| Parameter | Value | Units |
|---|---|---|
| Smax | 7.24E+05 | Counts |
| C0.5 | 5.02E+01 | ng/mL |
| D | 5.72E+00 | ng/mL |
| f | 3.83E−04 | |

Data can be then be viewed according to the dilution used to achieve the final concentration in each assay tip, and for each dilution level the responses fit to the same response showing that the dilutions are accurate and precise as shown in FIG. 32.

The model as described herein can be used to compute responses for any given dilution and set up algorithms to ensure that the analyte concentration is only computed from tips within the calibration range. Graphic means of representing the data are shown in FIG. 33, wherein the normalized assay response (B/Bmax) is plotted against the log normalized concentration (C/C0.5) for relative dilutions: 1:1

(solid line), 5:1 (dashed line), and 25:1 (dotted line). FIGS. 34 and 35 illustrate a similar example as FIG. 33 at different normalized concentrations. Simple pattern recognition algorithms can be used to identify data for high concentration samples. For example, for most of the dose-response, the signal decreases with dilution. When signal for any dilution equal or exceed that of the next higher dilution, the lower dilution result is rejected. In another example, concentrations derived by using the calibration function shown above, should correspond within some system imprecision with the known dilutions. If the calculated concentration for a low dilution is lower than would correspond with those for higher dilutions, the lower dilution result can be rejected.

When the assay dose-response approaches a maximum, the slope of the concentration ($\Delta C/\Delta S$) versus signal increases. For assays in which the relative variation in signal ($\Delta S/S$) is essentially constant (for example some instances of the system as described) this translates to a bigger variation in the calculated concentration result at higher concentrations. As provided herein, dilution or serial dilution of sample can provide a desired concentration precision (for example <10% CV) at signal levels significantly greater (for example, >10-fold) higher than the blank (zero analyte) signal but not close to the maximum signal (for example <0.3*Max. signal). Serial dilution enables the assay signal to be moved into this range for any relevant sample concentration.

By making several estimates of the analyte concentration from different dilutions, an average value can be obtained. An average value can also be achieved by making replicate measurements at a single dilution level. In some instances, a serial dilution approach as offered by the methods, systems, and device described herein can often eliminate errors due to non-linearity of dilution due to (for example) matrix effects from the sample.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for modeling a progression of a disease within a population, the system comprising:
 a point-of-care sample processing device including:
  a cartridge receptacle configured to receive a testing cartridge, the testing cartridge configured to facilitate performance of an assay in the point-of-care sample processing device;
  a memory that stores assay instructions and assay results; and
  a transceiver; and
 a central computing device that includes:
  a communication subsystem configured to receive the assay results from the memory, and to transmit the assay instructions to the point-of-care sample processing device;
  a modeling system configured to generate a model of the progression of the disease within the population based on the received assay results, the generating of the model including:
   calculating a weighting factor associated with a corresponding first age group and a second age group;
   calculating a ratio of infectious individuals based on a first number of individuals in the second age group, and a second number of individuals in the second age group who comingle with individuals of another age group; and
   multiplying the weighting factor by the ratio of infectious individuals; and
  a processing unit configured to generate the assay instructions based on the generated model, the assay instructions including machine-readable instructions for causing the point-of-care sample processing device to interact with the testing cartridge,
 wherein the point-of-care sample processing device is positioned at a location physically separate from the central computing device.

2. The system of claim 1, further comprising:
 a static database that stores static data relating to the disease; and
 a dynamic database that stores dynamic data relating to the population and individuals within the population.

3. The system of claim 2, wherein the dynamic data includes indications of disease states of the individuals within the population.

4. The system of claim 2, wherein the modeling system is further configured to generate the model based on the data in the static database and the dynamic database.

5. The system of claim 4, wherein the modeling system is further configured to propose a course of action for responding to the disease based on the generated model.

6. The system of claim 4, wherein the modeling system is further configured to:
 propose a plurality of courses of actions for responding to the disease based on the generated model, and
 rank the plurality of courses of actions according to at least one of cost, number of affected individuals, quality-adjusted life year (QALY), or QALY per economic cost unit.

7. The system of claim 1, wherein the performance of the assay includes measuring a biomarker in a sample of bodily fluid of an individual.

8. A system for modeling a progression of a disease within a population, the system comprising:
 a plurality of point-of-care sample processing devices, each of the plurality of point-of-care sample processing devices including:
  a testing receptacle configured to receive a testing apparatus and a testing sample, the testing apparatus configured to facilitate performance of an assay on the testing sample in the point-of-care sample processing device;
  a memory that stores assay parameters and assay results; and
  a transceiver; and
 a central computing device that includes:
  a communication subsystem configured to receive the assay results from the memory, and to transmit the assay parameters to the plurality of point-of-care sample processing devices;
  a disease modeling system configured to generate a model of the progression of the disease within the population based on the received assay results, and to generate the assay parameters based on the generated model, the assay parameters being machine readable for causing the plurality of point-of-care sample processing devices to interact with their respective testing apparatuses, the generating of the model including:
   calculating a weighting factor associated with a corresponding first age group and a second age group;
   calculating a ratio of infectious individuals based on a first number of individuals in the second age group, and a second number of individuals in the second age group who comingle with individuals of another age group; and
   multiplying the weighting factor by the ratio of infectious individuals,
wherein each of the plurality of point-of-care sample processing devices are positioned at distributed locations physically separate from the central computing device.

9. The system of claim 8, further comprising:
a static database that stores static data relating to the disease; and
a dynamic database that stores dynamic data relating to the population and individuals within the population.

10. The system of claim 9, wherein the dynamic data includes indications of disease states of the individuals within the population.

11. The system of claim 9, wherein the disease modeling system is further configured to generate the model based on the static data in the static database and the dynamic data in the dynamic database.

12. The system of claim 11, wherein the disease modeling system is further configured to propose a course of action for responding to the disease based on the generated model.

13. The system of claim 11, wherein the disease modeling system is configured to:
   propose a plurality of courses of actions for responding to the disease based on the generated model, and
   rank the plurality of courses of actions according to at least one of cost, number of affected individuals, quality-adjusted life year (QALY), or QALY per economic cost unit.

14. The system of claim 8, wherein the performance of the assay includes measuring a biomarker in the testing sample, wherein the testing sample is bodily fluid of an individual.

15. A system for modeling a progression of a disease within a population, the system comprising:
a plurality of point-of-care sample processing devices located at a plurality of distributed locations, each of the plurality of point-of-care sample processing devices including:
   a testing receptacle configured to receive a testing apparatus that facilitates performance of an assay;
   a sample receptacle configured to receive a testing sample on which the assay is to be performed;
   a memory that stores assay parameters and assay results; and
   a transceiver; and a central computing device positioned at a location that is physically remote from the plurality of point-of-care sample processing devices and configured to communicate with a plurality of databases, the central computing device including:
   a communication subsystem configured to receive the assay results from the memory, and to transmit the assay parameters to the plurality of point-of-care sample processing devices; and
   a disease modeler configured to generate a model of the disease based on information received from the plurality of databases and the assay results, and to generate the assay parameters based on the model, the assay parameters being machine-readable for causing the plurality of point-of-care sample processing devices to interact with their respective testing apparatuses, the generating of the model including:
      calculating a weighting factor associated with a corresponding first age group and a second age group;
      calculating a ratio of infectious individuals based on a first number of individuals in the second age group, and a second number of individuals in the second age group who comingle with individuals of another age group; and
      multiplying the weighting factor by the ratio of infectious individuals.

16. The system of claim 15, wherein the plurality of databases includes a static database that stores static information relating to the disease, the population, and individuals within the population, and a dynamic database that stores information relating to the disease that is updated in real-time.

17. The system of claim 16, wherein the disease modeler is configured to automatically generate an updated model in response to information in the dynamic database being updated, and to generate updated assay parameters based on the updated model.

18. The system of claim 17, wherein the communication subsystem is configured to transmit the updated assay parameters to the plurality of point-of-care sample processing devices, and
   wherein each of the plurality of point-of-care sample processing devices are configured to automatically implement the updated assay parameters in response to receiving the updated assay parameters.

19. The system of claim 15, wherein the disease modeler is further configured to generate a plurality of proposed courses of action for responding to the disease based on the model, and a plurality of sets of assay parameters corresponding to each of the plurality of proposed courses of action.

20. The system of claim 15, wherein the testing apparatus is a modular testing cartridge.

* * * * *